US012537071B1

(12) United States Patent
Bermudes

(10) Patent No.: US 12,537,071 B1
(45) Date of Patent: Jan. 27, 2026

(54) BACTERIA HAVING BOOLEAN CONTROL PATHWAYS EXPRESSING THERAPEUTIC PROTEINS INCLUDING IMMUNOTHERAPEUTIC CYTOTOXINS

(71) Applicant: David Gordon Bermudes, Woodland Hills, CA (US)

(72) Inventor: David Gordon Bermudes, Woodland Hills, CA (US)

( * ) Notice: Subject to any disclaimer, the term of this patent is extended or adjusted under 35 U.S.C. 154(b) by 1224 days.

(21) Appl. No.: 17/383,301

(22) Filed: Jul. 22, 2021

Related U.S. Application Data

(60) Provisional application No. 63/055,327, filed on Jul. 22, 2020.

(51) Int. Cl.
*G16B 5/10* (2019.01)
*C12N 1/20* (2006.01)
*C12N 15/74* (2006.01)

(52) U.S. Cl.
CPC ............... *G16B 5/10* (2019.02); *C12N 1/205* (2021.05); *C12N 15/74* (2013.01)

(58) Field of Classification Search
CPC ........... G16B 5/10; C12N 1/205; C12N 15/74
See application file for complete search history.

(56) References Cited

U.S. PATENT DOCUMENTS

| | | | |
|---|---|---|---|
| 4,190,495 | A | 2/1980 | Curtiss, III |
| 4,735,801 | A | 4/1988 | Stocker |
| 4,888,170 | A | 12/1989 | Curtiss, III |
| 4,968,619 | A | 11/1990 | Curtiss, III |
| 5,066,596 | A | 11/1991 | Manning et al. |
| 5,098,998 | A | 3/1992 | Mekalanos et al. |
| 5,143,830 | A | 9/1992 | Holland et al. |
| 5,294,441 | A | 3/1994 | Curtiss, III |
| 5,330,753 | A | 7/1994 | Mekalanos et al. |
| 5,387,744 | A | 2/1995 | Curtiss, III et al. |
| 5,424,065 | A | 6/1995 | Curtiss, III et al. |
| 5,468,485 | A | 11/1995 | Curtiss, III |
| 5,470,719 | A | 11/1995 | Meng et al. |
| 5,508,192 | A | 4/1996 | Georgiou et al. |
| 5,527,678 | A | 6/1996 | Blaser et al. |
| 5,627,067 | A | 5/1997 | Siadak et al. |
| 5,628,996 | A | 5/1997 | Siadak et al. |
| 5,643,771 | A | 7/1997 | Stocker |
| 5,654,184 | A | 8/1997 | Curtiss, III et al. |
| 5,656,488 | A | 8/1997 | Curtiss, III et al. |
| 5,662,905 | A | 9/1997 | Siadak et al. |
| 5,672,345 | A | 9/1997 | Curtiss, III |
| 5,679,564 | A | 10/1997 | Pace et al. |
| 5,679,880 | A | 10/1997 | Curtiss, III et al. |
| 5,686,079 | A | 11/1997 | Curtiss, III et al. |
| 5,695,983 | A | 12/1997 | Miller et al. |
| 5,717,071 | A | 2/1998 | Raff |
| 5,731,196 | A | 3/1998 | Miller, III et al. |
| 5,736,367 | A | 4/1998 | Haun et al. |
| 5,747,028 | A | 5/1998 | Calderwood et al. |
| 5,770,214 | A | 6/1998 | Dougan et al. |
| 5,773,007 | A | 6/1998 | Penney et al. |
| 5,811,105 | A | 9/1998 | Dougan et al. |
| 5,824,502 | A | 10/1998 | Honjo et al. |
| 5,824,538 | A | 10/1998 | Branstrom et al. |
| 5,830,702 | A | 11/1998 | Portnoy et al. |
| 5,837,509 | A | 11/1998 | Israelsen et al. |
| 5,837,541 | A | 11/1998 | Raff |
| 5,840,483 | A | 11/1998 | Curtiss, III |
| 5,843,426 | A | 12/1998 | Miller et al. |
| 5,855,879 | A | 1/1999 | Curtiss III |
| 5,855,880 | A | 1/1999 | Curtiss, III et al. |
| 5,869,066 | A | 2/1999 | Pace et al. |
| 5,874,088 | A | 2/1999 | Mekalanos |
| 5,877,159 | A | 3/1999 | Powell et al. |
| 5,888,799 | A | 3/1999 | Curtiss, III |
| 5,989,868 | A | 11/1999 | Harrison et al. |
| 6,024,961 | A | 2/2000 | Curtiss, III et al. |
| 6,030,624 | A | 2/2000 | Russell et al. |
| 6,051,237 | A | 4/2000 | Paterson |
| 6,051,416 | A | 4/2000 | Pace et al. |
| 6,077,678 | A | 6/2000 | Pace et al. |
| 6,080,849 | A | 6/2000 | Bermudes et al. |
| 6,083,715 | A | 7/2000 | Georgiou et al. |
| 6,100,388 | A | 8/2000 | Casas et al. |

(Continued)

FOREIGN PATENT DOCUMENTS

| | | |
|---|---|---|
| EP | 0973911 | 1/2000 |
| EP | 1270730 | 1/2003 |
| EP | 1402036 | 3/2004 |
| EP | 1407052 | 4/2004 |
| EP | 1068339 B1 | 7/2008 |
| WO | WO020832149 | 12/1899 |
| WO | WO0047222 | 8/2000 |
| WO | WO0125397 | 4/2001 |
| WO | WO02067983 | 9/2002 |
| WO | WO02074336 | 9/2002 |
| WO | WO2002070645 | 9/2002 |
| WO | WO02087494 | 11/2002 |
| WO | WO03014380 | 2/2003 |
| WO | WO2004016281 | 2/2004 |
| WO | WO2005005630 | 1/2005 |
| WO | WO2005018332 | 3/2005 |
| WO | WO2005054477 | 6/2005 |
| WO | WO2006017929 | 2/2006 |
| WO | WO2006048344 | 5/2006 |
| WO | WO2008073148 | 6/2008 |
| WO | WO2008089132 | 7/2008 |
| WO | WO2009021548 | 2/2009 |
| WO | WO2009126189 | 10/2009 |

*Primary Examiner* — Iqbal H Chowdhury
(74) *Attorney, Agent, or Firm* — Hoffberg & Associates; Steven M Hoffberg

(57) ABSTRACT

Tumor-selective expression of therapeutic molecules by bacteria is achieved by one or more AND, NOR, OR, NOT and/or NAND gate genetic circuits. The therapeutic molecules can be proteins, metabolites or catabolites, and may also be immunotherapeutics or immunotherapeutic cytotoxins. Single or multiple expression components may be used. Tumor selective expression of multimeric proteins utilizes multimerization as to complete the genetic circuit. Genetic circuits that are unlinked, function to achieve a combined effect on specificity of delivery of antitumor therapeutic molecules. Compositions and methods to generate silica, PEG and Poly-HPMA coated bacteria are also provided. Compositions and methods for selectively sensing or imaging tumors are also described.

20 Claims, 9 Drawing Sheets

Specification includes a Sequence Listing.

(56) References Cited

U.S. PATENT DOCUMENTS

| | | | |
|---|---|---|---|
| 6,129,917 | A | 10/2000 | Potempa et al. |
| 6,130,082 | A | 10/2000 | Majarian et al. |
| 6,150,170 | A | 11/2000 | Powell et al. |
| 6,153,203 | A | 11/2000 | Holmgren et al. |
| 6,177,083 | B1 | 1/2001 | Lubitz |
| 6,190,657 | B1 | 2/2001 | Pawelek et al. |
| 6,207,167 | B1 | 3/2001 | Ou et al. |
| 6,207,648 | B1 | 3/2001 | Waxman et al. |
| 6,245,338 | B1 | 6/2001 | Kyd et al. |
| 6,254,875 | B1 | 7/2001 | Kyd et al. |
| 6,284,477 | B1 | 9/2001 | Kyd et al. |
| 6,294,655 | B1 | 9/2001 | Ford et al. |
| 6,306,387 | B1 | 10/2001 | Galan |
| 6,309,861 | B1 | 10/2001 | Ambrosius et al. |
| 6,329,172 | B1 | 12/2001 | Rhee et al. |
| 6,337,072 | B1 | 1/2002 | Ford et al. |
| 6,339,141 | B1 | 1/2002 | Ballinger et al. |
| 6,365,163 | B1 | 4/2002 | Holmgren et al. |
| 6,365,723 | B1 | 4/2002 | Blattner et al. |
| 6,365,726 | B1 | 4/2002 | Ballinger et al. |
| 6,372,892 | B1 | 4/2002 | Ballinger et al. |
| 6,376,281 | B1 | 4/2002 | Kohler et al. |
| 6,383,496 | B1 | 5/2002 | Curtiss, III et al. |
| 6,410,012 | B1 | 6/2002 | Sizemore et al. |
| 6,413,523 | B1 | 7/2002 | Clements |
| 6,426,191 | B1 | 7/2002 | Ford et al. |
| 6,444,445 | B2 | 9/2002 | Nikolich et al. |
| 6,447,784 | B1 | 9/2002 | Bermudes et al. |
| 6,455,279 | B1 | 9/2002 | Ambrosius et al. |
| 6,471,964 | B1 | 10/2002 | Biering et al. |
| 6,475,482 | B1 | 11/2002 | Bermudes et al. |
| 6,495,661 | B1 | 12/2002 | Glisson et al. |
| 6,500,419 | B1 | 12/2002 | Hone et al. |
| 6,506,550 | B1 | 1/2003 | Fulton et al. |
| 6,511,666 | B1 | 1/2003 | Reynolds et al. |
| 6,531,313 | B1 | 3/2003 | Goudsmit et al. |
| 6,537,558 | B2 | 3/2003 | Kaniga |
| 6,541,623 | B1 | 4/2003 | Ford et al. |
| 6,548,287 | B1 | 4/2003 | Powell et al. |
| 6,566,121 | B1 | 5/2003 | Jacobs, Jr. et al. |
| 6,593,147 | B1 | 7/2003 | Barbet et al. |
| 6,596,509 | B1 | 7/2003 | Bauer et al. |
| 6,596,510 | B1 | 7/2003 | Lubitz et al. |
| 6,599,509 | B2 | 7/2003 | Fox et al. |
| 6,605,697 | B1 | 8/2003 | Kwon et al. |
| 6,610,300 | B1 | 8/2003 | Segers et al. |
| 6,610,529 | B1 | 8/2003 | Curtiss, III et al. |
| 6,635,246 | B1 | 10/2003 | Barrett et al. |
| 6,642,027 | B2 | 11/2003 | Diaz-Torres |
| 6,653,128 | B2 | 11/2003 | Barbet et al. |
| 6,673,569 | B1 | 1/2004 | Kurokawa et al. |
| 6,682,729 | B1 | 1/2004 | Powell et al. |
| 6,685,935 | B1 | 2/2004 | Pawelek et al. |
| 6,719,980 | B1 | 4/2004 | Weston et al. |
| 6,737,521 | B1 | 5/2004 | Fischetti et al. |
| 6,749,831 | B1 | 6/2004 | Bennett-Guerrero et al. |
| 6,752,994 | B2 | 6/2004 | Jacobs, Jr. et al. |
| 6,770,632 | B1 | 8/2004 | Aghi et al. |
| 6,780,405 | B1 | 8/2004 | Curtiss, III et al. |
| 6,798,684 | B2 | 9/2004 | Low et al. |
| 6,825,028 | B1 | 11/2004 | Von Eichel-Streiber et al. |
| 6,828,121 | B2 | 12/2004 | Chen |
| 6,852,512 | B2 | 2/2005 | Choi et al. |
| 6,855,814 | B2 | 2/2005 | Blattner et al. |
| 6,861,403 | B2 | 3/2005 | Sanders |
| 6,863,894 | B2 | 3/2005 | Bermudes et al. |
| 6,872,547 | B1 | 3/2005 | Curtiss, III |
| 6,887,483 | B2 | 5/2005 | Apicella et al. |
| 6,905,691 | B1 | 6/2005 | Chatfield et al. |
| 6,913,753 | B2 | 7/2005 | Ramachandran et al. |
| 6,916,478 | B2 | 7/2005 | Kadurugamuwa et al. |
| 6,916,918 | B2 | 7/2005 | Yu et al. |
| 6,919,198 | B1 | 7/2005 | Korpela et al. |
| 6,921,659 | B2 | 7/2005 | Joly |
| 6,923,958 | B2 | 8/2005 | Xiang et al. |
| 6,923,972 | B2 | 8/2005 | Bermudes et al. |
| 6,934,176 | B2 | 8/2005 | Low et al. |
| 6,962,696 | B1 | 11/2005 | Bermudes et al. |
| 6,992,237 | B1 | 1/2006 | Habben et al. |
| 6,994,860 | B1 | 2/2006 | Ruelle et al. |
| 7,005,129 | B1 | 2/2006 | Apicella et al. |
| 7,015,027 | B1 | 3/2006 | Redshaw |
| 7,018,835 | B2 | 3/2006 | Hone |
| 7,026,155 | B2 | 4/2006 | Mahan et al. |
| 7,039,956 | B1 | 5/2006 | Hsia |
| 7,045,336 | B1 | 5/2006 | Branstrom et al. |
| 7,052,867 | B2 | 5/2006 | Kwon et al. |
| 7,056,700 | B2 | 6/2006 | Galen |
| 7,056,732 | B2 | 6/2006 | Hua et al. |
| 7,063,850 | B1 | 6/2006 | Dale |
| 7,070,989 | B2 | 7/2006 | Lee et al. |
| 7,079,879 | B1 | 7/2006 | Sylvester et al. |
| 7,080,116 | B2 | 7/2006 | Purpura |
| 7,083,791 | B2 | 8/2006 | Sleeman et al. |
| 7,083,794 | B2 | 8/2006 | Curtiss, III et al. |
| 7,084,105 | B2 | 8/2006 | Chakrabarty et al. |
| 7,092,803 | B2 | 8/2006 | Kapolka et al. |
| 7,092,819 | B2 | 8/2006 | Odachi et al. |
| 7,094,410 | B2 | 8/2006 | Reisfeld et al. |
| 7,094,579 | B2 | 8/2006 | Gray et al. |
| 7,094,941 | B2 | 8/2006 | Das et al. |
| 7,095,430 | B2 | 8/2006 | Kato et al. |
| 7,095,524 | B2 | 8/2006 | Ogawa |
| 7,105,327 | B1 | 9/2006 | Kuppusamy et al. |
| 7,108,130 | B2 | 9/2006 | Herelier et al. |
| 7,108,139 | B2 | 9/2006 | Nguyen |
| 7,108,922 | B2 | 9/2006 | Lyu et al. |
| 7,112,434 | B2 | 9/2006 | Cannon et al. |
| 7,115,269 | B2 | 10/2006 | Darji et al. |
| 7,118,634 | B2 | 10/2006 | Goldsteinas et al. |
| 7,119,032 | B2 | 10/2006 | Ji et al. |
| 7,125,718 | B2 | 10/2006 | Powell et al. |
| 7,127,800 | B2 | 10/2006 | Dinan et al. |
| 7,130,192 | B2 | 10/2006 | Wang et al. |
| 7,144,580 | B2 | 12/2006 | Confer et al. |
| 7,144,982 | B2 | 12/2006 | Mayo |
| 7,159,299 | B1 | 1/2007 | McMunigal et al. |
| 7,165,470 | B2 | 1/2007 | Sakamoto et al. |
| 7,167,720 | B2 | 1/2007 | Takahashi et al. |
| 7,183,105 | B2 | 2/2007 | Sabbadini et al. |
| 7,195,757 | B2 | 3/2007 | Curtiss, III et al. |
| 7,202,059 | B2 | 4/2007 | Habermann et al. |
| 7,211,843 | B2 | 5/2007 | Low et al. |
| 7,226,588 | B2 | 6/2007 | Apicella et al. |
| 7,235,234 | B1 | 6/2007 | Branstrom et al. |
| 7,247,296 | B2 | 7/2007 | Redshaw |
| 7,264,812 | B2 | 9/2007 | Claerebout et al. |
| 7,279,464 | B2 | 10/2007 | Xiang et al. |
| 7,291,325 | B2 | 11/2007 | Lee et al. |
| 7,341,725 | B2 | 3/2008 | Weston et al. |
| 7,341,841 | B2 | 3/2008 | Metzger et al. |
| 7,341,860 | B2 | 3/2008 | Curtiss, III et al. |
| 7,344,710 | B2 | 3/2008 | Dang et al. |
| 7,354,592 | B2 | 4/2008 | Bermudes et al. |
| 7,393,525 | B2 | 7/2008 | Powell et al. |
| 7,404,963 | B2 | 7/2008 | Sotomayor et al. |
| 7,407,790 | B2 | 8/2008 | Hone |
| 7,410,788 | B2 | 8/2008 | Beckwith et al. |
| 7,425,438 | B2 | 9/2008 | Sung et al. |
| 7,452,531 | B2 | 11/2008 | Bermudes et al. |
| 7,459,161 | B2 | 12/2008 | Galen |
| 7,470,667 | B2 | 12/2008 | Luo et al. |
| 7,473,247 | B2 | 1/2009 | Mikszta et al. |
| 7,491,528 | B2 | 2/2009 | Lee et al. |
| 7,510,717 | B2 | 3/2009 | Apicella et al. |
| 7,514,089 | B2 | 4/2009 | Bermudes et al. |
| 7,514,415 | B2 | 4/2009 | Klinman et al. |
| 7,531,723 | B2 | 5/2009 | Habben et al. |
| 7,541,043 | B2 | 6/2009 | Kopecko et al. |
| 7,569,219 | B2 | 8/2009 | Hone |
| 7,569,552 | B2 | 8/2009 | Luo et al. |
| 7,569,682 | B2 | 8/2009 | Adler et al. |
| 7,588,767 | B2 | 9/2009 | Szalay et al. |
| 7,588,771 | B2 | 9/2009 | Szalay et al. |

(56) References Cited

U.S. PATENT DOCUMENTS 7,601,804 B2 10/2009 Nuijten et al.
7,611,712 B2 11/2009 Karp
7,611,883 B2 11/2009 Cranenburgh
7,622,107 B2 11/2009 Horwitz et al.
7,625,572 B2 12/2009 Sun et al.
7,657,380 B2 2/2010 Lazar et al.
7,662,398 B2 2/2010 Szalay et al.
7,666,656 B2 2/2010 Sun et al.
7,687,474 B2 3/2010 Matin et al.
7,691,383 B2 4/2010 Chakrabarty et al.
7,691,393 B2 4/2010 Dubensky, Jr. et al.
7,695,725 B2 4/2010 Dubensky, Jr. et al.
7,700,091 B2 4/2010 Von Eichel-Streiber et al.
7,700,104 B2 4/2010 Hensel et al.
7,718,179 B2 5/2010 Claerebout et al.
7,718,180 B2 5/2010 Karp
7,732,187 B2 6/2010 Cochran et al.
7,736,898 B1 6/2010 Fulton et al.
7,740,835 B2 6/2010 Fujimori et al.
7,754,221 B2 7/2010 Szalay et al.
7,758,876 B2 7/2010 Klinman et al.
7,763,420 B2 7/2010 Stritzker et al.
7,772,386 B1 8/2010 Jungblut et al.
7,776,527 B2 8/2010 Hsu et al.
7,786,288 B2 8/2010 Karp
7,790,177 B2 9/2010 Karp
7,794,734 B2 9/2010 Ayalew et al.
7,803,531 B2 9/2010 Fulton et al.
7,803,990 B2 9/2010 Abbitt
7,807,184 B2 10/2010 Vermeij
7,807,456 B2 10/2010 Cochran et al.
7,820,184 B2 10/2010 Stritzker et al.
7,829,104 B2 11/2010 Sun et al.
7,833,775 B2 11/2010 Dubensky, Jr. et al.
7,842,289 B2 11/2010 Dubensky, Jr. et al.
7,842,290 B2 11/2010 Holden
7,850,958 B2 12/2010 Hone
7,850,970 B2 12/2010 Shapiro
7,871,604 B1 1/2011 Curtiss, III et al.
7,871,815 B2 1/2011 Sabbadini et al.
7,871,816 B2 1/2011 Sung et al.
7,887,816 B2 2/2011 Feldman et al.
7,915,218 B2 3/2011 Capecchi et al.
7,919,081 B2 4/2011 Maier et al.
7,927,606 B2 4/2011 Dubensky, Jr. et al.
7,930,107 B2 4/2011 Lazar et al.
7,939,319 B2 5/2011 Polack et al.
7,951,386 B2 5/2011 Chang
7,951,786 B2 5/2011 Klinman et al.
7,955,600 B2 6/2011 Hensel et al.
7,960,518 B2 6/2011 Throsby et al.
7,972,604 B2 7/2011 Cochran et al.
7,985,573 B2 7/2011 Yacoby et al.
7,993,651 B2 8/2011 Hanke et al.
7,998,461 B2 8/2011 Forbes et al.
8,008,283 B2 8/2011 Hochman et al.
8,012,466 B2 9/2011 Morita et al.
8,021,662 B2 9/2011 Szalay et al.
8,021,848 B2 9/2011 Straus
8,034,359 B2 10/2011 Gunn
8,043,857 B2 10/2011 Sun et al.
8,048,428 B2 11/2011 Reisfeld et al.
8,049,000 B2 11/2011 Helentjaris et al.
8,053,181 B2 11/2011 Lewinsohn et al.
8,053,421 B2 11/2011 Luo et al.
8,066,987 B2 11/2011 Moore et al.
8,071,084 B2 12/2011 Kopecko et al.
8,071,319 B2 12/2011 Metzger et al.
8,076,099 B2 12/2011 Chambers et al.
8,101,396 B2 1/2012 Sabbadini et al.
8,114,409 B2 2/2012 Weston et al.
8,114,414 B2 2/2012 Paterson et al.
8,124,068 B2 2/2012 Horwitz et al.
8,124,408 B2 2/2012 Cai et al.
8,133,493 B2 3/2012 Curtiss, III
8,137,904 B2 3/2012 Szalay et al.
8,147,820 B2 4/2012 Hawke et al.
8,168,421 B2 5/2012 Quinn et al.
8,173,773 B2 5/2012 He et al.
8,187,610 B2 5/2012 Waller et al.
8,198,430 B2 6/2012 Prior et al.
8,202,516 B2 6/2012 Padmanabhan et al.
8,207,228 B2 6/2012 Mayo et al.
8,211,431 B2 7/2012 Throsby et al.
8,221,769 B2 7/2012 Szalay et al.
8,227,584 B2 7/2012 Claerebout et al.
8,241,623 B1 8/2012 Bermudes
8,241,631 B2 8/2012 Throsby et al.
8,241,637 B2 8/2012 Reisfeld et al.
8,257,713 B2 9/2012 Poobalane et al.
8,273,361 B2 9/2012 Reed et al.
8,282,919 B2 10/2012 Eisenstark et al.
8,287,883 B2 10/2012 Dubensky, Jr. et al.
8,288,359 B2 10/2012 Klinman et al.
8,318,661 B2 11/2012 Ny et al.
8,323,668 B2 12/2012 Fleckenstein
8,323,959 B2 12/2012 Szalay et al.
8,329,685 B1 12/2012 Meyer
8,337,832 B2 12/2012 Kopecko et al.
8,337,861 B2 12/2012 Paterson et al.
8,343,509 B2 1/2013 Stritzker et al.
8,343,512 B2 1/2013 Reed et al.
8,349,586 B1 1/2013 Hamer
8,357,486 B2 1/2013 Stritzker et al.
8,357,533 B2 1/2013 Cai et al.
8,361,707 B2 1/2013 Lewinsohn et al.
8,367,055 B2 2/2013 Talaat et al.
8,399,618 B2 3/2013 Lazar et al.
8,440,207 B2 5/2013 Bermudes
8,445,254 B2 5/2013 Curtiss, III et al.
8,445,426 B2 5/2013 De Vos et al.
8,445,662 B2 5/2013 He et al.
8,460,666 B2 6/2013 Throsby et al.
8,465,755 B2 6/2013 Curtiss, III et al.
8,470,551 B2 6/2013 Sung et al.
8,481,055 B2 7/2013 Klinman et al.
8,501,198 B2 8/2013 Gunn
8,524,220 B1 9/2013 Bermudes
8,551,471 B2 10/2013 Filutowicz et al.
8,551,497 B2 10/2013 Quinn et al.
8,557,789 B2 10/2013 Klinman et al.
8,568,707 B2 10/2013 Szalay et al.
8,580,280 B2 11/2013 Dominowski et al.
8,586,022 B2 11/2013 Szalay et al.
8,591,862 B2 11/2013 Brahmbhatt et al.
8,604,178 B2 12/2013 Bottje et al.
8,609,114 B2 12/2013 Reed
8,623,350 B1 1/2014 Bermudes
8,628,776 B2 1/2014 Throsby et al.
8,632,783 B2 1/2014 Bagnoli et al.
8,633,305 B2 1/2014 Shapiro
8,642,257 B2 2/2014 Szalay et al.
8,642,656 B2 2/2014 Mayo et al.
8,647,642 B2 2/2014 Bermudes
8,658,350 B2 2/2014 Lewinsohn et al.
8,663,634 B2 3/2014 Koenig et al.
8,663,940 B2 3/2014 Granoff et al.
8,669,355 B2 3/2014 Poobalane et al.
8,673,311 B2 3/2014 Cutting et al.
8,679,505 B2 3/2014 Bagnoli et al.
8,685,939 B2 4/2014 Wei et al.
8,703,153 B2 4/2014 Telfer et al.
8,715,641 B2 5/2014 Filutowicz et al.
8,715,929 B2 5/2014 Benghezal et al.
8,716,254 B2 5/2014 Xiang et al.
8,716,343 B2 5/2014 Mayo et al.
8,722,064 B2 5/2014 Reed et al.
8,722,668 B2 5/2014 Hochman
8,734,779 B2 5/2014 Hamaji et al.
8,748,150 B2 6/2014 Padmanabhan et al.
8,758,766 B2 6/2014 Oloo et al.
8,771,669 B1 7/2014 Bermudes
8,772,013 B2 7/2014 Brahmbhatt et al.
8,778,683 B2 7/2014 Nano

(56) References Cited

U.S. PATENT DOCUMENTS 8,784,829 B2 7/2014 Morsey et al.
8,784,836 B2 7/2014 Szalay et al.
8,790,909 B2 7/2014 Benghezal et al.
8,822,194 B2 9/2014 Zhao et al.
8,828,681 B2 9/2014 Bell, III et al.
8,840,908 B2 9/2014 Reed et al.
8,853,382 B2 10/2014 Hammarstrom et al.
8,859,256 B2 10/2014 Szalay et al.
8,877,212 B2 11/2014 Robinson et al.
8,883,147 B2 11/2014 Lazar et al.
8,889,121 B2 11/2014 Curtiss, III et al.
8,889,150 B2 11/2014 Malouin et al.
8,895,062 B2 11/2014 De Leeuw et al.
8,916,372 B2 12/2014 Bereta et al.
8,926,993 B2 1/2015 Dubensky, Jr. et al.
8,937,074 B2 1/2015 Meyer
8,951,531 B2 2/2015 Oloo et al.
8,956,618 B2 2/2015 Berghman et al.
8,956,621 B2 2/2015 Paterson et al.
8,956,859 B1 2/2015 Bermudes
8,961,989 B2 2/2015 Lewinsohn et al.
8,980,279 B2 3/2015 Gunn et al.
8,992,943 B2 3/2015 Kopecko et al.
9,005,665 B2 4/2015 Gourapura et al.
9,011,870 B2 4/2015 Leenhouts et al.
9,012,213 B2 4/2015 Fruehauf et al.
9,017,986 B2 4/2015 Sabbadini et al.
9,023,635 B2 5/2015 Bayer et al.
9,040,059 B2 5/2015 Curtiss, III et al.
9,040,233 B2 5/2015 Lewinsohn et al.
9,045,528 B2 6/2015 Ruker et al.
9,045,742 B2 6/2015 Curtiss, III et al.
9,050,285 B2 6/2015 Curtiss, III et al.
9,050,319 B2 6/2015 Maj et al.
9,051,574 B2 6/2015 Galen et al.
9,056,909 B2 6/2015 Chu et al.
9,062,297 B2 6/2015 Curtiss, III et al.
9,068,187 B1 6/2015 Bermudes
9,107,864 B2 8/2015 Gunn
9,140,698 B2 9/2015 Orth et al.
9,161,974 B2 10/2015 Dubensky et al.
9,163,219 B2 10/2015 Curtiss, III et al.
9,169,302 B2 10/2015 Carboulec et al.
9,173,930 B2 11/2015 Lewinsohn et al.
9,173,935 B2 11/2015 Maj et al.
9,173,936 B2 11/2015 Maj et al.
9,180,183 B2 11/2015 Maj et al.
9,181,546 B2 11/2015 Li et al.
9,198,960 B2 12/2015 Dubensky, Jr. et al.
9,200,251 B1 12/2015 Bermudes
9,200,289 B1 12/2015 Bermudes
9,205,142 B2 12/2015 Bagnoli et al.
9,220,764 B2 12/2015 Talaat et al.
9,248,177 B2 2/2016 Tang et al.
9,255,149 B2 2/2016 Himmler et al.
9,255,283 B2 2/2016 Curtiss, III et al.
9,265,804 B2 2/2016 Newman
9,267,108 B2 2/2016 Giacalone
9,289,481 B2 3/2016 Ramachandran et al.
9,297,015 B2 3/2016 Curtiss, III et al.
9,303,264 B2 4/2016 Curtiss et al.
9,309,493 B2 4/2016 Ilg et al.
9,315,817 B2 4/2016 Bermudes
9,320,787 B2 4/2016 Gunn
9,320,788 B2 4/2016 Gunn
9,333,251 B2 5/2016 Kopecko et al.
9,339,533 B2 5/2016 Beck et al.
9,358,283 B2 6/2016 Corbeil et al.
9,364,528 B1 6/2016 Giuliani et al.
9,365,625 B1 6/2016 Bermudes
9,376,686 B2 6/2016 Campos-Neto et al.
9,408,880 B2 8/2016 Kovarik et al.
9,415,077 B2 8/2016 Alonso et al.
9,415,098 B2 8/2016 Lubenau
9,421,252 B2 8/2016 Bermudes
9,428,572 B2 8/2016 Throsby et al.
9,441,204 B2 9/2016 Voorhees et al.
9,453,227 B2 9/2016 Diamond et al.
9,457,074 B2 10/2016 Gourapura et al.
9,457,077 B2 10/2016 Kovarik et al.
9,463,238 B2 10/2016 Chaplin et al.
9,474,831 B2 10/2016 Boyden et al.
9,480,740 B2 11/2016 Reed et al.
9,481,884 B2 11/2016 Li
9,481,888 B2 11/2016 Curtiss, III et al.
9,486,513 B1 11/2016 Bermudes
9,487,577 B2 11/2016 Schwarz et al.
9,492,534 B2 11/2016 Szalay et al.
9,499,606 B2 11/2016 Shapiro
9,504,750 B2 11/2016 Harel et al.
9,506,922 B2 11/2016 Lewinsohn et al.
9,526,778 B2 12/2016 Alonso et al.
9,529,005 B2 12/2016 Orth et al.
9,539,313 B2 1/2017 Sad et al.
9,540,407 B2 1/2017 Maj et al.
9,546,199 B2 1/2017 Oloo et al.
9,549,956 B2 1/2017 Fujiwara et al.
9,556,442 B2 1/2017 Le Gouellec et al.
9,561,270 B2 2/2017 Kohler et al.
9,562,080 B2 2/2017 Urbanowicz et al.
9,562,837 B2 2/2017 Link
9,566,321 B2 2/2017 Giacalone
9,566,322 B2 2/2017 Malouin et al.
9,567,375 B2 2/2017 Luo et al.
9,580,478 B2 2/2017 Nano
9,580,718 B2 2/2017 Curtiss, III et al.
9,592,283 B2 3/2017 Kolander et al.
9,593,339 B1 3/2017 Bermudes
9,597,379 B1 3/2017 Bermudes
9,598,697 B2 3/2017 Curtiss, III et al.
9,603,799 B2 3/2017 Sorayya et al.
9,610,342 B2 4/2017 Giuliani et al.
9,616,114 B1 4/2017 Bermudes
9,622,486 B2 4/2017 Padmanabhan et al.
9,636,386 B2 5/2017 Husseiny Elsayed et al.
9,642,881 B2 5/2017 Honda et al.
9,642,904 B2 5/2017 Bagnoli et al.
9,649,345 B2 5/2017 Honda et al.
9,651,559 B2 5/2017 Himmler et al.
9,655,815 B2 5/2017 Xiang et al.
9,657,085 B1 5/2017 Bermudes
9,657,327 B2 5/2017 Metzger et al.
9,662,385 B2 5/2017 Dominowski et al.
9,663,758 B2 5/2017 Talaat
9,670,270 B2 6/2017 Sabbadini et al.
9,695,229 B2 7/2017 Shapiro
9,714,426 B2 7/2017 Fruehauf et al.
9,717,782 B2 8/2017 Lewinsohn et al.
9,730,996 B2 8/2017 Gauduin et al.
9,737,592 B1 8/2017 Bermudes et al.
9,737,601 B2 8/2017 Schwarz et al.
9,739,773 B1 8/2017 Bermudes
9,750,802 B2 9/2017 Kovarik et al.
9,758,572 B2 9/2017 Schwarz et al.
9,764,021 B2 9/2017 Ilg et al.
9,775,896 B2 10/2017 Gunn
9,795,641 B2 10/2017 Nardelli Haefliger et al.
9,796,762 B2 10/2017 Kelly et al.
9,801,930 B2 10/2017 Ramachandran et al.
9,808,517 B2 11/2017 Putnam et al.
9,814,772 B2 11/2017 Reed et al.
9,827,305 B2 11/2017 Qiao et al.
9,844,592 B2 12/2017 Blander et al.
9,845,342 B2 12/2017 Thompson et al.
9,855,336 B2 1/2018 O'Connell et al.
9,856,311 B2 1/2018 Ruker et al.
9,867,785 B2 1/2018 Brahmbhatt et al.
9,872,898 B2 1/2018 Gourapura et al.
9,878,023 B1 1/2018 Bermudes
9,878,024 B2 1/2018 Dubensky, Jr. et al.
9,878,043 B2 1/2018 Brahmbhatt et al.
9,884,108 B2 2/2018 Campos-Neto et al.
9,885,051 B2 2/2018 Curtiss, III et al.
9,889,165 B2 2/2018 Taylor et al.

(56) References Cited

U.S. PATENT DOCUMENTS 9,901,082 B2 2/2018 Flavell et al.
9,907,755 B2 3/2018 Kabadi et al.
9,907,845 B2 3/2018 Reed et al.
9,913,893 B2 3/2018 Berghman et al.
9,925,257 B2 3/2018 Campos-Neto et al.
9,950,063 B2 4/2018 Reed et al.
9,951,340 B2 4/2018 Lesser et al.
9,986,724 B2 6/2018 Flavell et al.
9,987,355 B2 6/2018 Reed et al.
9,994,809 B2 6/2018 Bhatia et al.
9,999,660 B2 6/2018 Mueller et al.
10,087,451 B2 10/2018 Bermudes
10,141,626 B2 11/2018 Tan et al.
10,188,722 B2 1/2019 Bermudes
10,286,051 B1 5/2019 Bermudes
10,973,908 B1 4/2021 Bermudes
2001/0014673 A1 8/2001 Nikolich et al.
2002/0025325 A1 2/2002 Chu et al.
2002/0026655 A1 2/2002 Bermudes et al.
2002/0028215 A1 3/2002 Kadurugamuwa et al.
2002/0044938 A1 4/2002 Fox et al.
2002/0068068 A1 6/2002 Mahan et al.
2002/0076417 A1 6/2002 Mahan et al.
2002/0077272 A1 6/2002 Mahan et al.
2002/0081317 A1 6/2002 Mahan et al.
2002/0086032 A1 7/2002 Mahan et al.
2002/0086332 A1 7/2002 Mahan et al.
2002/0090376 A1 7/2002 Kaniga et al.
2002/0102242 A1 8/2002 Briles et al.
2002/0132789 A1 9/2002 Barbet et al.
2002/0146430 A1 10/2002 Galen
2002/0151063 A1 10/2002 Lasham et al.
2002/0151462 A1 10/2002 Lissolo
2002/0156009 A1 10/2002 Ballinger et al.
2002/0176848 A1 11/2002 Sizemore et al.
2003/0008839 A1 1/2003 van Rooij et al.
2003/0009015 A1 1/2003 Ulrich et al.
2003/0017162 A1 1/2003 Warren et al.
2003/0022835 A1 1/2003 Watson et al.
2003/0023075 A1 1/2003 Blattner et al.
2003/0031628 A1 2/2003 Zhao et al.
2003/0036644 A1 2/2003 Ulrich
2003/0045492 A1 3/2003 Tang et al.
2003/0059400 A1 3/2003 Szalay
2003/0065039 A1 4/2003 Kharazmi et al.
2003/0068328 A1 4/2003 Vladoianu et al.
2003/0100100 A1 5/2003 Jacobs, Jr. et al.
2003/0108562 A1 6/2003 Hanke et al.
2003/0108957 A1 6/2003 Otvos et al.
2003/0109026 A1 6/2003 Bermudes et al.
2003/0113293 A1 6/2003 Bermudes et al.
2003/0124516 A1 7/2003 Chung et al.
2003/0125278 A1 7/2003 Tang et al.
2003/0130827 A1 7/2003 Bentzien et al.
2003/0143676 A1 7/2003 Strachan et al.
2003/0152589 A1 8/2003 Ramachandran et al.
2003/0153527 A1 8/2003 Powell et al.
2003/0157637 A1 8/2003 Reynolds et al.
2003/0166099 A1 9/2003 Sabbadini et al.
2003/0166279 A1 9/2003 Sabbadini et al.
2003/0170211 A1 9/2003 Goudsmit et al.
2003/0170276 A1 9/2003 Bermudes et al.
2003/0170613 A1 9/2003 Straus
2003/0176377 A1 9/2003 Xiang et al.
2003/0180260 A1 9/2003 Clancy et al.
2003/0180304 A1 9/2003 Ullrich et al.
2003/0180320 A1 9/2003 Darji et al.
2003/0185802 A1 10/2003 Reisfeld et al.
2003/0186908 A1 10/2003 Goldway
2003/0190601 A1 10/2003 Sabbadini et al.
2003/0190683 A1 10/2003 Sabbadini et al.
2003/0190749 A1 10/2003 Surber et al.
2003/0194714 A1 10/2003 Sabbadini et al.
2003/0194755 A1 10/2003 Schnabel et al.
2003/0194798 A1 10/2003 Surber et al.
2003/0198995 A1 10/2003 Sabbadini et al.
2003/0198996 A1 10/2003 Surber et al.
2003/0199005 A1 10/2003 Sabbadini et al.
2003/0199088 A1 10/2003 Sabbadini et al.
2003/0199089 A1 10/2003 Surber et al.
2003/0202937 A1 10/2003 Sabbadini et al.
2003/0203411 A1 10/2003 Sabbadini et al.
2003/0203481 A1 10/2003 Surber et al.
2003/0207833 A1 11/2003 Berkley et al.
2003/0211086 A1 11/2003 Berkley et al.
2003/0211103 A1 11/2003 Buyse et al.
2003/0211461 A1 11/2003 Kariv et al.
2003/0211476 A1 11/2003 O'Mahony et al.
2003/0211599 A1 11/2003 Sabbadini et al.
2003/0219408 A1 11/2003 Sabbadini et al.
2003/0219888 A1 11/2003 Segall et al.
2003/0224369 A1 12/2003 Surber et al.
2003/0224444 A1 12/2003 Sabbadini et al.
2003/0232335 A1 12/2003 Surber et al.
2003/0235577 A1 12/2003 Shapiro et al.
2004/0005695 A1 1/2004 Miksch et al.
2004/0005700 A1 1/2004 Surber et al.
2004/0009540 A1 1/2004 Soohoo et al.
2004/0009936 A1 1/2004 Tang et al.
2004/0013658 A1 1/2004 Fulton et al.
2004/0013689 A1 1/2004 Kadurugamuwa et al.
2004/0023310 A1 2/2004 Kariv et al.
2004/0033539 A1 2/2004 Schnabel et al.
2004/0037117 A1 2/2004 Low et al.
2004/0042274 A1 3/2004 Low et al.
2004/0052817 A1 3/2004 Geldhof et al.
2004/0053209 A1 3/2004 Kariv et al.
2004/0054142 A1 3/2004 Cassart et al.
2004/0058849 A1 3/2004 Sleeman et al.
2004/0077067 A1 4/2004 Sin et al.
2004/0115174 A1 6/2004 Gilboa et al.
2004/0121307 A1 6/2004 Schnabel et al.
2004/0121474 A1 6/2004 SooHoo et al.
2004/0126871 A1 7/2004 Barbet et al.
2004/0131641 A1 7/2004 Mikszta et al.
2004/0132678 A1 7/2004 Hone
2004/0137003 A1 7/2004 Curtiss, III
2004/0156865 A1 8/2004 Confer et al.
2004/0192631 A1 9/2004 Xiang et al.
2004/0202648 A1 10/2004 Cabezon et al.
2004/0202663 A1 10/2004 Hu et al.
2004/0213804 A1 10/2004 Michon et al.
2004/0219169 A1 11/2004 Bermudes et al.
2004/0228877 A1 11/2004 Dubensky, Jr. et al.
2004/0229338 A1 11/2004 King
2004/0234455 A1 11/2004 Szalay
2004/0237147 A1 11/2004 Habben et al.
2004/0258703 A1 12/2004 Glenn et al.
2004/0258707 A1 12/2004 Weston et al.
2004/0265337 A1 12/2004 Zsebo et al.
2004/0266003 A1 12/2004 Powell et al.
2005/0008618 A1 1/2005 Kaufman et al.
2005/0009750 A1 1/2005 Sleeman et al.
2005/0010032 A1 1/2005 Hardham et al.
2005/0026866 A1 2/2005 Pawelek
2005/0036987 A1 2/2005 Pawelek et al.
2005/0042755 A1 2/2005 Von Eichel-Streiber et al.
2005/0048076 A1 3/2005 Apicella et al.
2005/0052892 A1 3/2005 Low et al.
2005/0064526 A1 3/2005 Ulrich et al.
2005/0069491 A1 3/2005 Szalay et al.
2005/0075298 A1 4/2005 Chen et al.
2005/0106151 A1 5/2005 Shapiro
2005/0106176 A1 5/2005 Curtis et al.
2005/0112139 A1 5/2005 Karp
2005/0112140 A1 5/2005 Karp
2005/0112642 A1 5/2005 Sleeman et al.
2005/0118193 A1 6/2005 Andino-Pavlovsky et al.
2005/0129711 A1 6/2005 Ramachandran et al.
2005/0163791 A1 7/2005 Adler et al.
2005/0175630 A1 8/2005 Raz et al.
2005/0180985 A9 8/2005 Vladoianu et al.
2005/0214317 A1 9/2005 Karp
2005/0214318 A1 9/2005 Karp

(56) References Cited

U.S. PATENT DOCUMENTS

| | | | |
|---|---|---|---|
| 2005/0222057 | A1 | 10/2005 | Brahmbhatt et al. |
| 2005/0229274 | A1 | 10/2005 | Habben et al. |
| 2005/0232937 | A1 | 10/2005 | Willemsen et al. |
| 2005/0233408 | A1 | 10/2005 | Pouwels et al. |
| 2005/0249706 | A1 | 11/2005 | Bermudes et al. |
| 2005/0249752 | A1 | 11/2005 | Sung et al. |
| 2005/0255088 | A1 | 11/2005 | Bermudes et al. |
| 2005/0255125 | A1 | 11/2005 | Nuijten et al. |
| 2005/0267103 | A1 | 12/2005 | Hochman |
| 2005/0271643 | A1 | 12/2005 | Sorokulova et al. |
| 2005/0271683 | A1 | 12/2005 | Claerebout et al. |
| 2005/0281841 | A1 | 12/2005 | Kopecko et al. |
| 2005/0287123 | A1 | 12/2005 | Xiang et al. |
| 2006/0018877 | A1 | 1/2006 | Mikszta et al. |
| 2006/0019239 | A1 | 1/2006 | Ivins et al. |
| 2006/0025387 | A1 | 2/2006 | Hochman |
| 2006/0057152 | A1 | 3/2006 | Marshall |
| 2006/0074039 | A1 | 4/2006 | Klinman et al. |
| 2006/0078572 | A1 | 4/2006 | Confer et al. |
| 2006/0083716 | A1 | 4/2006 | Kaufman et al. |
| 2006/0089350 | A1 | 4/2006 | Hochman et al. |
| 2006/0104955 | A1 | 5/2006 | Redshaw |
| 2006/0115483 | A1 | 6/2006 | Sleeman et al. |
| 2006/0115494 | A1 | 6/2006 | Sun et al. |
| 2006/0121045 | A1 | 6/2006 | Iverson et al. |
| 2006/0121054 | A1 | 6/2006 | Sun et al. |
| 2006/0127408 | A1 | 6/2006 | Young et al. |
| 2006/0140971 | A1 | 6/2006 | Sung et al. |
| 2006/0140975 | A1 | 6/2006 | Curtiss et al. |
| 2006/0147418 | A1 | 7/2006 | Hone |
| 2006/0147461 | A1 | 7/2006 | Galen |
| 2006/0153875 | A1 | 7/2006 | Adler et al. |
| 2006/0171960 | A1 | 8/2006 | Chu et al. |
| 2006/0182754 | A1 | 8/2006 | Horwitz et al. |
| 2006/0189792 | A1 | 8/2006 | Ruelle et al. |
| 2006/0193874 | A1 | 8/2006 | Jones |
| 2006/0233835 | A1 | 10/2006 | Paterson et al. |
| 2006/0240494 | A1 | 10/2006 | Otvos et al. |
| 2006/0246083 | A1 | 11/2006 | Dale |
| 2006/0257415 | A1 | 11/2006 | Sirard et al. |
| 2006/0269570 | A1 | 11/2006 | Hone |
| 2006/0270043 | A1 | 11/2006 | Blattner et al. |
| 2007/0004666 | A1 | 1/2007 | Lasham et al. |
| 2007/0009489 | A1 | 1/2007 | Bermudes et al. |
| 2007/0031382 | A1 | 2/2007 | Powell et al. |
| 2007/0031458 | A1 | 2/2007 | Favre et al. |
| 2007/0037225 | A1 | 2/2007 | Metzger et al. |
| 2007/0048331 | A1 | 3/2007 | Apicella et al. |
| 2007/0059323 | A1 | 3/2007 | Reisfeld et al. |
| 2007/0104689 | A1 | 5/2007 | Gillies et al. |
| 2007/0104733 | A1 | 5/2007 | Gunn |
| 2007/0104736 | A1 | 5/2007 | Apicella et al. |
| 2007/0110717 | A1 | 5/2007 | Luo et al. |
| 2007/0110721 | A1 | 5/2007 | Cranenburgh |
| 2007/0110752 | A1 | 5/2007 | Murison et al. |
| 2007/0116725 | A1 | 5/2007 | Vladoianu et al. |
| 2007/0122881 | A1 | 5/2007 | Surber |
| 2007/0128216 | A1 | 6/2007 | Horwitz et al. |
| 2007/0134214 | A1 | 6/2007 | Xu |
| 2007/0134264 | A1 | 6/2007 | Marshall |
| 2007/0134272 | A1 | 6/2007 | Ayalew et al. |
| 2007/0141082 | A1 | 6/2007 | Sung et al. |
| 2007/0154495 | A1 | 7/2007 | Gorringe et al. |
| 2007/0169226 | A1 | 7/2007 | Habben et al. |
| 2007/0189982 | A1 | 8/2007 | Reynolds et al. |
| 2007/0191262 | A1 | 8/2007 | Racila et al. |
| 2007/0202591 | A1 | 8/2007 | Ulrich |
| 2007/0258901 | A1 | 11/2007 | Boschert et al. |
| 2007/0281328 | A1 | 12/2007 | Hsu et al. |
| 2007/0286874 | A1 | 12/2007 | Cochran et al. |
| 2007/0287171 | A1 | 12/2007 | Inouye |
| 2007/0298012 | A1 | 12/2007 | King et al. |
| 2008/0008718 | A1 | 1/2008 | Schuijffel et al. |
| 2008/0020441 | A1 | 1/2008 | Brahmbhatt et al. |
| 2008/0038296 | A1 | 2/2008 | Brahmbhatt et al. |
| 2008/0063655 | A1 | 3/2008 | Adler et al. |
| 2008/0064062 | A1 | 3/2008 | Leonhartsberger et al. |
| 2008/0076157 | A1 | 3/2008 | Leonhartsberger et al. |
| 2008/0095794 | A1 | 4/2008 | Sun et al. |
| 2008/0107653 | A1 | 5/2008 | Vermeij |
| 2008/0112974 | A1 | 5/2008 | Czerkinsky et al. |
| 2008/0124355 | A1 | 5/2008 | Bermudes |
| 2008/0131466 | A1 | 6/2008 | Reed et al. |
| 2008/0138359 | A1 | 6/2008 | Steeghs et al. |
| 2008/0166757 | A1 | 7/2008 | Bron et al. |
| 2008/0166764 | A1 | 7/2008 | Schloesser et al. |
| 2008/0181892 | A1 | 7/2008 | Ledbetter et al. |
| 2008/0182295 | A1 | 7/2008 | Patkar et al. |
| 2008/0187520 | A1 | 8/2008 | Polack et al. |
| 2008/0188436 | A1 | 8/2008 | Brahmbhatt et al. |
| 2008/0193373 | A1 | 8/2008 | Stritzker et al. |
| 2008/0193974 | A1 | 8/2008 | Coleman et al. |
| 2008/0206284 | A1 | 8/2008 | Williams et al. |
| 2008/0206814 | A1 | 8/2008 | Lee et al. |
| 2008/0206818 | A1 | 8/2008 | Wich et al. |
| 2008/0213308 | A1 | 9/2008 | Valiante et al. |
| 2008/0241179 | A1 | 10/2008 | Weston et al. |
| 2008/0241858 | A1 | 10/2008 | Metzger et al. |
| 2008/0249013 | A1 | 10/2008 | Cabezon et al. |
| 2008/0254058 | A1 | 10/2008 | Glenting et al. |
| 2008/0254511 | A1 | 10/2008 | Dassler et al. |
| 2008/0260769 | A1 | 10/2008 | Capecchi et al. |
| 2008/0261869 | A1 | 10/2008 | Shapiro |
| 2008/0280346 | A1 | 11/2008 | de Lorenzo Prieto et al. |
| 2008/0286852 | A1 | 11/2008 | Sun et al. |
| 2008/0311081 | A1 | 12/2008 | Fruehauf et al. |
| 2008/0317742 | A1 | 12/2008 | Chambers et al. |
| 2009/0011995 | A1 | 1/2009 | Lee et al. |
| 2009/0017000 | A1 | 1/2009 | Cai et al. |
| 2009/0017048 | A1 | 1/2009 | Adler et al. |
| 2009/0028890 | A1 | 1/2009 | Karp |
| 2009/0028892 | A1 | 1/2009 | Claerebout et al. |
| 2009/0053186 | A1 | 2/2009 | Hu et al. |
| 2009/0068226 | A1 | 3/2009 | Ulrich et al. |
| 2009/0074816 | A1 | 3/2009 | Gunn |
| 2009/0081250 | A1 | 3/2009 | Paterson et al. |
| 2009/0081257 | A1 | 3/2009 | Maier et al. |
| 2009/0104204 | A1 | 4/2009 | Throsby et al. |
| 2009/0117047 | A1 | 5/2009 | Szalay et al. |
| 2009/0117048 | A1 | 5/2009 | Szalay et al. |
| 2009/0117049 | A1 | 5/2009 | Szalay et al. |
| 2009/0117151 | A1 | 5/2009 | Sung et al. |
| 2009/0117152 | A1 | 5/2009 | Chu et al. |
| 2009/0123382 | A1 | 5/2009 | Szalay et al. |
| 2009/0123426 | A1 | 5/2009 | Li et al. |
| 2009/0136542 | A1 | 5/2009 | Karp |
| 2009/0142310 | A1 | 6/2009 | Klinman et al. |
| 2009/0148473 | A1 | 6/2009 | Quinn et al. |
| 2009/0169517 | A1 | 7/2009 | Bermudes et al. |
| 2009/0169562 | A1 | 7/2009 | Throsby et al. |
| 2009/0175829 | A1 | 7/2009 | Forbes et al. |
| 2009/0180955 | A1 | 7/2009 | Stritzker et al. |
| 2009/0180987 | A1 | 7/2009 | Stritzker et al. |
| 2009/0181078 | A1 | 7/2009 | Reed et al. |
| 2009/0196887 | A1 | 8/2009 | Morita et al. |
| 2009/0208534 | A1 | 8/2009 | Xu et al. |
| 2009/0214476 | A1 | 8/2009 | Pretzer et al. |
| 2009/0215754 | A1 | 8/2009 | Hochman et al. |
| 2009/0220540 | A1 | 9/2009 | Marshall |
| 2009/0227013 | A1 | 9/2009 | Helentjaris et al. |
| 2009/0253778 | A1 | 10/2009 | Reisfeld et al. |
| 2009/0263414 | A1 | 10/2009 | Leenhouts et al. |
| 2009/0263418 | A1 | 10/2009 | Speelman-Van Der Wel et al. |
| 2009/0285844 | A1 | 11/2009 | Apicella et al. |
| 2009/0297552 | A1 | 12/2009 | Aderem et al. |
| 2009/0297561 | A1 | 12/2009 | Pasternack et al. |
| 2009/0300779 | A1 | 12/2009 | Zhao et al. |
| 2009/0304750 | A1 | 12/2009 | Hone et al. |
| 2009/0305398 | A1 | 12/2009 | Hone |
| 2009/0317404 | A1 | 12/2009 | Markham |
| 2009/0324503 | A1 | 12/2009 | Lewinsohn et al. |
| 2009/0324576 | A1 | 12/2009 | Padmanabhan et al. |
| 2009/0324638 | A1 | 12/2009 | Dattwyler et al. |
| 2009/0324641 | A1 | 12/2009 | Dominowski et al. |

(56) References Cited

U.S. PATENT DOCUMENTS

2010/0047286 A1 2/2010 Sun et al.
2010/0055082 A1 3/2010 Bauer et al.
2010/0055127 A1 3/2010 Venegas
2010/0068214 A1 3/2010 Rood et al.
2010/0092438 A1 4/2010 Fruehauf et al.
2010/0092518 A1 4/2010 Horwitz et al.
2010/0099600 A1 4/2010 Ny et al.
2010/0120124 A1 5/2010 Fernandez Herrero et al.
2010/0129406 A1 5/2010 Lauer et al.
2010/0135961 A1 6/2010 Bermudes
2010/0135973 A1 6/2010 Eisenstark et al.
2010/0136048 A1 6/2010 Bermudes
2010/0136055 A1 6/2010 Luo et al.
2010/0136058 A1 6/2010 Luo et al.
2010/0137192 A1 6/2010 Shapiro
2010/0166786 A1 7/2010 He et al.
2010/0166800 A1 7/2010 Cochran et al.
2010/0172938 A1 7/2010 Pouwels et al.
2010/0172976 A1 7/2010 Satishchandran et al.
2010/0189691 A1 7/2010 Fruehauf et al.
2010/0196524 A1 8/2010 Meindert De Vos et al.
2010/0209446 A1 8/2010 Claerebout et al.
2010/0226891 A1 9/2010 Sung et al.
2010/0226931 A1 9/2010 Valiante et al.
2010/0226941 A1 9/2010 Klinman et al.
2010/0233195 A1 9/2010 Delisa et al.
2010/0233212 A1 9/2010 Dubensky, Jr. et al.
2010/0233213 A1 9/2010 Sun et al.
2010/0239546 A1 9/2010 Fruehauf et al.
2010/0272748 A1 10/2010 Kopecko et al.
2010/0272759 A1 10/2010 Beck et al.
2010/0285592 A1 11/2010 Curtiss et al.
2010/0291148 A1 11/2010 Bernardini et al.
2010/0297184 A1 11/2010 Waller et al.
2010/0297740 A1 11/2010 Li et al.
2010/0303862 A1 12/2010 Ramachandran et al.
2010/0310602 A1 12/2010 Reed et al.
2010/0322957 A1 12/2010 Aderem et al.
2011/0008389 A1 1/2011 Cochran et al.
2011/0014274 A1 1/2011 Reed et al.
2011/0020401 A1 1/2011 Gunn
2011/0021416 A1 1/2011 Shapiro
2011/0027349 A1 2/2011 Sable et al.
2011/0052628 A1 3/2011 Hone
2011/0059126 A1 3/2011 Kohler et al.
2011/0064723 A1 3/2011 Truong-Le et al.
2011/0064766 A1 3/2011 Hawke et al.
2011/0070290 A1 3/2011 Reed et al.
2011/0086059 A1 4/2011 Galen et al.
2011/0091493 A1 4/2011 Moahamadzadeh et al.
2011/0104186 A1 5/2011 Valiante et al.
2011/0104196 A1 5/2011 Karp
2011/0110979 A1 5/2011 Nardelli Haefliger
2011/0111481 A1 5/2011 Li
2011/0111496 A1 5/2011 Li
2011/0123565 A1 5/2011 Weston et al.
2011/0165680 A1 7/2011 Blattner et al.
2011/0183342 A1 7/2011 Lewinsohn et al.
2011/0195093 A1 8/2011 Gunn
2011/0200631 A1 8/2011 Morsey et al.
2011/0201092 A1 8/2011 Dubensky, Jr. et al.
2011/0201676 A1 8/2011 Klinman et al.
2011/0206694 A1 8/2011 Fleckenstein
2011/0209228 A1 8/2011 Cocks et al.
2011/0212090 A1 9/2011 Pedersen et al.
2011/0213129 A1 9/2011 Reynolds et al.
2011/0217323 A1 9/2011 Valiante et al.
2011/0223241 A1 9/2011 Tardi et al.
2011/0243992 A1 10/2011 Kernodle
2011/0256214 A1 10/2011 Martin et al.
2011/0268661 A1 11/2011 Markiv et al.
2011/0268739 A1 11/2011 Throsby et al.
2011/0274719 A1 11/2011 Marshall
2011/0275585 A1 11/2011 Brahmbhatt et al.
2011/0281330 A1 11/2011 Sabbadini et al.
2011/0287046 A1 11/2011 Oloo et al.
2011/0293662 A1 12/2011 Blattner et al.
2011/0312020 A1 12/2011 Granoff et al.
2011/0318308 A1 12/2011 Ragolia
2012/0003298 A1 1/2012 Barberis et al.
2012/0009247 A1 1/2012 Maj et al.
2012/0014881 A1 1/2012 Lewinsohn et al.
2012/0020883 A1 1/2012 Stritzker et al.
2012/0021517 A1 1/2012 Jin et al.
2012/0027811 A1 2/2012 Edwards et al.
2012/0036589 A1 2/2012 Poobalane et al.
2012/0039931 A1 2/2012 Reisfeld et al.
2012/0039994 A1 2/2012 Reed et al.
2012/0058142 A1 3/2012 Kopecko et al.
2012/0071545 A1 3/2012 Shapiro
2012/0077206 A1 3/2012 Metzger et al.
2012/0083587 A1 4/2012 Gallo et al.
2012/0093773 A1 4/2012 Li et al.
2012/0093850 A1 4/2012 Bagnoli et al.
2012/0093865 A2 4/2012 Blattner et al.
2012/0100177 A1 4/2012 Ilg et al.
2012/0107340 A1 5/2012 Bagnoli et al.
2012/0108640 A1 5/2012 Hochman et al.
2012/0115223 A1 5/2012 Cai et al.
2012/0121647 A1 5/2012 Alonso et al.
2012/0128594 A1 5/2012 Choy et al.
2012/0135039 A1 5/2012 Aldwell et al.
2012/0135503 A1 5/2012 Sabbadini et al.
2012/0141493 A1 6/2012 Throsby et al.
2012/0142079 A1 6/2012 Sabbadini et al.
2012/0142080 A1 6/2012 Bermudes
2012/0144509 A1 6/2012 Benghezal et al.
2012/0148601 A1 6/2012 Ulrich et al.
2012/0164687 A1 6/2012 Bereta et al.
2012/0177682 A1 7/2012 Marshall
2012/0189572 A1 7/2012 Wei et al.
2012/0189657 A1 7/2012 Quinn et al.
2012/0189661 A1 7/2012 Nano
2012/0208866 A1 8/2012 Brahmbhatt et al.
2012/0225454 A1 9/2012 Benghezal et al.
2012/0237491 A1 9/2012 Padmanabhan et al.
2012/0237537 A1 9/2012 Lewinsohn et al.
2012/0237544 A1 9/2012 Cutting et al.
2012/0244621 A1 9/2012 Weiss et al.
2012/0258128 A1 10/2012 Dowling et al.
2012/0258129 A1 10/2012 He et al.
2012/0258135 A1 10/2012 Gunn et al.
2012/0276167 A1 11/2012 Lam et al.
2012/0282181 A1 11/2012 Lewinsohn et al.
2012/0282291 A1 11/2012 Berghman et al.
2012/0288523 A1 11/2012 Jacobs
2012/0294948 A1 11/2012 Poobalane et al.
2012/0301422 A1 11/2012 Meyer
2012/0315278 A1 12/2012 Throsby et al.
2013/0004547 A1 1/2013 Lam et al.
2013/0018089 A1 1/2013 Klinman et al.
2013/0040370 A1 2/2013 Genin
2013/0058997 A1 3/2013 Reed et al.
2013/0064845 A1 3/2013 Malouin et al.
2013/0078275 A1 3/2013 Tao
2013/0078278 A1 3/2013 Kopecko et al.
2013/0084307 A1 4/2013 Reed et al.
2013/0095131 A1 4/2013 Campos-Neto et al.
2013/0096103 A1 4/2013 Valiante et al.
2013/0101523 A1 4/2013 Lewinsohn et al.
2013/0110249 A1 5/2013 Schwarz et al.
2013/0121968 A1 5/2013 Quay
2013/0130292 A1 5/2013 Szalay et al.
2013/0149321 A1 6/2013 Ny et al.
2013/0156809 A1 6/2013 Sad et al.
2013/0164307 A1 6/2013 Markham
2013/0164380 A1 6/2013 Durum et al.
2013/0177589 A1 7/2013 Nano
2013/0177593 A1 7/2013 Gunn et al.
2013/0209405 A1 8/2013 Roy et al.
2013/0217063 A1 8/2013 Metzger et al.
2013/0236948 A1 9/2013 Barreira et al.
2013/0251719 A1 9/2013 Muller et al.
2013/0266635 A1 10/2013 Maj et al.

(56) References Cited

U.S. PATENT DOCUMENTS

2013/0267481 A1 10/2013 Maj et al.
2013/0273144 A1 10/2013 Maj et al.
2013/0287810 A1 10/2013 Mohamadzadeh et al.
2013/0295054 A1 11/2013 Huang et al.
2013/0302380 A1 11/2013 Fujiwara et al.
2013/0315950 A1 11/2013 Dubensky et al.
2013/0330824 A1 12/2013 Li
2013/0336990 A1 12/2013 Meyer
2013/0337012 A1 12/2013 Gunn
2013/0337545 A1 12/2013 Sabbadini et al.
2013/0345114 A1 12/2013 Williams et al.
2014/0004178 A1 1/2014 Morici
2014/0004193 A1 1/2014 Gourapura et al.
2014/0010844 A1 1/2014 Gunn
2014/0017279 A1 1/2014 Brito et al.
2014/0017285 A1 1/2014 Brito et al.
2014/0037691 A1 2/2014 Reed et al.
2014/0056940 A1 2/2014 Dominowski et al.
2014/0065187 A1 3/2014 Carboulec et al.
2014/0086950 A1 3/2014 Pascual et al.
2014/0093477 A1 4/2014 Orth et al.
2014/0093885 A1 4/2014 Hua et al.
2014/0093954 A1 4/2014 Giacalone
2014/0099320 A1 4/2014 Throsby et al.
2014/0112951 A1 4/2014 Tang et al.
2014/0134662 A1 5/2014 Flavell et al.
2014/0148582 A1 5/2014 Gallo et al.
2014/0155343 A1 6/2014 Brahmbhatt et al.
2014/0178341 A1 6/2014 Zhao et al.
2014/0178425 A1 6/2014 Bagnoli et al.
2014/0186398 A1 7/2014 Blander et al.
2014/0186401 A1 7/2014 Diamond et al.
2014/0187612 A1 7/2014 Agrez et al.
2014/0193459 A1 7/2014 Reed et al.
2014/0205538 A1 7/2014 Wei et al.
2014/0206064 A1 7/2014 Bayer et al.
2014/0212396 A1 7/2014 Newman
2014/0220661 A1 8/2014 Bermudes
2014/0234310 A1 8/2014 Shapiro
2014/0234379 A1 8/2014 Fujiwara et al.
2014/0256922 A1 9/2014 David et al.
2014/0271563 A1 9/2014 Alonso et al.
2014/0271719 A1 9/2014 Talaat
2014/0294883 A1 10/2014 Poobalane et al.
2014/0322249 A1 10/2014 Xiang et al.
2014/0322265 A1 10/2014 Chaplin et al.
2014/0322267 A1 10/2014 Haiwick et al.
2014/0322268 A1 10/2014 Reed et al.
2014/0335125 A1 11/2014 Le Gouellec et al.
2014/0341921 A1 11/2014 Honda et al.
2014/0341942 A1 11/2014 Oloo et al.
2014/0341970 A1 11/2014 Reed et al.
2014/0341974 A1 11/2014 Sorayya et al.
2014/0356415 A1 12/2014 DeShong et al.
2014/0369986 A1 12/2014 Padmanabhan et al.
2014/0370036 A1 12/2014 Shapiro
2014/0370057 A1 12/2014 Curtiss et al.
2014/0371428 A1 12/2014 Schwarz et al.
2015/0017138 A1 1/2015 Fruehauf et al.
2015/0017191 A1 1/2015 Fox et al.
2015/0017204 A1 1/2015 Bermudes
2015/0030573 A1 1/2015 Fruehauf et al.
2015/0037370 A1 2/2015 Corbeil et al.
2015/0050311 A1 2/2015 Schubert et al.
2015/0056246 A1 2/2015 Putnam et al.
2015/0071994 A1 3/2015 Schentag et al.
2015/0093824 A1 4/2015 Satishchandran et al.
2015/0125485 A1 5/2015 Dubensky, Jr. et al.
2015/0125921 A1 5/2015 Kotelko et al.
2015/0132335 A1 5/2015 Malouin et al.
2015/0140028 A1 5/2015 Sad et al.
2015/0140034 A1 5/2015 Dominowski et al.
2015/0140037 A1 5/2015 Galan et al.
2015/0165011 A1 6/2015 Lubenau
2015/0174178 A1 6/2015 Kovarik et al.
2015/0182611 A1 7/2015 Kopecko et al.
2015/0184167 A1 7/2015 Fruehauf et al.
2015/0190500 A1 7/2015 Berghman et al.
2015/0196659 A1 7/2015 Leenhouts et al.
2015/0202276 A1 7/2015 Lewinsohn et al.
2015/0204845 A1 7/2015 De Armas et al.
2015/0218254 A1 8/2015 Sabbadini et al.
2015/0219645 A1 8/2015 Lewinsohn et al.
2015/0225692 A1 8/2015 Bhatia et al.
2015/0238589 A1 8/2015 Gunn et al.
2015/0258190 A1 9/2015 Grandi
2015/0265696 A1 9/2015 Gourapura et al.
2015/0273045 A1 10/2015 Kolander et al.
2015/0316567 A1 11/2015 Salha et al.
2015/0321037 A1 11/2015 Li et al.
2015/0335736 A1 11/2015 Reed et al.
2015/0343050 A1 12/2015 Gunn
2015/0359909 A1 12/2015 O'Sullivan et al.
2015/0376242 A1 12/2015 Oloo et al.
2016/0000896 A1 1/2016 Carboulec et al.
2016/0022592 A1 1/2016 Kabadi et al.
2016/0028148 A1 1/2016 Tan et al.
2016/0030494 A1 2/2016 Henn et al.
2016/0045591 A1 2/2016 Campos-Neto et al.
2016/0054299 A9 2/2016 De Armas et al.
2016/0058860 A1 3/2016 Reed et al.
2016/0074505 A1 3/2016 Kovarik et al.
2016/0090395 A1 3/2016 Maj et al.
2016/0101168 A1 4/2016 Husseiny Elsayed et al.
2016/0103127 A1 4/2016 Lewinsohn et al.
2016/0108096 A1 4/2016 Thompson et al.
2016/0136285 A1 5/2016 Gozdziewicz et al.
2016/0136294 A1 5/2016 Leenhouts et al.
2016/0158334 A1 6/2016 Giacalone
2016/0158335 A1 6/2016 Bagnoli et al.
2016/0169921 A1 6/2016 Orth et al.
2016/0175415 A1 6/2016 Dubensky, Jr. et al.
2016/0175428 A1 6/2016 Tang et al.
2016/0193256 A1 7/2016 Honda et al.
2016/0193257 A1 7/2016 Honda et al.
2016/0199422 A1 7/2016 Newman
2016/0199474 A1 7/2016 Ramachandran et al.
2016/0206727 A1 7/2016 Haiwick et al.
2016/0208261 A1 7/2016 Satishchandran et al.
2016/0213770 A1 7/2016 Ilg et al.
2016/0220652 A1 8/2016 Petit et al.
2016/0222393 A1 8/2016 Bermudes
2016/0228523 A1 8/2016 Newman
2016/0228530 A1 8/2016 Paterson
2016/0243204 A1 8/2016 Ny et al.
2016/0250311 A1 9/2016 Lubenau
2016/0263209 A1 9/2016 Gunn
2016/0289287 A1 10/2016 Hancock et al.
2016/0317637 A1 11/2016 Agrawal et al.
2016/0324783 A1 11/2016 Fox et al.
2016/0324939 A1 11/2016 Allan
2016/0346381 A1 12/2016 Qiao et al.
2016/0354462 A1 12/2016 Campos-Neto et al.
2016/0366862 A1 12/2016 Flavell et al.
2016/0367650 A1 12/2016 Paterson
2016/0369282 A1 12/2016 Li et al.
2017/0007683 A1 1/2017 Mueller et al.
2017/0014513 A1 1/2017 O'Connell et al.
2017/0015735 A1 1/2017 Schwarz et al.
2017/0021011 A1 1/2017 Kovarik et al.
2017/0028048 A1 2/2017 Lewinsohn et al.
2017/0042987 A1 2/2017 D'Souza
2017/0042996 A1 2/2017 Wallecha et al.
2017/0051260 A1 2/2017 Bermudes et al.
2017/0072042 A1 3/2017 Fergen et al.
2017/0080078 A1 3/2017 Gourapura et al.
2017/0081642 A1 3/2017 Chaplin et al.
2017/0081671 A1 3/2017 Diamond et al.
2017/0095548 A1 4/2017 Malouin et al.
2017/0106028 A1 4/2017 Fujiwara et al.
2017/0106074 A1 4/2017 Alonso et al.
2017/0114319 A1 4/2017 Le Gouellec et al.
2017/0129942 A1 5/2017 Plante et al.
2017/0136102 A1 5/2017 Sharma

(56) References Cited

U.S. PATENT DOCUMENTS

| | | | |
|---|---|---|---|
| 2017/0136111 | A1 | 5/2017 | Nano |
| 2017/0143815 | A1 | 5/2017 | Giacalone |
| 2017/0145061 | A1 | 5/2017 | Lu et al. |
| 2017/0145065 | A1 | 5/2017 | Haagsman et al. |
| 2017/0151321 | A1 | 6/2017 | Luo et al. |
| 2017/0157232 | A1 | 6/2017 | Bremer et al. |
| 2017/0157239 | A1 | 6/2017 | Bermudes |
| 2017/0174746 | A1 | 6/2017 | Sad et al. |
| 2017/0182155 | A1 | 6/2017 | Reed et al. |
| 2017/0191058 | A1 | 7/2017 | De Armas et al. |
| 2017/0209502 | A1 | 7/2017 | Honda et al. |
| 2017/0216378 | A1 | 8/2017 | Honda et al. |
| 2017/0240615 | A1 | 8/2017 | Shapiro |
| 2017/0246281 | A1 | 8/2017 | Super et al. |
| 2017/0258885 | A1 | 9/2017 | Luirink et al. |
| 2017/0290889 | A1 | 10/2017 | Loke et al. |
| 2017/0290901 | A1 | 10/2017 | Talaat |
| 2017/0304434 | A1 | 10/2017 | Dominowski et al. |
| 2017/0318817 | A1 | 11/2017 | Padmanabhan et al. |
| 2017/0327830 | A1 | 11/2017 | Curtiss et al. |
| 2017/0340720 | A1 | 11/2017 | Bagnoli et al. |
| 2017/0350890 | A1 | 12/2017 | Cirillo et al. |
| 2017/0360540 | A1 | 12/2017 | Jackwood et al. |
| 2017/0368156 | A1 | 12/2017 | Husseiny Elsayed et al. |
| 2017/0368166 | A1 | 12/2017 | Gunn |
| 2018/0008701 | A1 | 1/2018 | Dominowski et al. |
| 2018/0021424 | A1 | 1/2018 | Dominowski et al. |
| 2018/0028642 | A1 | 2/2018 | Cherpes et al. |
| 2018/0028649 | A1 | 2/2018 | Reed et al. |
| 2018/0043021 | A1 | 2/2018 | Schwarz et al. |
| 2018/0044406 | A1 | 2/2018 | Schwarz et al. |
| 2018/0049413 | A1 | 2/2018 | Flavell et al. |
| 2018/0050099 | A1 | 2/2018 | Gunn et al. |
| 2018/0066041 | A1 | 3/2018 | Szijárto et al. |
| 2018/0066225 | A1 | 3/2018 | Choi et al. |
| 2018/0071377 | A1 | 3/2018 | Putnam et al. |
| 2018/0087060 | A1 | 3/2018 | Fruehauf et al. |
| 2018/0099999 | A1 | 4/2018 | Thompson et al. |
| 2018/0104328 | A1 | 4/2018 | Qiao et al. |
| 2018/0140665 | A1 | 5/2018 | Giacalone |
| 2018/0147278 | A1 | 5/2018 | Klocke et al. |
| 2018/0164221 | A1 | 6/2018 | Singh et al. |
| 2018/0168488 | A1 | 6/2018 | Jones et al. |
| 2018/0168489 | A1 | 6/2018 | Jones et al. |
| 2018/0168490 | A1 | 6/2018 | Jones et al. |
| 2018/0169222 | A1 | 6/2018 | Lopez |
| 2018/0169226 | A1 | 6/2018 | Reed et al. |
| 2018/0185469 | A1 | 7/2018 | Gourapura et al. |
| 2018/0193003 | A1 | 7/2018 | Jones et al. |
| 2018/0193441 | A1 | 7/2018 | Rubio Nistal et al. |
| 2018/0206726 | A1 | 7/2018 | Singh et al. |
| 2018/0206769 | A1 | 7/2018 | Pak et al. |
| 2018/0221286 | A1 | 8/2018 | Kabadi et al. |
| 2018/0221470 | A1 | 8/2018 | Reed et al. |
| 2018/0236063 | A1 | 8/2018 | Reed et al. |
| 2018/0243347 | A1 | 8/2018 | Agrawal et al. |
| 2018/0243348 | A1 | 8/2018 | Honda et al. |
| 2018/0271787 | A1 | 9/2018 | Tardi et al. |
| 2019/0017057 | A1 | 1/2019 | Bermudes |
| 2019/0055569 | A1 | 2/2019 | Lesser et al. |

| Input 1 | Input 2 | Output Q |
|---|---|---|
| 0 | 0 | 0 |
| 0 | 1 | 0 |
| 1 | 0 | 0 |
| 1 | 1 | 1 |

2-input AND Gate

| Input 1 | Input 2 | Input 3 | Output Q |
|---|---|---|---|
| 0 | 0 | 0 | 0 |
| 0 | 0 | 1 | 0 |
| 0 | 1 | 0 | 0 |
| 0 | 1 | 1 | 0 |
| 1 | 0 | 0 | 0 |
| 1 | 0 | 1 | 0 |
| 1 | 1 | 0 | 0 |
| 1 | 1 | 1 | 1 |

3-Input AND Gate

| Input 1 | Input 2 | Output |
|---|---|---|
| 0 | 0 | **0** |
| 0 | 1 | **1** |
| 1 | 0 | **1** |
| 1 | 1 | **1** |

OR Gate

| Input 1 | Output Q |
|---|---|
| 0 | 1 |
| 1 | 0 |

NOT Gate

| Input 1 | Input 2 | Output 1 | |
|---|---|---|---|
| 0 | 0 | **0** | |
| 0 | 1 | **1** | |
| 1 | 0 | **0** | |
| 1 | 1 | **0** | |

NOT AND Gate

| Input 1 | Input 2 | Output 1 | Output 2 |
|---|---|---|---|
| 0 | 0 | 0 | 0 |
| 0 | 1 | 0 | 1 |
| 1 | 0 | 1 | 0 |
| 1 | 1 | 0 | 0 |

NOT AND

| Input 1 | Input 2 | Input 3 | Output Q |
|---|---|---|---|
| 0 | 0 | 0 | 0 |
| 0 | 0 | 1 | 1 |
| 0 | 1 | 0 | 0 |
| 0 | 1 | 1 | 0 |
| 1 | 0 | 0 | 0 |
| 1 | 0 | 1 | 0 |
| 1 | 1 | 0 | 0 |
| 1 | 1 | 1 | 0 |

NOR AND

| Input 1 | Input 2 | Input 3 | Output Q |
|---|---|---|---|
| 0 | 0 | 0 | **0** |
| 0 | 0 | 1 | **0** |
| 0 | 1 | 0 | **0** |
| 0 | 1 | 1 | **1** |
| 1 | 0 | 0 | **0** |
| 1 | 0 | 1 | **0** |
| 1 | 1 | 0 | **0** |
| 1 | 1 | 1 | **0** |

NOT AND GATE (one inhibitory input and two positive inputs; not in normal tissue but yes in tumor)

NOR Gate

| Input 1 | Input 2 | Output Q |
|---|---|---|
| 0 | 0 | 1 |
| 0 | 1 | 0 |
| 1 | 0 | 0 |
| 1 | 1 | 0 |

NOT AND Gate

| Input 1 | Input 2 | Output |
|---|---|---|
| 0 | 0 | 0 |
| 0 | 1 | 1 |
| 1 | 0 | 0 |
| 1 | 1 | 0 |

pSTM 1787
RBS
CNF1
+/- ACDCRGDCFCG
YSL
709-730
ggggsACDCRGDCFCGggggsg
CNF1 1-539
LEU Z
2. pTet
YebF
CNF1 540-1013
CNF1 1, 53-539
CNF1 1, 190-539
Lysis
CNF1 1-53, 190-1013
TGFα
RGD

BACTERIA HAVING BOOLEAN CONTROL PATHWAYS EXPRESSING THERAPEUTIC PROTEINS INCLUDING IMMUNOTHERAPEUTIC CYTOTOXINS

CROSS REFERENCE TO RELATED APPLICATIONS

The present application is a non-provisional under 35 U.S.C. § 119(e) of U.S. Provisional Patent App. No. 63/055,327, filed Jul. 22, 2020, the entirety of which is expressly incorporated herein by reference.

FIELD OF THE INVENTION

This invention is generally in the field of genetically engineered bacteria, having genetic control pathways that lead to transcription based on satisfaction of Boolean conditions.

BACKGROUND OF THE INVENTION

Citation or identification of any reference herein, or any section of this application shall not be construed as an admission that such reference is available as prior art to the present application. The disclosures of each of these publications and patents are hereby incorporated by reference in their entirety in this application and shall be treated as if the entirety thereof forms a part of this application. Such references are provided for their disclosure of technologies to enable practice of the present invention, to provide written description basis for claim language, to make clear applicant's possession of the invention with respect to the various aggregates, combinations, and subcombinations of the respective disclosures or portions thereof (within a particular reference or across multiple references), and inform of the best mode for practicing the invention. The citation of references is intended to be part of the disclosure of the invention, and not merely supplementary background information. The incorporation by reference does not extend to teachings which are inconsistent with a embodiment of the invention as expressly described herein. The incorporated references also serve as evidence of a proper interpretation of the specification and claims, by persons of ordinary skill in the art at the time of the invention, of the terms, phrase and concepts discussed herein, without being limiting as the sole interpretation available.

It is known that homeostatic systems in organisms rely on direct or indirect feedback, or in some cases, threshold response. Further, the inherent mechanisms of organisms permit convergent regulatory pathways, i.e., multiple factors leading to a result. Thus, there is some intelligence even in prokaryotes. However, these pathways are endogenous, and interact with the organism metabolism, rendering them difficult to repurpose for arbitrary application, without adversely affecting the organism, e.g., causing off target effects when attempting to employ as a form of logic. Further, the endogenous pathways tend to operate in a linear regime, where partial response, often with feedback, is apparent. However, when genetically engineering organisms, it is possible to overcome these issues by including new or decoupled pathways that are not intrinsic to the homeostatic regulation of the metabolism or physiology of the organism.

The logically-responsive organisms may then be "programmed" to produce a product or biological response based on controllable conditions, which for example are bioorthogonal or extrinsic to the organism. One example is cancer or neoplasm therapy, where a first condition may be a pH of the tissue. The organism, for example, may grow in both neoplastic and non-neoplastic tissue, while a pathway within the organism may be made sensitive to the pH and produce or suppress a gene product dependent on pH. However, pH is non-specific, and this threshold response alone may insufficiently target the neoplastic tissue. Therefore, a second criteria may be applied, for example, redox potential, presence of receptors, receptor agonists, presence of receptor antogonists, presence of enzymes, presence of enzyme substrates or inhibitors, temperature, osmolarity, light, presence of deuterated water or other isotopes, etc. Further, in addition to functional signals and conditions, organisms may also be responsive to informational signals and conditions, i.e., nucleic acid sequences, peptide sequences, and modulated physical condition signals.

Cancer or neoplastic diseases including solid tumors, lymphomas, leukemias or leukemic bone marrow, is a devastating condition of uncontrolled cell growth, which often has the ability to spread throughout the body (metastases) resulting in death. Tumor-targeted bacteria offer tremendous potential advantages for the treatment of solid tumors, including the targeting from a distant inoculation site and the ability to express therapeutic agents directly within the tumor (Pawelek et al., 1997, Tumor-targeted *Salmonella* as a novel anticancer agent, Cancer Research 57: 4537-4544; Low et al., 1999, Lipid A mutant *Salmonella* with suppressed virulence and TNF-alpha induction retain tumor-targeting in vivo, Nature Biotechnol. 17: 37-41).

The primary shortcoming of tumor-targeted bacteria investigated in the human clinical trials (*Salmonella* strain VNP20009 and its derivative TAPET-CD; Toso et al., 2002, Phase I study of the intravenous administration of attenuated *Salmonella* typhimurium to patients with metastatic melanoma, J. Clin, Oncol. 20:142-152; Meir et al., 2001, Phase 1 trial of alive, attenuated *Salmonella* typhimurium (VNP20009) administered by direct Intra-tumoral (IT) injection, Proc Am Soc Clin Oncol 20: abstr 1043); Nemunaitis et al., 2003, Pilot trial of genetically modified, attenuated *Salmonella* expressing the *E. coli* cytosine deaminase gene in refractory cancer patients, Cancer Gene Therapy 10: 737-744) was that no significant antitumor activity was observed, even in patients where the bacteria was documented to target the tumor. In addition, an important factor was also that bacterial colonization of tumors, both in the form of the percentage of tumors that were colonized and amount of the bacteria that accumulated within the tumors, was usually lower compared to the preclinical studies using mice. One method of increasing the ability of the bacteria to expand their numbers within tumors is to kill tumor cells by engineering the bacteria to express conventional bacterial toxins (e.g., WO2009/126189, WO03/014380, WO/2005/018332, WO/2008/073148, US 2003/0059400 U.S. Pat. Nos. 7,452,531, 7,354,592, 6,962,696, 6,923,972, 6,863,894, 6,685,935, 6,475,482, 6,447,784, 6,190,657 and 6,080,849).

The present technology, according to various embodiments, further consists of modified forms of toxins, or chimeric toxins, with improved secretion, surface display and/or release by the bacteria, and/or modifications that improve the overall activity and/or specificity of the toxin for tumor tissue and lack of activity in normal tissues, and to act as immunological co-stimulatory agents. Such toxins may be further co-expressed with protease inhibitors as previously described (See, U.S. Pat. Nos. 8,241,623; 8,524,220; 8,771,669; 8,524,220).

Toxins, therapeutic cytokines and other molecules, homologues or fragments thereof useful in conjunction with the present technology having an antitumor effect, according to various embodiments, includes small lytic peptides, larger lytic peptides, pore-forming toxins, protein inhibitors, extracellular DNAases (DNase), intracellular DNAases, apoptosis inducing peptides, cytokines, prodrug converting enzymes, metabolite destroying enzymes, ribonucleases, antibody inactivating toxins and other anticancer peptides. In a preferred embodiment, the toxins include those that are naturally secreted, released and/or surface displayed, or heterologously secreted, released and/or surface displayed, and that can be modified uniquely to suit the delivery by a bacterium and may be further engineered to have the tumor, lymphoma, leukemic bone marrow or proximity-selective targeting system described herein, including but not limited to the proteins azurin and azurin derivatives, carboxylesterase Est55 (a prodrug-converting enzyme from *Geobacillus stearothermophilus* that activates CPT-11 to SN-38; Liu et al., 2007, Crystal structure of the *Geobacillus stearothermophilus* carboxyesterase Est55 and its activation of the prodrug CPT-11, J. Mol. Biol. 367: 212-223; Ewis et al., 2004, Molecular cloning and characterization of two thermostable carboxyl esterases from *Geobacillus stearothermophilus*, Gene 329:187-195) as well as carboxylesterases from *Bacillus* and related genera and species (e.g., *B. andreraoultii, B. kribbensis, B. coagulans*, B. MRMR6, *Tuberibacillus* sp. *B. persicus, B. thermoamylovorans, Geobacillus* sp., *B. dakarensis, B. niacin, Oceanobacillus caeni, B. massilionigehensis, Virgibicillus* sp., *Bacilli bacterium* VT-13-104, *B. bataviensis, B. bororiensis, B. coagulans*, firmicutes bacterium, *Thermaerobacterium* sp., *Thermaerobacter subterraneus, Thermaerobacter mahanensis, Alicyclobacillus macrosporangiidus, Thermoactinomyces* sp., *Parageobacillus thermantarcticus, Parageobacillus caldoxylosilyticus, Parageobacillus genomosp, Geobacillus thermoleovorans, Geobacillus thermodenitificans, Geobacillus kaustophilus, G. vulcani, G. jurassicus, G. zalihae, Anoxybacillus amylolyticus*) thiaminase (e.g., from *Bacillus*), methionase (methioninase), asparaginase, tryptophanase, apoptin, Torquetnovirus (TTV) derived apoptosis-inducing protein TAIP and with gyrovirus VP3 bax, bim, p53, BAK, BH3 peptide (BCL2 homology domain 3), cytochrome C, thrombospondin, platlet factor 4 (PF4) peptide, *Bacillus* sp. cytolysins, nheABC toxins, cytolethal distending toxins (cldt) including those cldts from *Haemophilus, Aggregatibacter, Salmonella, Escherichia, Shigella, Campylobacter; Helicobacter, Hahella* and *Yersinia*, typhoid toxins (with pertussis like toxin components) (pltAB), pertussis toxin, cldt:plt hybrids, actAB, cytolethal distending toxin anthrax toxin fusions (Bachran et al., 2014, Cytolethal distending toxin B as a cell-killing component of tumor-targeted anthrax toxin fusion proteins, Cell Death and Disease 5, e1003, 2014), cytotoxic nectrotic factor 1, (cnf1), cytotoxic nectrotic factor 2, (cnf2); cytotoxic nectrotic factor 3, (cnf3) *Bordetella* dermonecrotic factor (dnf) and related toxins in *Yersinia* (CNFY; Knust and Schmidt 2010 Toxins 2:116-127), shiga toxins and shiga-like toxins, bacteriocins, (colicins and microcins; Hen and Jack, Chapter 13 Microcins, in Kastin (ed), 2006, Handbook of Biologically Active Peptides, Academic Press; Nes et al., Chapter 17, The nonlantibiotic heat-stable bacteriocins in gram-positive bacteria, in Kastin (ed), 2006, Handbook of Biologically Active Peptides, Academic Press; Sharma et al., Chapter 18 in Kastin (ed), 2006, Handbook of Biologically Active Peptides, Academic Press) including membrane depolarizing (or pore-forming), DNAases (including colicin DNase, Staphylococcal Nuclease A:OrnpA fusions (Takahara et al., 1985 J. Biol. Chem 260: 2670-2674), *Serratia marcescens* DNase (Clegg and Allen, 1985, FEMS Microbiology Letters 27: 257-262; *Vibrio* DNase Newland et al., 1985 Infect Immun 47: 691-696) or other bacterial DNase), RNAases, and tRNAases, including but not limited colicin A, colicin D, colicin E5, colicin E492, microcin M24, colE1, colE2, colE3, colE5 colE7, coleE8, colE9, col-la, colicin N and colicin B, membrane lytic peptides from Staphalococcus (listed below) and sea anemones, P15 peptide and other TGF-beta mimics, repeat in toxin (RTX) family members (together with the necessary acylation and secretion genes) including *Actinobacillus* leucotoxins, a leuckotoxin: *E. coli* HlyA hybrid, *E. coli* HlyA hemolysin, *Bordetella* adenylate cyclase toxin, heat stable enterotoxins (HSTs) from *E. coli* and *Vibrio* sp. (Dubreuil 2006, Chapter 48, *Escherichia coli, Vibrio* and *Yersinia* species heat stable enterotoxins, Alouf and Popoff (eds), 2006, Comprehensive Sourcebook of Bacterial Protein Toxins, Third Edition, Academic Press; Lin et al., 2010, Bacterial heat-stable enterotoxins: Translation of pathogenic peptides into novel targeted diagnostics and therapeutics, Toxins (Basil) 2: 2028-2054), autotransporter toxins including but not limited to IgA protease, picU espC, and sat, Staphalococcus protein A, *Clostridium* enterotoxin, *Clostridium difficile* toxin A, scorpion chlorotoxin, aerolysin, subtilase, cereolysin, Staphalococcus leukotoxins (e.g. LukAB, 'LukF-PV, LukF- R, LukF-I, LukM, HIgB) and the other, to class S (e.g. LukS-PV, LukS-R, LukS-1, HIgA, HIgC). Best known are the toxins produced by *S. aureus*: γ-haemolysins, HIgA/HIgB and HIgC/HIgB and leukocidin Panton-Valentine, LukS-PV/LukF-PV (Luk-PV, PVL)) TRAIL, fasL, IL-18, CCL-21, human cyokine LIGHT, agglutinins (*Maackia amurensis*, wheat germ, *Datura stramonium, Lycopersicon* (tomato) plant lectin, leukoagglutinin (L-PHA, *Helix pomatia*) saporin, ricin, pertussus toxin, and porB, as well as other toxins and peptides (Kastin (ed), 2006, Handbook of Biologically Active Peptides, Academic Press; Alouf and Popoff (eds), 2006, Comprehensive Sourcebook of Bacterial Protein Toxins, Third Edition, Academic Press). Metabolite toxins such as the *Chromobacterium violacium* dipsepeptides (Shigeatsu et al., 1994, FR901228, a novel antitumor bicyclic depsipeptide produced by *Chromobacterium violaceum* No. 968. II. Structure determination. J Antibiotics (Tokyo) 47(3): 311-4) or those from *Serratia* are also of use in the present technology. Also included are *Pseudomonas* type III toxins ExoS, ExoT, ExoU and ExoY (Hauser et al., 2009, The type III secretion system of *Pseudomonas aeruginosa*: infection by injection, Nature Reviews Microbiology 7: 654-665: doi: 10.1028/nrmicro2199; Goldufsky et al., 2015, *Pseudomonas aeruginosa* exotoxin T induces potent cytotoxicity against a variety of murine and human cancer cell lines, J Med Microbiol 64: 164-173). Other toxin include those described by Nour-Imene Zahaf and Gudula Schmidt 2017 (Bacterial toxins for cancer therapy, Toxins (Basil) 9(8): 236) and Zahaf et al., 2017 Targeted delivery of an ADP-ribosylating bacterial toxin into cancer cells, Sci Rep 2017; 7:41252). The effector may also be *Burkholderia* TecA (e.g., UniProtKB-B4EMB9 (B4EMB9_BURCJ)), *Vibrio* thermostable pore-forming hemolysins (TDHs; TdhA and TdhS) *Francisella* mviN and ripA, *Shigella* IpaB, Chylamidia CPAF (Cunha and Zamboni 2013, Subversion of inflammasome activation and pyroptosis by pathogenic bacteria, Frontiers in Cellular and Infection Microbiology doi: 10:3389/fcimb.2013.00076) and cause pyroptosis.

Cytotoxins having an antitumor effect also include phenol soluble modulins (PSMs; U.S. Pat. No. 8,771,669) and related delta toxins (or delta-lysins or delta-hemolysins) and related toxins and variants from organisms with PSM related peptides including but not limited to *Staphylococcus aureus, Staphylococcus aureus* subsp. *aureus* RN4220, *Staphylococcus simiae, Staphylococcus epidermidis, Staphylococcus saccharolyticus, Staphylococcus caprae, Staphylococcus pasteuri, Staphylococcus carnosus, Staphylococcus massiliensis, Staphylococcus auricularis, Staphylococcus capitis, Staphylococcus intermedius, Staphylococcus pseudintermedius, Staphylococcus delphini, Staphylococcus warneri, Staphylococcus schleiferi, Staphylococcus simulans, Staphylococcus schleiferi, Staphylococcus muscae, Staphylococcus microti, Staphylococcus hyicus, Staphylococcus felis, Listeria monocytogenes, Terrabacteria* group, Hyphomonadaceae bacterium, Chthoniobacterales bacterium, Bacteroidetes bacterium, *Flavobacterium columnare, Candidatus Mycoplasma* haemohominis bacterium E08(2017), Verrucomicrobia bacterium, *Flavisolibacter* sp. XTX, Acidobacteria bacterium, *Elizabethkingia ursingii.*

Preferred toxins, enzymes and immunotherapeutics especially include *Pseudomonas* ToxA with targeting ligands and immunotherapeutic derivatives as well as co-expression with enhancer molecules such as apoptin, cytolethal distending toxins (CLDTs) and its chimeras including those with C-terminal cysteines and N-terminal or C-terminal fusions and immunotherapeutic derivatives, CLDT and its apoptotic derivatives (e.g., CLDT-apoptin), hybrid ArtAB:CLDTs, hybrid ArtAB:pertussis toxin S3 subunit, hybrid CLDT: pertussis S3 subunit, other hybrid CLDTs as described herein, cytotoxic necrotic factors and derivatives described herein, including those of cytotoxic necrotic factor 1, (cnf1), cytotoxic necrotic factor 2, (cnf2); cytotoxic necrotic factor 3, (cnt3) *Bordetella* dermonecrotic factor (dnf) and related cytotoxic necrotic factors toxins in *Yersinia* (CNFY) each of which may be modified as an immunotherapeutic, phenol soluble modulin toxins (PSMs) and PSM immunotherapeutics, parasporins, *Staphylococcus* leukotoxins, *Staphylococcus aureus* hemolysin (SAH), *Pasteurella* multocita toxins (PMT) and PMT immunotherapeutics, *Actinobacillus* leucotoxins and leukotoxin immunotherapeutics, leukoagglutinin (L-PHA, *Phaseolus vulgaris*) *Helix pomatia* lectin (HPA), mistletoe lectin, including the modifications described herein, GMCSF, human cGAS, *Vibrio* DncV, *Salmonella* AdrA, mistletoe lectin and hybrid mistletoe lectin, a K-Ras inhibitory peptide, as well as carboxylesterase Est55 and its C408V and C408A mutants, granulocyte colony stimulating factor alone or coexpressed with a lysis protein or colicin E3, secreted adenosine deaminase, tryptophanase, and antibodies and peptides to checkpoint inhibitors. Preferably, these therapeutic proteins, toxins enzymes and immunotherapeutics are at least 50%, preferably at least 60%, more preferably at least 70%, even more preferably at least 80%, still even more preferably at least 90%, most preferably at least 95%, such as 96%, 97%, 98% or 99%, even most preferably 100% identical in their amino acid sequence.

The chimeras may be fashioned by addition of one or more multimerization domains, such as the T4 foldon trimerization domain (Meier et al., 2004, Journal of Molecular Biology, 344:1051-1069; Bhardwaj et al., Protein Sci. 2008 17:1475-1485) or tetramerization domains such as VASP (Kühnel et al., 2004 PNAS 101:17027-17032). Chimeric toxins may be further modified by the addition of known cell penetrating (ferry) peptide which further improves their entry into target cells. Cell penetrating peptides include those derived from the human immunodeficiency virus (HIV) TAT protein amino acids 47-57 (SEQ ID NO 001: YGRKKRRQRRR) and used in fusion proteins (e.g., TAT-apoptin, TAT-bim, TAT-p53), the antennapedia homeodomain (penetraxin), Kaposi fibroblast growth factor (FGF) membrane-translocating sequence (MTS), herpes simplex virus VP22, hexahistidine, hexalysine, hexaarginine or "Chariot" (Active Motif, Carlsbad, Calif.; U.S. Pat. No. 6,841,535). Nuclear localization signals (NLSs) may also be added, including but not limited to that from herpes simplex virus thymidine kinase, the SV40 large T antigen monopartite NLS, or the nucleoplamin bipartite NLS or more preferably, the NLS from apoptin, a tumor associated (tumor-selective) NLS. The tumor- selective nuclear export signal from apoptin may be used alone or together with NLS from apoptin (Heckl et al., 2008, Value of apoptin's 40-amino-acid C-terminal fragment for the differentiation between human tumor and non-tumor cells, Apoptosis 13: 495-508; Backendor et al., 2008, Apoptin: Therapeutic potential of an early sensor of carcinogenic transformation, Ann Rev Pharmacol Toxicol 48:143-69).

Another modality to increase antitumor activity is through immunotherapeutics delivered by *Salmonella* or other type of bacteria (Diamond et al., U.S. Pat. No. 9,453,227B2; Blache et al., 2012, Systemic delivery of *Salmonella* typhimurium transformed with IDO shRNA enhances intratumoral vector colonization and suppresses tumor growth, Cancer Res 72: 6447-6456; Manuel et al., 2011 Enhancement of cancer vaccine therapy by systemic delivery of a tumor-targeting *Salmonella*-based STAT3 shRNA suppresses the growth of established melanoma tumors, Cancer Res 71P 4183-4191; Bermudes, U.S. Pat. No. 9,616,114; Thanos et al., US Patent Application 20190017050), Falb et al., Microorganisms programmed to produce immune modulators and anti-cancer therapeutics in tumor cells, US Patent Application 2019/0336544. Included in the present application are peptides and antibodies that bind to and result in antagonism to co-inhibitory molecules PD-1 (CD279), PD-L1 (B7-H1; CD274), PDL2 (B7-DC; CD273), CD80 (B7-1), CD86 (B7-2), B7-H3 (CD276)/B7H4 (VTCN1); CLTA4 (CD152), LAG-3, $KIR_L$, CD200, CD200R, CD112 (PVRL2; Nection-2), butyrophilin family members (e.g., Btn12, Skint1, MOG, CD277), HVEM (TNFSRSF14; CD270)VISTA (B7H5; PD-IH; Gi24), CD155 (PVR; Necl-5), CD112 (PVRL2; Nection-2), LAG3 (CD223), TIGIT, TIM-3 (HAVcr-2), A2aR BTLA, CD 96, CD112R, CD160, CD200R, VISTA B7/H3, and the macrophage antiphagocytosis molecules CD47 and SIRP□ (Sim et al., 2019, Discovery of high affinity, pan-allelic, and pan-mammalian reactive antibodies against the myeloid checkpoint receptor SIRP, MABS, doi.org/10.1080/19420862.2019.1624123). Also encompassed are antibodies and peptides that bind to and agonize co-stimulatory, CD27 (TNFRSF7), CD28, CD40, CD40L (TNSFSF; CD154), OX40 (TNFRSF4; CD134), GITR (TNFRSF18; CD357), CD226 (DNAM-1), 2B4 (CD244), (TNFRSF7), ICOS (CD278), CD28H, CD137 (TNFRSF-9; 41BB), TCR, TMIGD2 (IGPR-1), KIRs, CD48 (BCM-1; BLAST-1), CD155 (PVR; Necl-5), GITRL (TNFSF18), CD70 (TNFSF7; CD27L), OX40L (TNFSF4; CD252), CD137L (TNFSF9; 4-1BBL), MHC Class I or II, B7-H7 (HHLA2), ICOSL (B7-H2; B7RP1), CD80 (B7-1), CD86 (B7-2).

Also included in the technology is expression of granulocyte macrophage colony stimulating factor (GMCSF) Greenberg et al., 1988, Expression of biologically active, mature human granulocyte-macrophage colony stimulating factor with an *E. coli* secretory expression system, Current Microbiol 17: 321-332; Babu et al., 2009, Single step intein-mediated purification of hGMCSF expressed in salt-inducible *E. coli*, Biotechnol Lett 31: 659-664).

Peptide ligands include affibodies (protein A affinity-based ligands), armadillo repeat protein-based scaffolds, adnectins, anticalins, lipocalins, Kunitz domain-based binders, avimers, knottins, fynomers, atrimers and DARPins (designed ankyrin repeat proteins) and cytotoxic T-lymphocyte associated protein-4 (CTLA4)-based binders (Weidle et al., 2013 The emerging role of new protein scaffold-based agents for treatment of cancer. Cancer Genomics Proteomics 10: 155-168). Antibodies include intrabodies and antibody derivatives including camelid antibodies, F(ab')2, Fab', Fab, Fc, Fv, FcFv, VHH, VHH/VH, rIgG, single domain (sdAB), $V_{NAR}$, probodies, and nanobodies. Peptide ligands include those of Bermudes (U.S. Pat. No. 9,068,187, Protease inhibitor: protease sensitivity expression system composition and methods improving the therapeutic activity and specificity of proteins delivered by bacteria). Targeting peptides include heat stable enterotoxins (e.g., SEQ ID NO 002: NSSNYCCELCCNPACTGCF) and precursors (e.g., UnitProtKP—P01559 (HST1_ECOLX) UniProtKB—Q2WE95 (Q2WE95_ECOLX); GenBank: PXF64785.1) analogs (Giblin et al., 2006, In vitro and in vivo evaluation of $^{111}$In-labeled *E. coli* heat-stable enterotoxin analogs for specific targeting of breast cancers, Breast Cancer Research and Treatment 98: 7-15), which may be engineered in their precursor form, and related hormones guanylin and uroguanylin (Dubreuil 2006, Chapter 48, *Escherichia coli, Vibrio* and *Yersinia* species heat stable enterotoxins, Alouf and Popoff (eds), 2006, Comprehensive Sourcebook of Bacterial Protein Toxins, Third Edition, Academic Press; Lin et al., 2010, Bacterial heat-stable enterotoxins: Translation of pathogenic peptides into novel targeted diagnostic and therapeutics, Toxins (Basil) 2: 2028-2054) Targeting peptides also include epidermal growth factor (EGF), including those of human, dog, cat, horse and mouse, tumor growth factor alpha (TGFα) including those of human, dog (NCBI XM_014117458.1, SEQ ID NO 003: MVRGHLVAAVGASSKVREESSPSACPSGHRVCGRQTRVRVLPELSRRDGLQGEARRDRSSSSPQRPPRGPWSA PPPPCRRPDPLALWREGTEHPRRRAWRPQYGAAAGAVIPSWQLRGKASVLLAAGQALENSTSALSARPPVAAAW SHFNDCPDSHSQFCFHGTCRFLVQEDKPACVCHSGYVGARCEHADLLAWAASQKKQAITALVWSIVALAVLIIACV LIHCCQVRKHCEWCQALLCRHEKPSALLKGRAACCHSETGKGRKGPRQGHSGRRSPLPPPLTSPGQGPGRGGLF NLQEPLKRPPQGC), cat, horse and mouse, clorotoxin targeting peptide, *Clostridium* enterotoxin C-terminal peptide 290-319 (SEQ ID NO: 004 SLDAGQYVLVMKANSSYSGNYPYSILFQKF; Black et al., 2015, CPE290-319 COOH-terminus fragment is adequate for high-affinity binding to target cell receptors, 7:1116-1125 doi:10.3390/toxins7041116, RGD-C4 (SEQ ID NO: 005 ACDCRGDCFCG); Muc (Hayashi et al., 2001, MUC1 mucin core protein binds to the domain 1 of ICAM-1, Chlorotoxin tumor binding peptide (Dardevet et al., 2015, Chlorotoxin: A helpful natural scorpion peptide to diagnose glioma and fight tumor invasion, Toxins (Basil) 7:1079-1101), sunflower trypsin inhibitor (SFTI), MMP2/9 inhibitor SEQ ID NO: 006 CTTHWGFTLC and its derivative SEQ ID NO: 007 RGDSYCTTHWGFTLC Huang et al., 2013, The synthetic peptide RGDSYCTTHWGFTLC inhibits metastasis and proliferation of breast cancer cells in vitro, Nan Fang Yi Ke Da Xue Xue Bao. 2013 September; 33(9):1367-71), Anthrax lethal factor (Zahaf and Schmidt 2017, Bacterial toxins for cancer therapy, Toxins (Basil) 9(8): 236 doi: 10.3390/toxins9080236; Bachram and Leppla, 2016, Cytolethal distending toxin subunit B conjugated or fused to *Bacillus anthracis* toxin lethal factor. US 2016/0145590), *Bordetella* filamentous hemagglutinin, peptides that bind to epithelial cell adhesion molecule (U.S. Pat. No. 9,815,866), including SEQ ID NO: 008 EHLHCLGSLCWP (EP133) and SEQ ID NO: 009 KHLQCVRNICWS (EP114), pertussis toxin S3 subunit and peptides derived from it, IL13 and peptides derived from it, hyaluronic acid, peptide-35 (U.S. Pat. No. 8,003,613), Pep42 (Liu et al., 2007, Mechanistic studies of a peptidic GRP78 ligand for cancer cell-specific drug delivery, Mol Pharm 4: 435-447), and those described by Brown (2010, tumor targeting agents: the road from phage display peptide selections to clinical applications, Curr Pharm Des 16: 1040-1054).

Bacteria modified for improved disulfide bonding are also encompassed (de Marco, 2009, Strategies for successful recombinant expression of disulfide bond-dependent proteins in *Escherichia coli*, Microb Cell Fact 2009; 8: 26, doi: 10.1186/1475-2859-8-26. These may include overexpression of Dsb, Skp, SurA, FkpA, DegP, surA, PpiA, PpiB, DnaKJE, GroELS, ClpB, SlyD, TorD. The bacteria may also be single or double mutants for trxB and gor. Disulfide bonding may be assessed experimentally using known methods or in silico, (e.g., Ceronia et al., 2006; DISULFIND: a disulfide bonding state and cysteine connectivity prediction server, Nucleic Acids Res 34 (Web Server issue): W177-81).

Lysis proteins are also useful in the present technology. Lysis protein E from bacteiophage phi-X174 is used as a biotechnological tool to generate non-replication competent bacterial-based vaccines (Langemann et al., 2010, The bacterial ghost platform system, Bioengineered Bugs 1, 326-336). Programmed loss of bacterial cell wall structural integrity can also be achieved in live replication competent vaccines by disruption of the asd gene, which is essential for cell wall peptidoglycan synthesis (Kong et al., 2008, Regulated programmed lysis of recombinant *Salmonella* in host tissues to release protective antigens and confer biological containment. *Proceedings of the National Academy of Science USA* 105: 9361-9366). Programmed lysis was engineered through arabinose control of the cell wall biosynthesis genes murA and asd coupled with expression of the p22 phage c2 gene. The absence of arabinose results in complete loss of viability and provides biological containment. The bacteriophage lambda lysis gene cluster SRRz has also been further provided (Camacho et al., 2016, Engineering *Salmonella* as intracellular factory for effective killing of tumor cells. Scientific Reports 6:30591. DOI: 10.1038/srep30591). Bacterial autolysis systems have also been developed based on the lambda phage holin-endolysin with the phi X174 gene E (Won et al., 2017; Won G, Hajam I A and Lee J W (2017) Improved lysis efficiency and immunogenicity of *Salmonella* ghosts mediated by co-expression of a lambda phage holin-endolysin and phi X174 gene E. Scientific Reports 7:45139. DOI: 10.1038/srep45139). Selective release of periplasmic proteins has also been accomplished by use of bacteriocin release proteins (BRPs; van der Wal et al., 1995, Bacteriocin release proteins: Mode of action, structure, and biotechnological application. *FEMS Microbiology Reviews* 17: 381-399). The colicin E3 lysis protein has been used to enhance release of a tumor-selective toxin based on *Pseudomonas* ToxA (Quintero et al., 2016; EGFR-targeted chimeras of *Pseudomonas* ToxA released into the extracellular milieu by attenuated *Salmonella* selectively kill tumor cells. Biotechnol Bioeng 113: 2698-2711. doi: 10.1002/bit.26026).

Use of secreted proteins in live bacterial vectors has been demonstrated by several authors. Holland et al. (U.S. Pat. No. 5,143,830) have illustrated the use of fusions with the C-terminal portion of the hemolysin A (hlyA) gene, a member of the type I secretion system. When co-expressed in the presence of the hemolysin protein secretion channel (HlyBD) and a functional TolC, heterologous fusions are readily secreted from the bacteria. The type I secretion system that has been utilized most widely, and although it is currently considered the best system available, is thought to have limitations for delivery by attenuated bacteria (Hahn and Specht, 2003, FEMS Immunology and Medical Microbiology, 37: 87-98). Those limitations include the amount of protein secreted and the ability of the protein fused to it to interfere with secretion. Improvements of the type I secretion system have been demonstrated by Sugamata and Shiba (2005 Applied and Environmental Microbiology 71: 656-662), using a modified hlyB, and by Gupta and Lee (2008 Biotechnology and Bioengineering, 101: 967-974), by addition of rare codons to the hlyA gene. Fusion to the gene clyA (Galen et al., 2004, Infection and Immunity, 72: 7096-7106 and Type III secretion proteins have also been used. Surface display has been used to export proteins outside of the bacteria. For example, fusion of the Lpp protein amino acids 1-9 with the transmembrane region B3-B7 of OmpA has been used for surface display (Samuelson et al., 2002, Display of proteins on bacteria, J. Biotechnology 96:129-154). The autotransporter surface display has been described by Berthet et al., WO/2002/070645. Other heterologous protein secretion systems utilizing the autotransporter family can be modulated to result in either surface display or complete release into the medium (see Henderson et al., 2004, Type V secretion pathway: the autotransporter story, Microbiology and Molecular Biology Reviews 68: 692-744; Jose, 2006 Applied Microbiol. Biotechnol. 69: 607-614; Jose J, Zangen D (2005) Autodisplay of the protease inhibitor aprotinin in *Escherichia coli*. Biochem Biophys Res Commun 333:1218-1226 and Rutherford and Mourez 2006 Microbial Cell Factories 5: 22). For example, Veiga et al. (2003 Journal of Bacteriology 185: 5585-5590 and Klauser et al., 1990 EMBO Journal 9:1991-1999), demonstrated hybrid proteins containing the b-autotransporter domain of the immunoglobulin A (IgA) protease of *Nisseria gonorrhea*. Fusions to flagellar proteins have been demonstrated. The peptide, usually of 15 to 36 amino acids in length, is inserted into the central, hypervariable region of the FliC gene such as that from *Salmonella muenchen* (Verma et al. 1995 Vaccine 13: 235-24; Wu et al., 1989 Proc. Natl. Acad. Sci. USA 86: 4726-4730; Cuadro et al., 2004 Infect. Immun. 72: 2810-2816; Newton et al., 1995, Res. Microbiol. 146: 203-216). Multihybrid FliC insertions of up to 302 amino acids have also been prepared (Tanskanen et al. 2000, Appl. Env. Microbiol. 66: 4152-4156). Trimerization of antigens and functional proteins can be achieved using the T4 fibritin foldon trimerization sequence (Wei et al. 2008 J. Virology 82: 6200-6208) and VASP tetramerization domains (Kühnel et al., 2004 PNAS 101: 17027-17032). The multimerization domains are used to create, bi-specific, tri-specific, and quadra-specific targeting agents, whereby each individual agent is expressed with a multimerization tag, each of which may have the same or separate targeting peptide, such that following expression, surface display, secretion and/or release, they form multimers with multiple targeting domains. The multimerization domains may also be used to multimerize FcFv and other antibody fragments in order to result in aggregation of their targets on the cell surface. Other secretion systems include C-terminal fusions to the protein YebF (Zhang et al., 2006, Extracellular accumulation of recombinant proteins fused to the carrier protein YebF in *Escherichia coli*, Nat Biotechnol 24:100-104), which is commercially available as a kit (pAES40; AthenaES, Baltimore, MD). Fusions to OmsY and other proteins are also capable of secreting proteins into the medium (Zian et al., 2008, Proteome-Based Identification of Fusion Partner for High-Level Extracellular Production of Recombinant Proteins in *Escherichia coli*, Biotechnol Bioengineer 101: 587-601). Other secretions systems usable according to the present technology include that of Kotzsch et al. 2011 (A secretory system for bacterial production of high-profile protein targets, Protein Science 20: 597-609) using OmpA, OmpF and OsmY, or those described by Yoon et al., 2010 (Secretory production of recombinant proteins in *Escherichia coli*, Recent Patents on Biotechnology 4: 23-29; 7094579B2, WO2009021548A1, EP1402036B1, 7070989B2, US20080193974A1, U.S. Pat. Nos. 7,052,867B2, 6,605,697B1, 5,470,719A, US20070287171A1, US20090011995A1, US20080076157A1, U.S. Pat. Nos. 7,112,434B2, 6,919,198B1, 6,455,279B1, 7,291,325B2, 7,410,788B2, US006083715A, EP1270730A1, U.S. Pat. Nos. 6,673,569B1, 6,309,861B1, 5,989,868A, 7,056,732B2, 6,852,512B2, 6,861,403B2, EP1407052B1, WO2008089132A2, U.S. Pat. No. 5,824,502A, EP1068339B1, US20080166757A1, U.S. Pat. Nos. 6,329,172B1, 6,596,509B1, 6,642,027B2, WO2006017929A1, U.S. Pat. No. 6,596,510B1, US20080280346A1, US20077202059B2, US20080280346A1, U.S. Pat. Nos. 7,202,059B2, 7,491,528B2, US20080206814A1, US20080166764A1, US20080182295A1, US20080254511A1, US20080206818A1, U.S. Pat. No. 7,105,327B1, US20040005695A1, U.S. Pat. No. 5,508,192A, EP866132A2, U.S. Pat. Nos. 6,921,659B2, 6,828,121B2, US20080064062A1, EP786009B1, US20060270043A1), and Habermann and Ertl (U.S. Pat. No. 7,202,059 Fusion proteins capable of being secreted into a fermentation medium), which uses fusions to hirudin.

Construction of the genetic elements described herein through synthetic chemistry (resulting in synthetic biology when combined with a living element) uses known techniques, including restriction endonuclease digestions and religations ("molecular cloning"), overlapping PCR and/or Gibson Assembly to generate single or multiple genes and/or gene fusions. It is understood that long DNA sequences can be custom ordered from commercial vendors, and thus the technology only need to describe the non-coding sequences, regulatory sequences, and coding sequences, or the amino acids of the coding sequences, with either wild type (naturally occurring) or codon optimized being specified to the vendor. It is also understood that the genetic elements may be expressed on a plasmid, the chromosome, or by a phage or phagemids, using for example molecular cloning and/or chromosomal integration techniques known to those skill in the art. Sequence identity is known to those skilled in the art, e.g., as described in Thanos et al., US Patent Application 2019001705.

For purposes herein, sequence identity can be determined by standard alignment algorithm programs used with default gap penalties established by each supplier. Default parameters for the GAP program can include: (1) a unary comparison matrix (containing a value of 1 for identities and 0 for non-identities) and the weighted comparison matrix of Gribskov et al. (1986) Nucl. Acids Res. 14: 6745, as described by Schwartz and Dayhoff, eds., Atlas of Protein Sequence and Structure, National Biomedical Research Foundation, pp. 353-358 (1979); (2) a penalty of 3.0 for each gap and an additional 0.10 penalty for each symbol in each gap; and (3) no penalty for end gaps. Whether any two nucleic acid molecules have nucleotide sequences or any two polypeptides have amino acid sequences that are at least 80%, 85%, 90%, 95%, 96%, 97%, 98% or 99% "identical," or other similar variations reciting a percent identity, can be determined using known computer algorithms based on local or global alignment (see e.g., wikipedia.org/wiki/Sequence_alignment_software, providing links to dozens of known and publicly available alignment databases and programs). Generally, for purposes herein sequence identity is determined using computer algorithms based on global alignment, such as the Needleman-Wunsch Global Sequence Alignment tool available from NCBI/BLAST (blast.ncbi.nlm.nih.gov/Blast.cgi?CMD=Web&Page_TYPE=BlastHome); LAlign (William Pearson implementing the Huang and Miller algorithm (Adv. Appl. Math. (1991) 12:337-357)); and program from Xiaoqui Huang available at deepc2.psi.iastate.edu/aa/align/align.html. Typically, the full-length sequence of each of the compared polypeptides or nucleotides is aligned across the full-length of each sequence in a global alignment. Local alignment also can be used when the sequences being compared are substantially the same length. Therefore, as used herein, the term "identity" represents a comparison or alignment between a test and a reference polypeptide or polynucleotide. In one non-limiting example, "at least 90% identical to" refers to percent identities from 90 to 100% relative to the reference polypeptide or polynucleotide. Identity at a level of 90% or more is indicative of the fact that, assuming for exemplification purposes a test and reference polypeptide or polynucleotide length of 100 amino acids or nucleotides are compared, no more than 10% (i.e., 10 out of 100) of amino acids or nucleotides in the test polypeptide or polynucleotide differ from those of the reference polypeptide. Similar comparisons can be made between a test and reference polynucleotides. Such differences can be represented as point mutations randomly distributed over the entire length of an amino acid sequence or they can be clustered in one or more locations of varying length up to the maximum allowable, e.g., 10/100 amino acid difference (approximately 90% identity). Differences also can be due to deletions or truncations of amino acid residues. Differences are defined as nucleic acid or amino acid substitutions, insertions or deletions. Depending on the length of the compared sequences, at the level of homologies or identities above about 85-90%, the result can be independent of the program and gap parameters set; such high levels of identity can be assessed readily, often without relying on software. In general, two biological molecules are considered insubstantially different if they share common relevant biological properties as measured on an organismal level with statistically insignificant differences at a reasonable threshold, e.g., $p<0.05$, or $p<0.01$, with a reasonable sample size to avoid undue experimentation, normalized for reasonably expected differences that are not directly related to the relevant biological property or properties at issue.

It is noted that, in some cases, these rules of thumb regarding sequence identity are obviated by functional limitations or thermodynamic laws. For example, some aspects of the technology may operate or be operable in cell-free systems, and in which a choice of organism, source organism for enzymes, media (temperature, pressure, ion concentrations, substrates, products, interfering substances, etc.) are measurable or controllable. As such, a relatively low sequence homology in such cases may be acceptable as being equivalent, while in other cases, a relatively high sequence homology may be unacceptable, for the stated purposes. Therefore, as a rule of construction, any expression or range qualified with a function is constrained by the function.

Compositions described in accordance with various embodiments herein include, without limitation, *Salmonella enterica* serovar Typhimurium ("*S. typhimurium*"), *Salmonella montevideo, Salmonella enterica* serovar Typhi ("*S. typhi*"), *Salmonella enterica* serovar Paratyphi A, Paratyphi B ("*S. paratyphi*"), *Salmonella enterica* serovar Paratyphi C ("*S. paratyphi* C"), *Salmonella enterica* serovar Hadar ("*S. hadar*"), *Salmonella enterica* serovar Enteriditis ("*S. enterditis*"), *Salmonella enterica* serovar Kentucky ("*S. kentucky*"), *Salmonella enterica* serovar Infantis ("*S. infantis*"), *Salmonella enterica* serovar Pullorum ("*S. pullorum*"), *Salmonella enterica* serovar Gallinarum ("*S. gallinarum*"), *Salmonella enterica* serovar Muenchen ("*S. muenchen*"), *Salmonella enterica* serovar Agona ("*S. agona*") *Salmonella enterica* serovar Anatum ("*S. anatum*"), *Salmonella enterica* serovar Dublin ("*S. dublin*"), *Salmonella enterica* serovar Derby ("*S. derby*"), *Salmonella enterica* serovar *Choleraesuis* var. *kunzendorf* ("*S. cholerae kunzendorf*"), and *Salmonella enterica* serovar minnesota (*S. minnesota*). A preferred serotype for the treatment of bone marrow related diseases is *S. dublin.*

By way of example, live bacteria in accordance with aspects of the technology include known strains of *S. enterica* serovar Typhimurium (*S. typhimurium*) and *S. enterica* serovar Typhi (*S. typhi*) which are further modified as provided by various embodiments of the technology. Such Strains include Ty21a, CMV906, CMV908, CMV906-htr, CMV908-htr, Ty800, $aroA^-/serC^-$, holavax, M01ZH09, VNP20009. See also, U.S. Pat. No. 6,548,287, and EP0973911. See also, US 20140256922; 20120108640; 20110318308; 20090215754; 20090169517; 20070298012; 20070110752; 20070004666; 20060115483; 20060104955; 20060089350; 20060025387; 20050267103; 20050249706; 20050112642; 20050009750; 20040229338; 20040219169; 20040058849; 20030143676; 20030113293; 20030031628; 20030022835; 20020151063; 20140220661; 20140212396; 20140186401; 20140178341; 20140155343; 20140093885; 20130330824; 20130295054; 20130209405; 20130130292; 20120164687; 20120142080; 20120128594; 20120093773; 20120020883; 20110275585; 20110111496; 20110111481; 20100239546; 20100189691; 20100136048; 20100135973; 20100135961; 20100092438; 20090300779; 20090180955; 20090175829; 20090123426; 20090053186; 20080311081; 20080124355; 20080038296; 20070110721; 20070104689; 20060083716; 20050026866; 20050008618; 20040202663; 20050255088; 20030109026; 20020026655; 20110223241; 20070009489; 20050036987; 20030170276; 20140148582; 20130345114; 20130287810; 20130164380; 20130164307; 20130078275; 20120225454; 20120177682; 20120148601; 20120144509; 20120083587; 20120021517; 20110274719; 20110268661; 20110165680; 20110091493; 20110027349; 20100172976; 20090317404; 20090220540; 20090123382; 20090117049; 20090117048; 20090117047; 20090068226; 20080249013; 20080206284; 20070202591; 20070191262; 20070134264; 20060127408; 20060057152; 20050118193; 20050069491; 20050064526; 20040234455; 20040202648; 20040054142; 20030170211; 20030059400; 20030036644; 20030009015; 20030008839; 20020176848; 20020102242; 20140205538; 20140112951; 20140086950; 20120244621; 20120189572; 20110104196; 20100233195; 20090208534; 20090136542; 20090028890; 20080260769; 20080187520; 20070031382; 20060140975; 20050214318; 20050214317; 20050112140; 20050112139; 20040266003; 20040115174;

20040009936; 20030153527; 20030125278; 20030045492; U.S. Pat. Nos. 8,828,681; 8,822,194; 8,784,836; 8,771,669; 8,734,779; 8,722,668; 8,715,641; 8,703,153; 8,685,939; 8,663,634; 8,647,642; 8,642,257; 8,623,350; 8,604,178; 8,591,862; 8,586,022; 8,568,707; 8,551,471; 8,524,220; 8,440,207; 8,357,486; 8,343,509; 8,323,959; 8,282,919; 8,241,623; 8,221,769; 8,198,430; 8,137,904; 8,066,987; 8,021,662; 8,008,283; 7,998,461; 7,955,600; 7,939,319; 7,915,218; 7,887,816; 7,842,290; 7,820,184; 7,803,531; 7,790,177; 7,786,288; 7,763,420; 7,754,221; 7,740,835; 7,736,898; 7,718,180; 7,700,104; 7,691,383; 7,687,474; 7,662,398; 7,611,883; 7,611,712; 7,588,771; 7,588,767; 7,514,089; 7,470,667; 7,452,531; 7,404,963; 7,393,525; 7,354,592; 7,344,710; 7,247,296; 7,195,757; 7,125,718; 7,084,105; 7,083,791; 7,015,027; 6,962,696; 6,923,972; 6,916,918; 6,863,894; 6,770,632; 6,685,935; 6,682,729; 6,506,550; 6,500,419; 6,475,482; 6,447,784; 6,207,648; 6,190,657; 6,150,170; 6,080,849; 6,030,624; and 5,877,159.

Strains encompassed by the technology may be attenuated in virulence by mutations in a variety of metabolic and structural genes, for example to achieve pharmacological acceptability permitting the attenuated bacteria to be administered to animals or humans without expected mortality, and low levels of morbidity and/or toxicity. Some strains may be "normal" (wild type) flora and/or probiotic, and therefore attenuation or modification of the normal organism biology and biochemical pathways may be unnecessary. The technology therefore may provide alive composition for treating cancer comprising alive attenuated bacterium that is a serovar of *Salmonella enterica* comprising an attenuating mutation in a genetic locus of the chromosome of said bacterium that attenuates virulence of said bacterium and wherein said attenuating mutation is the Suwwan deletion (Murray et al., 2004. Hot spot for a large deletion in the 18-19 Cs region confers a multiple phenotype in *Salmonella enterica* serovar Typhimurium strain ATCC 14028. Journal of Bacteriology 186: 8516-8523 (2004)) or combinations with other known attenuating mutations. Other attenuating mutation useful in the *Salmonella* bacterial strains described herein may be in a genetic locus selected from the group consisting of phoP, phoQ, edt, cya, crp, poxA, tpoS, htrA, nuoG, pmi, pabA, pts, damA, pur, purA, purB, purI, purF, zwf, aroA, aroB, aroC, aroD, serC, gua, cadA, rfc, rjb, rfa, ompR, msbB, leucine and arginine, and combinations thereof. Strains of *Salmonella* deleted in msbB and Suwwan and msbB, Suwwan and purF and/or purI and optionally zwf and Strain VNP20009 are particularly preferred.

The technology also encompasses attenuated gram-positive bacteria. For example, *Staphylococcus epidermidis*, group B *Streptococcus* including *S. agalactiae*, and *Listeria* species including *L. monocytogenes* may be employed. It is known to those skilled in the art that variations in molecular biology techniques such as use of gram-positive origins of replication, gram-positive signal sequences and gram-positive promoters and filamentous phage (e.g., phage B5; Chopin et al., 2002 J. Bacteriol. 184: 2030-2033, described further below) may be employed and substituted as needed. Other bacterial strains may also be encompassed, including non-pathogenic bacteria of the gut skin (such as *Staphylococcus epidermidis, Proprioni bacteria* spp.) and other body locations known as the human microbiome (Grice et al., Topographical and temporal diversity of the human skin microbiome, Science 324:1190-1192; A framework for human microbiome research; The Human Microbiome Project Consortium, 14 Jun., 2012 Nature 486, 215-221; Spor et al., 2011, Unravelling the effects of the environment and host genotype on the gut microbiome, Nature Reviews Microbiology 9: 279-290) such as *E. coli* strains, *Bacteriodies* spp., *Bifidobacterium* spp. and *Bacillus* spp., attenuated pathogenic strains of *E. coli* including enteropathogenic and uropathogenic isolates, *Enterococcus* sp. and *Serratia* sp. as well as attenuated *Neisseria* sp., *Shigella* sp., *Staphylococcus* sp., *Staphylococcus camosis, Yersinia* sp., *Streptococcus* sp. and *Listeria* sp. including *L. monocytogenes*. Bacteria of low pathogenic potential to humans and other mammals or birds or wild animals, pets and livestock, such as insect pathogenic *Xenorhabdus* sp., *Photorhabdus* sp. and human wound *Photorhabdus* (*Xenorhabdus*) are also encompassed. Probiotic strains of bacteria are also encompassed, including *Lactobacillus* sp. (e.g., *Lactobacillus acidophilus, Lactobacillus salivarius*) *Lactococcus* sp., (e.g., *Lactococcus lactis, Lactococcus casei*) *Leuconostoc* sp., *Pediococcus* sp., *Streptococcus* sp. (e.g., *S. salivariu, S. thermophilus*), *Bacillus* sp., *Bifidobacterium* sp., *Bacteroides* sp., and *Escherichia coli* such as the 1917 Nissel strain. It is known to those skilled in the art that minor variations in molecular biology techniques such as use of gram-positive origins of replication, gram-positive signal sequences gram-positive promoters (e.g., *Lactococcus* expression, Mohamadzadeh et al., PNAS Mar. 17, 2009 vol. 106 no. 11 4331-4336) may be used and substituted as needed. The bacteria may be further modified to be internalized into the host cell (Guimaraes et al., 2006, Use of Native Lactococci as Vehicles for Delivery of DNA into Mammalian Epithelial Cells, Appl Environ Microbiol. 2006 November; 72(11): 7091-7097; Innocentin et al., 2009, *Lactococcus lactis* Expressing either *Staphylococcus aureus* Fibronectin-Binding Protein A or *Listeria monocytogenes* Internalin A Can Efficiently Internalize and Deliver DNA in Human Epithelial Cells Appl Environ Microbiol. 2009 July; 75(14): 4870-4878). The bacteria *Faecalibacterium prausnitzii*, US patent application 20190030089 and *Akkermansia* spp. (WO2014075745A1; U.S. Pat. No. 6,468,525B1) may also be used.

Tumor Selective Expression. The technology also encompasses tumor selective expression, including novel combinations and methods to achieve improved expression combined with reduced expression in normal tissues through enhanced tumor targeting and decreased numbers of bacteria in normal tissues. Hypoxic-inducible promoters have been indicated as useful for tumor selective expression. It is known that tumors are hypoxic due to ineffective/insufficient blood supply through neo-angiogenesis. Several investigators have indicated the use of hypoxic promoters. Bermudes et al. (U.S. Pat. No. 6,962,696) have indicated the use of the pepT promoter for tumor-selective activation by tumor-targeted bacteria which is known to be activated under hypoxic conditions. Other hypoxic and anaerobic promoters have also been described (Membrillo-Hernandez and Lin 1999, Regulation of expression of adhE gene, encoding ethanol oxidoreductase in *Escherichia coli*: transcription from a downstream promoter and regulation by Fnr and RpoS, J Bacteriol 181: 7571-7579). A flexible and potent hypoxic promoter based on pepT for tumor-selective gene expression was further developed by Mangesha et al., 2006 (Development of a flexible and potent hypoxic-inducible promoter for tumor-targeted gene expression in attenuated *Salmonella*, Cancer Bio Ther 5:1120-1128), which was enhanced by engineering TATA- and FNR-boxes, with induction up to 200-fold. Kim et al., 2011 (Exploiting hypoxia-inducible promoter for tumor-specific gene expression in tumor-targeting bacteria, J. Nucl Med 52, Suppl 1690, Abstract 1690) used the pepT, pflE, ansB and vhb promoters for bacterial expression in tumors. Huang et al., 2013 (US Patent Application 20130295054) have also used hypoxia regulation for bacterial treatment of cancer. Anderson et al., 2006, Environmentally controlled invasion of cancer cells by engineered bacteria, *J Mol Biol.* 2006 Jan. 27; 355(4):619-627) used the fdhF promoter.

The present technology also encompasses quorum sensing regulated gene expression circuits. The application of synthetic biology and artificial gene circuits is being applied to bacterial delivery systems (Prindle et al., 2012, Genetic circuits in *Salmonella typhimurium*. ACS Synthetic Biology 1: 458-464). Quorum sensing is a gene expression system based on density-dependent induction by an autoinducer produced by the bacteria. When concentrations of the inducer are high, indirectly due to high concentrations of the bacteria, the inducer interacts with the quorum gene expression regulon to initiate expression. Because bacteria such as *Salmonella* localize within tumors to numbers exceeding $10^9$ CFU/g, the preferential localization of the bacteria offers a concentration-dependent phenomenon that can be coupled to a quorum sensing circuit Bacterial quorum sensing circuits have been reengineered to control bacterial invasion of host cells (Anderson et al., 2006) Environmentally controlled invasion of cancer cells by engineered bacteria. *Journal of Molecular Biology* 355: 619-627) and was suggested to be useful for tumor-selective expression. Quorum sensing has been used to induce tumor-localized expression (Swofford et al., 2015, Quorum-sensing *Salmonella* selectively trigger protein expression within tumors. *Proceedings of the National Academy of Sciences USA* 112: 3457-3462; Din et al., 2016, Synchronized cycles of bacterial lysis for in vivo delivery. *Nature* 536: 81-85.), and synchronized tumor-localized lysis combined with expression (Din et al., 2016). An *E. coli* modified to express the *Yersinia* invasion gene under inducible control of the *Vibrio fisheri* quorum sensing lux operon has been used to induce uptake of non-invasive *E. coli*, which they further tuned using a ribosomal binding site library and showed that concentration dependent invasion occurred based on quorum-based induction (Anderson et al., 2006). The *Vibrio fisheri* quorum sensing lux operon was used to preferentially expressing a GFP reporter within murine tumors (Swofford et al., 2015). Above a high-level threshold (4.2 $10^{10}$ CFU/g), expression was triggered to the same levels as constitutive controls, while below 0.6 $10^{10}$, expression levels were only at 3%. The colonization level within liver of these bacterially infected mice was completely below the level required to initiate expression, thereby preventing liver-associated expression and establishing that expression is tumor-selective. Coupling of expression of a therapeutic protein (HlyE; Ryan et al., 2009, Bacterial delivery of a novel cytolysin to hypoxic areas of solid tumors. Gene Therapy 16:329-339) and the φX174 gene E with a *Vibrio fisheri* quorum sensing circuit that resulted in oscillatory expression of the effector gene, individual cycles of protein expression followed by cell lysis occurred on a cyclical basis, and resulted in repeated rounds of protein expression and release that led to a therapeutic protein-dependent (HlyE) antitumor effect (Din et al., 2016). The system may also be used to express an anti-CD47 antibody (Chowdhury et al., Programable bacteria induce durable tumor regression and systemic antitumor immunity, Nature Medicine, doi.org/10.1038/s41591-019-0498-z). This system has the additional potential to be used for expression control of other effector systems such as those outlined above. The present technology provides modified and alternative genetic regulatory circuits for the expression of therapeutic genes by bacteria, including tumor-specific density dependence and normal tissue density independence.

The term "preferentially activated in cancerous cells and/or tissues" as used herein refers to a nucleotide sequence that expresses a polypeptide from a coding sequence in tumors and/or in proximity to tumors, neoplastic or cancerous cells at a level of at least two-fold more than the same polypeptide from the same coding sequence is expressed in or in proximity to non-tumors and/or non-tumorous, non-cancerous or non-neoplastic cells (i.e., normal cells and/or tissues). As further defined in this specification, "preferential repression non-cancerous cells and/or tissues" refers to a nucleotide sequence that expresses a polypeptide repressor from a coding sequence in or in proximity to non-tumor, non-cancerous or non-neoplastic cells and/or non-tumor, non-neoplastic or non-cancerous tissues (i.e., normal cells and/or tissues) at a level of at least two-fold more than the same polypeptide from the same coding sequence is expressed in cancerous cells and/or tissues.

The use of these nucleotide sequences is affected by operably linking such heterologous promoters which promoter is preferentially activated in solid tumors. Hua et al., 2011 (Proteomic screening of anaerobically regulated promoters from *Salmonella* and its antitumor applications, Mol Cell Proteomics DOI: 10.1074/mcp.M111.009399) identified alcohol dehydrogenase E, pyruvate dehydrogenase, carbamoyl phosphate synthase large subunit, periplasmic murein peptide-binding protein precursors, trp-repressor binding protein, Chain A *Salmonella* typhimurium liganded by phosphate ion, acetate kinase, mannose-specific enzyme IIAB, phosphoglycerate kinase and glycerophosphodiester phosphodiesterase, and Hua et al., 2017 (U.S. Pat. No. 9,708,617) have demonstrated the alcohol dehydrogenase (padhE) anaerobic-specific expression.

Yu et al., 2012 (Explicit hypoxia targeting with tumor suppression by creating and "obligate" anaerobic *Salmonella* typhimurium strain, Scientific Reports 2: 436, DOI: 10.1038/srep00436; Huang et al., U.S. Pat. No. 9,127,284) by putting an essential gene under hypoxic regulation of the pepT promoter, and uses the podA promoter to drive an antisense expression of the same gene under oxygenic conditions, and also claim use of ansB and fdhR promoters. The fdhF promoter is known commonly in the iGem registry of standard biological parts as part BBa_K2538000.

Several different sources have indicated methods for generating tumor-selective gene expression of therapeutic proteins for therapy by bacterial vectors. Pawelek, Bermudes and Low, (1997, Vectors for the diagnosis and treatment of solid tumors including melanoma, U.S. Pat. No. 6,190,657) indicated bacterial activation of gene expression for therapeutic proteins in tumor cells selected through the IVET promoter-trap system (Slauch et al., 1994, Methods Enzymol. 235:481-492; Mahan et al., 1993, Science 259: 686-688), or through use of identifying tumor-specific protein expression by two-dimensional electrophoresis. Pawelek et al., further indicated use of transposon mutation to select mutants for survival within tumors but not in normal (epithelial) cells. Arrach et al. (2010, High-throughput screening for *Salmonella* avirulent mutants that retain targeting of solid tumors, Cancer Research 70: 2165-2170) have used the approach of screening for avirulent transposon mutants that retain tumor targeting, and identified two classes consisting of htrA, SPI-2 and STM3120, which had reduced fitness toward normal tissue and unchanged against tumors. Arrach et al., 2010 also found a second class with reduced fitness towards both tumor tissues and normal tissues, with STM3120 showing an overall competitive advantage. Tumors provide niche-specific conditions for preferential growth which is aided by the chemotaxis gene cheY, motility genes motAB and the ethanolamine metabolic pathway eutC gene (Silva-Valenzuela et al., 2016; Solid tumors provide niche-specific conditions that lead to preferential growth of *Salmonella*, Oncotarget 7: 35169-35180).

Arrach et al. (2008, *Salmonella* promoters preferentially activated inside tumors, Cancer Research 68: 4827-4832; Arrach and McClelland US patent application 2011/0195847 Methods to treat solid tumors) used a promoter trap and identified promoters preferentially induced in tumors (Cancer Research 68: 4827-4832, Table 2), those expressed in both tumors and normal tissues, and those expressed preferentially in normal tissues (i.e., spleen). US2011/0195847 also describes use of a promoter trap to identified promoters preferentially induced in tumors (US 2011/0195847 Tables 2A and 2B), as well as intergenic regions that induce higher GFP expression in tumor than in spleen, those expressed in both tumors and normal tissues (US 2011/0195847 Tables 3A and 3B, Regions that induce GFP expression in both tumor and spleen), those expressed preferentially in normal tissues (US 2011/0195847 Tables 4, Intergenic regions that induce higher GFP expression in spleen than in tumor), and tumor selective promoters (US 2011/0195847 Tables 6A and 6B, Cloned candidate intergenic tumor-specific *Salmonella* promoters, and Table 7 Intragenic regions that induce higher GFP expression in tumor than in spleen).

Flentie et al., (2012, A bioluminescent transposon reporter-trap identifies tumor-specific microenvironment-induced promoters in *Salmonella* for conditional bacterial-based tumor therapy. *Cancer Discovery* 2: 624-637) have also described tumor-selective promoters. Deyneko et al., (2016, Composing a tumor specific bacterial promoter. *PLoS ONE* DOI:10.1371/journal.pone.0155338) and Leschner et al., (2012, Identification of tumor-specific *Salmonella* typhimurium promoters and their regulatory logic. *Nucleic Acids Research* 40(7) DOI: 10.1093/nar/gkr1041).

Arrach et al. also suggest the use of multiple promoters in combination, each of which alone express a peptide that do not make a functional protein, which combine to make a functional protein when co-expressed. However, Arrach et al. did not specifically indicate any such functional combinations to which that approach would be applicable or their use to express modified peptides. Arrach et al. also did not provide positive functional repression of expression in non-cancerous tissues combined with expression in cancerous tissues.

Several other investigators have also identified tumor-selective promoters. Weiss et al., (US Patent Application 20120244621, Tumor-specific bacterial promoter elements) describes several nucleic acid sequences, although these sequences are mostly hypoxic/anaerobic Fnr regulated sequences. Others include Leschner et al., (2012, Identification of tumor-specific *Salmonella* Typhimurium promoters and their regulatory logic, Nucleic Acids Research 40: 2984-2994; Flentie et al., 2012, A bioluminescent transposon reporter-trap identified tumor-specific microenvironment-induced promoters in *Salmonella* for conditional bacterial-based tumor therapy, Cancer Discov 2: 624-637, doi: 10.1158/2159-8290.CD-11-0201, or Dyneko et al., 2016, (Composing a tumor specific bacterial promoter, 11(5): e0155338, doi:10.1371/journal.pone.0155338). Other investigators (Bhatia and Danino, U.S. Pat. No. 9,994,809) have suggested the use of at least one nucleic acid sequence consisting of non-constitutive promoter operably linked to a second nucleic acid sequence that encodes a therapeutic agent. Nissim and Bar-Ziv 2010 (A tunable dual-promoter integrator for targeting of cancer cells, Molecular Systems Biology 6: Article 444; doi:10.1038/msb.2010.99) also developed a eukaryotic dual promoter system for cancer specific expression. The Kiang et al., 2011 (J Nucl Med 52 Suppl 1, Abstract 585, Dual expression of therapeutic and imaging reporter gene in attenuated *Salmonella* typhimurium using bi-directional Tet expression system), and a similar approach was utilized by Chien et al., 2019 (Multiplexed biosensors for precision bacteria tropism in vivo, bioRxiv doi.org/10.1101/851311).

Prior investigations of tumor-selective promoters did not indicate any such functional combinations to which that approach would be applicable or their use to express modified peptides, nor did they provide positive functional repression of expression in non-cancerous tissues combined with expression in cancerous tissues. It also did not use two tumor-selective promoters, whereby one results in positive expression in the tumor, while the other is used as an inverter to repress growth and expression in non-tumor tissue.

Mapping of transcriptional start locations is known, and includes RACE; rapid amplification of cDNA ends (e.g., Mattaeu and Rodrigue 2015, Precise Identification of Genome-Wide Transcription Start Sites in Bacteria by 5'-Rapid Amplification of cDNA Ends (5-RACE), Methods Mol Biol 143-159; Klerk et al., 2014, RNA sequencing: from tag-based profiling to resolving complete transcript structure, Cell Mol Life Sci 71: 3537-3551).

Operator sequences and their use in transcriptional control have been described (Engstrom and Pfleger 2017, Transcription control engineering and applications in synthetic Biology, Synthetic and Systems Biotechnology 2:176-191; (Deadman And Passcode Microbial Kill Switches US 20190040398), and are known to include triplet palindromic lac operators, symmetric lac operators, scrO operators, hinge-helix (HH) motif that alter the orientation of the helix-turn-helix (HTH) motif to weaken DNA operator binding, pLlacO promoter containing a lacO operator site that bind by the LacI DNA recognition module (DRM), GalR-LacI or CelR-LacI that bind the lacO operator. Operators are coupled with repressors adjacent to the promoter in order to block transcription and exert control over gene expression (Lewis 2011, A tale of two repressors—a historical perspective, J Mol Biol 409: 14-27; Ramos et al., 2005, The TetR family of transcriptional repressors, Microbiology and Molecular Biology Reviews, DOI: 10.1128/MMBR.69.2.326-356.2005; Molina-Henares et al., 2006, Members of the lclR family of bacterial transcriptional regulators function as activators and/or repressors; *FEMS Microbiology Reviews*, Volume 30, Issue 2, March 2006, Pages 157-186). Repressor and operator systems also include the *Pseudomonas* cymate (cym) repressor and operator (Choi et al., 2010, Novel, versatile, and tightly regulated expression system for *Escherichia coli* strains, Applied and Environ Microbiology 76: 5058-5066, doi: 10.1128/AEM.00413-10.

Exogenously Inducible Promoters. "Exogenously inducible" refers to the addition of an additional agent in order to affect gene expression (See: Brautaset et al, 2009, Positively regulated bacterial expression systems, Microb Biotechnol 2(1): 15-30; Chen et al., 2018, Tuning the dynamic range of bacterial promoters regulated by ligand-inducible transcription factors, Nature Communications 9, Article number: 64 (2018)). Application or administration of exogenous inducing agents may include oral, gaseous (inhaled), parenteral, including subcutaneous, intravenous, intratumoral, intramuscular, intraperitoneal, intrathecal, and intralymphatic. The promoters utilized may be of the same or of different types, with different genes expressed by any of the different promoters including constitutive, environmentally inducible, exogenously inducible, tumor specific, eukaryotic, normal tissue, normal environment, quorum sensing, and/or growth phase dependent promoters. Use of two or more separate promoters for more than one therapeutic protein, or therapeutic protein subcomponent (e.g., of a multimeric protein) allows, for example, when sufficient induction by X-ray, tetracycline, arabinose, methylsalicylate or other inducer(s) is/are administered following administration of the bacterial vector, to result in the expression of the therapeutic protein in a controlled and/or targeted manner. A variety of inducible promoters are known including arabinose ($Ara_{BAD}$) (Lossner et al., 2007, Cell Microbiol. 9:1529-1537; WO2006/048344; EP1,655,370 A1, ("pAra")), tetracycline inducible promoter (TET promoter; "pTet"), SOS-response promoters responsive to DNA damaging agents such as mitomycin, alkylating agents, X-rays and ultraviolet (UV) light such as the recA promoter, colicin promoters, sulA promoters and others ("pSOS"), the methylsalicylate inducible promoter (Royo et al., 2007, Nature Methods 4: 937-942; WO/2005/054477), PrpR/PprpB (Lee and Keasling 2005, A propionate-inducible expression system for enteric bacteria Appl Environ Microbiol, 71:6856-6862; Lee and Keasling 2006, Effect of glucose or glycerol as the sole carbon source on gene expression from the *Salmonella* prpBCDE promoter in *Escherichia coli*. Biotechnol Prog. 22:1547-1551), XylR/Pu and XylS/Pm (Blatny et al., 1997, Construction of a versatile set of broad-host-range cloning and expression vectors based on the RK2 replicon, Appl Environ Microbiol, 63: 370-379; Blatny et al., 1997, Improved broad-host-range RK2 vectors useful for high and low regulated gene expression levels in gram-negative bacteria, Plasmid. 38:35-51), the cym (cumate) inducible system (Choi et al., 2010, Novel, versatile, and tightly regulated expression system from *Escherichia coli* strains, Appl Environ Microbiol 76: 5058-5066)). The use of a dual expression system based on bidirectional tet expression was described by Jiang et al., 2011 (J Nucl Med 52 Suppl 1, Abstract 585, Dual expression of therapeutic and imaging reporter gene in attenuated *Salmonella* typhimurium using bi-directional Tet expression system).

Constitutively Expressed Promoters. Constitutively expressed promoters ("pConstitutive" have been extensively described (see, Shimada et al., 2014, The Whole Set of Constitutive Promoters Recognized by RNA Polymerase RpoD Holoenzyme of *Escherichia coli*, PLoS One doi.org/10.1371/journal.pone.0090447; Gilman and Love, 2016, Synthetic promoter design for new microbial chassis, Biochem Soc Trans 44: 731-737).

Environmentally Induced Promoters. Bacteria such as *E. coli* and *Salmonella* have been shown to respond to a variety of environmental stimuli (Forst and Inouye, 1988, environmentally regulated gene expression for membrane proteins in *Escherichia coli*, Ann Rev Cell Biol 4: 21-42; Lopez-Maury et al., 2008, Tuning gene expression to changing environments: from rapid responses to evolutionary adaptation, Nature Rev Genetics 9: 583-593; Vijayakumar et al., 2004, RpoS-regulated genes of *Escherichia coli* identified by random lacZ fusion mutagenesis, J Bacteriol 186: 8499-8507), with certain promoters useful in the present technology. Hypoxic-inducible promoters including but are not limited to the PepT promoter (Bermudes et al., WO 01/25397), and those identified herein including tumor, spleen, hypoxia, acid, ROS and quorum promoters and expression systems.

Acid stress response, xasA/gadC and ROS. Hersh et al., 1996 (A glutamate-dependent acid resistance gene in *Escherichia coli*. J. Bacteriol. 178:3978-3981) and Ryan et al., 2015 (Global transcriptome and mutagenesis analysis of the acid tolerance response of *Salmonella enterica* Serovar Typhimurium AEM 81: 8054-8065) described acidic promoters ("pAcidic" and ROS (reactive oxygen species; "pROS"), induced, including peroxide (H2O2) superoxide ($O2\cdot^-$), nitric oxide (·NO; "pNitric") SoxRS ("pSOX" peroxynitrite ($ONOO^-$) and ·OH have also been described (Touati 2000, Sensing and protecting against superoxide stress in *Escherichia coli*—how many ways are there to trigger soxRS response? Redox Rep 5: 287-293; Krapp et al., 2011, The soxRS response of *Escherichia coli* can be induced in the absence of oxidative stress and oxygen by modulation of NADPH content, Microbiology 157: 957-965).

Hypoxic Inducible Promoters. Use of hypoxic-inducible promoters ("pHypoxic" is also encompassed. These promoters include but not limited to the PepT promoter (Bermudes et al., WO 01/25397). Other hypoxic and anaerobic promoters have also been described (Membrillo-Hernandez and Lin 1999, Regulation of expression of adhE gene, encoding ethanol oxidoreductase in *Escherichia coli*: transcription from a downstream promoter and regulation by Fnr and RpoS, J Bacteriol 181: 7571-7579). A flexible and potent hypoxic promoter based on pepT for tumor-selective gene expression was further developed by Mangesha et al., 2006 (Development of a flexible and potent hypoxic-inducible promoter for tumor-targeted gene expression in attenuated *Salmonella*, Cancer Bio Ther 5:1120-1128), which was enhanced by engineering TATA- and FNR-boxes, with induction up to 200-fold. Kim et al., 2011 (Exploiting hypoxia-inducible promoter for tumor-specific gene expression in tumor-targeting bacteria, J. Nucl Med 52, Suppl 1690, Abstract 1690) used the pepT, pflE, ansB and vhb promoters for bacterial expression in tumors. Huang et al., 2013 (US Patent Application 20130295054) have also used hypoxia regulation for bacterial treatment of cancer.

Normal Tissue Promoters. Use of promoters activated in normal, non-cancerous tissues is also encompassed. Bile induction ("pBile" is used to repress bacterial growth through expression of SulA and other genes having inhibitory effects such as lysis genes. Bile induction is accomplished by linking the promoter for micF and/or osmY (Berstein et al., 1999, Bile salt activation of stress response promoters in *Escherichia coli*, Current Microbiol 39: 68-72) or the promoter of the CS5 operon (csfA-F) or homologues (Joffre et al., 2019, The bile salt glycocholate induces global changes in gene expression and activates virulence in enterotoxigenic *Escherichia coli*, Scientific Repots 9, Article number 108 (2019). Spleen activated promoters are those described by US 2011/0195847, e.g., Table 4 (Intergenic regions that induce higher GFP expression in spleen than in tumor; "pSpleen"), including but not limited to the promoters from the genes: STM0006 yaaJ, STM0006, STM0007 talB, STM0080, STM0080, STM0081, STM0390 aroM, STM0391 yaiE, STM0605 ybdN, STM0605, STM0606 ybdO, STM0892 ybjP, STM0893, STM1044 sodC, STM1044, STM1045, STM1231 phoP, STM1231, STM1232 purB, STM1249, STM1249, STM1250, STM1583, STM1583, STM1584, STM1584 ansP, STM1736 yciA, STM1736, STM1737, STM1737 tonB, STM1868, STM1876 holE, STM1876, STM1877, STM2153 yehE, STM2153, STM2154, STM2154 mrp, STM2169 yohC, STM2169, STM2170 yohD, STM2349 yfcG, STM2349, STM2350, STM2366 accD, STM2367 dedA, STM3047 ygfY, STM3047, STM3048, STM3048 ygfZ, STM3231 yqjK, STM3231, STM3232, STM3805 yidH, STM3805, STM3806, STM4286 lpxO, STM4286, STM4287, STM4290 proP, STM4290, STM4291, STM4291 basS, STM4328 yjeH, STM4329, STM4362 hflX, STM4362, STM4363, STM4363 hflK, PSLT006, PSLT007, PSLT024, PSLT025, PSLT025, PSLT026, PSLT040 spvA, PSLT040, PSLT041, PSLT045, PSLT046, PSLT047.

Inverter systems. Positively regulated elements may be converted into negative regulation (inverter) by using the positive element to drive the expression of a negative element (NOT function), such as a repressor. Naturally occurring repressor systems or artificial repressor systems with a constitutive promoter can be negatively regulated by addition of the operator sequence and cognate repressor (Wang et al., 2013, Synthetic biology: advancing the design of diverse genetic systems, Ann Rev Chem Biomol eng 2013, doi: 10.1146/annurev-chembioeng-061312-103351; Tabor et al., A synthetic genetic edge detection program, Cell, 137: 1272-1281, doi: 10.1016/j.cell.2009.04.048; Voigt 2006, Genetic parts to program bacteria, Current Opinion in Biotechnology 17: 548-557). Thus, the parts of an inverter include the ribosome binding site, repressor, terminator and an operator, such as PartBBa_Q01121. Others include symmetrical lacO SEQ ID NO: 010 tgtgtggaattgtgagcgctcacaattccacaca (Sadler et al., 1983 A perfectly symmetric lac operator binds the lac repressor very tightly, Proc. Natl. Acad. Sci. USA 80: 6785-6789).

The lac operator functions with the Lac gene product of lac/UniProtKB—P03023 (LACI_ECOLI)

A. Constitutive promoters: Promoters Recognized by RNA Polymerase RpoD Holoenzyme, Shimada et al., 2014; Synthetic constitutive promoters, Gilman and Love, 2016.
B. Growth phase dependent promoters: Lag phase (Madar et al., 2013); Log phase; Vijayakumar et al., 2004; Stationary phase; Vijayakumar et al., 2004.
C. Environmentally inducible prokaryotic elements: ROS response and NO induction, Touati 2000; Krapp et al., 2011; Crawford et al., 2016; Acidic pH response, Hersh, et al., 1996.; Ryan et al., 2015; Thiol activated genes—GST activated genes, DKSA Tapscott et al., 2016; Hypoxic and anaerobic, induction, e.g., adhE; Chen et al., 2011; Liu et al., 2011; pepT, Bermudes et al., WO 01/25397 and others.
D. Exogenously inducible prokaryotic elements: pAra, Lossner et al., 2007; Tetracyclin-inducible (tet); Berens and Hillen, 2003, 2008; SOS-response inducible, Kreuzer 2013; Kubiak et al., 2017; e.g., sulA Bermudes U.S. Pat. No. 9,616,114; Salicylate, methylsalicylate inducible, Royo et al., 2007; Cumate induction, Choi et al., 2010.
E. Tumor specific inducible prokaryotic elements: Arrach et al., 2008; US 2011/0195847; Weiss et al., US patent application 20120244621; EP2258844A1; Flentie et al., 2012; Leschner et al., 2012; Deyneko et al., 2016.
F. Normal environmental and normal tissue induced elements: Aarach et al., 2008; US 2011/0195847; Bile, yciF, Prouty et al., 2004; Tpx, Kim et al., 1999.
G. Quorum sensing elements: Anderson et al., 2006; Prindle et al., 2012; Swofford et al., 2015; Din et al., 2016.

Crawford et al., 2016, DksA-dependent transcriptional regulation of *Salmonella* experiencing Nitrosative stress, Frontiers in Microbiology Volume 7, Article 444.

Kim et al., 1999, Involvement of AcrA and Fnr in expression of *Escherichia coli* thiol peroxidase gene, IUBMB Life 48: 215-218.

Madar et al., 2013, Promoter activity dynamics in the lag phase of *Escherichia coli*, BMC Systems Biology 7, 136 (2013).

Miksch and Dobrowolski 1995, Growth phase dependent induces of stationary-phase promoters of *Escherichia coli* in different gram-negative bacteria, J Bacteriol 177: 5374-5378

Prouty et al., 2004, Transcriptional regulation of *Salmonella enterica* serovar Typhimurium genes by bile FEMS Immunology and Medical Microbiology 41: 177-185.

Ryan et al., 2015, global transcriptome and mutagenic analysis of the acid tolerance response of *Salmonella* enteriac serovar typhimurium Applied Environmental Microbiol, 81: 8054-8065.

Tapscott TG 2016, Contribution of Thiol-Based Sensor DksA to *Salmonella* Pathogenesis A thesis submitted to the faculty of the Graduate School of the University of Colorado in partial fulfillment of the requirements for the degree of Doctor of Philosophy Molecular Biology Program 2016.

Measurements of gene expression. Assessment of circuit function utilizes known methods. Fluorescent proteins have been used extensively (Young, Jonathan W., James C W Locke, Alphan Altinok, Nitzan Rosenfeld, Tigran Bacarian, Peter S. Swain, Eric Mjolsness, and Michael B. Elowitz. "Measuring single-cell gene expression dynamics in bacteria using fluorescence time-lapse microscopy." Nature protocols 7, no. 1 (2012): 80-88.; He, Li, Richard Binari, Jiuhong Huang, Julia Falo-Sanjuan, and Norbert Perrimon. "In vivo study of gene expression with an enhanced dual-color fluorescent transcriptional timer." Elife 8 (2019): e46181.). Where environmental conditions may limit fluorescent protein detection, such as acidic (Rekas et al., 2002. Crystal Structure of Venus, a Yellow Fluorescent Protein with Improved Maturation and Reduced Environmental Sensitivity J Biological Chem 277: 50573-50578) or hypoxic conditions (Landete et al., 2015, Use of anaerobic green fluorescent protein versus green fluorescent protein as reporter in lactic acid bacteria. Appl Microbiol Biotechnol 99: 6865-6877 (evoglo-Pp1); Seo et al., 2018, Development of an oxygen-independent flavin mononucleotide-based fluorescent reporter system in *Clostridium beijerinckii* and its potential applications, J Biotechnol 256:119-126, (CbFbFP)), appropriate reporters may be utilized.

Orthogonal gene expression. It is known that orthogonal, or non-crossover stimulation or repression, expression components may represent optimal precision of the expression system (Brophy and Voigt, 2014, Principles of Genetic Circuit Design, Nat Methods 11: 508-520). Promoter elements, including the −35 and −10 regions may be precisely controlled (Chen et al, Tuning the dynamic range of bacterial promoters regulated by ligand-inducible transcription factors, Nature Communications 9, Article number 64 (2018)). Methods to achieve orthogonality include but are not limited to optimizing sigma factors (Pinto et al., 2018, Engineering orthogonal synthetic timer circuits based on extracytoplasmic function σ factors, *Nucleic Acids Research,* 46: 7450-7464; Bervoets et al., A sigma factor toolbox for orthogonal gene expression in *Escherichia coli*, Nucleic Acids Research 46: 2133-2144 doi: 10.1093/nar/gky010), orthogonal tet repressors (Rusk et al., 2014, Orthogonal logic gates, Nature Methods, 11, 132 (2014)), alteration of the 16S ribosomes (An and Chin, 2009, Synthesis of orthogonal transcription-translation networks, Proc Natl Acad Sci USA 106: 8477-8482), control of RNA levels, transcriptional activators, enhancer binding proteins, phage RNAPs, transcriptional repressors, TALE repressors, riboswitches, UAA control of transcription, optogenetics, RNA control of transcription, pT181-based transcriptional repression, STARs, tna adaptor, dCas9 transcriptional repression, dCas9:RNAP w transcriptional activation, RNA degradation, Cys4 cleavage, self-cleaving aptazymes, RBSs (including the RBS calculator and reverse engineer function RBS calculator (salislab.net/software/Salis et al., 2009, Automated design of synthetic ribosome binding sites to control protein expression, Nature Biotechnology 27, 946-950; Salis H M 2011, The ribosome binding site calculator, Methods in Enzymology 498, 19-42, doi:10.1016/B978-0-12-385120-8.00002-4; Borujeni et al., *Nucleic Acids Research*, Volume 45, Issue 9, 19 May 2017, Pages 5437-5448, doi.org/10.1093/nar/gkx061), orthogonal ribosomes, ribosomal variants (Deadman And Passcode Microbial Kill Switches United States Patent Application 20190040398), taRNAs, sRNAs, IS10 repression, toehold switches, protein degradation, inducible ssrA-tagged degradation, *M. florum* Ion degradation, protein splicing, protein cleavage, protein scaffolds, RNA scaffolds, inducible association of proteins, recombinases, retron encoded analogue memory (Bradley et al., 2016, Tools and principles for microbial gene circuit engineering, J Molecular Biol 428: 862-888).

The technology also encompasses combinations with known agents, including imatinib and reticuloendothelial system (RES) blocker such as clodronate (dichloromethylene-bisphosphonate; Compositions and methods comprising genetically enhanced obligate and facultative anaerobic bacteria for oncopathic cancer therapy, WO 2009111177) which have the potential to improve the circulation time of the bacteria, vascular permeability inducing agents such as bradykinin, hyperthermia or carbogen which have the potential to improve the permeability of the tumor enhancing entry of the bacteria, or aldose reductase inhibitors.

Chemotherapeutic agents for use in combination with the present technology include: Alkylating agents: (Mustard gas derivatives: Mechlorethamine, Cyclophosphamide, Chlorambucil, Melphalan, and Ifosfamide; Ethylenimines: (Thiotepa and Hexamethylmelamine; Alkylsulfonates: Busulfan; Hydrazines and Triazines: Altretamine, Procarbazine, Dacarbazine and Temozolomide; Nitrosureas: Carmustine, Lomustine and Streptozocin) Nitrosureas: (note that nitrosureas are unique because, unlike most types of chemo treatments, they can cross the blood-brain barrier and can be useful in treating brain tumors); Metal salts: Carboplatin, Cisplatin, and Oxaliplatin), plant alkaloids: (Vinca alkaloids: Vincristine, Vinblastine and Vinorelbine); Taxanes: (Paclitaxel and Docetaxel and alburment bound taxol (Abraxane); Podophyllotoxins) Etoposide and Tenisopide; Camptothecan analogs: (Irinotecan and Topotecan), Antitumor antibiotics: (Anthracyclines: Doxorubicin, Daunorubicin, Epirubicin, Mitoxantrone, and Idarubicin; Chromomycins: Dactinomycin and Plicamycin); Miscellaneous: (Mitomycin and Bleomycin); Antimetabolites: (Folic acid antagonist, Methotrexate); Pyrimidine antagonist: (5-Fluorouracil, Foxuridine, Cytarabine, Capecitabine, and Gemcitabine) Purine antagonist: (6-Mercaptopurine and 6-Thioguanine); Adenosine deaminase inhibitor: (Cladribine, Fludarabine, Nelarabine and Pentostatin); Topoisomerase inhibitors: (Topoisomerase I inhibitors, Ironotecan, topotecan); Topoisomerase II inhibitors: (Amsacrine, etoposide, etoposide phosphate, teniposide); Proteosome inhibitors: (Bortezomib, carfilzomib, Ixazomib); Other agents: (Ribonucleotide reductase inhibitor, Hydroxyurea); Adrenocortical steroid inhibitor (Mitotane); Enzymes: (Asparaginase and Pegaspargase); Antimicrotubule agent: (Estramustine); Retinoids: (Bexarotene, Isotretinoin, Tretinoin, ATRA); Antibodies: (Alemtuzumab, transtuzumab, cetuximab, brentuximab vedotin, ado-transtuzumab emtasine, Denileukin difitox, blinatumomab, bevacizumab, alemtuzumab, ipilimumab, nivolumab, ofatumumab, pembrolizumab, rituximab); Kinase inhibitors: (inhibitors of ALK (Crizotinib, Ceritinib, Alectinib, Brigatinib), BCR-Abl (Crizotinib, Ceritinib, Alectinib, Brigatinib), B-Raf (Crizotinib, Ceritinib, Alectinib, Brigatinib), BTK (Ibrutinib), CDK family (Palbociclib, Sorafenib, Ribociclib), c-Met (Crizotinib, Cabozantinib), EGFR family (Gefitinib, Erlotinib, Lapatinib, Vandetanib, Afatinib, Osimertinib), JAK family (Ruxolitinib, Tofacitinib), Mek1/2 (Trametinib), PDGFR a/b (Axitinib, Gefitinib, Imatinib, Lenvatinib, Nintedanib, Pazopanib, Regorafenib, Sorafenib, Sunitinib), RET (Vandetanib), Src family (Bosutinib, Dasatinib, Ponatinib, Vandetanib), VEGFR family (Axitinib, Lenvatinib, Nintedanib, Regorafenib, Pazopanib, Sorafenib, Sunitinib)).

The technology also encompasses combinations with protease inhibitors and targeted toxins and chimeric toxins and antitumor enzymes and/or genetically engineered phage and phagemids (Bermudes U.S. Pat. No. 8,524,220, Protease Inhibitor: Protease sensitivity expression system composition and methods improving the therapeutic activity and specificity of proteins delivered by bacteria; U.S. Pat. No. 8,241,623, Protease Sensitivity Expression System; U.S. Pat. No. 8,623,350 Protease inhibitor: protease sensitivity expression system and method improving the therapeutic activity and specificity of proteins and phage and phagemids delivered by bacteria).

The technology further encompasses combinations with antivascular agents, such as platelet factor 4 and thrombospondin, alone or in combination (Bermudes et al., U.S. Pat. Nos. 6,962,696, 7,452,531 Compositions and Methods for Tumor-Targeted Delivery of Effector Molecules).

The present technology provides genetic regulatory circuits for the expression of therapeutic genes by bacteria. The present technology also provides, according to various embodiments, live attenuated therapeutic bacterial strains that have improved ability compared to a parental strain in regard to the pharmacokinetic properties of enhanced circulation in the bloodstream and entry into, persistence and growth within tumors, by resisting immune elimination or lytic destruction, increased numbers of foci within tumors, increased colonization, expansion and persistence within tumors.

Immunotherapeutic cytotoxins alone and in combination with immunotherapeutics are provided for expression using known inducible promoters or the gene circuits provided herein as well as their combination with therapeutic enhancers. Novel targeted forms of the immunotherapeutic cytotoxins are provided. Novel mechanisms of adapting the immunotherapeutic cytotoxins to the inducible promoters or the gene circuits are also provided. It is the intention of these changes that the result in an overall increase in 1) the tumor selectivity of expression, 2) the percentage of tumors targeted, 3) the number of individual locations (foci) within a tumor that are targeted, 4) the number of CFU/g that are found within the tumor, 5) the tumor to normal tissue ratio of the bacteria and/or the bacterially expressed therapeutic, 6) the length of time that they reside within the tumor and 7) enhanced immunotherapeutic effects, and, alone or collectively 8) increased antitumor activity.

Logical operations performed by bacteria are known: evolutionnews.org/2013/05/bacteria_perfor/; Li, Zhongjian, et al. "Bacteria-based AND logic gate: a decision-making and self-powered biosensor." Chemical Communications 47.11 (2011): 3060-3062; Sherlock, Madeline E., et al. “Tandem riboswitches form a natural Boolean logic gate to control purine metabolism in bacteria.” Elife 7 (2018): e33908.; Silva-Rocha, Rafael, et al. “The logicome of environmental bacteria: merging catabolic and regulatory events with Boolean formalisms.” Environmental Microbiology 13.9 (2011): 2389-2402.; Arugula, Mary Anitha, et al. “Molecular AND logic gate based on bacterial anaerobic respiration.” Chemical Communications 48.82 (2012): 10174-10176.; TerAvest, Michaela A., Zhongjian Li, and Largus T. Angenent. “Bacteria-based biocomputing with Cellular Computing Circuits to sense, decide, signal, and act.” Energy & Environmental Science 4.12 (2011): 4907-4916.; Silva-Rocha, Rafael, and Victor de Lorenzo. “Engineering multicellular logic in bacteria with metabolic wires.” ACS synthetic biology 3.4 (2014): 204-209.; Yuan, Yong, et al. “Multiple logic gates based on reversible electron transfer of self-organized bacterial biofilm.” Electrochemistry communications 18 (2012): 62-65.; Ji, Weiyue, et al. “A formalized design process for bacterial consortia that perform logic computing.” PLoS One 8.2 (2013): e57482.; Martins, Daniel P., Michael Taynnan Barros, and Sasitharan Balasubramaniam. “Quality and Capacity Analysis of Molecular Communications in Bacterial Synthetic Logic Circuits.” IEEE transactions on nanobioscience 18.4 (2019): 628-639.; Li, Xie, et al. “A single-component light sensor system allows highly tunable and direct activation of gene expression in bacterial cells.” Nucleic acids research 48.6 (2020): e33-e33.; Guiziou, Sarah, Pauline Mayonove, and Jerome Bonnet. “Hierarchical composition of reliable recombinase logic devices.” Nature communications 10.1 (2019): 1-7.; Peng, Lei, et al. “Integration of logic gates to CRISPR/Cas12a system for rapid and sensitive detection of pathogenic bacterial genes.” Analytica Chimica Acta (2020).; Wei, Zhao, et al. “Construction of Boolean logic gates based on dual-vector circuits of multiple gene regulatory elements.” Molecular Genetics and Genomics 294.2 (2019): 277-286.; Sarkar, Kathakali, Deepro Bonnerjee, and Sangram Bagh. “A single layer artificial neural network with engineered bacteria.” arXiv preprint arXiv:2001.00792 (2020).; Goni-Moreno, Angel, and Pablo I. Nikel. “High-performance biocomputing in synthetic biology-integrated transcriptional and metabolic circuits.” Frontiers in bioengineering and biotechnology 7 (2019): 40.; Yerudkar, Amol, Carmen Del Vecchio, and Luigi Glielmo. “Control of switched Boolean control networks by state feedback.” 201918th European Control Conference (ECC). IEEE, 2019.; Monteiro, Lummy Maria Oliveira, et al. “Modulating Fis and IHF binding specificity, crosstalk and regulatory logic through the engineering of complex promoters.” bioRxiv (2019): 614396.; Yu, Diane, and Ronald R. Breaker. “A bacterial riboswitch class senses xanthine and uric acid to regulate genes associated with purine oxidation.” RNA (2020): rna-075218.; Stav, Shira, et al. “Genome-wide discovery of structured noncoding RNAs in bacteria.” BMC microbiology 19.1 (2019): 1-18.; Han, Laichuang, et al. “Development of a novel strategy for robust synthetic bacterial promoters based on a stepwise evolution targeting the spacer region of the core promoter in *Bacillus subtilis*.” Microbial cell factories 18.1 (2019): 1-14.; Zamat, Ali, Linshan Zhu, and Yingxiao Wang. “Engineering Molecular Machines for the Control of Cellular Functions for Diagnostics and Therapeutics.” Advanced Functional Materials (2019): 1904345.; Banal, James L., et al. “Arbitrary Boolean logical search operations on massive molecular file systems.” bioRxiv (2020).; Banal, James L., et al. “Random access DNA memory in a scalable, archival file storage system.” bioRxiv (2020).

SUMMARY AND OBJECTS OF THE INVENTION

For reasons of clarity, the detailed description is divided into the following subsections: 1) bacterial gene expression, promoters and regulation, 2) bacterial pharmacokinetic enhancers, 3) immunotherapeutics, GMCSF, adenosine deaminase, lectins and KRAS inhibition 4) multifunctional immunotherapeutic cytotoxic proteins, 5) targeting moieties, 6) therapeutic enhancers, 7) bacterial genetic backgrounds improving immunotherapeutic effects.

Bacterial gene expression and promoters. Bacterial promoters useful in the technology include but are not limited to constitutive, exogenously inducible, quorum sensing, and tissue or environmentally inducible promoters such as hypoxic promoters, acidic promoters, tumor-selective promoters, ROS promoters, NOS promoters, normal tissue promoters, inducible promoters including but not limited to Tet, Ara, salicylate, SOS, Sox, as well as constitutive promoters, repressors, inverters, and terminators, and, if used in combination, may have the same orientation, opposite orientation, and may be proximal or distal, and may be at independent locations. The promoters are used alone or in combination to effectively result I expression of an effector gene having an anticancer effect selectively within the cancerous tissue, while limiting expression in non-cancerous or normal tissues. Expression within normal tissues includes division inhibitor gene expression of division inhibitors of *E. coli* and the *Salmonella* homologues (SulA, SfiC, MinC-MinD, DicB-MinD, bacteriophage Kil genes such as DicF, and StfZ (Joseleau-Petit et al., 1999, Metabolic alarms and cell division in *Escherichia coli*, J Bacteriol 181: 9-14; Dewachter et al., 2018, An integrative view of cell cycle control in *Escherichia coli*, FEMS Microbiol Revs 42:116-136, doi: 10.1093/femsre/fuy005; Riley 1993, Functions of the gene products of *Escherichia coli*, Microbiological Reviews 57: 862-952). Optionally, SOS response promoters may be utilized in strains in which the DNA polymerase V, an error-prone polymerase activated by the SOS response, has be partially or completely inactivated by deletion or altered gene expression (e.g., encoded by the umuC gene). While growth inhibitors are preferred in the present technology because they do not kill the cells, and thus the cells remain viable and capable of relocating to a tumor where they resume growth, inhibition within non-tumor tissue may also be achieved by expression of a lysis protein (e.g., φX174E lysis protein) or a protein lethal to bacteria (Yamaguchi et al., 2011, Toxin-antitoxin systems in bacteria and archeae, Ann Rev Genet 45: 61-79) without its corresponding antitoxin.

The promoter combinations have dual or tripartite or greater requirements for expression and may optionally be combined with reduced normal tissue expression or colonization and have the effect of increased antitumor activity and reduced toxicity to normal tissues. The promoters are useful for expression of cytotoxins, artificially split cytotoxins, immunotherapeutic cytotoxins, peptides, affibodies (protein A affinity-based ligands), armadillo repeat protein-based scaffolds, adnectins, anticalins, lipocalins, Kunitz domain-based binders, avimers, knottins, fynomers, atrimers and DARPins (designed ankyrin repeat proteins) and cytotoxic T-lymphocyte associated protein-4 (CTLA4)-based binders (Weidle et al., 2013 The emerging role of new protein scaffold-based agents for treatment of cancer. Cancer Genomics Protomics 10: 155-168), intrabodies, antibodies including camelid antibodies, F(ab')2, Fab', Fab, Fc, Fv, FcFv, VHH, VHH/VH, rIgG, single domain (sdAB), $V_{NAR}$, probodies, nanobodies, minibodies, diabodies, triabodies, tetrabodies, bispecific sc(Fv)2, and bPD-L1 and metabolic genes.

In some embodiments, the first promoter nucleotide sequence, the second promoter nucleotide sequence, or the first promoter nucleotide sequence and the second promoter nucleotide sequence can comprise (i) a nucleotide sequence of US2011/0195847, including but not limited to tumor-selective and spleen-selective, a nucleotide sequence of Weiss et al., US patent application 2012/0244621, Leschner et al., Identification of tumor-specific *Salmonella* typhimurium promoters and their regulatory logic, Nucleic Acids Research 40: 2984-2994; Weiss et al., US Patent Application US 201244621A1, Tumor-specific bacterial promoter elements, identified SEQ ID NO: 011 YHNYDTKTTWTTWANASRWAM, wherein non-standard nucleotides are represented as follows: R is G or A, Y is T or C, M is A or C, K is G or T, W is A or T, S is G or C, B is T or G or C, V is A or G or C, H is A or T or C, D is A or T or G, and N is A or T or G or C, and to the reverse complementary of this sequence. They also identified

```
                                 SEQ ID NO: 012
CAGTATTTTATTTAAAGGTAA;

                                 SEQ ID NO: 013
CCATATTTTATTTAGAGGTAA;

                                 SEQ ID NO: 014
TTTTGTTTAAAAAAAAATACAG;

                                 SEQ ID NO: 015
TTACCTCTAAATAAAATATGG;

                                 SEQ ID NO: 016
CACTGTGATTTTTTGAGGTAA;

                                 SEQ ID NO: 017
TTACGTGTAAAAAAACAAATG;

                                 SEQ ID NO: 018
TTACTTTTAAAAAACCAACCTG;

                                 SEQ ID NO: 019
TCTCATTTTTTCTCAACGTGA;

                                 SEQ ID NO: 020
GCACGTTTTAATAAATTGGG;

                                 SEQ ID NO: 021
CAGCATTTTGTGTATAAATTA;

                                 SEQ ID NO: 022
TAATCTTTATATGAAATAAGA;

                                 SEQ ID NO: 023
TTGTATGTTATTTGTACAAAC;

                                 SEQ ID NO: 024
GTATCTTTTTATAAAACACAA.
```

Flentie et al., 2012, A bioluminescent transposon reporter-trap identified tumor-specific microenvironment-induced promoters in *Salmonella* for conditional bacterial-based tumor therapy, Cancer Discov 2: 624-637, doi:10.1158/2159-8290.CD-11-0201) identified the promoters of STM1787, STM1791 and STM1793 as tumor selective.

Dyneko et al., 2016, (Composing a tumor specific bacterial promoter, 11(5): e0155338) identified FNR" SEQ ID NO: 025 CGTTGATCAATGATCAA with −35''' and −10''' SEQ ID NO: 026 TTTTAAGA . . . TTGATTTAATT as resulting in a functional tumor-selective promoter. doi: 10.1371/journal.pone.0155338. Deyneko et al., 2016 identified expression of ydiH, lpT csG mltD mdh mtfA frdA pfkA pflE nirB ptsG glpA ydiH as being tumor specific. They disclose the following tumor selective promoter elements:

```
                                                 SEQ ID NO: 025
CGTTGATCAATGATCAA with -35''' and -10'''

                                                 SEQ ID NO: 026
TTTTAAGA...TTGATTTAAATT

                                                 SEQ ID NO: 027
taacgcctCTTTGTCAGAacctctccattcGTTGACGCACATCAAgaTAG

CTTtcattcgaaagtaaTTTAATCTTTATATGAAATAAGAGaggccgttt

mutation of NagC:
                                                 SEQ ID NO: 028
taacgcctCTTTGTCAGAacctctccattcGTTGACGCACATCAAgaTAG

CTTtcattcgaaagtaaTTTAATCTTTATATGAAATGCGAGaggccgttt

deletion in TGIF:
                                                 SEQ ID NO: 029
taacgcctCTTTTCAGAacctctccattcGTTGACGCACATCAAgaTAGC

TTtcattcgaaagtaaTTTAATCTTTATATGAAATAAGAGaggccgttt

mutation of insignificant nucleotides in FNR and
NagC:
                                                 SEQ ID NO: 030
taacgcctCTTTGTCAGAacctctccattcGTTGATCATGATCAAgaTAG

CTTtcattcgaaagtaaTTTAATCTTTTATGATACATAAGAGaggccgtt

t

mutation of regions between motifs:
                                                 SEQ ID NO: 031
taagtcacCTTTGTCAGAacaacgctactcGTTGACGCACATCAAgaTAG

CTTtcactagtaagtaaTTTAATCTTTATATGAAATAAGAGaggccgttt

                                                 SEQ ID NO: 032
agaccaatggacatccacggcgattattaCGTTGATCATGATCAAgcagT

TTTAAGActataccaacTTGATTTAATTcttgtAATAAACgaatgcc
```

A functional promoter nucleotide sequence at least 50%, preferably at least 60%, more preferably at least 70%, even more preferably at least 80%, still even more preferably at least 90%, most preferably at least 95%, such as 96%, 97%, 98% or 99%, even most preferably 100% identical to the identical to a nucleotide sequence, or (iii) or a functional promoter subsequence of (i) or (ii). In certain embodiments, the functional promoter subsequence is about 20 to about 500 nucleotides in length. In some embodiments, expression systems described herein may be contained in recombinant host cells, and in certain embodiments, the recombinant host cells can be an attenuated *Salmonella.*

In certain embodiments, the promoters can be *Salmonella* promoters and the recombinant host cells can be *Salmonella*. In some embodiments, the candidate promoters are from other bacteria, especially *E coli*, are at least 50%, preferably at least 60%, more preferably at least 70%, even more preferably at least 80%, still even more preferably at least 90%, most preferably at least 95%, such as 96%, 97%, 98% or 99%, even most preferably 100% identical to promoters from bacteria. In certain embodiments, the bacteria can be Enterobacteriaceae, and in some embodiments the Enterobacteriaceae can be *Salmonella*. Also provided, in some embodiments, is an expression system which comprises a nucleotide sequence encoding a toxic or therapeutic protein or a protein that participates in generating a desired toxin or therapeutic agent operably linked to a promoter identified as described herein. In certain embodiments, recombinant host cells may comprise an expression system described herein.

Also provided, in some embodiments, is an expression system which may comprise a first promoter nucleotide sequence operably linked to a first coding sequence and second promoter nucleotide sequence operably linked to a second coding sequence, where: the first coding sequence and the second coding sequence encode polypeptides that individually do not inhibit tumor growth; polypeptides encoded by the first coding sequence and the second coding sequence, in combination, inhibit tumor growth; and the first promoter nucleotide sequence and the second promoter nucleotide sequence can be preferentially activated in solid tumors of living organisms. In certain embodiments, one or more of the promoter nucleotide sequences can be preferentially activated in solid tumors (e.g., one promoter is constitutive, or exogenously inducible, and one promoter is preferentially activated in solid tumors). In some embodiments, the first promoter nucleotide sequence and the second promoter nucleotide sequence can be in the same nucleic acid molecule. In certain embodiments, the first promoter nucleotide sequence and the second promoter nucleotide sequence may be in different nucleic acid molecules. In some embodiments, the first promoter nucleotide sequence and the second promoter nucleotide sequence can be bacterial nucleotide sequences. In certain embodiments, the bacterial sequences may be Enterobacteriaceae sequences, and in some embodiments the Enterobacteriaceae sequences can be *Salmonella* sequences. In certain embodiments, the different nucleic acid molecules can be disposed in the same recombinant host cell, and in some embodiments, the different nucleic acid molecules can be disposed in different recombinant host cells of the same species. In some embodiments, the different recombinant host cells can be different bacterial species.

The technology may be used to control bacteria to sequence a therapy, provide alternate therapies, select a site of action, select patents for therapy, etc. For example, the bacteria may be therapeutically controlled by local endogenous conditions within the patient, as well as exogenous conditions and agents. Because these endogenous and exogenous factors may change over time, the control may be dynamic and/or oscillatory. In addition, the vector may comprise multiple interacting bacteria, which each influence others, to provide interactive activity.

An expression system may comprise a first promoter nucleotide sequence operably linked to a first coding sequence and second promoter nucleotide sequence operably linked to a second coding sequence, where: the first coding sequence and the second coding sequence encode polypeptides where one coding sequence does not inhibit tumor growth, but where it limits the growth of the bacteria in normal tissues, and the second polypeptide or peptides encoded by the second coding sequence inhibit tumor growth; and the first promoter nucleotide sequence is preferentially activated in normal tissue and the second promoter nucleotide sequence can be preferentially activated in solid tumors of living organisms. In certain embodiments, one or more of the promoter nucleotide sequences can be preferentially activated in solid tumors (e.g., one promoter is constitutive, or exogenously inducible, and one promoter is preferentially activated in solid tumors). In some embodiments, the first promoter nucleotide sequence and the second promoter nucleotide sequence can be bacterial nucleotide sequences. In certain embodiments, the bacterial sequences may be Enterobacteriaceae sequences or non-Enterobacteriaceae, or mammalian, and in some embodiments the Enterobacteriaceae sequences can be *Salmonella* sequences. In certain embodiments, the different nucleic acid molecules can be disposed in the same recombinant host cell, and in some embodiments, the different nucleic acid molecules can be disposed in different recombinant host cells of the same species. In some embodiments, the different recombinant host cells can be different bacterial species.

The nucleic acid sequences can be used to generate genetic circuits, including but not limited to various AND, NOR, OR, NOT, NOT AND, XOR and/or NAND gates (e.g., FIGS. 1A-13B). These gates, of their functional equivalents, may be used to implement flip-flops (D, R/S, etc.) and memory storage units, and hysteresis. The technology may provide amplification of signals, in some cases with linear proportional changes between input and output, and threshold/comparator units. The implemented logic may also include timers and counters, oscillators, and the like. Therefore, complex logical aggregations such as phase-locked loops are possible. In some cases, the logic is contained in a single cell, i.e., the state of one cell does not directly control the state of an adjacent cell, while in other cases, there is a consensus mechanism to provide a consistent state for an entire colony of like cells. Where heterogeneous populations of cells are provided, advantageously they may interact to provide logical chains. The regulatory pathways may be chained together to form complex logic. Thus, when bioorthogonal regulators and gene products are employed, their generation, sending, and the pathways they control may be reasonable independent of the biology of the organism, except as may be a desired end effect. The product of one logical mechanism may be the regulator/input of the subsequent mechanism. XOR may be obtained by $A\cdot\overline{B}+\overline{A}\cdot B$ or $(A+B)\cdot(\overline{A}+\overline{B})$.

The present technology provides modified and alternative quorum sensing genetic regulatory circuits for the expression of therapeutic genes by bacteria, including tumor-specific density dependence and normal tissue density independence. The technology does so by replacing the quorum producing gene that is normally a low-level constitutive promoter with a low-level tumor-selective promoter, and the tumor selective promoter has been further modified to have an operator sequence that is repressed by a normal tissue inverter.

The mechanisms may provide feedback, e.g., an amplified proportional response output, or an oscillatory output. Further, some mechanisms may be state dependent, and as a result, provide memory and memory readout A simple example is a divide by two flip-flop. Therefore, relatively complex logic, with multiple inputs, multiple outputs, and complex logic transformations, may be implemented.

Typically, the goal is not simply performance of computation, and therefore the organism also include an effector output that delivers a desired effect in selective dependent on a logical state or series of states.

Improved Pharmacokinetics and Tumor Colonization: The present technology provides compositions and methods to enhance bacterial half-life in the bloodstream, passage out of the vasculature into the target tissue, targeting of tumors and lymphomas, colonization of tumors and lymphomas, expansion within tumor or lymphoma and persistence within tumor and lymphomas, each of which, alone or in combination or subcombination, result in an overall increase in 1) the percentage of tumors and lymphomas targeted, 2) the number of individual locations (foci) within a tumor or lymphoma that are established, 3) the number of colony forming units (CFU/g) that are found within the tumor or lymphoma, 4) the length of time that they reside within the tumor or lymphoma and 5) reduced immune clearance from the tumor or lymphoma, and, alone or collectively, and/or 6) increased anticancer activity.

The present technology embodies previously described compositions and methods (Bermudes, U.S. Ser. No. 10/286,051, Modified bacteria having improved pharmacokinetics and tumor colonization enhancing antitumor activity). The compositions or genetically engineered bacteria may optionally comprise at least one of the following that has the effect of reduced binding of antibodies, and/or other components of the immune system including innate immunity (mannose binding proteins, CRPs, ficolins, colectins, complement, scavenger receptor; Howard et al., 2018, Semin Immunopathol 40: 75-85; doi: 10.1007/s00281-017-0642-0).

Bacteria that produce polysilicate coats. Bacteria may produce polysilicate coats based on expression of silicatein from diatoms and/or sponges including the *Pseudomonas* ice nucleation protein (INP) fusion with the truncated form (known as BBa_K265009) (Pozzolini et al., 2004, Molecular cloning of silicatein gene from marine sponge *Petrosia ficiformis* (Porifera, Demospongiae) and development of primmorphs as a model for biosilicification studies, Mar Biotechnol (NY). 2004 6:594-603; Muller et al., 2008, Bioencapsulation of living bacteria (*Escherichia coli*) with poly(silicate) after transformation with silicatein-alpha gene, Biomaterials 29: 771-779; Schroder et al., Silicatein: acquisition of structure-guiding and structure-forming properties during maturation from the pro-silicatein to the silicatein form, Journal of Biological Chemistry doi: 10.1074/jbc.M112.351486; van Bloois et al., 2011, Decorating microbes: surface display of proteins on *Escherichia coli*. Trends in Biotechnology 29:79-86.; Brutchey and Morse 2008, Silicatein and the translation of its molecular mechanism of biosilicification into low temperature nanomaterial synthesis. American Chemical Society. 108 (11): 4915-4934; Iler 1979, The Chemistry of Silica: Solubility, Polymerization, Colloid and Surface Properties, and Biochemistry. New York: Wiley, 1979; Rai and Perry, 2009, Facile fabrication of uniform silica films with tunable physical properties using silicatein protein from sponges. Languir 26(6): 4152-4159).

PEGylated Bacteria. In another embodiment, the bacteria may optionally be coated with polyethylene glycol (PEG), i.e., PEGylation. Previously, several authors have taught away from pegylating bacteria. Greco et al., 2010 (PEGylation prevents bacteria-induced platelet activation and biofilm formation in platelet concentrates, Vox Sanguinus 100, issue 3 doi.org/10.1111/j.1423-0410.2010.01419.x) taught that PEGylation of platelets prevented activation by bacteria. Kingshot et al. 2003 (Covalent attachment of poly (ethylene glycol) to surfaces critical for reducing bacterial adhesion, Langmuir 19, 17, 6912-6921) and Nie et al., 2017 (A comparative analysis of antibacterial properties and inflammatory responses for the KR-12 peptide on titanium and PEGylated titanium surfaces, RSC Advances 7:34321-34330) taught that pegylation interferes with the activities of bacteria.

PEGylation may be accomplished by any known means (e.g., amine-reactive PEGs, C-terminal-reactive PEGs, Thiol-reactive PEGs, homobifunctional crosslinkers, heterobifunctional crosslinkers, multi-arm PEGs, membrane-inserting FSL-PEGs, monomethoxypoly(ethylene) glycols activated by cyanuric chloride, succinimidyl succinate, and tresyl chloride; Suk et al., 2017, PEGylation as a strategy for improving nanoparticle-based drug and gene delivery, Adv Drug Deliv Rev 99(Pt A): 28-51; Tesfay et al., 2013, PEGylation of vesicular stomatis virus extends virus persistence in blood circulation of passively immunized mice, J Virol 87: 3752-3759; Wonganan and Croyle, 2010, PEGylated Adenoviruses: From Mice to Monkeys, Viruses 2: 468-502); Wortmann et al., 2008, Fully detargeted polyethylene glycol-coated adenovirus vectors are potent genetic vaccines and escape from preexisting anti-adenovirus antibodies, Mol Ther 16: 154-162; Kim et al., 2008, PEGylation of bacteriophages increases blood circulation time and reduces T-helper type 1 immune response. Microbial Biotechnology 1: 247-257; Kreppel and Kochanek 2007, Modification of adenovirus gene transfer vectors with synthetic polymers: A scientific review and technical guide, Molecular Therapy 16:16-29). A technical guide is provided by Lee et al., 2007 (Investigations of PEGylated recombinant adenovirus, using fluorescein-labeled polyethylene glycol. Hum Gene Ther 18: 286-300).

HPMAylated Bacteria. In another embodiment, the bacteria may optionally be coated with poly-N-(2-hydroxypropyl) methacrylamide (poly-HPMA). Attachment is achieved by using amino-reactive N-(2-hydroxypropyl) methacrylamide copolymer, which couples the polymer to the amino groups of the bacterial cell wall exposed to the aqueous milieu. The hydrophilic HPMA polymer is chemically activated by the incorporation of amino-reactive 4-nitrophenoxy groups on diglycyl side chains under generation of a 21 kd random copolymer (Rihova and Kubackova 2003, Clinical implications of N-(2-hydroxypropyl) methacrylamide copolymers, Curr Pharm Biotechnol 4: 311-322; Vasey et al., 1999, Phase I clinical and pharmacokinetic study of PK1 [N-(2-hydroxypropyl) methacrylamide copolymer doxorubicin]: first member of a new class of chemotherapeutic agents-drug-polymer conjugates. Cancer Research Campaign Phase I/II Committee Clin Cancer Res, 5: 83-94). This results in up to 10 reactive 4-nitrophenyl groups per 100 monomers and can therefore attach to the bacteria at multiple amines, closely attaching the polymer. The result is greater than 10%, more preferably up to 30%, more preferably up to 50%, more preferably up to 70% of the amino groups may be reacted with (Fisher et al., 2001, Polymer-coated adenovirus permits efficient retargeting and evades neutralizing antibodies. Gene Ther 8: 341-348).

Combinations of bacterial coatings. In another embodiment, the bacteria are optionally genetically modified to express sialic acid (Bermudes U.S. Pat. No. 9,616,114B1), in combination with genetic modification of producing silica. Alternatively, the bacteria are optionally genetically modified to express sialic acid, in combination with genetic modification with PEG and/or HPMA.

In another embodiment, the bacteria are coated with poly(allylamine hydrochloride) (PAH) (Lee et al., 2013, A polymer coating applied to *Salmonella* prevents the binding of *Salmonella*-specific antibodies, Int J Cancer. 2013 Feb. 1; 132(3):717-25. doi: 10.1002/ijc.27700) alone or in combination with PEG and/or poly-HPMA. Polymer coated bacteria, such as coating with polyallylamine hydrochloride or conjugated polyelectrolyte (CP) and polymyxin B (PLB) and combinations (Zhu et al., 2013, Conjugated polymer-coated bacteria for multimodal intracellular and extracellular anticancer activity, Advanced Materials 25:1203-1208; DOI: 10.1002/adma.201204550) are also encompassed. The PHA may be between 5000 and 50,000 MW, more preferably 15000 MW.

Cytotoxins, peptides, antibodies and enzymes resulting in immunogenic cell death, loss if immune evasion, and inhibition of K-RAS.

Checkpoint Inhibitors. The immunotherapeutics of the present technology include checkpoint inhibitors, including antibodies and peptides and antibody-like peptides (U.S. Pat. No. 7,018,801B2) that bind to and result in antagonism to co-inhibitory molecules PD-1 (CD279), PD-L1 (B7-H1; CD274), PDL2 (B7-DC; CD273), CD80 (B7-1), CD86 (B7-2), B7-H3 (CD276)/B7H4 (VTCN1); CLTA4 (CD152), LAG-3, $KIR_L$, CD200, CD200R, CD112 (PVRL2; Nection-2), butyrophilin family members (e.g., Btn12, Skint1, MOG, CD277), HVEM (TNFSRSF14; CD270)VISTA (B7H5; PD-IH; Gi24), CD155 (PVR; Necl-5), CD112 (PVRL2; Nection-2), LAG3 (CD223), TIGIT, TIM-3 (HAVcr-2), A2aR BTLA, CD 96, CD112R, CD160, CD200R, VISTA B7/H3, and the macrophage antiphagocytosis molecules CD47 and SIRPa. Also encompassed are antibodies and peptides that bind to and agonize co-stimulatory, CD27 (TNFRSF7), CD28, CD40, CD40L (TNSFSF; CD154), OX40 (TNFRSF4; CD134), GITR (TNFRSF18; CD357), CD226 (DNAM-1), 2B4 (CD244), (TNFRSF7), ICOS (CD278), CD28H, CD137 (TNFRSF-9; 41BB), TCR, TMIGD2 (IGPR-1), KIRs, CD48 (BCM-1; BLAST-1), CD155 (PVR; Necl-5), GITRL (TNFSF18), CD70 (TNFSF7; CD27L), OX40L (TNFSF4; CD252), CD137L (TNFSF9; 4-1BBL), MHC Class I or II, B7-H7 (HHLA2), ICOSL (B7-H2; B7RP1), CD80 (B7-1), CD86 (B7-2). as well as general stimulators of the immune system, engineered for expression by tumor-targeted bacteria. Immunotherapeutics may be done alone, or in combination or in sequence (e.g., anti-OX40 followed by anti-PD-1, Messenheimer et al., 2017 Timing of PD-1 blockade is critical to effective combination immunotherapy with Anti-Ox40, doi: 10.1158/1078-0432.CCR-16-2677). The peptides may be expressed as overlapping peptide panels (i.e., pepmixes) that stimulate immunity. Other stimulators of the immune system include c-di-GMP (cyclic di-GMP), and desaminotyrosine (also known as phloreate or phloretic acid, Hydro-p-coumaric acid, 3-(4-Hydroxyphenyl)propanoic acid or 3-(4-Hydroxyphenyl)propanoic acid), alone or in combination.

Mistletoe Lectin. Expression of the mistletoe lectin may stimulate mitogenicity, e.g., *Phaseolus vulgaris* photohemagglutinin (PHA; LPHA; PHA-L, including the isoforms such as PHA-L4) Hoffman and Donalsdon, 1987 (Synthesis of mitogenic phytohemagglutinin-L in *Escherichia coli*, Bio/Technology 5:157-160). Stimulation of mitogenicity also encompasses expression of concanavalin A Min et al, 1992 (non-glycosylated recombinant pro-concanavalin A is active without peptide cleavage, EMBO Journal 11: 1303-1307). The mistletoe lectin may comprise the A and B chains as independent genes, or the A and B chains as a single fused gene (Eck et al., 1999, Cloning of the mistletoe lectin gene and characterization of the recombinant A-chain, Eur. J. Biochem 264: 775-784; Eck et al., 1999; Hajto et al., 1998, Effect of a recombinant lectin, *Viscum album* agglutinin on the secretion of interleukin-12 in cultured human peripheral blood mononuclear cells and on NK-cell-mediated cytotoxicity of rat splenocytes in vitro and in vivo," Natural Immunity, 16: 34-46, 1998; Lee et al., 2009, Immunomodulating effects of Korean mistletoe lectin in vitro and in vivo," International Immunopharmacology 9:1555-1561). In a preferred embodiment, the mistletoe lectin lacks ribonuclease activity, including active site inactivation in the A chain, or by solely expressing the B chain (Eck et al., 1999, Characterization of recombinant and plant-derived mistletoe lectin and their B-chains, Eur. J. Biochem 265: 788-797). In another preferred embodiment, the mistletoe lectin may be expressed as a fusion with *Shigella* toxin or shiga-like toxin, which thereby enhances secretion. In another embodiment, the mistletoe lectin is released by induced bacterial periplasmic release with a colicin lysis protein, or by whole bacterial lysis through lysis gene expression.

GMSCF. Also included in the technology is expression, secretion, display and/or release of granulocyte macrophage colony stimulating factor (GMCSF) with signal sequence, SEQ ID NO: 033

MWLQSLLLLGTVACSISAPARSPSPSTQPWEHVNAIQEARRLLNLSRDTAAEMNETVEVISEMFDQEPTCL QTRLELYKQGLRGSLTKLKGPLTMMASHYKQHCPPTPETSCATQIITFESFKENLKDFLLVIPFDCWEPVQE and/or the mature form without signal sequence, SEQ ID NO: 034

APARSPSPST QPWEHVNAIQ EARRLLNLSR DTAAEMNETV EVISEMFDLQEPTCLQTRLELYKQGLRGSL TKLKGPLTMM ASHYKQHCPP TPETSCATQIITFESFKENL KDFLLVIPFD CWEPVQE

Expression methods include known bacteria expression systems (e.g., Greenberg et al., 1988, Expression of biologically active, mature human GMCSF with an *E. coli* secretory expression system, Current Microbiol 17: 321-332; Babu et al., 2009, Single step intein-mediated purification of hGMCSF expressed in salt-inducible *E. coli*, Biotechnol Lett 31: 659-664; Oloomi et al., 1998, PCR-mediated expression of the human GM-CSF gene in *Escherichia coli*, Iranian Biomedical Journal 2: 21-25; Gronski et al., 1988, *E. coli* derived human granulocyte-macrophage colony-stimulating factor (rh GM-CSF) available for clinical trials, Behring Inst Mitt 83: 246-249; Armitage 1998, Emerging applications of recombinant human granulocyte-macrophage colony-stimulating factor, Blood 92: 4491-4508; Malekian et al., 2019, Improvement of soluble expression of GM-CSF in the cytoplasm of *Escherichia coli* using chemical and molecular chaperones, Protein Expression and Purification 160: 66-72; Malikian et al., 2017, High-yield production of granulocyte-macrophage colony-stimulating factor in *E. coli* BL21 (DE2) by an auto-induction strategy, IJPR (2019), 18 (1): 469-478), as well as novel fusions to *Pseudomonas* INP or *E. coli* YebF, with or without an leucine lysine (LK) cleavage signal, an enterokinase signal SEQ ID NO: 165 DDDDK followed by a leucine lysine cleavage signal, or an enterokinase signal followed by glycine and threonine plus a leucine lysine cleavage signal (SEQ ID NO: 035 DDDDKGTLK).

Over expression of adenosine deaminase. The object of over expressing adenosine deaminase is to deplete adenosine by its destruction, inactivation, or conversion to inosine. Over expression may be accomplished by the regulatory elements described herein, with or without bacterial lysis or release factors. The adenosine deaminase may be a cytoplasmic adenosine deaminase, a genetically engineered secreted adenosine deaminase, a surface displayed, or a secreted bacterial adenosine deaminase such as those from *Chryseobacterium* spp, *Niastella* spp, *Flexithrix* spp., *Hymenobacter*, spp. *Catalinimonas* spp., *Hymenobacer* spp., and *Elizabethkingia* spp. (Skaldin et al., 2018; Secreted bacterial adenosine deaminase is an evolutionary precursor of adenosine deaminase growth factor, Molecular Biology and Evolution 35: 2851-2861; Riedmaier et al., 2010, Crystal structure of a *Legionella pneumophila* ecto-triphosphate diphosphohydrolase, a structural and functional homolog of the eukaryotic NTPDases Structure 18: 228-238; Fan et al., 2012; Ecto-5'-nucleotidase: a candidate virulence factor in *Streptococcus sanguinis* experimental endocarditis, PLoS One 7(6):e38059; Firon et al., 2014, Extracellular nucleotide catabolism by the Group B *Streptococcus* ectonucleotidase NudP increases bacterial survival in blood J Biol Chem. 289 (9): 5479-5489; Zheng et al., 2015. Streptococcal 5'-nucleotidase A (S5nA), a novel *Streptococcus pyogenes* virulence factor that facilitates immune evasion, J Biol Chem 290 (52): 31126-31137). The adenosine deaminases may also be those described by Thanos US Patent Application 20180216095.

K-Ras inhibitory peptide. In another embodiment, the bacteria may express, secrete, display and/or release a K-Ras inhibitory peptide. Expression may be coupled to any of the expression systems described herein, and may be expressed as a YebF fusion, a YebF(LK) fusion, a YebF enterokinase SEQ ID NO: 154 DDDDK followed by an LK fusion, an ice nucleation (inaZ Part:BBa_K584021 or Bba_K811003) fusion, an ice nucleation (LK) fusion, an ice nucleation enterokinase SEQ ID NO: 165 DDDDK followed by an LK fusion, or an enterokinase signal followed by glycine and threonine plus a leucine lysine cleavage signal, a N-terminal signal sequence fusion (e.g., OmpA), a C-terminal secretion system (e.g., that of *E. coli* hemolysin), or may be released by coexpression with a lysis gene and/or a colicin lysis gene. Ras inhibitory peptides include those of Sakamoto et al., 2017 (K-Ras(G12D)-selective inhibitory peptides generated by random peptide T7 phage display technology, Biochem Biophys Res com 484: 605-611).

Phloretin hydrolase. In another embodiment, the bacteria may express, secrete, display and/or release phloretin hydrolase. Phloretin hydrolase (EC 3.7.1.4) is an enzyme that catalyzes the chemical reaction phloretin+$H_2O$ to phloretate+phloroglucinol. The phloretin hydrolases are known phloretin hydrolases (phy gene), especially those that function in tumor-targeted bacteria, including but not limited to *Salmonella, E. coli, Bifidobacteria* spp., *Clostridium* spp. and *Listeria* spp. (e.g., Schoefer et al., 2004, Cloning and expression of a phloretin hydrolase gene from *Eubacterium ramulus* and characterization of the recombinant enzyme. Appl Environ Microbiol. 70(10):6131-7. The deduced amino acid sequence of phy showed similarities to a putative protein of the 2,4-diacetylphloroglucinol biosynthetic operon from *Pseudomonas fluorescens*, which is also encompassed by the present technology. Also included are homologues in *Clostridium orbiscindens*, and other *Clostridium* spp.

Expression of the phy gene is further accompanied by expression of the pathway(s) for the phloretin biosynthesis. Watts et al. (2004. Exploring recombinant flavonoid biosynthesis in metabolically engineered *Escherichia coli*. ChemBioChem 5, 500-507) showed that phloretin, the substrate for phy, was generated in double transgenic *E. coli* over expressing hydroxycinnamate:CoA ligase and a chalcone synthese from p-dihydrocoumaric acid. Single transgenic *E. coli* expressing a hydroxycinnamate:CoA ligase or chalcone synthase revealed the presence of an endogenous dehydrogenase. Jiang et al., 2005 (Metabolic engineering of the phenylpropanoid pathway in *Saccharomyces cerevisiae*. Appl. Environ. Microbiol. 71, 2962-2969) showed that overexpressing a phenylalanine ammonia lyase, a hydroxycinnamate:CoA ligase and a chalcone synthase resulted in the phy substrate phloretin from either phenylalanine or tyrosine, amino acids available within tumors. It is known that the pathway uses endogenous 4-coumaroyl-CoA biosynthesis, followed by EC 1.3.1.117 hydroxycinnamoyl-CoA reductase, and EC 3.7.1.4 phloretin hydrolase which generates phlorate and naringenin. Alternatively, the production of phloretate can begin with phlorizin, followed by EC 3.2.1.62 glycosylceramidase to make the phloretin substrate for the EC 3.7.1.4 phloretin hydrolase. The enzymes necessary for phloridzin biosynthesis in apples have been described by Gosch et al., 2010 (Phloridzin: Biosynthesis, distribution and physiological relevance in plants, Phytochemistry, 71: 8383-843), which include NADPH-dependent dehydrogenase, chalcone synthase and UDP-glucose: phloretin 2'-O-glycosyltransferase. The generation of cinnomoyl-CoA and naringenin has also been described by Hwang et al., 2003, Production of plant-specific favones by *Escherichia coli* containing an artificial gene cluster, Appl Environ Microbiol DOI: 10.1128/AEM.69.5.2699-2706.2003).

Multifunctional immunotherapeutic cytotoxins. The object of the multifunctional immunotherapeutic cytotoxins is to coordinately kill tumor cells and recruit the immune system to further eliminate cancerous cells, including causing immunogenic cell death. The immunotherapeutic cytotoxins of the technology may have inherent immune stimulation, including but not limited to stimulation of interferon and/or stimulation of T-cell proliferation, and are further activated by coexpression or co-administration of the above immune stimulators, c-di-GMP and/or desaminotyrosine or adenosine deaminase. The immunotherapeutic cytotoxins may be further activated by creating a chimeric protein that optionally has a protease cleavage site and releases an antigen or peptide that results in immune stimulation leading to anti-cancer effects.

Toxins. A non-limiting list of toxins particularly useful in this embodiment of the present technology, and may also be incorporated into other embodiments of the technology include cytolethal distending toxins (CDTs), typhoid toxins, typhoid toxin:pertussis toxin S3 hybrids, *E coli* cytotoxic necrotizing factors CNF1, CNF2, CNF3, *Yersinia* CNF, YCNF ($CNF_Y$), *Bordetella* dermonecrotic factor (DNF), Phenol soluble modulins of *Staphylococcus*, streptococal super antigens (Proft and Fraser 2016, Streptococcal superantigens: Biological properties and potential role in disease, In: Ferretti et al (editors) *Streptococcus pyogenes*: Basic Biology to Clinical Manifestations [Internet]. Oklahoma City (OK): University of Oklahoma Health Sciences Center; 2016-. 2016 Feb. 10; e.g., SPE-A, SPE-B, SPE-C, SPE-D, SPE-E, SPE-G, SPE-H, SPE-I, SPE-J, SPE-K, SPE-L, SPE-M, SSA, SMEZ1, SMEZ2), Alouf and Popoff (eds), 2015, Comprehensive Sourcebook of Bacterial Protein Toxins, Fourth Edition, Academic Press, Chapter 32, Bacterial superantigens and superantigen-like toxins (SPE-A, SPE-B, SPE-C, SPE-D, SPE-E, SPE-G, SPE-H, SPE-I, SPE-J, SPE-K, SPE-L, SPE-M, SPE-N, SPE-O, SPE-P, SPE-Q, SER, SESkSET SEIU, SEIU2, SEIV SEIX, TSST-1); staphylococcal super antigens (Xu and McCormick 2012, Staphylococcal superantigens in colonization and disease, Fron. Cell Infect Microbiol 2012; 2: 52. doi: 10.3389/fcimb.2012.00052), cytolethal distending toxin family members, CLDT-anthrax LF fusion (Bachran et al., 2014, Cytolethal distending toxin B as a cell-killing component of tumor-targeted anthrax fusion proteins, Cell Death and Disease 5, e1003 (2014), *Pseudomonas* ToxA and ToxA derivatives (Quintero et al., 2016, EGFR-targeted chimeras of *Pseudomonas* ToxA released into the extracellular milieu by attenuated *Salmonella* selectively kill tumor cells. Biotechnol Bioeng 113: 2698-2711. doi: 10.1002/bit.26026), cholera toxin, diphtheria toxin, pertussis toxin, pertussis adenylate cyclase toxin, pertussis filamentous hemagglutinin, *Agregatebacter* Ltx, *Agregatebacter* Ltx: *E. coli* HlyA C-terminus hybrids, ArtAB toxin, subtilase, shiga and shiga-like toxins together with the Q gene, anthrax toxin, including anthrax lethal factor, botulinum toxin, tetanus toxin, *Pasteurella* multocita toxin (PMT), parasporins including PS1, PS2, PS3 and PS4 family members (Ohba et al., 2009, Parasporin, a new anticancer protein group from *Bacillus thuringiensis*, Anticancer Research 29: 427-434), leukocydin family members, e.g., LukAB.

Cytoxins such as CNF1, PMT, cldtB, OTG-PE38K (derived from ToxA) are further modified by creating gene fusions with immune peptides such as YSL (Yao et al., 2005, Tripeptide tyroserleutide enhances the antitumor effects of macrophages and stimulates macrophage secretion of IL-1beta, TNF-alpha, and NO in vitro. Cancer Immunol Immunohter 55: 56-60), survivin, Bcl-2, Mcl-1 (Garg et al., 2016, Survivin: a unique target for tumor therapy, Cancer Cell Int 2016; 16: 49; Onodi et al., 2018, High therapeutic efficacy of a new survivin LSP-cancer vaccine containing CD4+ and CD8+ T-cell epitopes, Frontiers in oncology 2018 doi: 10.3389/fonc.2018.00517' Ciesielski et al., 2008, Therapeutic effect of a T-helper cell supported CTL response induced by a survivin peptide vaccine against murine cerebral glioma, Cancer Immunol Immunother 57:1827-1835; Mohammad et al., 2015, Broad targeting of resistance to apoptosis in cancer, Seminars in Cancer Biology 35: S78-S103). The survivin peptides are known immunogenic peptides, including but not limited to SEQ ID NO: 036 $SVN_{9-16}$ AWQPFLKD, SEQ ID NO: 037 $SVN_{18-52}$ RISTFKNW, SEQ ID NO: 038 $SVN_{39-46}$ AEAGFIHC, SEQ ID NO: 039 $SVN_{53-67}$ DLAQCFFCFKELEGW, SEQ ID NO: 040 $SVN_{56-64}$ AQCFFCFKEL, SEQ ID NO: 041 $SVN_{56-64}$ QCFFCFKEL, SEQ ID NO: 042 $SVN_{57-64}$ CFFCFKEL, SEQ ID NO: 043 $SVN_{82-89}$ SGCAFLSV, SEQ ID NO: 044 $SVN_{97-104}$ TLGEFLKL (Ciesielski et al., Cancer Immunol Immunother. 2008 December; 57(12): 1827-1835, doi: 10.1007/s00262-008-0510-9). The peptides also include those of U.S. Pat. No. 7,943,138B2; SEQ ID NO: 042 $SVN_{57-64}$ CFFCFKEL, SEQ ID NO: 045 $SVN_{57-64}$/M57 MFFCFKEL, SEQ ID NO: 046 $SVN_{82\_89}$/L82 LGCAFLSV, and Onodi et al., 2018, High Therapeutic Efficacy of a New Survivin LSP-Cancer Vaccine Containing CD4+ and CD8+ T-Cell Epitopes, Front. Oncol., 13 Nov. 2018| doi.org/10.3389/fonc.2018.00517), $SVN_{17-31}$ SEQ ID NO: 047 HRISTFKNWPFLEGC, $SVN_{20-34}$ SEQ ID NO: 048 STFKNWPFLEGCACT, $SVN_{84-98}$ SEQ ID NO: 049 CAFLSVKKQFEELTL, $SVN_{90-104}$ SEQ ID NO: 050 KKQFEELTLGEFLKL, $SVN_{93-107}$ or SEQ ID NO: 051 FEELTLGEFLKLDRE, $SVN_{96-110}$ SEQ ID NO: 052 LTLGEFLKLDREFAK, $SVN_{122-136}$ SEQ ID NO: 053 KEFEETAKKVRRAIE, $SVN_{128-142}$ SEQ ID NO: 054 AKKVRRAIEQLAAMD. Especially preferred peptides are $SVN_{57-64}$ and $SVN_{82-89}$, and more specially preferred is $SVN_{53-67}$, or its extended peptide SEQ ID NO: 055 $SVN_{49-71}$ ENEPDLAQCFFCFKELEGWEPDD, which may be expressed alone or in combination. Also encompassed is CVD908ssb (ClinicalTrials.gov Identifier: NCT03762291). Other peptides include but are not limited to melanoma associated antigens Melan A/MART 1, tyrosinase, gp100, tyrosine-related protein-2 (TRYP-2). Also included are human epidermal receptor-2 (HER2), carcinoembryonic antigen (CEA), mucin 1 (MUC-1) and New York- esophageous (NY-ESO) and mesothelin. Mesothelin peptides include but are not limited to amino acids 540-549 SEQ ID NO: 056 KLLGPHEVGL, 530-538 SEQ ID NO: 057 VLPLTVAEV, 20-28 SEQ ID NO: 058 SLLFLLFSL, 435-443 SEQ ID NO: 059 FYPGYLCSL, 83-91 SEQ ID NO: 060 ELAVALAQK, 225-233 SEQ ID NO: 061 ALQGGGPPY (Wang et al., 2010, The human cancer antigen mesothelin is more efficiently presented to the mouse immune system when targeted to the DEC-205/CD205 receptor on dendritic cells, Ann NY Acad Sci 1174: 6-17). The invention also encompasses the N-domain of carcinoembryonic antigen (CEA; Abdul-Wahid et al., US Patent Application 20150044218). CltB requires addition of a C-terminal cysteine (C) and OTG-PE38K is modified with a C-terminal KDEL endoplasmic reticulum retention signal. Additional antigens include EMR2, CD33, IL10RB, PLXNC1, PIEZO1, CD300LF, CPM, ITFG3, TTYH3, ITGA4, SLC9A1, MBOAT7, CD38, SLC6A6, ENG, SIRPB1, MRP1, ITGA5, SLC43A3, MYADM, ICAM1, SLC44A1, CCR1, SLC22A5, TFR2, KCNN4, LILRB4, LTB4R, CD70, GYPA, FCGR1A, CD123, CLEC12A, ITGB5, PTPRJ, SLC30A1, EMC10, TNFRSF1B, CD82, ITGAX, CR1, DAGLB, SEMA4A, TLR2, P2RY13, LILRB2, EMB, CD96, LILRB3, LILRA6, LILRA2, WT1, PRAME and SLC19A1.

In another embodiment, the toxins that recruit the immune system, including but not limited to PMT and CNF, are mitogenic, and may also cause the cancer cells to temporarily grow faster, but therefore to become susceptible to chemotherapeutic agents, such as paclitaxel.

CLDT. Regarding use of tumor-targeted bacteria expressing wild type cytolethal distending toxin and chimeras, there have been several earlier descriptions (Bermudes et al., 2005, Compositions and methods for tumor-targeted delivery of effector molecules, U.S. Pat. No. 6,962,696; Bermudes et al., 2008, Compositions and methods for tumor-targeted delivery of effector molecules, U.S. Pat. No. 7,452,531; Bermudes, 2013, Protease sensitivity expression system, U.S. Pat. No. 8,241,623; Bermudes 2013, Protease inhibitor protease sensitivity expression system composition and methods improving the therapeutic activity and specificity of proteins delivered by bacteria U.S. Pat. No. 8,524,220; Bermudes 2014, Protease inhibitor: protease sensitivity expression system and method improving the therapeutic activity and specificity of proteins and phage and phagemids delivered by bacteria U.S. Pat. No. 8,623,350; Bermudes 2014, Immunization and/or treatment of parasites and infectious agents by live bacteria U.S. Pat. No. 8,771,669; Bermudes and Quintero 2017, Chimeric protein toxins for expression by therapeutic bacteria, US Patent Application 20170051260).

Under most nomenclature systems, the CdtB gene product is the DNase. *Salmonella* CLDTs are also known to possess an ADP-ribosylating activity within the "A" (PltA) subunit (Miller and Wiedmann, 2016, Dynamic duo—The *Salmonella* cytolethal distending toxin combines ADP-robosyltransferase and nuclease actividites in a novels form of cytolethal distending toxin, Toxins 2016, 8, 121; doi: 10.3390/toxins8050121; Scuron et al, 2016, The cytolethal distending toxin contributes to microbial virulence and disease pathogenesis by acting as a tri-perditious toxin, Frontiers in Cellular and Infection Microbiology doi: 10.3389/fcimb.2016.00168).

CLDTs are known to occur in phage ("phage CLDT") and a number of bacterial genera including *Haemophilus* sp., *Haemophilus parasuis, Haemophilus ducreyi, Aggregatibacter* sp., *Aggregatibacter actinomycetemcomitans, Salmonella* sp., *Salmonella bongon, Salmonella arizonae, Salmonella enterica, Salmonella enterica* serotypes (Agbeni, Arechavaleta, Arizonae, Barranquilla, Brandenburg, Bredeney, Corvallis, Cotham, Cubana, Freetown, Gaminara, Georgia, Give, Glostrup, Indiana, Inverness, Javiana, Johannesburg, Kiambu, Kintambo, Kisarawe, Luciana, Miami, Minnesota, Mississippi, Montevideo, Muenster Oranienburg, Overschie, Panama, Paratyphi A, Pomona, Poona, Reading, Rubislaw, Sandiego, Schwarzengrund, Telelkebir, Typhi, Urbana, Wandsworth), *Escherichia* sp., *Escherichia coli, Escherichia albertii, Shigella* sp., *Shigella dysenteriae, Shigella boydii, Campylobacter* sp., *Campylobacter fetus, Campylobacter lari, Campylobacter upsaliensis, Campylobacter coli, Campylobacter jejuni, Campylobacter hyointestinalis, Helicobacter* sp., *Helicobacter bilus, Helicobacter canis, Helicobacter cinaedi, Helicobacter callitrichis, Helicobacte hepaticus, Helicobacter mastomyrinus, Helicobacter pylon, Helicobacter pullorum, Helicobacter winghamsensis, Providencia* sp., *Providencia alcalifaciens, Hahella* sp., *Hahella chejuensis, Pseudomonas* sp., *Pseudomonas entomophila* and *Yersinia* sp., *Yersinia ruckeri, Yersinia bercovieri, Yersinia enterocolitica*, (Gargi et al., 2012 Bacterial toxin modulation of the eukaryotic cell cycle: are all cytolethal distending toxins created equally? Frontiers in Cellular and Infection Microbiol. 2:124. doi: 10.3389/fcimb.2012.00124), although CLDT does not exist in the VNP20009 strain of *Salmonella* used in human clinical studies (Toso et al. 2002. Phase I Study of the Intravenous Administration of Attenuated *Salmonella* typhimurium to Patients with Metastatic Melanoma. J. Clin. Oncol. 20, 142-152; Low et al., 2004, Construction of VNP20009, a novel, genetically stable antibiotic sensitive strain of tumor-targeting *Salmonella* for parenteral administration in humans. Methods Mol Med 90: 47-60).

Cytolethal distending toxins have been explored as potential cancer therapeutics in their isolated and purified forms (Lai et al., 2016, Molecular Mechanisms and Potential Clinical Applications of *Campylobacter jejuni* Cytolethal Distending Toxin, Frontiers in Cellular and Infection Microbiol doi: 10.3389/fcimb.2016.00009). CLDT conjugated toxins for cancer therapy have also been described (Bachran et al., 2014, Cytolethal distending toxin B as a cell-killing component of tumor-targeted anthrax toxin fusion proteins, Cell Death and Disease (2014) 5, e10003; doi: 10.1038/cddis.2013.540; Bachran and Leppla 2016, Cytolethal distending toxin subunit B conjugated or fused to *Bacillus anthracis* toxin lethal factor, US Patent Application 2016/0145590; Dirienzo 2015, Chimeria comprising bacterial cytotoxin and methods using the same, US Patent Application 20150291667; Purdy et al., 2008, Use of lytic toxins and toxin conjugates, US Patent Application 20080213310).

Cytolethal distending toxins (CDT or CLDTs) comprise a family of heterotrimeric holotoxins produced by bacteria that are internalized into mammalian cells and are translocated into the nucleus. Depending upon both the specific CLDT and the mammalian cells type, different effects have been documented. All CLDTs have homology to exonuclease III and several have been directly shown to exhibit DNase activity in vitro (Ewell and Dreyfus 2000 DNase I homologous residues in CdtB are critical for cytolethal distending toxin-mediated cell cycle arrest. Mol Microbiol 37, 952-963; Lara-Tejero and Galen, 2000 A bacterial toxin that controls cell cycle progression as a deoxyribonuclease I-like protein. Science 290, 354-357), which is believed to be the primary effect of the toxin. The DNase activity results in double-stranded DNA breaks that activates the cell's DNA damage response and interrupts the cell cycle at G2M. Non-hematopoietic cells tend to enlarge, hence part of the toxin name distending, and in many cases the cells subsequently undergo apoptosis. In hematopoietic cells apoptosis is more rapidly produced (Jinadasa et al., 2011, Cytolethal distending toxin: a conserved bacterial genotoxin that blocks cell cycle progression, leading to apoptosis of a broad range of mammalian cell lineages. Microbiology 157: 1851-1875; Gargi et al., 2012).

Most of the CLDTs are organized in a unidirectional operon of cldtA, cldtB and cldtC genes, where the cldtB encodes the active subcomponent, and cldtA and cldtC encode peptides that are involved in cell binding and translocation. In *Salmonella* however, the genes exist as a bidirectional operon consisting of cldtB together with a two pertussis like toxin subunits oriented in the opposite direction, pltA and pltB, as well as sty and ttsA, also in opposing directions of each other, that are reported to be required for secretion of the toxin (Hodak and Galan 2013 A *Salmonella typhi* homologue of bacteriophage muramidase controls typhoid toxin secretion. EMBO Reports 14: 95-102). However, in the present technology, according to various embodiments, the presence of sty and ttsA are not required for secretion of the active toxin when the operon is reorganized into a unidirectional operon of cldtB, pltB and pltA, but optionally may be present and may augment activity under some circumstances.

Translocation of *E. coli* CLDTs to the nucleus, which constitutes the target location for the endonuclease activity, requires the presence of a nuclear localization signal (NLS). In *Escherichia coli* CLDT-II for example, the NLS is bipartite and located at the C-terminus (McSweeney and Dreyfus, 2004). Nishikubo et al., 2003 identified an NLS occurring in the 48-124 amino acid region in *Actinobacillus actinomycetemcomitans.*

Targeting moieties. Bermudes and Quintero have described the use of construction of cldt:plt hybrids (US 20170051260). For clarification and distinction from the present technology however, the following description of Bermudes and Quintero is provided. The naturally occurring *Salmonella typhi* (and other *Salmonella* serotypes, but not present (entirely absent) for example in tumor-targeted *Salmonella* typhimurium strain VNP20009) consists of 5 genes, cltdB, sty 1887, ttsA, pltA and pltB in that particular sequence. Most of the non-*Salmonella* CLDTs are organized in a unidirectional operon of cldtA, cldtB and cldtC genes, where the cldtB encodes the active subcomponent, and cldtA and cldtC encode peptides that are involved in cell binding and translocation. In *Salmonella* however, the genes exist as a bidirectional operon consisting of cldtB together with a two pertussis like toxin subunits oriented in the opposite direction, pltA and pltB, as well as sty and ttsA, also in opposing directions of each other, that are reported to be required for secretion of the toxin (Hodak and Galan 2013 A *Salmonella* Typhi homologue of bacteriophage muramidase controls typhoid toxin secretion. EMBO Reports 14: 95-102). The genes of the *S. typhi* CLDT operon, pltB and pltA derive their name from their similarity to pertussis toxin (hence, pertussis like toxin B=pltB). However the cldt:plt hybrids described by Bermudes and Quintero are of whole gene and operon nature in that they consist of separate genes of the *Salmonella typhi* (and/or other serotypes) reoriented from the naturally occurring [cltdB, sty 1887, ttsA, pltA and pltB] to [cldtB, pltB and pltA], in that novel sequence with a deletion in sty and ttsA and a reversal of the transcriptional orientation of pltB and pltA. The present technology may use either operon organization.

The pertussis toxin from *Bordetella* species, including *B. pertussis*, is a multi-subunit (S1, S2, S3, S4 and S5 subunits) that is both secreted and cell-bound. Pawelek (US Patent Application 2005/0026866), has suggested the use of pertussis toxin and *Bordetella* sp. as anticancer agents. However, Pawelek did not suggest chimeric CLDTs with pertussis toxin S2 or S3 subunits, which are non-covalently bound subunits, nor did he suggest CLDT pertussis PltBs protein chimeras with S2, S3 or both, neither of which contains the pertussis toxin cytotoxic activity. Furthermore, Pawelek did not suggest chimeric proteins of the ArtAB subtilase with pertussis S2 or S3 subunits, or chimeras of ArtAB subtilase with CLDT.

The present technology, according to various embodiments, consists of either the wild type 5 gene CLDT operon or the modified 3 gene *Salmonella* CLDT operon, from any *Salmonella* serotype, or, modified forms of any form of cytolethal distending toxin, and forms of cytolethal distending toxins that are chimeric with the S2 or S3 subunits of pertussis toxin, or both, or PltB:S2 or PltS3 chimeras, or both, or ArtAB chimeric with S2 or S3, or both, or ArtAB chimeric with CLDTs. The S2 and/or S3, or PltB:S2 or PltB:S3 chimeras may be co-expressed with the CLDT operon, or may replace the CLDT operon PltB. The present technology also provides multiple forms of chimeras, consisting of chimeras with modified N-terminal secretion signals, and/or internal and/or C-terminal disulfide bonds within the pltB hydrophobic and helical anchor area consisting of 1) only those of pltB, 2) hybrid disulfide bonds of pltB hydrophobic and helical anchor with S3 hydrophobic and helical anchor, and 3) hybrids with only hydrophobic and helical anchor area disulfides of S3.

Fusions may be either at the N-terminus (post hydrophobic signal sequence cleavage) or C-terminal (pre-cysteine if cysteine is the terminal amino acid involved in disulfide bonding), or internally. Translocation of *E. coli* CLDTs to the nucleus, which constitutes the target location for the endonuclease activity, requires the presence of a nuclear localization signal (NLS). In *Escherichia coli* CLDT-II for example, the NLS is bipartite and located at the C-terminus (McSweeney and Dreyfus, 2004). Nishikubo et al., 2003 identified an NLS occurring in the 48-124 amino acid region in *Actinobacillus actinomycetemcomitans.*

The present technology also provides multiple forms of chimeras, consisting of chimeras with the N-terminal secretion signal, and/or internal and/or C-terminal disulfide bonds within the pltB hydrophobic and helical anchor area consisting of 1) only those of pltB, 2) hybrid disulfide bonds of pltB hydrophobic and helical anchor with S3 hydrophobic and helical anchor, and 3) hybrids with only hydrophobic and helical anchor area disulfides of S3. The present technology also include, in addition to pltB:S3 hybrids, pltB:S3 hybrids with non-hybrid amino acids that improve disulfide bonding as determined by an algorithm (Ceroni et al, 2006, DISULFIND: a disulfide bond state and cysteine connectivity prediction server, Nucleic Acids Research 2006 Jul. 1; 34 doi: 10.1093/nar/gkl266).

Peptide Ligands: Other peptide ligands include those of Bermudes (U.S. Pat. No. 9,068,187, Protease inhibitor protease sensitivity expression system composition and methods improving the therapeutic activity and specificity of proteins delivered by bacteria). Targeting peptides include heat stable enterotoxins (SEQ ID NO: 002 NSSNYCCELCCNPACTGCF) precursors (e.g., UnitProtKP—P01559 (HST1_ECOLX) UniProtKB—Q2WE95 (Q2WE95_ECOLX); GenBank: PXF64785.1) and related hormones guanylin and uroguanylin (Dubreuil 2006, Chapter 48*, Escherichia coli, Vibrio* and *Yersinia* species heat stable enterotoxins, Alouf and Popoff (eds), Comprehensive Sourcebook of Bacterial Protein Toxins, Third Edition, Academic Press; Alouf and Popoff (eds), 2015, Comprehensive Sourcebook of Bacterial Protein Toxins, Third Edition, Academic Press, Chapter 31, *Escherichia coli* heat-stable enterotoxins (Dubreuil JD); Lin et al., 2010, Bacterial heat-stable enterotoxins: Translation of pathogenic peptides into novel targeted diagnostics and therapeutics, Toxins (Basil) 2: 2028-2054) Targeting peptides also include epidermal growth factor (EGF), including those of human, dog, cat, horse and mouse, tumor growth factor alpha (TGF ▯) including those of human, dog, cat, horse and mouse, clorotoxin targeting peptide, *Clostridium* enterotoxin C-terminal peptide 290-319 (SEQ ID NO: 004 SLDAGQYVLVMKANSSYSGNYPYSILFQKF; Black et al., 2015, CPE290-319 COOH-terminus fragment is adequate for high-affinity binding to target cell receptors, 7:1116-1125 doi:10.3390/toxins7041116, RGD-C4 (SEQ ID NO: 005 ACDCRGDCFCG); Muc (Hayashi et al., 2001, MUC1 mucin core protein binds to the domain 1 of ICAM-1 (mature peptide) SEQ ID NO: 062 QTSVSPSKVILPRGGSVLVTCSTSCDQPKLLGIETPLPKKELLLPGNNRKVYELSNVQEDSQPMCYSNCPDGQ, Chlorotoxin tumor binding peptide (Dardevet et al., 2015, Chlorotoxin: A helpful natural scorpion peptide to diagnose glioma and fight tumor invasion, Toxins (Basil) 7:1079-1101) SEQ ID NO: 063 MCMPCFTTDHQMARKCDDCCGGKGRGKCYGPQCLCR, sunflower trypsin inhibitor (SFTI) SEQ ID NO: 064 GRCTKSIPPICFPD, BulA conotoxin SEQ ID NO: 065 GCCSTPPCAVLYC, MMP2/9 inhibitor SEQ ID NO: 006 CTTHWGFTLC and its derivative SEQ ID NO: 007 RGDSYCTTHWGFTLC Huang et al., 2013, The synthetic peptide inhibits metastasis and proliferation of breast cancer cells in vitro, Nan Fang Yi Ke Da Xue Xue Bao. 2013 September; 33(9):1367-71), inhibits metastasis and proliferation of breast cancer cells in vitro, Nan Fang Yi Ke Da Xue Xue Bao. 2013 September; 33(9):1367-71), Anthrax lethal factor (Zahaf and Schmidt 2017, Bacterial toxins for cancer therapy, Toxins (Basil) 9(8): 236 doi: 10.3390/toxins9080236; Bachram and Leppla, 2016, Cytolethal distending toxin subunit B conjugated or fused to *Bacillus anthracis* toxin lethal factor. US Patent application 2016/0145590), *Bordetella* filamentous hemagglutinin, peptides that bind to epithelial cell adhesion molecule (U.S. Pat. No. 9,815,866), including SEQ ID NO: 008 EHLHCLGSLCWP (EP133) and SEQ ID NO: 009 KHLQCVRNICWS (EP114), pertussis toxin S3 subunit and peptides derived from it, IL13 and peptides derived from it, hyaluronic acid, peptide-35 (U.S. Pat. No. 8,003,613), Pep42 (Liu et al., 2007, Mechanistic studies of a peptidic GRP78 ligand for cancer cell-specific drug delivery, Mol Pharm 4: 435-447), and those described by Brown (2010, tumor targeting agents: the road from phage display peptide selections to clinical applications, Curr Pharm Des 16: 1040-1054). Ligands also include antibodies and antibody derivatives, affibodies (protein A affinity-based ligands), armadillo repeat protein-based scaffolds, adnectins, anticalins, lipocalins, Kunitz domain-based binders, avimers, knottins, fynomers, atrimers and DARPins (designed ankyrin repeat proteins) and cytotoxic T-lymphocyte associated protein-4 (CTLA4)-based binders (Weidle et al., 2013 The emerging role of new protein scaffold-based agents for treatment of cancer. Cancer Genomics Protomics 10: 155-168).

Therapeutic enhancers. The therapeutic enhancers of the technology are able to enhance the immunostimulatory and/or cytotoxicity of the immunotherapeutics and cytotoxins, directly or indirectly, including enhancing the spread of the bacteria within the tumor. Therapeutic enhancers may be expressed independently or dependently (polycistronically) with the immunotherapeutics and cytotoxins. Therapeutic enhancers include but are not limited to hyaluronidase (including human (HYAL1, HYAL2, HYAL3, HYAL4, and HYAL5, as well as those of bacteria, especially *Staphylococcus* sp., including but not limited to *S. aureus, Streptococcus* sp., including but not limited to *S. pyogenes* and *S. hyalurolyticis*, and *Clostridium* sp., including but not limited to *C. perfringens*, as well as those of lizards, snakes and honeybees). In a preferred embodiment, the hyaluronidase is surface displayed as described by Orlando et al., 2015 (Autodisplay of human hyaluronidase Hyal-1 on *Escherichia coli* and identification of plant-derived enzyme inhibitors, Molecules 2015, 20, 15449-15468; doi:10.3390/molecules200915449) and may be further tailored using the vector described by Jose et al., 2016 (US 20160108407). Hyalurondase may also be expressed as described by Kaebler et al., 2010 (Autodisplay of catalytically active human hyaluronidase PH-20a and testing of enzyme inhibitors, European Journal of Pharmaceutical Sciences, doi:10.1016/j.ejps.2010.11.004; Jose et al., United States Patent Application 20160108407, Improved surface display of functional proteins in a broad range of gram negative bacteria). The hyaluronidase may also be expressed as described by Ebelt et al., Hyaluronidase-expressing *Salmonella* effectively targets tumor-associated hyaluronic acid in pancreatic ductal adenocarcinoma, Molecular Cancer Therapeutics doi: 10.1158/1535-7163.MCT-19-0556 or by Ebelt et al., 2019 Hyaluronidase-expressing *Salmonella* effectively targets tumor-associated hyaluronic acid in pancreatic ductal adenocarcinoma, DOI: 10.1159/1535-7163.MCT-19-0556.

In another preferred embodiment the hyaluronidase is surface displayed by the *Pseudomonas* INP (UniProtKB—P06620 (ICEN_PSESY), or its truncated form Part: BBa_K265008), and by be released through cleavage of a proteolytic linker. TAT-apoptin (Bermudes et al., U.S. Pat. No. 7,452,531), TAT-bim, TAT-bax, TAT-p53 peptide (Justesen et al., 2007, Immunology 122: 326-334; (as well as other therapeutic peptides and cell penetrating peptides, see Table 2, Marqus et al., 2017, Evaluation of the use of therapeutic peptides for cancer treatment, J Biomed Sci 24: Article number: 21 (2017); Protease inhibitors (e.g., Bermudes U.S. Pat. No. 9,878,023; Quimbar et al., 2013, High-affinity cyclic peptide matriptase inhibitors, J. Biological Chemistry doi/10.1074/jbc.M113.460030; Korsinczky et al., 2001, Solution Structures by 1H NMR of the Novel CyclicTrypsin Inhibitor SFTI-1 from Sunflower Seeds and an Acyclic Permutant, J. Mol. Biol. (2001) 311, 579±591), E3 periplasmic lysis, the peptide pentastatin-1 (SEQ ID NO: 066 LRRFSTMPFMFCNINNVCNF) (Koskimaki et al., 2010 Pentastating-1, a collagen IV derived 20-mer peptide, suppresses tumor growth in a small cell lung cancer xenograft model, BMC Cancer 10: 29 doi: 10.1186/1471-2407-10-29, and Noxa (Jeong et al., Anti-tumoral effect of the mitochondrial target domain of Noxa delivered by an engineered *Salmonella typhimurium*, PLoS One (2014) 9, issue 1, e80050).

The hyaluronidase may also be delivered exogenously, via a purified protein (e.g., PH20 hyaluronidase (rHuPH20)), as a liposome, or viral vector (e.g., VCN-01).

Bacterial genetic backgrounds improving immunotherapeutic effects. The present technology also provides a combination of bacteria that enhance the immune stimulation by preventing inhibition of proinflammatory response together with agents and enhancers described above. These mutations include but are not limited to steE, ssaV, and combinations of steE and ssaV (Stapels et al., *Salmonella* persisters undermine host immune defenses during antibiotic treatment, Science 362:1156-1160). The bacteria may be further deleted in lytB, disrupting the mevalonate pathway and enhancing ▯▯T-cell responses (Workalemahu et al., 2014, metabolic engineering of *Salmonella* vaccine bacteria to boost human V▯2V▯2 T cell immunity, J Immunol 15: 193: 708-721).

The types of cancers or neoplasias to which the present technology is directed include all neoplastic malignancies, including solid tumors such as those of Blood: acute lymphoblastic leukemia, acute myeloid leukemia, AIDS-related lymphoma, Burkitt lymphoma, central nervous system lymphoma, childhood acute myeloma, childhood multiple myeloma/plasma cell neoplasm, chronic lymphocytic leukemia, chronic myelogenous leukemia, chronic myeloid leukemia, chronic myeloproliferative disorders, cutaneous T-cell lymphoma, hairy cell leukemia, Hodgkin lymphoma, Langerhans cell histiocytosis, leukemia, macroglobulinemia, mycosis fungoides, multiple myeloproliferative disorders, myelodysplastic syndromes, myeloproliferative diseases, myelogenous leukemia, non-Hodgkin lymphoma, plasma cell neoplasm/multiple myeloma, primary central nervous system lymphoma, small cell lymphoma, Sezary syndrome, thymoma and thymic carcinoma, Waldenström macroglobulinemia, Waldenström malignant fibrous histiocytoma of bone and osteosarcoma, T-cell lymphoma, Gastrointestinal: adult (primary) liver cancer, anal cancer, appendix cancer, bile duct cancer, colon cancer, colorectal cancer, esophageal cancer, extrahepatic bile duct cancer, extrahepatic bladder cancer, gallbladder cancer, gastric (stomach) cancer, gastrointestinal cancers, gastrointestinal carcinoid tumor, gastrointestinal stromal cell tumor, gastrointestinal stromal tumor (gist), head and neck cancer, hepatocellular (liver) cancer, hypopharyngeal cancer, laryngeal cancer, lip and oral cavity cancer, lip and oropharyngeal cancer, metastatic stomach (gastric) cancer, metastatic squamous neck cancer with occult primary, mouth cancer, nasal cavity and paranasal sinus cancer, nasopharyngeal cancer, oral cavity cancer, pancreatic cancer, paranasal sinus and nasal cavity cancer, pharyngeal cancer, primary hepatocellular (liver) cancer, rectal cancer, salivary gland cancer, small intestine cancer, throat cancer, Respiratory: lung cancer, bronchial tumors, non-small cell lung cancer, pleuropulmonary blastoma, respiratory tract carcinoma involving the nut gene on chromosome 15, small cell lung cancer, Neural and Endocrine: adrenocortical carcinoma adrenocortical carcinoma, astrocytomas, brain stem glioma, brain tumor, breast cancer, carcinoid tumor, central nervous system atypical teratoid/rhabdoid tumor, central nervous system embryonal tumors, central nervous system tumors, craniopharyngioma, eye cancer, glioma, islet cell tumors (endocrine pancreas), medulloblastoma, medulloepithelioma, multiple endocrine neoplasia syndrome, nervous system atypical teratoid/rhabdoid tumor, neuroblastoma, parathyroid cancer, pineal parenchymal tumors, pineal parenchymal tumors of intermediate differentiation, pineoblastoma, pituitary tumor, retinoblastoma, supratentorial primitive neuroectodermal tumors, spinal cord tumors, thyroid cancer, Skin and Connective Tissue: sarcoma, basal cell carcinoma, bone cancer, chordoma, Ewing sarcoma family of tumors, intraocular melanoma, Kaposi sarcoma, melanoma, Merkel cell carcinoma, osteosarcoma and malignant fibrous histiocytoma of bone, papillomatosis, rhabdomyosarcoma, skin cancer (nonmelanoma), soft tissue sarcoma, squamous cell carcinoma, squamous neck cancer with occult primary, Urinary Track: bladder cancer, kidney (renal cell) cancer, kidney cancer, renal cell (kidney) cancer, renal pelvis and ureter cancer, transitional cell cancer of the renal pelvis and ureter, ureter and renal pelvis, urethral cancer, Wilms tumor, Reproductive Organs: cervical cancer, germ cell tumor, embryonal tumors, endometrial cancer, endometrial uterine sarcoma, ependymoblastoma, ependymoma, extracranial germ cell tumor, extragonadal germ cell tumor, ovarian cancer, ovarian epithelial cancer, ovarian germ cell tumor, ovarian gestational trophoblastic tumor, ovarian low malignant potential tumor, penile cancer, primary cervical cancer, prostate cancer, uterine cancer, uterine sarcoma, vaginal cancer, vulvar cancer, teratoid/rhabdoid tumor, testicular cancer, trophoblastic tumor, mesothelioma.

Issues related to bacterial targeting and efficacy have previously been addressed by Bermudes (Protease sensitivity expression system, U.S. Pat. No. 8,241,623 B1). Survival under $CO_2$ conditions, high osmolarity and acidic conditions has also been addressed (U.S. Pat. No. 8,647,642).

As cited above, the primary shortcoming of tumor-targeted bacteria investigated in the human clinical trials (*Salmonella* strain VNP20009 and its derivative TAPET-CD; Toso et al., 2002, Phase I study of the intravenous administration of attenuated *Salmonella* typhimurium to patients with metastatic melanoma, J. Clin, Oncol. 20:142-152; Meir et al., 2001, Phase 1 trial of alive, attenuated *Salmonella* typhimurium (VNP20009) administered by direct Intra-tumoral (IT) injection, Proc Am Soc Clin Oncol 20: abstr 1043; Nemunaitis et al., 2003, Pilot trial of genetically modified, attenuated *Salmonella* expressing the *E. coli* cytosine deaminase gene in refractory cancer patients, Cancer Gene Therapy 10:737-744) is that no antitumor activity was observed, even in patients that were documented to have had tumors that were colonized by the bacteria. An additional divergence between the murine studies (e.g., Pawelek et al., 1997, Tumor-targeted *Salmonella* as a novel anticancer agent, Cancer Research 57:4537-4544; Low et al., 1999, Lipid A mutant *Salmonella* with suppressed virulence and TNF-alpha induction retain tumor-targeting in vivo, Nature Biotechnol. 17:37-41), is that in most patients, the levels of the bacteria were significantly lower. For example, whereas in the murine models the bacteria frequently achieved levels of $1\times10^9$ colony forming units (CFU) per gram of tumor tissue, in humans the levels were significantly lower, e.g., $1\times10^6$ CFU/g was achieved in 3 patients (Meir et al., 2001). Generally, it has been perceived that the murine studies should precede using bacteria with the greatest amount of tumor targeting. For example, Pawelek et al., WO/1996/040238, selected “super infective” bacteria by cycling through tumors. The novel cycling and selection procedure they employed selected for increased targeting numbers which was correlated with a greater antitumor effect. A similar study using the strain AR-1 was performed by Zhao et al., 2005 (Tumor-targeting bacterial therapy with amino acid auxotrophs of GFP-expressing *Salmonella typhimurium*) Proc Natl Acad Sci USA. 102: 755-760). In the development of the *Salmonella* strain A1-R by re-isolation form a tumor, as described by the same group in a later study (Hayashi et al., 2009, Cancer metastasis directly eradicated by targeted therapy with a modified *Salmonella typhimurium*, Journal of Cellular Biochemistry 106: 992-998) “The idea was to increase the tumor targeting capability of the bacteria.” Thus, developing and testing bacteria with enhanced tumor targeting using known genetic backgrounds that already exhibit high levels of tumor targeting has been a focus within the field. However, while it is desirable to find ways to improve the levels of bacteria within tumors, including the present technology, the importance of selecting an appropriate tumor model and/or bacterial genetic background to assess the contribution that an effector system might have in a human, or how it might improve tumor colonization levels, wherein the tumor model and/or bacterial genetic background should provide low (rather than high) levels of tumor colonization, has not been appreciated. It has not been understood that to evaluate how an effector system such as the herpes simplex thymidine kinase or cytosine deaminase described by Pawelek et al., WO/1996/040238, or those provided in the present technology, would function in humans where lower targeting numbers might be expected (at least at the outset; greater number could be achieved if the effector system is effective), such that the murine tumor system and lor bacterial genetic background where the tumor-targeting level is similar to the level achieved in humans represents an appropriate model.

firA is a mutation within the gene that encodes the enzyme UDP-3-O(R-30 hydroxymyristoyl)-glycocyamine N-acyltransferase, that regulates the third step in endotoxin biosynthesis (Kelley et al., 1993, J. Biol. Chem. 268:19866-19874). *Salmonella* typhimurium and *E. coli* strains bearing this type of mutation produce a lipid A that differs from wild type lipid A in that it contains a seventh fatty acid, a hexadecanoic acid (Roy and Coleman, 1994, J. Bacteriol. 176:1639-1646). Roy and Coleman demonstrated that in addition to blocking the third step in endotoxin biosynthesis, the firA mutation also decreases enzymatic activity of lipid A 4' kinase that regulates the sixth step of lipid A biosynthesis. *Salmonella* typhimurium strain SH5014 and its firA' derivative SH7622 are described in Hirvas et al, 1991, EMBO J. 10:1017-1023. The genotypes of these strains are as follows: strain SH5014 ilv-1178 thr-914ήis-6116 metA22 metE551 trpB2 xyl-404 HI-b H2-e, n, x flaA66 rpsL120 rfaJ4041; strain SH7622 ilv-1178 thr-914 his-6116 metA22 metE551 trpB2 xyl-404 HI-b H2-e, n, x flahββ rpsL120 rfaJ4041, ssc-I ($firA^{ts}$). A derivative of *Salmonella* typhimurium firA' strain SH7622 was picked, designated SH7622-64, and used as the firA' strain for the experiments. SH7622-64 was selected for its supersensitivity to the antibiotic novobiocin and temperature-sensitive growth, characteristics of the firA' SH7622 strain. When studies in two different tumor models, Pawelek et al. found *Salmonella*/g tissue: Primary Tumor of M27 lung cancer, $2.9\times10^6$ per gram and in B16 melanoma, $3.2\times10^5$ per gram, yet retaining a similar 3200: 1 tumor to liver targeting ratio. This strain, while never used in any subsequent studies, represents a surprising solution to translating murine to human studies wherein both systems tend to have the same number of bacteria per gram of target tissue.

In an alternative approach to selecting bacterial mutants using strain backgrounds with high tumor-targeting and antitumor effects as is commonly applied (Zhao et al., 2005, Tumor-targeting bacterial therapy with amino acid auxotrophs of GFP-expressing *Salmonella typhimurium*. Proc Natl Acad Sci USA. 102: 755-760), bacterial mutants with suboptimal targeting or low antitumor effects are used for selection of improved antitumor effects. The bacterial mutants can be generated by any standard method of mutation (e.g., UV, nitrosoguanadine, Tn10, Tn5), or can be a spontaneous mutation such as a suppressor mutation (e.g., Murray et al., 2001, Extragenic suppressors of growth defects in msbB *Salmonella*, J. Bacteriol. 183: 5554-5561), or those of the present technology.

The present technology provides, according to various embodiments, live attenuated therapeutic bacterial strains that have improved ability compared to a parental strain in regard to the pharmacokinetic properties of enhanced circulation in the bloodstream and entry into, persistence and growth within tumors, by resisting immune elimination or lytic destruction, increased numbers of foci within tumors, increased colonization, expansion and persistence within tumors. It is the intention of these changes that the result in an overall increase in 1) increased serum half-life, 2) the percentage of tumors targeted, 3) the number of individual locations (foci) within a tumor that are established, 4) the number of CFU/g that are found within the tumor, 5) the ratio of tumor to liver, with increased ratio within the tumor, 6) the length of time that they reside within the tumor and 7) reduced immune clearance from the tumor, and, alone or collectively 8) increased antitumor activity directly and/or indirectly through the immune system. Administration of the genetically engineered bacterium to the human or animal may also result in reduced immune elimination following repeated dosing compared to its parental strain.

The live genetically engineered bacterium may be provided in a pharmaceutically acceptable formulation suitable for administration to a human or animal and have improved specificity and enhanced toxicity an immune-stimulation. The bacterium may comprise at least one gene which enhances serum half-life, tumor colonization and specificity, cytotoxicity and/or antitumor immune-stimulation.

It is therefore an object to provide alive genetically engineered bacterium functionally implementing a Boolean logic gate, comprising: a first heterologous gene inducible or repressible via a first promoter; and a second heterologous gene inducible or repressible via a second promoter, wherein the first promoter and the second promoter are independent and different; and wherein combined promotion or repression of the first gene and promotion or repression of the second gene selectively interact to provide a different functional outcome than independent promotion or repression of the first gene or promotion or repression of the second gene, the live genetically engineered bacterium being adapted for administration to a human or animal and colonization of at least one tissue under non-lethal conditions, wherein the different functional outcome has a therapeutic effect on the human or animal.

The first promoter may be preferentially expressed within a tumor of a host; and the second promoter may be exogenously administered to the host, the first gene and the second gene being inducible in combination to provide an antitumor effect and being inducible independently without providing the antitumor effect. The first promoter may be induced or preferentially expressed in a tumor and the second promoter is induced or preferentially expressed in normal tissue, reducing the bacterial growth or expression of the first gene in normal tissue and preferentially expressing the gene in tumor tissue. The first promoter may be induced or preferentially expressed within a tumor, and the second promoter is induced or preferentially expressed in normal tissue, acting to negatively regulate growth of the live genetically engineered bacterium and/or expression of the first gene in normal tissue. The first promoter may comprises a tumor selective promoter selected from the group consisting of: STM1787, STM1791 STM1793, ydiH, IpT, csG, mltD, mdh, mtfA, frdA, pfkA, pflE, nirB, ptsG, glpA, and ydiH. The second promoter may comprise a normal tissue-selective promoter. The first heterologous gene may be selected from the group consisting of Pseudomonase ToxA, cytolethal distending toxins (CLDTs), hybrid ArtAB: CLDTs, hybrid ArtAB:pertussis toxin S3 subunit, hybrid CLDT:pertussis S3 subunit, cytotoxic nectrotic factors (cnf1, cnf2, cnf3, dnf, CNFY) phenol soluble modulin toxins (PSMs), parasporins, *Staphylococcus* leukotoxins, *Pasteurella* multocita toxins (PMT) *Actinobacillus* leucotoxins leukoagglutinin (L-PHA, *Phaseolus vulgaris*) *Helix pomatia* lectin (HPA), mistletoe lectin, GMCSF, human cGAS, *Vibrio* DncV, *Salmonella* AdrA, K-Ras inhibitory peptides, carboxylesterase Est55 and its C408V and C408A mutants, secreted adenosine deaminase, tryptophanase, and antibodies and peptides to checkpoint inhibitors. The second promoter may comprise MarA, which is induced by presence of acetyl salicylic acid.

The first heterologous gene may comprise a plurality of therapeutic genes which are adapted to be co-expressed with an enhancer selected from the group comprising of TAT-apoptin, TAT-bim, TAT-bax, and TAT-p53.

The first heterologous gene may encode a therapeutic toxin modified with an immunotherapeutic peptide selected from the group consisting of tyroserleutide, survivin peptides, melanoma associated antigens Melan A/MART 1, tyrosinase, gp100, tyrosine-related protein-2 (TRYP-2), EGFR, human epidermal receptor-2 (HER2), carcinoembryonic antigen (CEA), mucin 1 (MUC-1) and New York-esophageous (NY-ESO) and mesothelin.

The live genetically engineered bacterium may have a selective tropism for at least one type of tumor in a human or animal, and the first heterologous gene encodes afunctional gene product effective for treating the at least one type of tumor, the live genetically engineered bacterium being provided within a pharmaceutically acceptable formulation for administration to the human or animal.

The live genetically engineered bacterium may be provided in a pharmaceutically acceptable formulation suitable for administration to a human or animal, and the genetically engineered bacterium is subject to PEGylation effective for increasing a serum half-life of the live genetically engineered bacterium after administration to the human or animal in the pharmaceutically acceptable formulation.

It is also an object to provide a method of treating a neoplasm, comprising: administering a pharmaceutically-acceptable formulation comprising alive genetically engineered bacterium with at least one synthetic gene encoding a logic function having at least two inputs, having at least two selectively induced promoters, each having at least one distinct gene product, wherein a first regulatory factor which interacts with a first promoter is produced by the neoplasm, and a second regulatory factor which interacts with a second promoter is exogenously administered.

The logic function may comprise AND, OR, NOT, NAND, NOR, XOR, Not-XOR, a D-type flip-flop, an R-S-type flip flop, an adder, a multiplier, gates with at least three inputs, feedback gates, various linear functions, etc.

It is a further object to provide alive genetically engineered bacterium, comprising: at least two different heterologous promoters, each being inducible or repressible via a respective different independent activator or repressor, being configured to functionally implement a Boolean logic function based on inputs represented by presence or absence of the respective promoters, and an output representing a gene product selectively transcribed in dependent on the presence or absence of respective different independent activators or repressors and the Boolean logic function, wherein the gene product output provides feedback to the input, the live genetically engineered bacterium being adapted for administration to a human or animal and colonization of at least one tissue under non-lethal conditions.

An object provides a bacterium genetically engineered to provide an acetylsalicylic acid (ASA) inducible promoter which promotes expression of at least one antitumor protein by the bacterium. The bacterium may also have a heterologous gene, selected or mutated, optionally responsive to an ASA inducible promoter or the same promoter as the at least one antitumor protein, which causes the bacterium to be decorated with carbohydrates in a heterologous decoration pattern. The at least one gene may comprise a plurality of genes, each responsive to an ASA inducible promoter, effective for causing the bacterium to selectively display a different heterologous antigen in response to presence of ASA. The ASA inducible promoter may be part of a Boolean logic system.

The bacterium may comprise at least one gene which is heterologous, selected or mutated, which causes the bacterium to be decorated with carbohydrates in a heterologous decoration pattern.

A still further object provides a method for treating a neoplastic disease in a living human or animal, comprising: administering a pharmaceutically acceptable formulation containing a genetically engineered bacterium to the living human or animal having the neoplastic disease, the genetically engineered bacterium may optionally be genetically engineered or selected to have a reduced size compared to its parental strain and which grows to a maximum size of about 650 nm, having at least one gene which causes or induces carbohydrate decoration of external components of the genetically engineered bacterium in a pattern different from the parental strain; permitting the genetically engineered bacterium to grow within and then be cleared from the living human or animal to cause antitumor effects, which are non-lethal to the living human or animal.

It is an object to provide alive genetically engineered bacterium, comprising: an AND gate consisting of at least one heterologous inducible gene via a promoter that is preferentially expressed within a tumor and at least a second gene independently preferentially expressed via a promoter within the same tumor, whereby the combined expression of both genes is required for functional therapeutic activity, the live genetically engineered bacterium being adapted for administration to a human or animal and colonization of at least one tissue under non-lethal conditions.

It is also an object to provide alive genetically engineered bacterium, comprising: two independent circuits that have a combined effect where at least one inducible gene is preferentially expressed via a promoter within a tumor and at least one gene is preferentially expressed via a promoter in normal tissue, reducing the bacterial growth or expression of the first gene in normal tissue and preferentially expressing the gene in tumor tissue, the live genetically engineered bacterium being adapted for administration to a human or animal and colonization of at least one tissue under non-lethal conditions.

It is a further object to provide alive genetically engineered bacterium, comprising: an integrated circuit consisting of least one inducible gene that is induced or preferentially expressed via a promoter within a tumor and at least one gene preferentially expressed via a promoter in normal tissue negatively regulating the bacterial growth and/or expression of the first gene in normal tissue, the live genetically engineered bacterium being adapted for administration to a human or animal and colonization of at least one tissue under non-lethal conditions.

A tumor selective promoter may be selected from the group comprising those of: STM1787, STM1791 STM1793, ydiH, lpT csG mltD mdh mtfA frdA pfkA pflE nirB ptsG glpA ydiH, A normal tissue-selective promoter may be selected from the group consisting of: bile activated gene promoterss (micF and/or osmY, CS5 operon csfA-F), spleen activated promoters (US 2011/0195847 Tables 4, Intergenic regions that induce higher GFP expression in spleen than in tumor) STM0006 yaaJ, STM0006, STM0007 talB, STM0080, STM0080, STM0081, STM0390 aroM, STM0391 yaiE, STM0605 ybdN, STM0605, STM0606 ybdO, STM0892 ybjP, STM0893, STM1044 sodC, STM1044, STM1045, STM1231 phoP, STM1231, STM1232 purB, STM1249, STM1249, STM1250, STM1583, STM1583, STM1584, STM1584 ansP, STM1736 yciA, STM1736, STM1737, STM1737 tonB, STM1868, STM1876 holE, STM1876, STM1877, STM2153 yehE, STM2153, STM2154, STM2154 mrp, STM2169 yohC, STM2169, STM2170 yohD, STM2349 yfcG, STM2349, STM2350, STM2366 accD, STM2367 dedA, STM3047 ygfY, STM3047, STM3048, STM3048 ygfZ, STM3231 yqjK, STM3231, STM3232, STM3805 yidH, STM3805, STM3806, STM4286 lpxO, STM4286, STM4287, STM4290 proP, STM4290, STM4291, STM4291 basS, STM4328 yjeH, STM4329, STM4362 hfDX, STM4362, STM4363, STM4363 hflK, PSLT006, PSLT007, PSLT024, PSLT025, PSLT025, PSLT026, PSLT040 spvA, PSLT040, PSLT041, PSLT045, PSLT046, PSLT047.

A gene may be provided, selected from the group consisting of Pseudomonase ToxA, cytolethal distending toxins (CLDTs), hybrid ArtAB:CLDTs, hybrid ArtAB:pertussis toxin S3 subunit, hybrid CLDT:pertussis S3 subunit, cytotoxic necrotic factors (cnf1, cnf2, cnf3, dnf, $CNF_Y$) phenol soluble modulin toxins (PSMs), parasporins, *Staphylococcus* leukotoxins, *Pasteurella* multocita toxins (PMT) *Actinobacillus leucotoxins* leukoagglutinin (L-PHA, *Phaseolus vulgaris*) *Helix pomatia* lectin (HPA), mistletoe lectin, GMCSF, human cGAS, *Vibrio* DncV, *Salmonella* AdrA, K-Ras inhibitory peptides, carboxylesterase Est55 and its C408V and C408A mutants, secreted adenosine deaminase, tryptophanase, and antibodies and peptides to checkpoint inhibitors. The therapeutic genes may be co-expressed with an enhancer. The therapeutic enhancer may be selected from the group consisting of TAT-apoptin, TAT-bim, TAT-bax, TAT-p53, *Burkholderia* TecA (e.g., UniProtKB—B4EMB9 (B4EMB9_BURCJ)).

A therapeutic toxin gene may be modified with an immunotherapeutic peptide.

An immunotherapeutic peptide may be selected from the group consisting of tyroserleutide, survivin peptides, melanoma associated antigens Melan A/MART 1, tyrosinase, gp100, tyrosine-related protein-2 (TRYP-2), EGFR, human epidermal receptor-2 (HER2), carcinoembryonic antigen (CEA), mucin 1 (MUC-1) and New York-esophageous (NY-ESO) and mesothelin.

An inducible promoter may comprise MarA, which is induced by presence of acetyl salicylic acid.

The live genetically engineered bacterium may be of genus *Salmonella.*

The live genetically engineered bacterium may have a selective tropism for at least one type of tumor in a human or animal, and the functional gene product is effective for treating the at least one type of tumor, the live genetically engineered bacterium being provided within a pharmaceutically acceptable formulation for administration to the human or animal.

The live genetically engineered bacterium may be provided in a pharmaceutically acceptable formulation suitable for administration to a human or animal, and the PEGylation of the genetically engineered bacterium is effective for increasing a serum half-life of the live genetically engineered bacterium after administration to the human or animal in the pharmaceutically acceptable formulation.

It is another object to provide a method for treating a neoplastic disease in a living human or animal, comprising: administering a pharmaceutically acceptable formulation containing a genetically engineered bacterium to the living human or animal having the neoplastic disease, the genetically engineered bacterium be genetically engineered to have at least one gene which causes an immunological response in the human or animal; and permitting the genetically engineered bacterium to grow within the living human or animal and then be cleared from the living human or animal, to cause antitumor effects resulting from the immunological response which are non-lethal to the living human or animal.

It is a further object to provide a method of treating a neoplasm, comprising: administering a pharmaceutically-acceptable formulation comprising alive genetically engineered bacterium with at least one synthetic gene encoding a logic function having at least two inputs, having at least two selectively induced promoters, each having at least one distinct gene product, wherein a first regulatory factor which interacts with a first promoter is produced by the neoplasm, and a second regulatory factor which interacts with a second promoter is exogenously administered. The logic function may comprise AND, OR, NOT, NAND, NOR or XOR.

It is another object to provide alive genetically engineered bacterium functionally implementing an AND gate, comprising: a first heterologous inducible gene via a first promoter that is preferentially expressed within a tumor; and a second inducible gene via a second promoter, the first gene and the second gene induced in combination to provide an antitumor effect and being induced independently without providing the antitumor effect; the live genetically engineered bacterium being adapted for administration to a human or animal and colonization of at least one tissue under non-lethal conditions.

It is a further object to provide alive genetically engineered bacterium functionally implementing a Boolean logic gate, comprising: a first heterologous gene inducible or repressible via a first promoter; and a second heterologous gene inducible or repressible via a second promoter, wherein the first promoter an the second promoter are independent and different; and wherein combined promotion or repression of the first gene and promotion or repression of the second gene selectively interact to provide a different functional outcome than independent promotion or repression of the first gene or promotion or repression of the second gene, the live genetically engineered bacterium being adapted for administration to a human or animal and colonization of at least one tissue under non-lethal conditions, wherein the different functional outcome has a therapeutic effect on the human or animal.

Administration of the pharmaceutically acceptable formulation containing a genetically engineered bacterium to the human or animal may result in at least one of: increased numbers of colony forming units within the solid tumor compared to its parental strain; increased serum half-life compared to its parental strain; increased numbers of colony forming units within the solid tumor compared to its parental strain; and reduced elimination following repeated dosing compared to its parental strain and increase antitumor toxicity and specificity, and/or increased antitumor immunity.

The inducible promoter may be composed of pMarA, which is induced by presence of acetyl salicylic acid. The inducible promoter may also be responsive to at least one of tet, arabinose, hypoxia, a cellular SOS response promoter, SOX promoter, ROS promoter, X-rays, and alkylating agents such as mitomycin.

The at least one heterologous inducible gene which causes or induces carbohydrate decoration of external components of the genetically engineered bacterium may comprise a plurality of inducible genes having respectively different inducers. At least one of the plurality of inducible genes having respectively different inducers may be responsive to a pharmacological inducer which is not naturally found in human tissue. The at least one heterologous inducible gene and the at least one gene producing a gene product under control of an inducible promoter may each induced by a common inducer. The at least one heterologous inducible gene may comprise a plurality of inducible genes, having respectively different inducible promoters induced by different pharmacological agents not naturally found in humans, to thereby provide the live genetically engineered bacterium having a plurality of different surface antigen patterns under control of a selective presence of the different pharmacological agents. The carbohydrate decoration may be subject to Boolean logic control.

The live genetically engineered bacterium may have a selective tropism for at least one type of tumor in a human or animal, and the functional gene product is effective for treating the at least one type of tumor, the live genetically engineered bacterium being provided within a pharmaceutically acceptable formulation for administration to the human or animal.

When administering self-replicating organisms, the minimum dose approximates a single in vivo replication competent organism or minimum infectious dose, which itself is approximated by an in vitro determined CFU. Suitable dosage ranges are generally from about 1.0 CFU/kg to about $1\times10^{10}$ CFU/kg; optionally from about 1.0 CFU/kg to about $1\times10^{8}$ CFU/kg; optionally from about $1\times10^{2}$ CFU/kg to about $1\times10^{8}$ CFU/kg; optionally from about $1\times10^{4}$ CFU/kg to about $1\times10^{8}$ CFU/kg; and optionally from about $1\times10^{4}$ CFU/kg to about $1\times10^{10}$ CFU/kg. Effective doses may be extrapolated from dose-response curves derived from in vitro or animal model test systems. However, higher doses are preferred, in order to permit prompt initiation of therapeutic effect and avoid host immune response suppression of the organisms before they reach full therapeutic potential. In some cases, replication incompetent organisms may be used, e.g., where the organisms remain competent to produce biologically active products as discussed herein while not being able to replicate, in which case a dose may be, for example, in the range $10^{8}$ to $10^{10}$ organisms and determined by nonculture-based methods (e.g., hemocytometer). The maximum dose of preferred organisms which display low toxicity and pathogenicity is in excess of $10^{10}$, and for orally or dermally administered probiotic species, gram scale doses may be administered.

The bacterial delivery vector may be attenuated, non-pathogenic, low pathogenic (including wild type), or a probiotic bacterium. The bacteria are introduced either systemically (e.g., parenteral, intravenous (IV), intramuscular (IM), intralymphatic (IL), intradermal (ID), subcutaneously (sub-q)), local-regionally (e.g., intralesionally, intratumorally (IT), intraperitoneally (IP), topically, intathecally (intrathecal), by inhaler or nasal spray) or to the mucosal system through oral, nasal, pulmonary intravessically, enema or suppository administration.

The bacteria may also be administered through exposure to myeloid derived suppressor cells (MDSC), where they spread from MDSC into tumor cells (Chandra et al., 2013, Myeloid-derived suppressor cells have a central role in attenuated *Listeria* moncytogenes-based immunotherapy against metastatic breast cancer in young and old mice. British J Cancer 108: 2281-2290. This process may occur through ex-vivo exposure to cells isolated from the patient, followed by reinfusion (Wells et al., 1979, A technique for the separation and cryopreservation of myeloid stem cells from human bone marrow, Cryobiology 16: 201-210; Casabuberta-Serra et al., 2017, Myeloid-derived suppressor cells can be efficiently generated from human hematopoietic progenitors and peripheral blood monocytes, Immunol Cell Biol 95: 538-548; Wyczechoska et al., 2015, Isolation and characterization of human MDSC from peripheral blood of patients with various malignancies (TUM6P.971), J. Immunol 194 (1 Supplement) 141.19.

The terms "oral", "enteral", "enterally", "orally", "non-parenteral", "non- parenterally", and the like, refer to administration of a compound or composition to an individual by a route or mode along the alimentary canal. Examples of "oral" routes of administration include, without limitation, swallowing liquid or solid forms by the mouth, administration of a composition through a nasojejunal or gastrostomy tube, intraduodenal administration of a composition, and rectal administration, e.g., using suppositories that release alive bacterial strain described herein to the lower intestinal tract of the alimentary canal. Upon administration, the bacteria are able to undergo limited or unlimited replication, express, surface display, secrete and/or release the effector molecules and/or protease inhibitors with anti-cancer thereby providing a therapeutic benefit by reducing or eliminating the malignancy and/or neoplasia.

Bacteria of the technology have recognizable attributes in regard to their serum half-life and presence within tumors. For example, Toso et al., 2002 (Phase I Study of the Intravenous Administration of Attenuated *Salmonella* typhimurium to Patients with Metastatic Melanoma, Journal of Clinical Oncology, 20:142-152) showed for example that a dose of $3\times10^{8}$ of the strain VNP20009 resulted in an average (in 6 patients) of approx. 65,000 CFU per ml of blood at 25 min, but only an average of 19 CFU/ml at 60 min., and only an average of 0.1 CFU/ml at 4 hrs, and only one patient in 6 had any CFU/ml at 12 hrs. Bacteria of the technology have significantly higher numbers of colony forming units at one or more times following 25 min, or have higher numbers of patients with greater than 0 CFU/ml at 12 hrs. A single patient in that treatment group received a second dose: that patient had 19,400 CFU/ml at 25 min for the first dose, but only 38 CFU/ml for the second dose. Bacteria of the technology have significantly greater numbers of CFU/ml at 25 min upon subsequent doses. Patients in that same treatment group were also assessed for the presence of CFU/g of tumor tissue. Only one in six patients had any CFU/g in their tumor. Bacteria of the technology have significantly greater percentages of tumors colonized by bacteria. The one tumor that was colonized by the bacteria had 11,000 CFU/g of tumor tissue, compared to $10^{9}$ CFU/g in tumor tissue of mice (Luo et al., 2001, Antitumor effect of VNP20009, an attenuated *Salmonella* in murine tumor models. Oncol. Res. 12: 501-508). Bacteria of the technology have significantly CFU/g of tumor tissue. In the study by Toso et al., 2002, no antitumor activity was observed, whereas the bacteria of the technology have improved antitumor activity.

The bacteria of the various embodiments of the technology are distinct from known bacteria. The bacteria of the technology can be recognized by their improved tumor targeting capabilities, or tumor specificity compared to their parental strains, with enhanced tumor to normal tissue ratios, determined by counting colony forming units (CFUs) in tumors compared to normal tissues. The enhanced specificity can also be measured by determining the activity of the effector proteins, such as by ELISA, in the respective tissues, using antibodies specific for the effector proteins. This is particularly true when the genetic circuits employed use normal tissue negative regulation to control bacterial growth. The bacteria of the technology can also be recognized by improved safety due to the gene regulatory circuits, which can be recognized in standard tolerability studies.

The bacteria of the technology can also be recognized by their improved pharmacokinetics tissue distribution and tumor colonization compared to their parental strains. The strains persist in the blood longer than the parental strains as determined by colony forming unit (CFU) assays. The strains also show higher initial tumor colonization rates (i.e., higher tumor CFU and/or greater numbers of tumors initially colonized). The bacteria also show reduced binding of innate and adaptive opsonizing agents, such as C-reactive protein, mannose binding protein, or antibodies, as determined by known methods, such as binding assays.

The bacteria of the technology are distinguished by their improved induction of anti-cancer immunity through one or more mechanisms when delivered systemically or locally. The bacteria deplete myeloid derived suppressor cells that improves host defenses and/or generate cytotoxic CD8+ T-cells that kill tumor cells. The result of the immune response is a durable response that resists recurrence of tumors. The bacteria of the technology improve upon and/or overcome unresponsiveness to known checkpoint inhibitors in combination with the cytotoxins and modified cytotoxins of the technology including but not limited to (*Pseudomonas* exotoxin A (ToxA; apoptosis), cytotoxic necrotizing factor (CNF; rho activation and necrosis); cytolethal distending toxin (CDT; DNA double stranded breaks and single strand DNA production and cGAS activation), *Aggregatebacter* leukotoxin (LTX; cytolytic), *Pasteurella multocita* toxin (PMT), T-cell proliferation, *Clostridium perfringens* enterotoxin C-terminus; cladin 3/4 binding). The therapy can result in immunogenic cell death (Obeid et al., 2006; Kroemer et al., 2013), and regulates the population of lymphoid and myeloid cells infiltrating the tumor as well as their function (Lazzari et al., 2018). These effects include upregulation of the B-cell enhancer of activation (NF-B), maturation of antigen presenting cells (APCs), an increase in CD8+ T-cells, and decrease in the population of immunosuppressive regulatory T-cells (T-regs) and myeloid derived suppressive cells (MDSCs). MDSCs are determined by key histological markers present on MDCSs of the macrophage lineage are CD11b, Ly-S6 and CD31, and Gr-1 of the granulocyte lineage. $Gr\text{-}1^{+}/CD11b^{+}$ is commonly used to define MDSCs.

T-cell responses are measured by known methods (e.g., Bercovici et al., 2000, New methods for assessing T-cell responses, Clin Diagn Lab Immunol 7: 859-864), such as limiting dilutions culture (frequency of t cells that mount a response to a specific antigen), ELISPOT (T-cell cytokine production), intracellular staining (cytokine staining), cytokine capture with bispecific antibodies (use of antibody heavy and light chain hybrids with one specific for T-cells and the other for specific cytokines), tetramer staining (determining MHC:peptide complexes), and spectratyping and biosensor assays (visualization of CDR3 by gel electrophoresis and biosensor assays that measure ligand receptor interactions).

The bacteria of the technology may further inhibit adenosine deaminase and KRAS, also measured by known methods (Sakamoto et al., 2017, K-Ras (G12D)-selective inhibitory peptides generated by random peptide T7 phage display technology, Biochem Biophys Res Comm 484: 605-611). KRAS inhibitory peptides expressed by therapeutic bacteria include KRpep-2 (SEQ ID NO: 067 RRCPLYI-SYDPVCRR), KRpep-2d (SEQ ID NO: 068 RRRRCPLYI- SYDPVCRRRR). Secretion, display and/or release of the peptides includes the known mechanisms such as YebF fusion, INP fusion, hlyA fusion, N-terminal Type II signal sequence fusion, Type III secretion fusion, autodisplay fusion and/or release, lysis protein mediated release, colicin release protein mediated release, and others. The peptide may be further modified with a ferry peptide as an in-frame fusion.

The cytotoxins of the technology are recognized by their alterations that improve immunogenicity, immunize against tumor antigens, enhance combination therapeutic efficacy with checkpoint inhibitors, and may optionally be engineered with tumor-selective ligands. These toxins are further enhanced in their antitumor activity by combination with enhancers that augment or promote their therapeutic efficacy. The bacteria may optionally be further modified to enhance the immune response, such as deletion steE and ssaV that make them more immunogenic, that further augments or promotes their therapeutic efficacy.

Pharmaceutically acceptable formulations.

Pharmaceutically acceptable formulations may be provided for delivery by other various routes e.g. by intramuscular injection, subcutaneous delivery, by intranasal delivery (e.g. WO 00/47222, U.S. Pat. No. 6,635,246), intradermal delivery (e.g. WO02/074336, WO02/067983, WO02/087494, WO02/0832149 WO04/016281) by transdermal delivery, by transcutaneous delivery, by topical routes, etc. Injection may involve a needle (including a microneedle), or may be needle-free. See, e.g., U.S. Pat. Nos. 7,452,531, 7,354,592, 6,962,696, 6,923,972, 6,863,894, 6,685,935, 6,475,482, 6,447,784, 6,190,657, 6,080,849 and US 2003/0059400.

Bacterial vector vaccines are known, and similar techniques may be used for the present bacteria as for bacterial vaccine vectors (U.S. Pat. No. 6,500,419, Curtiss, In: New Generation Vaccines: The Molecular Approach, Ed., Marcel Dekker, Inc., New York, N.Y., pages 161-188 and 269-288 (1989); and Mims et al, In: Medical Microbiology, Eds., Mosby-Year Book Europe Ltd., London (1993)). These known vaccines can enter the host, either orally, intranasally or parenterally. Once gaining access to the host, the bacterial vector vaccines express an engineered prokaryotic expression cassette contained therein that encodes a foreign antigen(s). Foreign antigens can be any protein (or part of a protein) or combination thereof from a bacterial, viral, or parasitic pathogen that has vaccine properties (New Generation Vaccines: The Molecular Approach, supra; Vaccines and Immunotherapy, supra; Hilleman, Dev. Biol. Stand., 82:3-20 (1994); Formal et al, Infect. Immun. 34:746-751 (1981); Gonzalez et al, J. Infect Dis., 169:927-931 (1994); Stevenson et al, FEMS Lett, 28:317-320 (1985); Aggarwal et al, J. Exp. Med., 172:1083-1090 (1990); Hone et al, Microbial. Path., 5:407-418 (1988); Flynn et al, Mol. Microbiol., 4:2111-2118 (1990); Walker et al, Infect. Immun., 60:4260-4268 (1992); Cardenas et al, Vacc., 11:126-135 (1993); Curtiss et al, Dev. Biol. Stand., 82:23-33 (1994); Simonet et al, Infect Immun., 62:863-867 (1994); Charbit et al, Vacc., 11:1221-1228 (1993); Turner et al, Infect Immun., 61:5374-5380 (1993); Schodel et al, Infect Immun., 62:1669-1676 (1994); Schodel et al, J. Immunol., 145:4317-4321 (1990); Stabel et al, Infect. Immun., 59:2941-2947 (1991); Brown, J. Infect Dis., 155:86-92 (1987); Doggett et al, Infect Immun., 61:1859-1866 (1993); Brett et al, Immunol., 80:306-312 (1993); Yang et al, J. Immunol., 145:2281-2285 (1990); Gao et al, Infect. Immun., 60:3780-3789 (1992); and Chatfield et al, Bio/Technology, 10:888-892 (1992)). Delivery of the foreign antigen to the host tissue using bacterial vector vaccines results in host immune responses against the foreign antigen, which provide protection against the pathogen from which the foreign antigen originates (Mims, The Pathogenesis of Infectious Disease, Academic Press, London (1987); and New Generation Vaccines: The Molecular Approach, supra). See also: Formal et al, Infect Immun., 34:746-751 (1981); Wick et al, Infect Immun., 62:4542-4548 (1994)); Hone et al, Vaccine, 9:810-816 (1991); Tacket et al, Infect Immun., 60:536-541 (1992); Hone et al, J. Clin. Invest, 90:412-420 (1992); Chatfield et al, Vaccine, 10:8-11 (1992); Tacket et al, Vaccine, 10:443-446 (1992); van Damme et al, Gastroenterol., 103:520-531 (1992) (*Yersinia pestis*), Noriega et al, Infect. Immun., 62:5168-5172 (1994) (*Shigella* spp), Levine et al, In: *Vibrio cholerae*, Molecular to Global Perspectives, Wachsmuth et al, Eds, ASM Press, Washington, D.C., pages 395-414 (1994) (*Vibrio cholerae*), Lagranderie et al, Vaccine, 11:1283-1290 (1993); Flynn, Cell. Molec. Biol., 40(Suppl.1):31-36 (1994) (*Mycobacterium* strain BCG), Schafer et al, J. Immunol., 149:53-59 (1992) (*Listeria monocytogenes*).

The bacteria are generally administered along with a pharmaceutically acceptable carrier and/or diluent. The particular pharmaceutically acceptable carrier and/or diluent employed is not critical to the present technology unless otherwise specific herein (or in a respective incorporated referenced relevant to the issue). Examples of diluents include a phosphate buffered saline, buffer for buffering against gastric acid in the stomach, such as citrate buffer (pH 7.0) containing sucrose, bicarbonate buffer (pH 7.0) alone (Levine et al, J. Clin. Invest., 79:888-902 (1987); and Black et al J. Infect Dis., 155:1260-1265 (1987)), or bicarbonate buffer (pH 7.0) containing ascorbic acid, lactose, and optionally aspartame (Levine et al, Lancet, II:467-470 (1988)). Examples of carriers include proteins, e.g., as found in skim milk, sugars, e.g., sucrose, or polyvinylpyrrolidone. Typically, these carriers would be used at a concentration of about 0.1-30% (w/v) but preferably at a range of 1-10% (w/v).

Set forth below are other pharmaceutically acceptable carriers or diluents which may be used for delivery specific routes. Any such carrier or diluent can be used for administration of the bacteria of the technology, so long as the bacteria are still capable of invading a target cell. In vitro or in vivo tests for invasiveness can be performed to determine appropriate diluents and carriers. The compositions of the technology can be formulated for a variety of types of administration, including systemic and topical or localized administration. Lyophilized forms are also included, so long as the bacteria are invasive upon contact with a target cell or upon administration to the subject. Techniques and formulations generally may be found in Remington's Pharmaceutical Sciences, Meade Publishing Co., Easton, Pa. For systemic administration, injection is preferred, including intramuscular, intravenous, intraperitoneal, and subcutaneous. For injection, the composition, e.g., bacteria, of the technology can be formulated in liquid solutions, preferably in physiologically compatible buffers such as Hank's solution or Ringer's solution.

For oral administration, the pharmaceutical compositions may take the form of, for example, tablets or capsules prepared by conventional means with pharmaceutically acceptable excipients such as binding agents (e.g., pregelatinized maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulfate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate.

Preparations for oral administration may be suitably formulated to give controlled release of the active compound. For buccal administration the compositions may take the form of tablets or lozenges formulated in conventional manner. For administration by inhalation, the pharmaceutical compositions for use according to the present technology are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin for use in an inhaler or insufflator may be formulated containing a powder mix of the composition, e.g., bacteria, and a suitable powder base such as lactose or starch.

The pharmaceutical compositions may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

The pharmaceutical compositions may also be formulated in rectal, intravaginal or intraurethral compositions such as suppositories or retention enemas, e.g., containing conventional suppository bases such as cocoa butter or other glycerides. See also U.S. Pat. No. 6,962,696.

The present technology provides a pharmaceutical composition comprising a pharmaceutically acceptable carrier and an attenuated tumor-targeted bacteria comprising one or more nucleic acid molecules encoding one or more primary effector molecules operably linked to one or more appropriate promoters. The present technology provides a pharmaceutical composition comprising a pharmaceutically acceptable carrier and an attenuated tumor-targeted bacteria comprising one or more nucleic acid molecules encoding one or more primary effector molecules and one or more secondary effector molecules operably linked to one or more appropriate promoters.

The present technology provides a pharmaceutical composition comprising a pharmaceutically acceptable carrier and a bacterium.

In a specific embodiment, the term “pharmaceutically acceptable” means approved by a regulatory agency of the Federal or a state government or listed in the U.S. Pharmacopeia or other generally recognized pharmacopeia for use in animals, and more particularly in humans. The term “carrier” refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil, olive oil, and the like. Saline is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in “Remington’s Pharmaceutical Sciences” by E. W. Martin. Such compositions will contain a therapeutically effective amount of the therapeutic attenuated tumor-targeted bacteria, in purified form, together with a suitable amount of carrier so as to provide the form for proper administration to the patient. The formulation should suit the mode of administration.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a suspending agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The amount of the pharmaceutical composition of the technology which will be effective in the treatment or prevention of a solid tumor cancer will depend on the nature of the cancer, and can be determined by standard clinical techniques. In addition, in vitro assays may optionally be employed to help identify optimal dosage ranges. The precise dose to be employed in the formulation will also depend on the route of administration, and the seriousness of the cancer, and should be decided according to the judgment of the practitioner and each patient’s circumstances. However, suitable dosage ranges are generally from about 1.0 CFU/kg to about $1\times10^{10}$ CFU/kg; optionally from about 1.0 CFU/kg to about $1\times10^{8}$ CFU/kg; optionally from about $1\times10^{2}$ CFU/kg to about $1\times10^{8}$ CFU/kg; optionally from about 1 $10^{4}$ CFU/kg to about $1\times10^{8}$ CFU/kg; and optionally from about $1\times10^{4}$ CFU/kg to about $1\times10^{10}$ CFU/kg. Effective doses may be extrapolated from dose-response curves derived from in vitro or animal model test systems.

Various delivery systems are known and can be used to administer a pharmaceutical composition of the present technology. Methods of introduction include but are not limited to intradermal, intramuscular, intraperitoneal, intravenous, subcutaneous, intrathecal, intranasal, epidural, and oral routes. Methods of introduction may also be intratumoral (e.g., by direct administration into the area of the tumor).

The compositions may be administered by any convenient route, for example by infusion or bolus injection, by absorption through epithelial or mucocutaneous linings (e.g., oral mucosa, rectal and intestinal-mucosa, etc.) and may be administered together with other biologically active agents. Administration can be systemic or local. In addition, it may be desirable to introduce the pharmaceutical compositions of the technology into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

In a specific embodiment, it may be desirable to administer the pharmaceutical compositions of the technology locally to the area in need of treatment; this may be achieved by, for example, and not by way of limitation, local infusion during surgery, by injection, by means of a catheter, or by means of an implant, said implant being of a porous, non-porous, or gelatinous material, including membranes, such as silastic membranes, or fibers. In one embodiment, administration can be by direct injection at the site (or former site) of a malignant tumor or neoplastic or pre-neoplastic tissue.

The attenuated tumor-targeted bacteria comprising one or more primary effector molecules and optionally, one or more secondary effector molecules may be delivered in a controlled release system. The attenuated tumor-targeted bacteria comprising one or more fusion proteins of the technology and optionally, one or more effector molecules may also be delivered in a controlled release system. In one embodiment, a pump may be used (see Langer, supra; Sefton, CRC Crit. Ref. Biomed. Eng. 14:201 (1987); Buchwald et al., 1980, Surgery 88:507; and Saudek et al., 1989, N. Engl. J. Med. 321:574). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, J. Macromol. Sci. Rev. Macromol. Chem: 23:61 (1983); see also Levy et al., 1985, Science 228:190; During et al., 1989, Ann. Neurol. 25:351; and Howard et al., 1989, J. Neurosurg. 71:105). In yet another embodiment, a controlled release system can be placed in proximity of the therapeutic target, i.e., the brain, thus requiring only a fraction of the systemic dose (see, e.g., Goodson, in Medical Applications of Controlled Release, supra, vol. 2, pp. 115-138 (1984)).

Other controlled release systems are discussed in the review by Langer (1990, Science 249:1527-1533) and may be used in connection with the administration of the attenuated tumor-targeted bacteria comprising one or more primary effector molecule(s) and optionally, one or more secondary effector molecule(s). Both chemical or biologic agents, and bacteria may be provided within controlled release systems.

The technology also provides a pharmaceutical pack or kit comprising one or more containers filled with one or more of the ingredients of the pharmaceutical compositions of the technology. Optionally associated with such container(s) can be a notice in the form prescribed by governmental agency regulating the manufacture, use or sale of pharmaceuticals or biological products, which notice reflects approval by the agency of manufacture, use or sale for human administration. Manufacture may include known methods (Collioud A, Rothen S A, Dietrih G, 2008. Developing and manufacturing attenuated live bacterial vaccines, BioPharm Inernational, Vol 2008, Supplement, Issue 6; Bajrovic et al., 2020, Novel technology for storage and distribution of live vaccines and other biological medicines at ambient temperature, Science Advances 2020:6:eaau4919). Typical manufacturing methods include growing the bacteria in a fermenter under controlled condition in medium containing casamino acids, yeast extract, mineral salts and an anti-foaming agent. The bacteria may be concentrated by centrifugation, diafiltered and stabilized with a solution containing ascorbic acid (an antioxidant), Hy-case SF (hydrolyzed casein; cryoprotectant), sodium chloride (a stabilizer), alternatively calcium and magnesium (stabilizers), and sucrose or trehalose (cryoprotectant).

The present technology also provides methods for treating a solid tumor comprising administering to a human or animal in need thereof, a pharmaceutical composition of the technology and at least one other known cancer therapy. In a specific embodiment, a human or animal with a solid tumor cancer is administered a pharmaceutical composition of the technology and at least one chemotherapeutic agent. Examples of chemotherapeutic agents include, but are not limited to, cisplatin, ifosfamide, taxanes such as taxol and paclitaxol, topoisomerase I inhibitors (e.g., CPT-11, topotecan, 9-AC, and GG-211), gemcitabine, vinorelbine, oxaliplatin, 5-fluorouracil (5-FU), leucovorin, vinorelbine, temodal, cytochalasin B, gramicidin D, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin homologs, and cytoxan.

The present technology includes the sequential or concomitant administration of pharmaceutical composition of the technology and an anti-cancer agent such as a chemotherapeutic agent. In a specific embodiment, the pharmaceutical composition of the technology is administered prior to (e.g., 2 hours, 6 hours, 12 hours, 1 day, 4 days, 6 days, 12 days, 14 days, 1 month or several months before) the administration of the anti-cancer agent. In another specific embodiment, the pharmaceutical composition of the technology is administered subsequent to (e.g., 2 hours, 6 hours, 12 hours, 1 day, 4 days, 6 days, 12 days, 14 days, 1 month or several months after) the administration of an anti-cancer agent. In a specific embodiment, the pharmaceutical composition of the technology is administered concomitantly with an anti-cancer agent. The technology encompasses combinations of anti-cancer agents and attenuated tumor-targeted bacteria engineered to express one or more nucleic acid molecules encoding one or more effector molecules and/or fusion proteins that are additive or synergistic.

The technology also encompasses combinations of anti-cancer agents and attenuated tumor-targeted bacteria engineered to express one or more nucleic acid molecules encoding one or more effector molecules and/or fusion proteins that have different sites of action. Such a combination provides an improved therapy based on the dual action of these therapeutics whether the combination is synergistic or additive. Thus, the novel combinational therapy of the present technology yields improved efficacy over either agent used as a single-agent therapy.

In one embodiment, an animal with a solid tumor cancer is administered a pharmaceutical composition of the technology and treated with radiation therapy (e.g., gamma radiation or x-ray radiation). In a specific embodiment, the technology provides a method to treat or prevent cancer that has shown to be refractory to radiation therapy. The pharmaceutical composition may be administered concurrently with radiation therapy. Alternatively, radiation therapy may be administered subsequent to administration of a pharmaceutical composition of the technology, preferably at least an hour, five hours, 12 hours, a day, a week, a month, more preferably several months (e.g., up to three months), subsequent to administration of a pharmaceutical composition.

The radiation therapy administered prior to, concurrently with, or subsequent to the administration of the pharmaceutical composition of the technology can be administered by any method known in the art Any radiation therapy protocol can be used depending upon the type of cancer to be treated. For example, but not by way of limitation, x-ray radiation can be administered; in particular, high-energy megavoltage (radiation of greater that 1 MeV energy) can be used for deep tumors, and electron beam and orthovoltage x-ray radiation can be used for skin cancers. Gamma ray emitting radioisotopes, such as radioactive isotopes of radium, cobalt and other elements may also be administered to expose tissues to radiation.

Additionally, the technology also provides methods of treatment of cancer with a pharmaceutical composition as an alternative to radiation therapy where the radiation therapy has proven or may prove too toxic, i.e., results in unacceptable or unbearable side effects, for the subject being treated.

The pharmaceutical compositions of the technology are preferably tested in vitro, and then in vivo for the desired therapeutic or prophylactic activity, prior to use in humans. For example, in vitro assays which can be used to determine whether administration of a specific pharmaceutical composition is indicated, include in vitro cell culture assays in which a patient tissue sample is grown in culture, and exposed to or otherwise administered a pharmaceutical composition, and the effect of such composition upon the tissue sample is observed.

Pharmaceutical compositions of the technology can be tested for their ability to augment activated immune cells by contacting immune cells with a test pharmaceutical composition or a control and determining the ability of the test pharmaceutical composition to modulate (e.g., increase) the biological activity of the immune cells. The ability of a test composition to modulate the biological activity of immune cells can be assessed by detecting the expression of cytokines or antigens, detecting the proliferation of immune cells, detecting the activation of signaling molecules, detecting the effector function of immune cells, or detecting the differentiation of immune cells. Techniques known to those of skill in the art can be used for measuring these activities. For example, cellular proliferation can be assayed by $^{3}$H-thymidine incorporation assays and trypan blue cell counts. Cytokine and antigen expression can be assayed, for example, by immunoassays including, but are not limited to, competitive and non-competitive assay systems using techniques such as western blots, immunohistochemistry radioimmunoassays (RIAs), ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A, immunoassays and FACS analysis. The activation of signaling molecules can be assayed, for example, by kinase assays and electromobility shift assays (EMSAs). The effector function of T-cells can be measured, for example, by a 51Cr-release assay (see, e.g., Palladino et al., 1987, Cancer Res. 47:5074-5079 and Blachere et al., 1993, J. Immunotherapy 14:352-356).

Pharmaceutical compositions of the technology can be tested for their ability to reduce tumor formation in animals suffering from cancer. Pharmaceutical compositions of the technology can also be tested for their ability to alleviate of one or more symptoms associated with a solid tumor cancer. Further, pharmaceutical compositions of the technology can be tested for their ability to increase the survival period of patients suffering from a solid tumor cancer. Techniques known to those of skill in the art can be used to analyze the function of the pharmaceutical compositions of the technology in animals.

In various specific embodiments, in vitro assays can be carried out with representative cells of cell types involved in a solid tumor cancer, to determine if a pharmaceutical composition of the technology has a desired effect upon such cell types.

Pharmaceutical compositions of the technology for use in therapy can be tested in suitable animal model systems prior to testing in humans, including but not limited to rats, mice, chicken, cows, monkeys, pigs, dogs, rabbits, etc. For in vivo testing, prior to administration to humans, any animal model system known in the art may be used.

DETAILED DESCRIPTION OF THE INVENTION

Figure 1A:
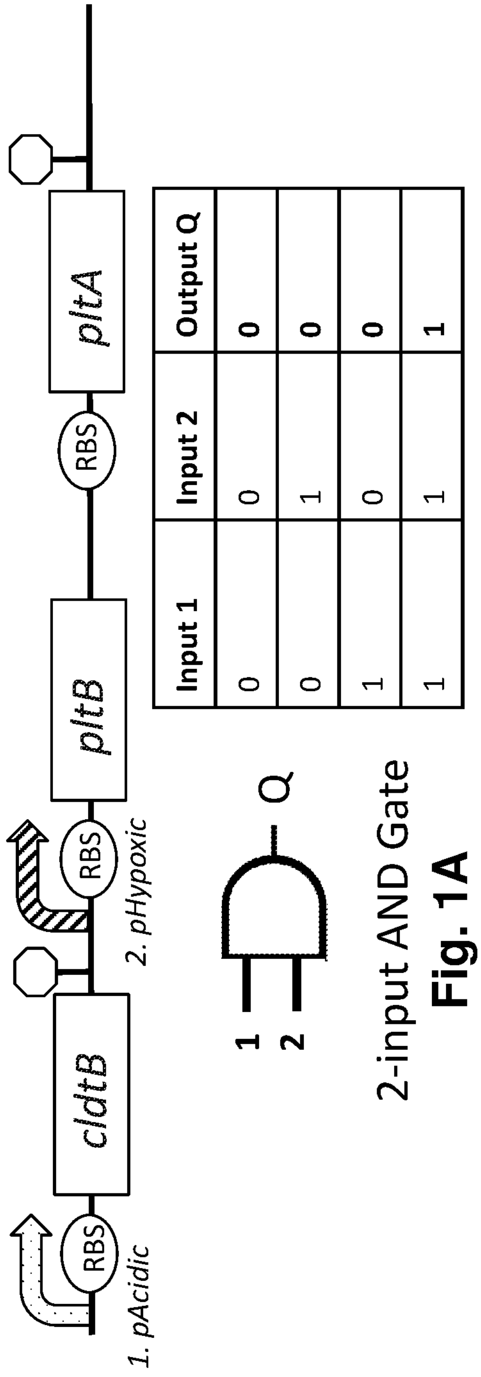
FIGS. 1A and 1B show two component and three component AND gates, respectively, for expression of multi-component therapeutics (e.g., typhoid cytolethal distending toxin).

The present technology provides, according to various embodiments, bacterial tumor-selective gene expression which may optionally be combined with non-tumorous tissue suppression. These bacteria may also be further enhanced in their blood circulation time, and express immunotherapeutic effectors and/or multifunctional immunotherapeutic cytotoxins with or without selective targeting moieties. The bacteria are also enhanced in their ability to deliver to tumor cells, tumor matrix and/or immune cells, and may have specific genetic backgrounds to enhance their immuno-oncology antitumor effects. These bacteria are improved in their tumor-selective pharmacokinetics, have improved ability to distribute systemically, persist longer within tumors, target tumors in multiple foci, targeted higher percentages of tumors, target tumors with increased numbers of bacteria, directly kill tumor cells and/or stimulate antitumor cell immune functions through gene expression, secretion, release or surface display of proteins, and thereby increase the antitumor immune response and have enhanced tumor cell killing that alone or in combination, and result in increased antitumor activity.

The present technology provides, according to various embodiments, improved live attenuated therapeutic bacterial strains that express one or more therapeutic molecules. The primary characteristic of the bacteria of certain embodiments of the technology are the improved targeting to tumors and reduced clearance from the blood (increased serum half-life) with enhanced antitumor activity through one or more anti-tumor mechanisms. In one embodiment, the percent increase in effect is approximately 2% to approximately 95%, approximately 2% to approximately 75%, approximately 2% to approximately 50%, approximately 2% to about 40%, approximately 2% to about 30%, approximately 2% to about 25%, approximately 2% to about 20% or about 2% to approximately 10% greater than the parental strain of bacteria without expressing one or more of the modifications described herein under the same conditions.

Bacterial Gene Expression and Promoters. Exemplary gene expression elements and therapeutic peptides that they express are shown in FIGS. 1A-13B.

An acetylsalicylic acid (aspirin)-inducible promoter in combination with one or more deletions in antibiotic resistance related efflux pumps (e.g., AcrAB; Baucheron et al., 2004, AcrAB-TolC directs efflux-mediated multidrug resistance in *Salmonella enterica* serovar typhimurium DT104, Antimicrob Agents Chemother 48: 3729-3735) is also encompassed based upon the *Salmonella* multiple antibiotic resistance operon (mar) promoter/operator regulon (Sulavik et al., 1997, The *Salmonella* typhimurium mar locus: molecular and genetic analyses and assessment of its role in virulence. J. Bacteriol. 179: 1857-1866; Barbosa and Levy, 2000 Differential expression of over 60 chromosomal genes in *Escherichia coli* by constitutive expression or MarA, J. Bacteriol 182: 3467-3474; Alekshun and Levy, 2004, The *Escherichia coli* mar locus-antibiotic resistance and more, ASM News 70: 451-456), Genbank accession number U54468.1 (which, by itself, does not confer antibiotic resistance). The regulon consists of the mar promoter/operator region, the MarR negative regulator, the MarA positive regulator, and the downstream start codon (ATG) that is used for expression of the gene(s) of interest, such as the monomeric or multimeric effectors described herein. Alternatively, use of the mar regulon also encompasses inducible expression of other anti-cancer proteins, protease inhibitors and targeted toxins and antitumor enzymes and/or genetically engineered phage and phagemids (Bermudes U.S. Pat. No. 8,524,220, Protease Inhibitor Protease sensitivity expression system composition and methods improving the therapeutic activity and specificity of proteins delivered by bacteria; U.S. Pat. No. 8,241,623, Protease Sensitivity Expression System; U.S. Pat. No. 8,623,350 Protease inhibitor: protease sensitivity expression system and method improving the therapeutic activity and specificity of proteins and phage and phagemids delivered by bacteria) or combinations with antivascular agents, such as platelet factor 4 and thrombospondin, alone or in combination (Bermudes et al., U.S. Pat. Nos. 6,962,696, 7,452,531 Compositions and Methods for Tumor-Targeted Delivery of Effector Molecules) and other anticancer agents (e.g., WO2009/126189, WO03/014380, WO/2005/018332, WO/2008/073148, US 2003/0059400 U.S. Pat. Nos. 7,452,531, 7,354,592, 6,962,696, 6,923,972, 6,863,894, 6,685,935, 6,475,482, 6,447,784, 6,190,657 and 6,080,849). The DNA containing the upstream regulon promoter/operator, the MarR and MarA genes and ending with the start codon (ATG; caps) to which may be fused as the initiating codon a gene or genes of interest is encompassed by SEQ ID NO: 069

```
cagtgtgcaagttaatatcctctacaacctataacctgtaattatcaatt
agttacaagttatcacagcacaataccccggacgcctittagcaaatcgt
ggcatcggccaattcatttagttgacttatacttgcctgggcaatagtat
ctgacgaaattaattacttgccggggcaaccattttgaaaagcaccagtg
atctgttcaATGaaatcattccgctgggtcgcttgatctacatggtaaat
cagaaaaaagatcgcctgttaaataactatttatccccgctggatatcac
cgcaacacagtttaaagtgctttgctcgatacgctgcgcgggatgtatta
ccccggttgaacttaaaaaagtgctgtctgtcgatctcggcgcattgacg
cggatgctcgaccgcctgctgtgcaaaggctggatcgaaagactgccgaa
tcctaatgacaaacgcggcgtactggtgaagctaacgccggacggcgcgg
caatttgtgagcaatgtcatcaacgaccagggcaagacctgcatcaggaa
ttaacaaaaaacttaacggcggacgaagtggcaacgcttgagtatttgct
caagaaaattctgccgtagacaaaaaagaggtATGacgatgtccagacgc
aacactgacgctattactattcatagcattttggactggatcgaggataa
cctggagtcgccgctctcactggaaaaagtgtctgagcgttcaggatatt
ccaaatggcacctgcaacggatgtttaaaaaagagaccggtcattcatta
ggccaatacatccgcagccgtaaaatgacggaaatcgcgcaaaaattaaa
agagagcaacgagcccattctctatctggcggaacgctatggctttgagt
cacagcaaacattgacccggacgttcaaaaactattttgatgtgccgcca
cacaaataccggatcaccaatatgcatggcgaatcacggtatatgctgcc
gctgaaccatggcaactactagtttgtttatgcgccacgcgaagagcacc
ATG
```

In another embodiment, the bp 1-209, with the ATG of MarR at 210-212 is used as the start codon. In a more preferred embodiment, the SEQ. ID NO: 003 bp 1-632, with the ATG of MarA at 633-635 is used as the start codon. Optionally, in any of the promoters described above, a bacterial termination sequence can be placed upstream of bp 1 (Peters et al., 2011 Bacterial transcriptional terminators: the RNA3' end chronical, J. Mol. Biol. 412: 793-813).

In another embodiment, promoters that are selectively activated within tumors are used alone or in combination with other promoters, including environmentally induced (e.g., hypoxic, acidic, ROS, SOX), exogenously induced (e.g., tet, salicylate, arabinose, DNA damage SOS), and may be optionally combined with normal tissue regulated promoters such as spleen and bile selective promoters that are inverted negatively regulate the expression and/or positively inhibit the growth and viability of the bacteria in normal tissues. See discussion of Arrach et al. (2008) supra.

The STM1787 promoter DNA of Flentie et al. (2012), is in general a "pTumor", or tumor-selective promoter. Other tumor activated ("pTumor") promoters include those of US2011/0195847 Table 2A, including but not limited to

STM1382-STM1383.

SEQ ID NO: 070

TGAAGCATACCTGATTTCTGGAAATAGCGTAGATCGGAACGAATAGTCTC

CTGGCTAACCTTATAAAGGTCTGAAAGTTTACTGACGCTAACACTATTAT

CCTTTATCAGTAAATTAATGATGGCATGACGTCTTTCTTCTTTAAACATA

TTGCCTCCGGGTAGTGAGTTGAATTGTATTTATGGCAATGTTGTCATGCG

GTGAATTCAATCACAGATTATGCGGTCACCGGAAGTAACCCCAAATGAAT

GTCAATAATCAGAAGCGCAGCCAATGTGTTAAATATTAATTGCTTACAGA

A hypoxic inducible promoter of Mengesha et al., 2006, Development of a flexible and potent hypoxia-inducible promoter for tumor-targeted gene expression in *Salmonella. Cancer Biology and Therapy* 5: 1120-1128), a "pHypoxic" is SEQ ID NO: 071

GGATAAAAGTGACCTGACGCAATATTTGTCTTTTCTTGCTTAATAATGTT

GTCA

An acid (low pH; "pAcidic") inducible promoter (Tucker et al., 2002, Gene expression profiling of the pH response in *Escherichia coli*, J Bacteriol 184: 6551-6558) GadA-RBS >BBa_K1231001 SEQ ID NO: 072 ctttcctgcacagtctgaacggggtgtacacgccgtatatgcaggataaa caataattaatttgatcgcccgaacagcaatgtttgggcgatttttatta cgataataaagtctgtttttaatattatcatgttaaatgtttatattata aaaagtcgtttttctgcttaggattttgttatttaaattaagcctgtaat gccttgcttccattgcggataaatcctactttttattgccttcaaataa atttaaggagttcg Transcriptional terminators, e.g., >BBa_B0004 SEQ ID NO: 073 cgccgaaaaccccgcttcggcggggttttgccgc, or >BBa_B0012 SEQ ID NO: 074 tcacactggctcacot-togggtgggcctttctgcgtttata, or double terminator, Part: BBa_B0015 (double terminator; B0010-B0012) SEQ ID NO: 075 Ccaggcatcaaataaaacgaaaggetcagtcgaaagactgggc-cittocgttttatctgitgtttgtcggtgaacgctctctactagagtcacactggetcac-citogggtgggcctitctgcgttt ata, are useful in the present technology.

A 5' untranslated (5'UT) region with a ribosomal binding site (RBS), e.g., SEQ ID NO: 076

ACCGTAGTTAAAGCACCTAACCGAGCTCggtaccAAAGGAGGTTGGCCC and the 5'UT deduced from US2011/0195847 PRL1-F1 SEQ ID NO: 077

TCGAGAGATCTCCATCGAATTCGTGGGTCGACCCCGGG*AGGCCT*AAAGA

GGAGAAATTAACT are also useful in the present technology.

pTet with TetR, Tet operator and 5' untranslated region with a ribosomal binding site SEQ ID NO: 078 ttaagacccactttcacatttaagttgtttttctaatccgcatatAatc aattcaaggccgaataagaaggctggctctgcaccttggtgatcaaata attcgatagcttgtcgtaataatggcggcatactatcagtagtaggtgt ttccctttcttctttagcgacttgatgctcttgatcttccaatacgcaa cctaaagtaaaatgccccacagcgctgagtgcatataatgcattctcta gtgaaaaaccttgttggcataaaaaggctaattgattttcgagagtttc atactgtttttctgtaggccgtgtacctaaatgtacttttgctccatcg cgatgacttagtaaagcacatctaaaacttttagcgttattacgtaaaa aatcttgccagctttccccttctaaagggcaaaagtgagtatggtgcct atctaacatctcaatggctaaggcgtcgagcaaagcccgcttattttt acatgccaatacaatgtaggctgctctacacctagcttctgggcgagtt tacgggttgttaaaccttcgattccgacctcattaagcagctctaatgc gctgttaatcactttacttttatctaatctcgacatcattaattCCTcA gcTtttg*tt*gacactctatcgttgatagagtta*tttt*accacTCCCTAT

CAGTGAT

AGAACCGTAGTTAAAGCACCTAACCGAGCTCggtac-cAAAGGAGGTTGGCCC, are also useful in the present technology.

An SOS (DNA damage, X-ray, alkylating agent) induced promoter, >BBa_K819017 sulA promoter SEQ ID NO: 079 cgaggctctttccgaaaatagggttgatctttgttgtcactggatgtaccgtacatc-catacggtaactcacaggggctgg Spleen activated ("pSpleen") promoters include those of US2011/0195847 Table 4, including but not limited to yaaJ. SEQ ID NO: 080

GTATTTCGTTAATAAAACTGAAAAACTCAGGCATTAACGTCCCTCTTGT

TGATGCCGGCACGCTTTGATAATCCTGTATAAGCGTGACCCATGATGTA

GATGACCTTGTCAGACTAATATTAACGGCAGTTTACCATAAATACGGTG

GTATCCTTTAATTGCGCATCAACCGTCGGCAGATACGCAAACAGTGCAC

AAGGGCAGCCAGGTGCATGTAGGCGGTTGCGCTGTGAGTGCGTCGTGTT

ATCATCAGGGTAGACCGGTTACATCCCCTAACAAGCTGTTTAAAGAGAA

ACTCTAT pSpleen promoters include those of US2011/0195847 Table 4, including but not limited to talB. SEQ ID NO: 081

TGCGAATAAACGGATGCCTGAACAGGCAGGGACGCCGGAAAACGTCGAA

ATACGTTAGACCATTCGCCCGTGTTCCCGCTTTCCCCACCGCGCTGTCC

GCTTACATGAGGTTACACTCATCGACATTTCTCTGAACAGCGGCTCAAC

ATTTCCCGGAAAAAAACATATCGCAGGGCATTTATCCTTATGATTAGGT

ATAAATGATGAGGTATAAGGAACAGGAGTCTGTAATGAAACCAATACCT

TTTTATTTGCTCGCGCTATTTTCTGCCGCCTCCGGGGCTACGGAGATAA

ACGTCTG

Spleen activated ("pSpleen") promoters include those of US2011/0195847 Table 4, including but not limited to aroM. SEQ ID NO: 082

TCAAGGCGCGGACGTCATTATGCTGGATTGTCTGGGTTTTCATCAGCGT

CATCGGGATATTTTACAGCAGGCGCTGGATGTGCCGGTTTTACTCTCTA

ACGTTTTGATTGCGCGGTTAGCTTCAGAACTGCTTGTCTAATTTTACGT

GACAGGCCGAACGTCAGGACTCTATATTGGGTGTTAATTTAATAATGAG

ACGGGGCCTGATTATGCTACAAAGCAATGAATACTTTTCCGGGAAAGTT

AAGTCTATTGGATTTACCAGCAGTAGCACCGGCCGGGCCAGCGTTGGTG

TGATGGC pSpleen promoters include those of US2011/0195847 Table 4, including but not limited to tonB. SEQ ID NO: 083

GTTCGCCGTCCATTTTTACCTCTGGGGCTGTTTCTTAGCGCGCCCTCCC

CCGGAAAAACAAAATATAATGAACAAAAAACATACAAACCATCATCTTT

TAAAAATAAATTACATTAAAACAGAGAGTTACAACATGATGATGATGCA

TGAAAAATCAAAAATGCGCCAAATCCCGCGCCGCTGCCGCCCCGTGGCA

GGCCGCCCCGCCGGGAGTACCTTTTTAAAATGCGAACAATTATCAACAA

CTACCACTTAATGATTATTTATTTCATTTTGCGATATTGATTATCATTT

TCAATAA

φX174E lysis protein gene ("Lysis"), BBa_K2685005 SEQ ID NO: 084 atggttcgttggaccctgtgggacaccctggctttcctgctgctgctgt ctctgctgctgccgtctctgctgatcatgttcatcccgtctaccttcaa acgtccggtttcttcttggaaagctctgaacctgcgtaaaaccctgctg atggcttcttctgttcgtctgaaaccgctgaactgctctcgtctgccgt gcgtttacgctcaggaaaccctgaccttcctgctgacccagaaaaaaac ctgcgttaaaaactacgttcgtaaagaataa The lac promoter ("pLac") BBa_K389050 sequence, consisting of the p(Lac) IQ promoter 114032, RBS B0034, LacI C0012, double stop B0010, and LacI regulated promoter R0010: SEQ ID NO: 085 tggtgcaaaacctttcgcggtatggcatgatagcgcctactagagaaag aggagaaatactagatggtgaatgtgaaaccagtaacgttatacgatgt -continued cgcagagtatgccggtgtctcttatcagaccgtttcccgcgtggtgaac caggccagccacgtttctgcgaaaacgcgggaaaaagtggaagcggcgat ggcggagctgaattacattcccaaccgcgtggcacaacaactggcgggc aaacagtcgttgctgattggcgttgccacctccagtctggccctgcacg cgccgtcgcaaattgtcgcggcgattaaatctcgcgccgatcaactggg tgccagcgtggtggtgtcgatggtagaacgaagcggcgtcgaagcctgt aaagcggcggtgcacaatcttctcgcgcaacgcgtcagtgggctgatca ttaactatccgctggatgaccaggatgccattgctgtggaagctgcctg cactaatgttccggcgttatttcttgatgtctctgaccagacacccatc aacagtattattttctcccatgaagacggtacgcgactgggcgtggagc atctggtcgcattgggtcaccagcaaatcgcgctgttagcgggcccatt aagttctgtctcggcgcgtctgcgtctggctggctggcataaatatctc actcgcaatcaaattcagccgatagcggaacgggaaggcgactggagtg ccatgtccggttttcaacaaaccatgcaaatgctgaatgagggcatcgt tcccactgcgatgctggttgccaacgatcagatggcgctgggcgcaatg cgcgccattaccgagtccgggctgcgcgttggtgcggatatctcggtag tgggatacgacgataccgaagacagctcatgttatatcccgccgttaac caccatcaaacaggattttcgcctgctggggcaaaccagcgtggaccgc ttgctgcaactctctcagggccaggcggtgaagggcaatcagctgttgc ccgtctcactggtgaaaagaaaaaccaccctggcgcccaatacgcaaac cgcctctccccgcgcgttggccgattcattaatgcagctggcacgacag gtttcccgactggaaagcgggcaggctgcaaacgacgaaaactacgctt tagtagcttaataactctgatagtgctagtgtagatctctactagagcc aggcatcaaataaaacgaaaggctcagtcgaaagactgggcctttcgtt ttatctgttgtttgtcggtgaacgctctctactagagccaggcatcaaa taaaacgaaaggctcagtcgaaagactgggcctttcgttttatctgttg tttgtcggtgaacgctctctactagagcaatacgcaaaccgcctctccc cgcgcgttggccgattcattaatgcagctggcacgacaggtttcccgac tggaaagcgggcagtgagcgcaacgcaattaatgtgagttagctcactc attaggcaccccaggctttacactttatgcttccggctcgtatgttgtg tggaattgtgagcggataacaatttcacaca A bile salt (normal gut) sensing promoter ("pBile") >BBa_K318514 Part-only sequence SEQ ID NO: 086 ttatcaggggggagccgttgaccgtcgacgcgcgcagcgtcggacacaat tgatacatctccagcaggatcgtgacgtaggcgcgagcttcttttttta aatcaaacgattgcggagcaaataaccagttttccatgagccctgaaat aaagctgcgcatcagtatcgccgcacgacgggtcagcagattttcaggc agcattttagcattaatacaatgttttaacgtttgttcaatccgatcgt aactttccagacaaaggctacgttgcgcctgttgaaccacaaccatttc tccgacaaactcacatttatggaatataatctccatcaataagcggcgt -continued cgtcttctgttacagtagcttcaagaatatgaactaaaatttctcttaa tacagatagtggatcgtcggggaattttgcctgatactcaatctcaagc tcaccaatattggattctgatagctcccagatctcactgaataaatccg acttatttttgaaatgccaatagattgcgccgcgcgtcacgccagcagc gttcgcaatctccgccagcgaggttgccgatacgccttgctgcgagaac aaacgcagggccacatccaggatgtgttgtcgtgtctccagcgcttgtt gtttggtttttcgtgccatatgtcggtgaatttacaggcgttagattta catacatttatggatgtatgtaccatagcacgacgataatataaacgca gcaatgggtttaaggacctttgaccattgaccaatttgaaatcggacac tcgaggtttacatatgaacaaaaacagagggttaacgcctctggcggtc g A constitutive (pConstitutive) promoter BBa_J23105: SEQ ID NO: 087 tttacggctagctcagtcctaggtactatgctagc The growth inhibitory gene sulA *Salmonella* amino acids SEQ ID NO: 088

MYTSGYANRSSSFPTTTHNAARTATENAAAGLVSEVVYHEDQPMMAQLL

LLPLLRQLGQQSRWQLWLTPQQKLSREWVQSSGLPLTKVMQISQLAPRH

TLESMIRALRTGNYSWIGWMTEELTEEEHASLVEAAKVGNAVGFIMRPV

RAHALPRRQHSGLKIHSNLYH

*Salmonella sulA* nucleotides SEQ ID NO: 089 atgtacacttcaggctatgcacatcgttcttcgtcgttctcatccgcag caagtaaaattgcgcgtgtctctacggaaaacactacagccgggcttat cagtgaagttgtctatcgcgaagatcagcccatgatgacgcaacttcta ctgttgccattgttacagcaactcggtcagcaatcgcgctggcaactct ggttaacaccgcaacaaaaactgagtcgggaatgggttcaggcatctgg gctacccttaacgaaagtaatgcagattagccagctctccccttgccac actgtggagtcaatggttcgcgctttacgcacgggcaattacagtgtgg tgatcggttggttggcagatgatttgactgaagaagagcatgctgaact tgttgatgcggcaaatgaaggtaacgctatggggtttattatgcgtccg gtaagcgcatcctctcacgccacgagacaactitccgggctaaaaattc actctaatttgtatcat Table 2. Bacterial growth inhibitory genes and/or proteins useful in the technology.

sulA SEQ ID NO: 089.

SulA SEQ ID NO: 088.

MinC

SEQ ID NO: 090

MSNTPIELKGSSFTLSWHLHEAEPEVIRQALEDKIAQAPAFLKHAPWIN
VSGLESPVNWPELHKIVTSTGLRIIGVSGCKDASLKVEIDRMGLPLLTE
GKEKAVRPAPVEPATPSEPPQNANPITKTRLIDVPVRSGQRIYAPQCDL
IVTSHVSAGAELIADGNIHVYGMMRGRALAGASGDREAQIFCTHLTAEL
VSIAGVYWLSDKIPAEFYGKAARLRLADNALTVQPLN

-continued

MinD

SEQ ID NO: 091

MARIIVVTSGKGGVGKTTSSAAIATGLAQKGKKTWVIDFDIGLRNLDLI
MGCERRWVYDFVNVIQGDATLNQALIKDKRTENLFILPASQTRDKDALT
REGVAKVLDSLKAMDFEFIVCDSPAGIETGALMALYFADEAIITTNPEV
SSVRDSDRILGILASKSRRAENGEEPIKEHLLLTRYNPGRVNKGDMLSM
EDVLEILRIKLVGVIPEDQSVLRASNQGEPVILDATADAGKAYADTVDR
LLGEERPFRFIEEEKKGFLKRLFGG

DicF encoding an antisense RNA

SEQ ID NO: 092 gaggacgcgataatgaaaacgttattaccaaacgttaatacgtctgaag
gttgttttgaaattggtgtcactatcagtaacccagtatttactgaaga
tgccattaacaagagaaaacaagaacgggagctattaaataaaatatgc
attgtttcaatgctggctcgtttacgtctgatgccaaaaggatgtgcac
aatga Salmonella P22 phage kil

SEQ ID NO: 093

MTIVPVNGTILVQQGNREFNKLYEASFPDTKEGNSAAYAWASSIAMGWE
DCQDEDWNRNHAA

Salmonella ST64T phage the cell division inhibitor kil

SEQ ID NO: 132

MDKSLMAIQSKFAIAVYLGDKIMYREAVEAFREWRLK

Enterobacteria phage UAB_Phi20

SEQ ID NO: 149

MSMKIGEHMKPVIELLEELNGNDTDAKLKLLALVISEYMLNADVTGFEV
SAGRMKVAVDISVED lamda kil

SEQ ID NO: 094

MPLQGGLLLAALPNLYLNESPVNYVTDGNALSTYLISQESQRMDQTLMA
IQTKFTIATFIGDEKMFREAVDAYKKWILILKLRSSKSI

Multispecies: host cell division inhibitory peptide Kil

SEQ ID NO: 095

MPLQGGLLLAALPNLYLNESPVNYVTDGNALSTYLISQESQRMDQTLMA
IQTKFTIATFIGDEKMFREAVDAYKKWILILKLRSSKSIH phage Mu cell division inhibitor gp5

SEQ ID NO: 096

MARNIKMATDAQNWLQARGSHVNESYLGVARPILEITYPPVELVKNAVR
IMEHKSGVARSVWTARLNGCQIIWR phage Rac cell division inhibitor KilR

SEQ ID NO: 097

MIAHHFGTDEIPRQCVTPGDYVLHEGRTYIASANNIKKRKLYIRNLTTK
TCITDCMIKVFLGRDGLPVKAESW

Salmonella (NCBI: EBU7160853)

SEQ ID NO: 098

MKHQHYGTMEVIRQCAVPGTMVKYNDRIYKATANTRGKLTLTNIRENIT

GenBank: ABF14997.1

SEQ ID NO: 186

TMEVIRQCAVPGTMVKYNDRIYKATANTRGKLTLTNIRENITIRDLVIE
IYLDGKGEPLTN

GenBank: EBY8247551.1

SEQ ID NO: 099

TMEVIRQCAVPGTMVKYNDRIYKATANTRGKLTLTNIRENITIRDLVIE
IYLDGKGEPLTNMKHQHYGTMEVIRQCAVPGTMVKYNDRIYKATANTRG
KLTLTNIRENITIRDLVIEIYLDGKG

GenBank: EBK1720184.1

SEQ ID NO: 100

MKHQHYGTMKVIRQCAVPGTMVKYNDRIYKATANTRGKLTLTNIRENIT
IRDLVIEIYLDGKGEPLTN

GenBank AKG31181.1

SEQ ID NO: 101

MQNTLTVIRQCVTPGMLVIHHGKPWRAAVNKDGKLHIHTLTEAKPLKDL
LVDIVLNHKNEPEII

-continued

```
GenBank: EBH8280910.1
                                             SEQ ID NO: 102
MKHQHYGTMEVIRQCAVPGTMVKYNDRIYKATANTRGKLTLTNIRENIT
IRDLVIEFYLDGKGEPLTN

GenBank: AHX77645.1
                                             SEQ ID NO: 103
MKHQHYGTMEVIRQCAVPGTMVKYNDRIYKATANTRGKLTLTNIRENIT
IRDLVIEIYLDGKGEPLTN

GenBank: CQB84553.1
                                             SEQ ID NO: 104
MKHQHYGTMEVIRQCAVPGTMVKYNDRIYKATANTRGKLTLTNIRENIT
IRDLVIEIYLDGKGEPLSN

GenBank: ECM3647222.1
                                             SEQ ID NO: 105
MKHQHYGTMEVIRQCAVPGTMVKYNDRIYKATANTRGKLTLTNIRENIT
IRDLVIEIYLDDKGEPLTN

GenBank: ECH8747869.1
                                             SEQ ID NO: 106
MKHQHYGTMEVIRQCAVPGTMVKYNDRIYKATANTKGKLTLTNIRENIT
IRDLVIEIYLDKGEPLTN

GenBank: ECM8575082.1
                                             SEQ ID NO: 107
EIPRQCITPGDYVIHDGRTYIASANNIKKRRLYIRDLTTQRCITDCMVK
VWLNRNGLPAKAESW

GenBank: EBU6838365.1
                                             SEQ ID NO: 108
MIAHHFGTDEIPRQCITPGDYVIHDGRTYIASANHIKKRRLYIRDLTTQ
RCITDCMVKVWLNRNGLPAKAESW

zinc sigma-54-dependent two-component system
Response regulator, GenBank: AUC49429.1
SEQ ID NO: 109
MIAHHFGTDEIPRQCITPGDYVIHDGRTYIASANNIKKRRLYIRDLTTQ
V

GenBank: EBB4754385.1
                                             SEQ ID NO: 110
MIAHHFGTDEIPRQCVTPGDYVLHEGRTYIASANNIKKRKLYIRSLTTK
TCISDCMIKVFLGRDGLPVKAESW
```

Tumor-selective genetic circuits, including but not limited to AND gates, OR gates, NOR gates and NAND gates, may be used for production of monomeric toxins, production of multimeric toxins, production of therapeutic RNA molecules and/or production of therapeutic DNA molecules, production of metabolites, catabolites, anabolites (e.g., lipidA). The gene circuits may be a known gene circuits, such as synchronized quorum genetic clocks (Danino et al., Nature 463: 326-330; Din et al., Nature 536: 81-85) or Chien et al., Multiplexed biosensors for precision bacteria tropism in vivo, bioRxiv doi: dx.doi.org/10.1101/851311, Hasty et al. (Engineered bacteria for production and release of therapeutics US Patent Application 20180148729), Falb et al., Microorganisms programmed to produce immune 15 modulators and anti-cancer therapeutics in tumor cells, US Patent Application 2019/0336544; Engstrom and Pfleger 2017, Transcription control engineering and applications in synthetic Biology, Synthetic and Systems Biotechnology 2: 176-191; (Deadman And Passcode Microbial Kill Switches US 20190040398), Bhatia and Danino, Programmable drug delivery profiles of tumor-targeted bacteria, U.S. Pat. No. 9,994,809, as modified herein.

Figure 1B:
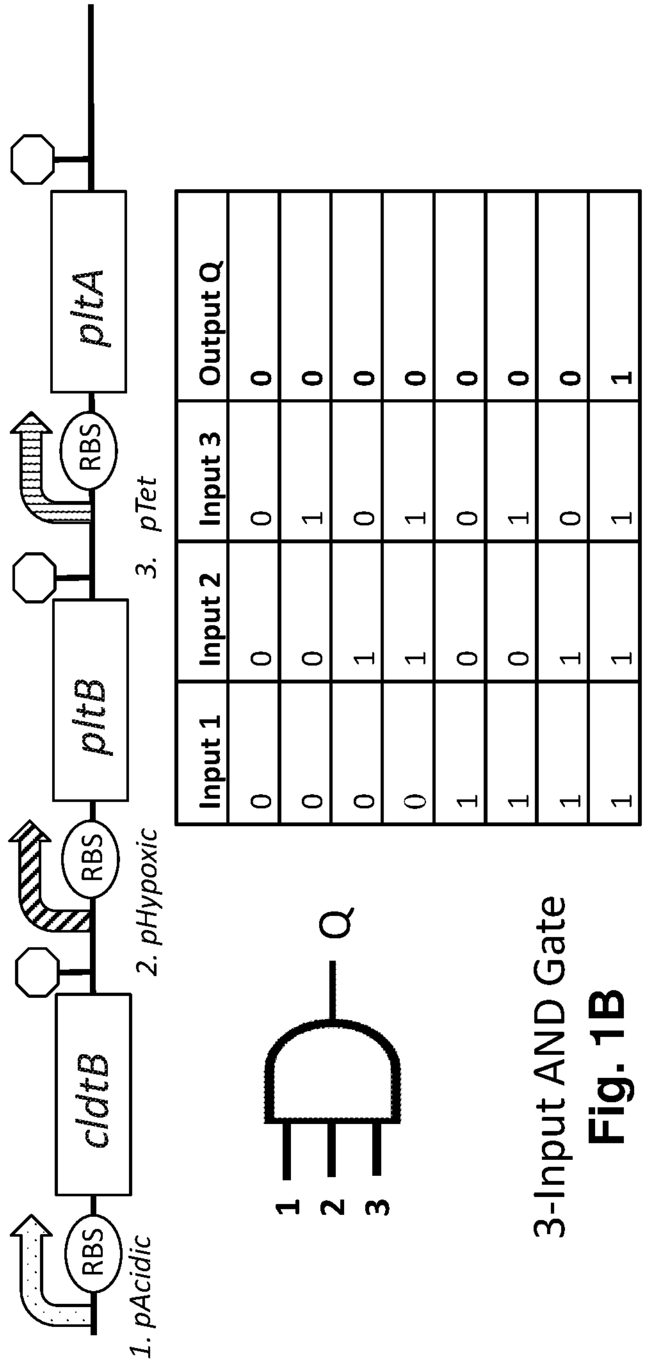

AND Gates: Expression circuit combinations consisting of multicomponent objects consisting of therapeutic toxins, artificially "split" toxins, multi-component "toxin enhancers" (i.e., toxin+enhancer), and nucleic acid delivery constructs independently expressed by multiple bacterial promoters, e.g., hypoxic, acidic, tumor specific, ROS induced, exogenously inducible (e.g., tetracycline, arabinose, salicylate, x-ray/RecA and LexA system) and others to independently drive the expression of a gene, which dependently, in combination, comprise the whole functional component, or enhanced component, such as a therapeutic molecule, biosensor or imaging agent (e.g., lux, of fluorescent protein; FIGS. 1A and 1B).

Figure 2A:
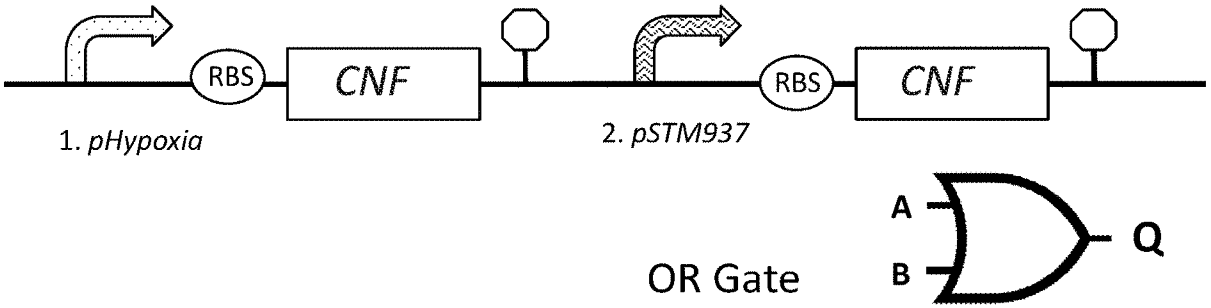
FIGS. 2A and 2B show OR gates and NOT gates, respectively.
Figure 2B:
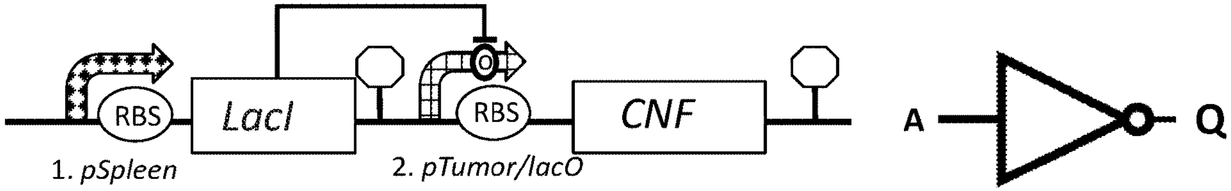

OR and NOT gates, by which expression circuits consist of multiple copies of the objects, single gene or polycistronic, with different single or independent promoters independently expressed by multiple bacterial promoters, e.g., hypoxic, acidic, tumor specific, ROS induced, exogenously inducible (e.g., tetracycline, arabinose, salicylate, x-ray/RecA and LexA system) and/or eukaryotic promoters (e.g., tumor-selective promoters and/or exogenously inducible promoters) or dual bacterial/eukaryotic promoters (examples or description), and others to singly (polycistronic) or independently drive the expression of a gene, which dependently or independently, alone or in combination, comprise the whole functional component, or enhanced component, such as a therapeutic molecule, biosensor or imaging agent (FIGS. 2A-2B).

A NOT gate uses positive expression to drive a repressor (an inverter system), that shuts down expression (FIG. 2B).

Figure 3:
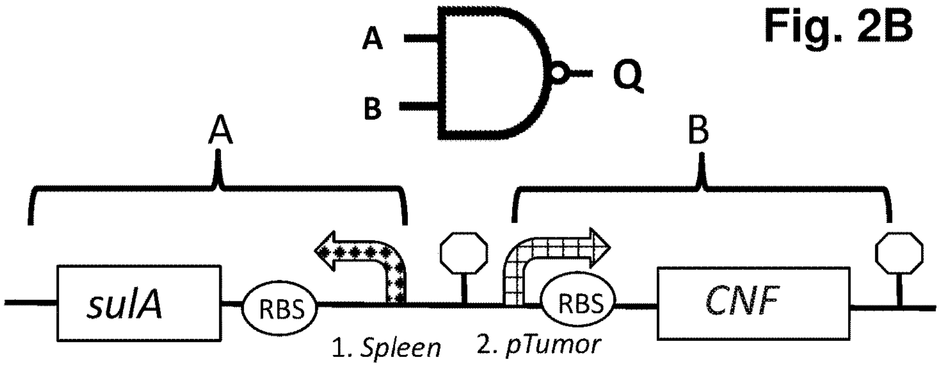
FIG. 3 shows two simple independent circuits (A & B) that collectively act as a NOT AND Gate.

Two simple independent circuits act together to collectively promote selective expression within tumors. Within normal tissue, such as spleen, growth, and therefore gene expression, is limited through expression of the SulA growth inhibitor. SulA does not result in cell death, and therefore allow the bacteria to survive, and if relocated within a tumor, to resume growth. The second simple circuit promotes expression within the tumor. Alternatively to SulA, a lysis, or bactericidal toxin may be expressed. Co-existence of the two circuits within the same organism collectively enhances tumor-selective expression (FIG. 3). The two-circuit system shown in FIG. 3 can be further combined with the two component and three component AND gates shown in FIGS. 1A-1B, such as for cytolethal distending toxin.

Figure 4A:
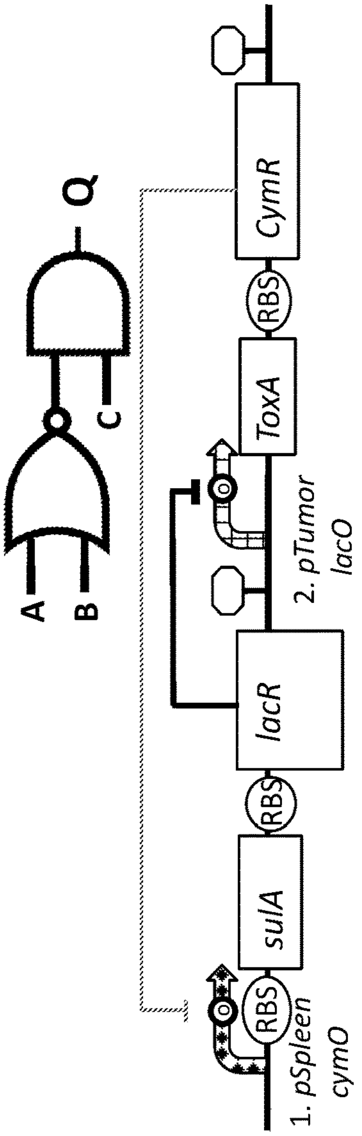
FIGS. 4A and 4B show NOT AND and NOR AND gates, respectively.
Figure 4B:
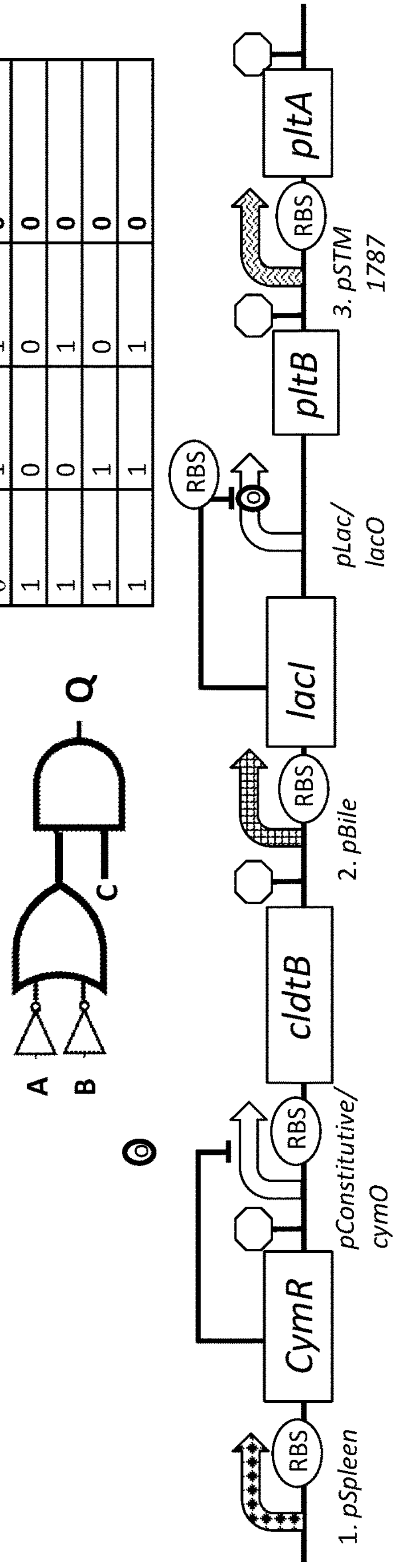

NOR gates, by which expression occurs Not in normal tissues (e.g., spleen) OR other normal OR bile induced, i.e., such that it is positive expression only with both are not present and that either one turns it off (FIG. 4B). NOT AND (FIG. 4A) and NOR AND (FIG. 4B), function not in normal tissue (inverter for one component normal tissue) and one or two ANDs, e.g., hypoxic and acidic (a 2-input AND gate plus a NOT gate) for expression of a three component toxin, such as CLDT.

Figure 5A:
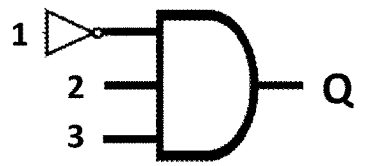
FIG. 5A shows a logical equivalent and logic chart of a NOT (1 negative) AND (2 positive input) gate.
Figure 5B:
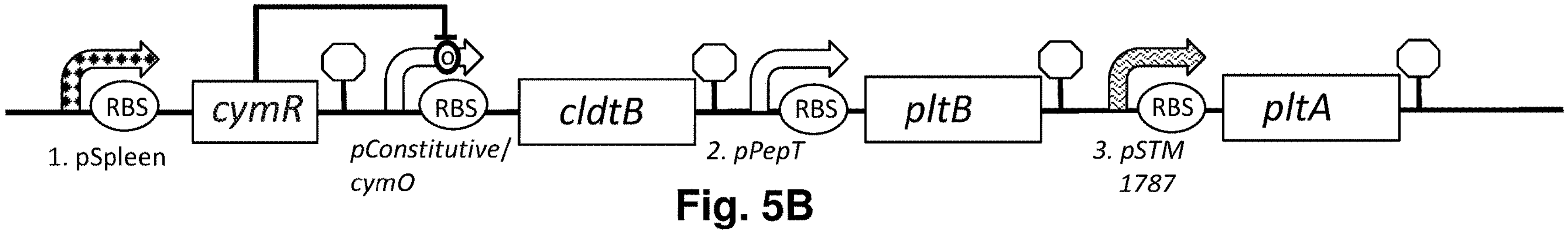
FIGS. 5B and 5C show alternate implementations of the NOT AND logic circuit.
Figure 5C:
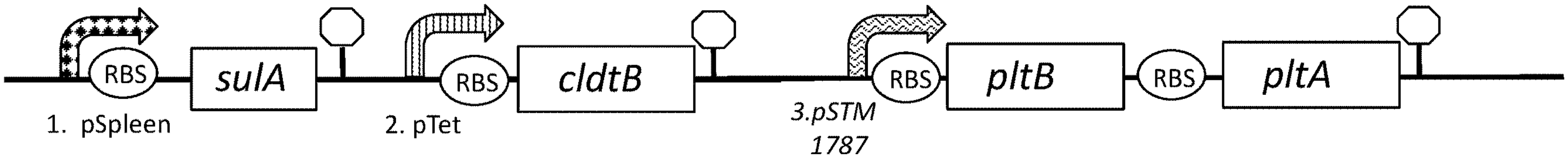

NOT AND can also function with two negative regulatory elements (FIGS. 5A-5C).

Figure 6A:
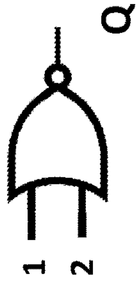
FIG. 6A shows a logical equivalent and logic chart and logic chart of a NOR gate.
Figure 7A:
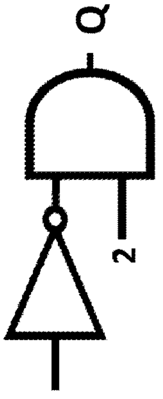
FIG. 7A shows a logical equivalent and logic chart and logic chart of a NOT AND gate (one input negative, one input positive).
Figure 6B:
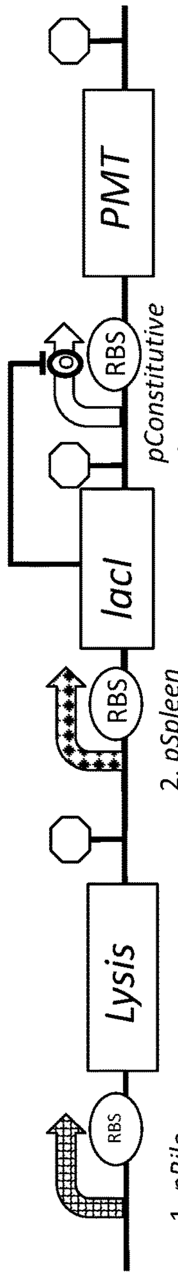
FIGS. 6B and 6C show alternate implementations of the NOR logic circuit.
Figure 6C:
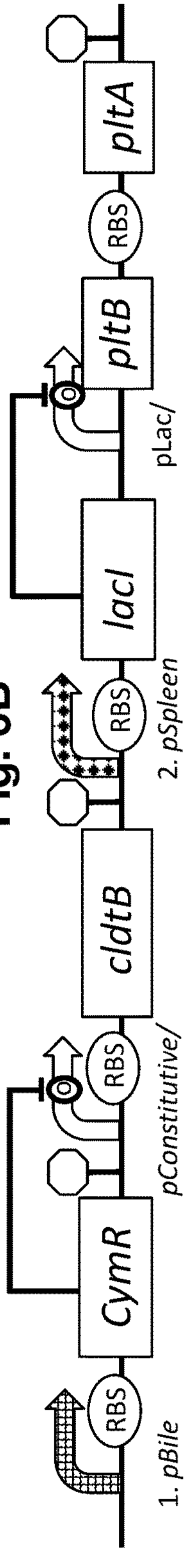
Figure 7B:
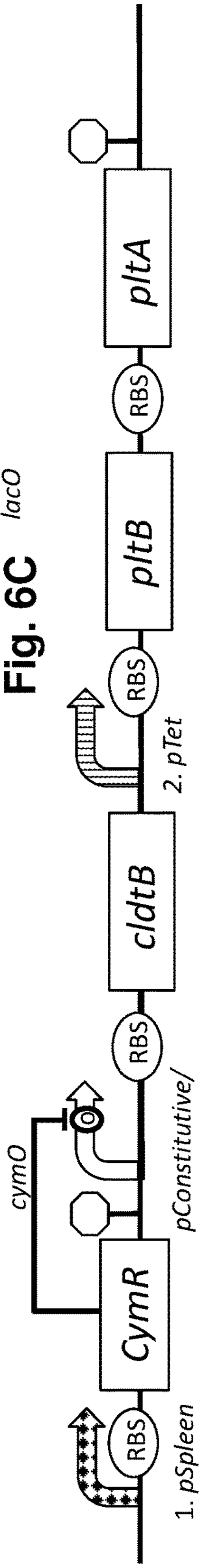
FIGS. 7B and 7C show alternate implementations of the NOT AND logic circuit.
Figure 7C:
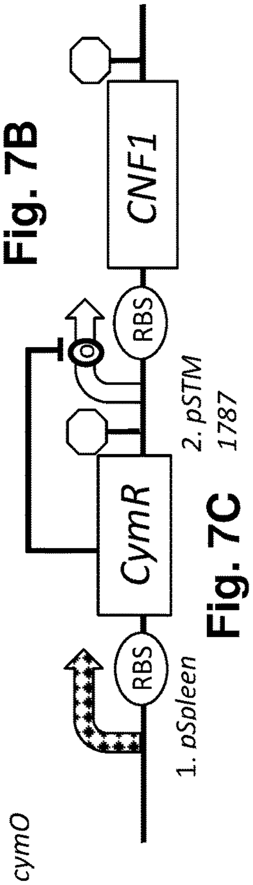

NOT OR (NOR) Gates are shown in FIGS. 6A-6C. Two promoters with expression associated with normal tissue (e.g., pBile and pSpleen) are used to negatively regulate expression of a therapeutic protein such as PMT (or with multiple RBSs, a multimeric protein such as typhoid cldtB pltAB). Alternatively, a promoter such as pBile is used to drive a repressor of an otherwise constitutive promoter, and results in repression of a first monomer (CldtB) in normal tissue, while a second normal tissue promoter (pSpleen) results in repression of the other cytolethal distending toxin components. Therapeutic protein expression occurs when there are no repressors expressed. Additional NOT AND gates are shown in FIGS. 7A-7C.

Quorum Sensing Regulated Gene Expression. Application of quorum sensing may allow for the expression of therapeutic genes to occur simultaneously, sequentially, or alternating (repeated). As a component of the present technology, quorum sensing may be combined with other promoter systems, such as tumor-selective, and negatively regulated for normal tissues and/or normal environments such as the gut. The present technology incorporates artificial gene circuits is being applied to bacterial delivery systems (Prindle et al., 2012 Genetic circuits in *Salmonella typhimurium. ACS Synthetic Biology* 1: 458-464) that utilizes concentration-dependent induction by an autoinducer produced by the bacteria in combination with the other promoter types. These known quorum sensing circuits include controlled bacterial invasion of host cells (Anderson et al., 2006 Environmentally controlled invasion of cancer cells by engineered bacteria. *Journal of Molecular Biology* 355: 619-627.), tumor-localized expression (Swofford et al., 2015 Quorum-sensing *Salmonella* selectively trigger protein expression within tumors. *Proceedings of the National Academy of Sciences USA* 112: 3457-3462.; Din et al., 2016 Synchronized cycles of bacterial lysis for in vivo delivery. *Nature* 536: 81-85.), and synchronized tumor-localized lysis combined with expression (Din et al., 2016). Coupling the therapeutic protein expression (HlyE; Ryan et al., 2009 Bacterial delivery of a novel cytolysin to hypoxic areas of solid tumors. *Gene Therapy* 16:329-339) with the φX174 gene E results in oscillatory expression of the effector gene, on a cyclical basis (Din et al., 2016).

Examples of reporter genes include but are not limited to bioluminescence operons, such as that from *Photorhabdus luminescences* luxCDABE which encode the fatty acid reductase complex and the bacterial luciferase, and split GFPs, including biomolecular and trimolecular complementation (biFC and tnFC using oligomerization including but not limited to that provided by TDP-43; Foglieni et al., 2017 Split GFP technologies to structurally characterize and quantify functional biomolecular interactions of FTD-related proteins, Scientific Reports 7, Article number: 14013 (2017)).

Figures 8A, 8B, 8C, 8D:
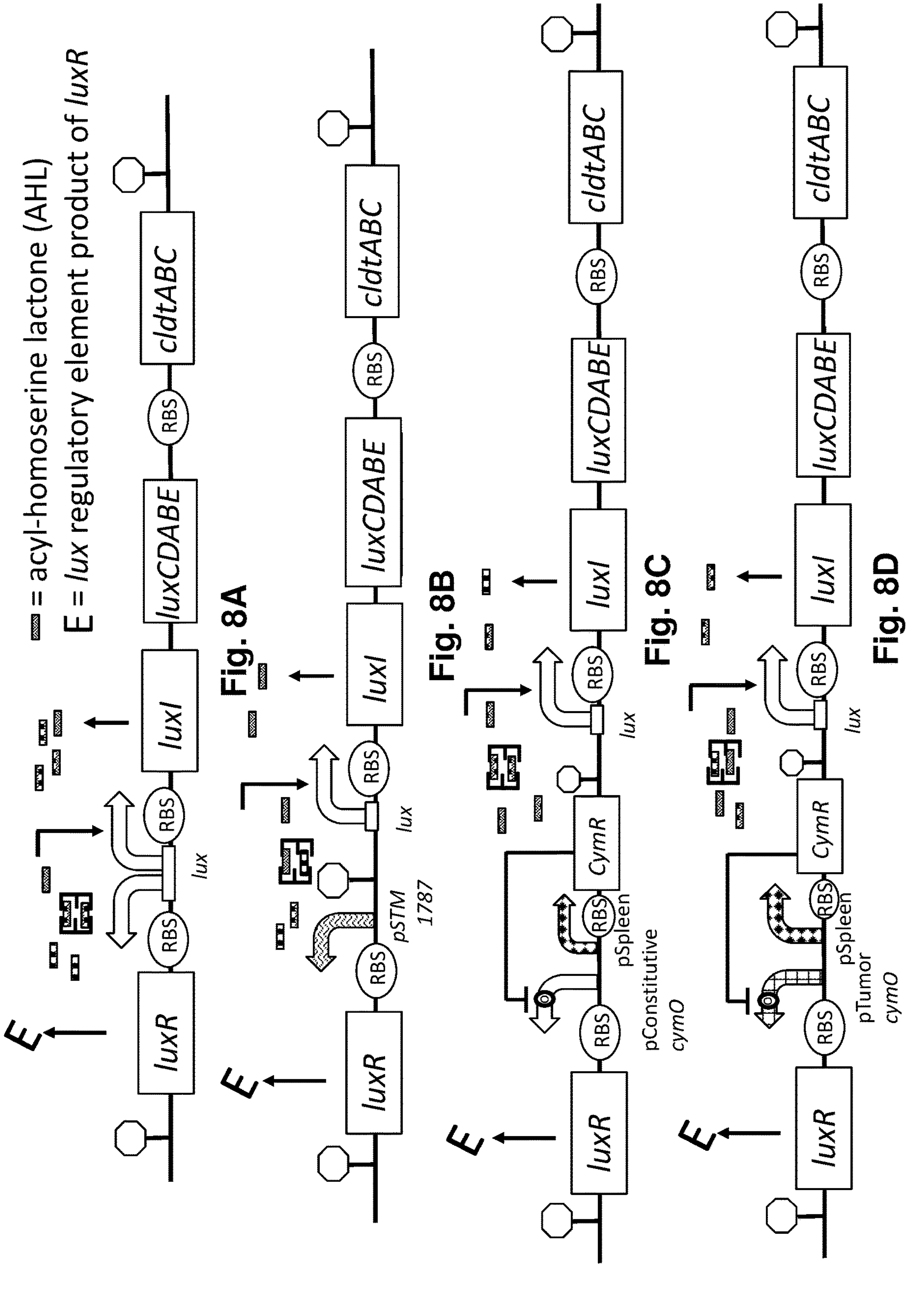
FIGS. 8A-8D show modified quorum sensing lux operons.

The present technology provides modified and alternative genetic regulatory circuits for the expression of therapeutic genes by bacteria, including tumor-specific density dependence and normal tissue density independence (FIGS. 8A-8D). As depicted in FIGS. 8C-8D, the luxR gene is under control of a spleen regulated pConstitutive cymO, thereby limiting the lux expression to tumors, rather than solely to high densities within the tumor, as high densities could occur at localized non-tumor sites of infection. The system can further employ both a pSpleen negative regulator with a pTumor positive and negative regulator, as shown in FIG. 8D. Coupling of quorum sensing to tumor selective and normal tissue repressed expression is shown in FIGS. 8A-8D.

Examples of multi-component therapeutic molecules such as therapeutic toxins include cytolethal distending toxins and hybrids or chimeras thereof, RTX toxins including but not limited to *Actinobacillus leuckotoxin* and *Bordetella* adenylate cyclase toxin (CyaA or ACT) and hybrids or chimeras thereof, *Salmonella* sp. ArtAB and hybrids or chimeras thereof, "split" *Pseudomonas* ToxA and hybrids or chimeras thereof, "split" *E. coli* cytotoxic necrotic factor (CNF) and hybrids or chimeras thereof, "split" *Bordetella* dermonecrotic factor (DNF) and hybrids or chimeras thereof, "split" *Pasteurella multocita* toxin (PMT) and hybrids or chimeras thereof.

Examples of toxin enhancers include apoptin, ferry peptide:apoptin fusions such as TAT-apoptin (Bermudes et al., 2000, U.S. patent application Ser. No. 09/645,415; Flinterman et al., 2009, Delivery of therapeutic proteins as secretable TAT fusion products, Molecular Therapy 17: 334-342), proapoptotic peptides including but not limited to bax, bad and p53 peptides, and ferry peptide fusions such as TAT-bax, TAT-bad and TAT-p53, and lysis and/or release peptides such as lysis proteins phiX129 E or periplasmic release such as ColE3. Kong et al., 2008 (Proc Nat Acad Sci USA 105: 9361-9366) used arabinose inducible control to maintain expression of essential genes asd and murA, whereby in their absence the cells lyse high efficiency was achieved by Camacho et al., 2016 (Scientific Reports 6:30591. DOI: 10.1038/srep30591) with the lambda gene cluster SRRz.

The promoters may also be of different types, with different genes or subunits of a multimeric protein expressed by different constitutive or inducible promoters. Use of two separate inducible promoter for more than one antigen allows, when sufficient X-ray, tetracycline, arabinose methysalicylate or other inducer is administered following administration of the bacterial vector, their expression to occur simultaneously, sequentially, or alternating (repeated). A variety of inducible promoters are known including arabinose, SOS-response promoters responsive to DNA damaging agents such as mitomycin, alkylating agents, X-rays and ultraviolet (UV) light such as the recA promoter, colicin promoters, sulA promoters and hypoxic-inducible promoters including but not limited to the pepT promoter (Bermudes et al., WO 01/25397, Nuyts et al., (2002, Radio-responsive recA promoter significantly increases TNF□ production in recombinant clostridia after 2 Gy irradiation. Gene Therapy 8, 1197-1201)), the arabinose inducible promoter ($Ara_{BAD}$) (Lossner et al., 2007, Cell Microbiol. 9:1529-1537; WO/2006/048344) the methylsalicylate inducible promoter (Royo et al., 2007, Nature Methods 4: 937-942; WO/2005/054477. A single promoter may be used to drive the expression of one or more gene, such that multiple genes, or multiple subunits of a multimeric protein, may be induced. To achieve multiple alternating gene expression, two independent (orthogonal) promoters are required. Thus, a tumor-targeted bacteria may be induced to have one or more proteins induced by a first inducer, and may be induced to have a second set of one or more proteins induced by a second inducer, and so on. Similarly, following a first induction with induced expression of one or more genes, the first inducer may be curtailed, and the inducer for the second set of one or more genes initiated, thus achieving a sequential combination effect.

Bacterial pharmacokinetic enhancers. Silica coated bacteria. The bacteria are engineered to have a silica coat by engineering them to express silicatin. Bacteria that produce polysilicate coats is based on expression of silicatein from diatoms and/or sponges including the *Pseudomonas* INP fusion with the truncated form (known as BBa_K265009 and Part:BBa_K265008) (Pozzolini et al., 2004, Molecular cloning of silicatein gene from marine sponge *Petrosia ficiformis* (Porifera, Demospongiae) and development of primmorphs as a model for biosilicification studies, Mar Biotechnol (NY). 2004 6:594-603; Muller et al., 2008, Bioencapsulation of living bacteria (*Escherichia coli*) with poly(silicate) after transformation with silicatein-alpha gene, Biomaterials 29: 771-779; Schroder et al., Silicatein: acquisition of structure-guiding and structure-forming properties during maturation from the pro-silicatein to the silicatein form, Journal of Biological Chemistry doi: 10.1074/jbc.M112.351486; van Bloois et al., 2011, Decorating microbes: surface display of proteins on *Escherichia coli*. Trends in Biotechnology 29:79-86.; Brutchey and Morse 2008, Silicatein and the translation of its molecular mechanism of biosilicification into low temperature nanomaterial synthesis. American Chemical Society. 108 (11): 4915-4934; Iler 1979, The Chemistry of Silica: Solubility, Polymerization, Colloid and Surface Properties, and Biochemistry. New York: Wiley, 1979; Rai and Perry, 2009, Facile fabrication of uniform silica films with tunable physical properties using silicatein protein from sponges. Languir 26(6): 4152-4159). SEQ ID NO: 111

```
atgaaggctacaaaattggtgttgggagcggtaatcctgggttcgactc
tgttggcaggctgttcttccaatgcgaagatcgaccagttatccagtga
tgtggggatcaacccatacgtcggtttcgagatgggttatgactggctg
ggccgcatgccatataagggatccgtggaaaacggcgcatataaggcac
aaggagtccaattgaccgcaaagttgggttaccccattactgatgattt
ggacatctacacgcgtctgggtgggatggtgtggcgcgcagacacaaaa
agtaatgtttatggtaagaatcacgatacaggagtttctcccgtttttg
ctggaggagtggagtatgcgatcacgccggaaatcgcgacgcgcttgga
gtaccaatggactaacaacattggcgacgcgcacacgattggcactcgt
cctgacaacggcatcccaggtatgtatctcggcacgttggttgttttgt
gtgttttgggggctgctattggagagccaatgcctcagtatgagttcaa
ggaggaatggcagctgtggaagaaacaacatgacaagtcttacagcacc
aacttggaggaactggagaaacatcttgtctggctctccaacaagaagt
acattgaactgcacaatgccaatgcagacacctttggattcactctagc
tatgaaccatctaggagatatgactgaccatgaatacaaggagagatac
ctcacatacactaacagcaaatctggtaactacaccaaggtgttcaaac
gtgagccatggatggcctacccggagactgtagattggagaacaaaggg
cgctgtgactggtatcaagagccagggagattgtggtgccagctatgca
ttcagtgccatgggtgcacttgaaggaatcaatgcacttgctactggaa
agctgacctatctcagtgaacagaacatcattgattgctctgtacctta
tggtaaccatggttgcaagggtggaaacatgtatgtggctttcctctat
gttgttgctaacgaaggagttgatgatgggggttcctatccatttagag
gaaagcaatccagttgtacgtatcaagagcagtaccgtggtgcaagtat
gtctggctcagttcaaatcaacagtggtagtgaatctgatctggaagca
gctgtagccaatgttggtccagttgcagtagctattgatggagagtcaa
atgctttcagattctattacagtggagtgtacgactcctccagatgttc
tagtagcagtctcaaccacgccatggtgatcactggctatggaatttca
aataaccaggaatactggcttgcaaagaacagctggggtgagaactggg
gagaactgggctatgtgaagatggccaggaacaagtacaatcaatgtgg
gattgctagtgatgcctcctaccccactctctag
```

PEGylated Bacteria. In another embodiment, the bacteria may optionally be coated with polyethylene glycol (PEG), i.e., PEGylation. Pegylation may be accomplished by any known means (e.g., amine-reactive PEGs, C-terminal-reactive PEGs, Thiol-reactive PEGs, homobifunctional crosslinkers, heterobifunctional crosslinkers, multi-arm PEGs, membrane-inserting FSL-PEGs, monomethoxypoly(ethylene) glycols activated by cyanuric chloride, succinimidyl succinate, and tresyl chloride; Suk et al., 2017, PEGylation as a strategy for improving nanoparticle-based drug and gene delivery, Adv Drug Deliv Rev 99(Pt A): 28-51; Tesfay et al., 2013, PEGylation of vesicular *stomatis* virus extends virus persistence in blood circulation of passively immunized mice, J Virol 87: 3752-3759; Wonganan and Croyle, 2010, PEGylated Adenoviruses: From Mice to Monkeys, Viruses 2: 468-502); Wortmann et al., 2008, Fully detargeted polyethylene glycol-coated adenovirus vectors are potent genetic vaccines and escape from preexisting anti-adenovirus antibodies, Mol Ther 16: 154-162; Kim et al., 2008, PEGylation of bacteriophages increases blood circulatin time and reduces T-helper type 1 immune response. Microbial Biotechnology 1: 247-257; Krepple and Kochanek 2007, Modification of adenovirus gene transfer vectors with synthetic polymers: A scientific review and technical guide, Molecular Therapy 16:16-29). A technical guide is provided by Lee et al., 2007 (Investigations of PEGylated recombinant adenovirus, using fluorescein-labeled polyethylene glycol. Hum Gene Ther 18: 286-300.)

HPMAylated Bacteria. In another embodiment, the bacteria may optionally be coated with poly-N-(2-hydroxypropyl)methacrylamide (poly-HPMA). Attachment is achieved by using amino-reactive N-(2-hydroxypropyl)methacrylamide copolymer, which couples the polymer to the amino groups of the bacterial cell wall exposed to the aqueous milieu. The hydrophilic HPMA polymer is chemically activated by the incorporation of amino-reactive 4-nitrophenoxy groups on diglycyl side chains under generation of a 21 kd random copolymer (Rihova and Kubackova 2003, Clinical implications of N-(2-hydroxypropyl) methacrylamide copolymers, Curr Pharm Biotechnol 4: 311-322; Vasey et al., 1999, Phase I clinical and pharmacokinetic study of PK1 [N-(2-hydroxypropyl)methacrylamide copolymer doxorubicin]: first member of a new class of chemotherapeutic agents-drug-polymer conjugates. Cancer Research Campaign Phase I/II Committee Clin Cancer Res, 5: 83-94). This results in up to 10 reactive 4-nitrophenyl groups per 100 monomers, and can therefore attach to the bacteria at multiple amines, closely attaching the polymer. The result is greater than 10%, more preferably up to 30%, more preferably up to 50%, more preferably up to 70% of the amino groups may be reacted with (Fisher et al., 2001, Polymer-coated adenovirus permits efficient retargeting and evades neutralizing antibodies. Gene Ther 8: 341-348).

Combinations of bacterial coatings. In another embodiment, the bacteria are optionally genetically modified to express sialic acid (Bermudes U.S. Pat. No. 9,616,114), in combination with genetic modification of producing silica. Alternatively, the bacteria are optionally genetically modified to express sialic acid, in combination with genetic modification with PEG and/or HPMA.

In another embodiment, the bacteria are coated with poly(allylamine hydrochloride) (PAH) (Lee et al., 2013, A polymer coating applied to *Salmonella* prevents the binding of *Salmonella*-specific antibodies, Int J Cancer. 2013 Feb. 1; 132(3):717-25. doi: 10.1002/ijc.27700) alone or in combination with PEG and/or poly-HPMA. Polymer coated bacteria, such as coating with polyallylamine hydrochloride or conjugated polyelectrolyte (CP) and polymyxin B (PLB) and combinations (Zhu et al., 2013, Conjugated polymer-coated bacteria for multimodal intracellular and extracellular anticancer activity, Advanced Materials 25:1203-1208; DOI: 10.1002/adma.201204550) are also encompassed. The PHA may be between 5000 and 50,000 MW, more preferably 15000 MW.

Bacteria that express immunotherapeutics. The immunotherapeutics of the present technology include checkpoint inhibitors (FIGS. 11A-11C), including antibodies and peptides and antibody-like peptides (U.S. Pat. No. 7,018,801) that bind to and result in antagonism to co-inhibitory molecules PD-1 (CD279), PD-L1 (B7-H1; CD274), PDL2 (B7-DC; CD273), CD80 (B7-1), CD86 (B7-2), B7-H3 (CD276)/B7H4 (VTCN1); CLTA4 (CD152), LAG-3, $KIR_L$, CD200, CD200R, CD112 (PVRL2; Nection-2), butyrophilin family members (e.g., Btn12, Skint1, MOG, CD277), HVEM (TNFSRSF14; CD270)VISTA (B7H5; PD-IH; Gi24), CD155 (PVR; Necl-5), CD112 (PVRL2; Nection-2), LAG3 (CD223), TIGIT, TIM-3 (HAVcr-2), A2aR BTLA, CD 96, CD112R, CD160, CD200R, VISTA B7/H3, and the macrophage antiphagocytosis molecules CD47 and SIRPa. Also encompassed are antibodies and peptides that bind to and agonize co-stimulatory, CD27 (TNFRSF7), CD28, CD40, CD40L (TNSFSF; CD154), OX40 (TNFRSF4; CD134), GITR (TNFRSF18; CD357), CD226 (DNAM-1), 2B4 (CD244), (TNFRSF7), ICOS (CD278), CD28H, CD137 (TNFRSF-9; 41BB), TCR, TMIGD2 (IGPR-1), KIRs, CD48 (BCM-1; BLAST-1), CD155 (PVR; Necl-5), GITRL (TNFSF18), CD70 (TNFSF7; CD27L), OX40L (TNFSF4; CD252), CD137L (TNFSF9; 4-1BBL), MHC Class I or II, B7-H7 (HHLA2), ICOSL (B7-H2; B7RP1), CD80 (B7-1), CD86 (B7-2). as well as general stimulators of the immune system, engineered for expression by tumor-targeted bacteria. Immunotherapeutics may be done alone, or in combination or in sequence (e.g., anti-OX40 followed by anti-PD-1, Messenheimer et al., 2017 Timing of PD-1 blockade is critical to effective combination immunotherapy with Anti-Ox40, doi: 10.1158/1078-0432.CCR-16-2677). The peptides may be expressed as overlapping peptide panels (i.e., pepmixes) that stimulate immunity. Other stimulators of the immune system include c-di-GMP (cyclic di-GMP), and desaminotyrosine (also known as phloreate or phloretic acid, Hydro-p-coumaric acid, 3-(4-Hydroxyphenyl)propanoic acid or 3-(4-Hydroxyphenyl)propanoic acid), alone or in combination.

Stimulation of mitogenicity also encompasses expression of the mistletoe lectin, *Phaseolus vulgaris* photohemagglutinin (PHA; LPHA; PHA-L, including the isoforms such as PHA-L4) Hoffman and Donaldson, 1987 (Synthesis of mitogenic phytohemagglutinin-L in *Escherichia coli*, Bio/Technology 5:157-160; Wimer 1990, Therapeutic activities of PHA-L4 the mitogenic isolectin of phytogemagglutinin as an ideal response modifier, Molecular Biotherapy 1: 311-317; Mody et al., 1995, Use of lectins as diagnostic and therapeutic tools for cancer, J Pharmacological and Toxicological Methods 33:1-10; Kaned et al., 2002, The high specificities of *Phaseolus vulgaris* erythro- and leukoagglutinating lectins for bisecting GlcNAc or α-1-6-linked branch structures, respectively, are attributable to Loop B, J Biol Chem 277:16928-16935). Pha-L SEQ ID NO: 112 MASSKFFTVLFLVLLTHANSSNDIYFSFDRFNETN-LILQGDASVSSSGQLRLTNVNSNGEPRVGSLGRAF-YSAPIQIW DNTTGTVASFATSFTFNIQVPNNAGPADG-LAFALVPVGSQPKDKGGFLGLFDGSNSNFHTVAVEF-DTLYNKDWDPT ERHIGIDVNSIRSIKTTRWDFVNGE-NAEVLITYESSTNLLVASLVYPSQKTSFIVSDTVD-LKSVLPEWVSVGFSATTGIN KGNVETNDVLSWS-FASKLSDGTTSEGLNLANLVLNQIL Stimulation of mitogenicity also encompasses expression of concanavalin A Min et al, 1992 (non-glycosylated recombinant pro-concanavalin A is active without peptide cleavage, EMBO Journal 11: 1303-1307).

Expression of checkpoint inhibitor antibodies. Examples of checkpoint inhibitor single chain variable fraction (ScFv) antibodies, modified by fusion to the HlyA secretion signal (HlyA C-terminal 60 amino acids), and co-expressed in trans with HlyBD (and TolC; Fernandez et al., 2000, Specific secretion of active single-chain Fv antibodies into the supernatants of *Escherichia coli* cultures by use of the hemolysin system. Appl. Environ. Microbiol. 66: 5024-5029) is SEQ ID NO: 113 LAYGSQGNLNPLINEISKIISAAGNFDV-KEERAAASLLQLSGNASDFSYGRNSITLTASA Expression and secretion of antibodies such as checkpoint inhibitor antibodies also includes other known secretion fusions, including membrane protein A (OmpA), lipoprotein (Lpp), and Lpp-OmpA hybrids (Georiou et al., 1997. Display of heterologous proteins on the surface of Microorganisms: From the screening of combinatorial libraries to live recombinant vaccines. Nature Biotechnology 15: 29-34), hemolysin fusions and fusions with the *Pseudomonas* INP (INP; also known as ICE). The OmpA-Lpp fusion approach has successfully been used for antibody secretion (Bereta et al., 2007; Massa et al., 2013 *Salmonella* engineered to express CD20-targeting antibodies and a drug-converting enzyme can eradicate human lymphomas. Blood 122, 705-714), including their use in tumor-targeted *Salmonella* VNP20009 (Bereta et al., 2007. Improving tumor targeting and therapeutic potential of *Salmonella* VNP20009 by displaying cell surface CEA-specific antibodies. Vaccine 25, 4183-4192. The *Pseudomonas* INP fusion has been successfully used for antibody export (Bassi et al., 2008. Expression of Single Chain Antibodies (ScFvs) for c-myc Oncoprotein in Recombinant *Escherichia coli* Membranes by Using the Ice-Nucleation Protein of *Pseudomonas syringae*. Biotechnology Progress 16: 557-563. doi.org/10.1021/bp000053k).

Over expression of adenosine deaminase. The object of over expressing adenosine deaminase is to deplete adenosine by its conversion to inosine. Over expression may be accomplished by the regulatory elements described herein, with or without bacterial lysis. In *Salmonella enterica* serotype Typhimurium, adenosine deaminase has the amino acid sequence: SEQ ID NO: 114 MIDITLPLTDIHRHLDGNI-RAQTILDLGRQFNIALPAQTLETLIPHVQVTSTEPD-LVSFLTKLDWGVKVLASLDACRRVAF ENIEDAAR-NGLHYVELRFSPGYMAMAHQLPIAGWEAVIDGVR-DGCNTFGVEARLIGIMSRTFGEAACLQELDALLAH RENITALDLAGDELGFPGSLFLSHFNRARDAG-WHITVHAGEAAGPESIWQAIRELGAERIGHGVKAVE-DRALMDFLA QQRIGIESCLTSNIQTSTVASLADH-PLKTFLEHGVLASLNTDDPAVQGVDIIHEYHVAAP-AAGLSREQIRQAQINGLEIA FLSDSEKRALREKVAEA The secreted adenosine deaminase of *Elizabethkingia anophelis/meningoseptica* amino acid sequence SEQ ID NO: 115

```
MMKKTLIYILLLGLPLTGNQYITAQELSYQQKINLLDQENQALGFDSDL
KLSDAESVLDKKLFQLRKEFLTETEKQKIPLYNSSFNQIKPLIENSKLF
NIIQSMPKGGLLHTHSGGITDAKWIIETARKYKESYIYVQKDNDQYIFG
QMAFFAKDKVPAGFVNLDEKLSADPGFEKQLQELLILKRDQLCNYTDYW
IEFEKRFKRTGSLLSYRPFFKAYYLKGFQDLIKDNVQHGEIRFIFDQLY
DFEHGKYSLNTSITDLQDILKEIHKTAPQFTLKLIYSSFKFLDPKGVDQ
QLEAAFQLKKEFPDMITGFDLVADEAAGNSIYSFRESWMKLNDLSKKYG
VDMPLFLHAGESNSVFNKNVVDLALLNNKRIGHGLNLIYFPKTLELIKK
QNKLVEVSPISNQILGYVSDMRNHPARVLLSNGVQCSINSDDPGVYGYE
GLSYDFWVAFVYWELDIKALKKLVYNSINYSSLNEKEKKEAILYLNKQW
TDFVTKMNQKLS
```

Phloretin hydrolase (EC 3.7.1.4) is an enzyme that catalyzes the chemical reaction phloretin+$H_2O$ to phloretate+phloroglucinol. The phloretin hydrolases are known phloretin hydrolases (phy gene), especially those that function in tumor-targeted bacteria, including but not limited to *Salmonella, E. coli, Bifidobacteria* spp., *Clostridium* spp. and *Listeria* spp. (e.g., Schoefer et al., 2004, Cloning and expression of a phloretin hydrolase gene from *Eubacterium ramulus* and characterization of the recombinant enzyme. Appl Environ Microbiol. 70(10):6131-7. The deduced amino acid sequence of phy showed similarities to a putative protein of the 2,4-diacetylphloroglucinol biosynthetic operon from *Pseudomonas fluorescens*, which is also encompassed by the present technology. Also included are homologues in *Clostridium orbiscindens*, and other *Clostridium* spp. The *Eubacterium ramulus* phloretin hydrolase (phy) gene GenBank: AF548616.1, has the amino acid sequence: SEQ ID NO: 116

```
MEEDFNMSTPGVKVGVXEEEKKLSYYKYYEQDLAPVPAEKIAILQGGPI
APEKCIPFDERNKFLKGEDDEYANIGFGVAADGTALVCNTTYMPGVTGE
MLDWWFPWHSVGSDLRYKIWDPEDHYFARAYPASYWDPNVPMNQKTWGV
DHYIMEDVGPGPEFLKLCFKRPADFGYDESIIGTEKCESLVCAIGESSC
AAAMTHKWHPYKDGVLFESRFWIGYRIDEEGNIVKAIPEGVSIPPFVPQ
GLFAHNIKEFTNLAAILPTLYAEEKDTF
```

Mistletoe B chain. The mistletoe B chain may be expressed alone or as a fusion. SEQ ID NO: 117

```
DDVTCTTSEPTVRFVGRNGLCLDVPEGDYHDGSRIQLWPCKSNSDQNQL
WTIRRDGTIRSNGRCLTTYGYTAGSYIMIYDCNRGGWDLTTWQIRGNGI
ILNPRSMMVIGTPSGSRGTRGTTFTLQTLGYSLGQGWLASNDTAPREVT
IYGFRDHCMETSGGKVWWVGTCVSGKQNQRWALYGDGSIRPKPYQDQCL
TSQGDSVRSVINLFSCTAGSPRQRWVFTNKGAILNLKNRLAMDVAESNP
SLRRIIIFSVTGNPNQMWLPVP. See Mistletoe Lectin,
supra.
```

Cyclic dinucleotides (CDNs). The dinucleotide cyclases of the technology are classified according to their enzymatic activity and by their amino acid and corresponding nucleotide sequences, and homologues and orthologues thereof. These enzymes condense nucleotides into cyclic dinucleotides (CDNs), which includes but is not limited to cyclic-di-GMP (c-di-GMP), cyclic-di-AMP, and cyclic AMP-GMP (cGAMP) (Jenal et al., 2017, Cyclic di-GMP: second messenger exraordinaire, Nature Reviews Microbiology 15: 271-284). Purified cyclic dinucleotides have been suggested as immunostimulatory agents against diseases including cancer (Dubensky Jr. et al., U.S. Pat. No. 9,724,408; Dubensky Jr. U.S. Pat. No. 9,770,467; Patel et al., U.S. Pat. No. 9,840,533).

Bacteria and other organisms naturally make CDNs (Cowles et al., 2016, Diguanylate cyclases AdrA and STM1987 regulate *Salmonella enterica* exopolysaccharide production during plant colonization in an environment-dependent manner, Appl Environ Microbiol 82:1237-1248; Kader et al., 2006, Hierarchical involvement of various GGDEF domain proteins in rdar morphotype development of *Salmonella enterica* serovar Typhimurium, Molecular Microbiology 60: 602-616). The diguanylate cyclases of the present technology may be those of either gram positive bacteria such as *Bifidobacterium, Clostridium, Lactococcus, Lactobacillus*, and/or *Listeria* (e.g., Zhu et al., 2016, Cyclic-di-AMP synthesis by the deadenylate cyclase CdaA is modulated by the peptidoglycan biosynthesis enzyme GlmM in *Lactococcus lactus*, Mol Microbiol 99:1015-1027), gram negative bacteria such as *Escherichia* and *Salmonella*, or of eukaryotes including those of the human cGAS gene and/or homologues and family members conserved in chimpanzee, Rhesus monkey, cow, mouse, rat, chicken, zebrafish, and frog described by Tao et al., 2017 (Nonspecific DNA binding of cGAS N terminus promotes cGAS activation, J Immunol DOI: doi.org/10.4049/jimmunol.1601909), or the *Vibrio cholera* DncV and/or homologues, the enzymes of which may be expressed in any bacterial vector species of the technology.

The dinucleotide cyclases including diguanylate cyclases useful for the technology useful include those of *Salmonella* species, such as those identified in the nucleotide sequence of *Salmonella enterica* serotype Tyhimurium genome (Jarvik et al., 2010, Short-term signatures of evolutionary change in the *Salmonella enterica* Serovar Typhimurium 14028 genome, J Bacteriol 192: 560-567), which includes STM14_0400, STM14_0455 (yaiC/AdrA), STM14_0552 (ylaB), STM14_0643, STM14_1632 (ydiV), STM14_1552, STM14_2047 (yeaJ), STM14_2209, STM14_2620 (yegE), STM14_2964 (yfeA), STM14_4086, STM14_5126 (yjcC) STM14_5467, or those listed by Cowles et al., 2016 STM1283 (yeaJ), STM1344 (ydiV), STM1697, STM1703 (yciR), STM1987 (Enzyme Commission EC: 2.7.7.65), STM2123 (yegE), STM2410 (yfeA), STM2503, STM2672 (yfiN), STM3375 (yhdA), STM3388, STM3615 (yhjK), STM4264 (yjcC), STM4551. In a preferred embodiment, the enzymes utilized lack phosphodiesterase activity, which is recognized by its "EAL" domain, and thereby do not degrade CDNs. The dinucleotide cyclases of the technology may optionally have their EAL domain genetically altered, disrupted or deleted, and thus artificially lack phosphodiesterase activity. Multiple diguanylate cyclases may be express using promoters of different activities.

In a preferred embodiment, the dinucleotide cyclase is the human enzyme cGAS, or homologue or orthologs thereof, which synthesizes the hybrid cyclic dinucleotide c-GMP-AMP (2',-3'-cGAMP) (Sun et al., 2013, Cyclic GMP-AMP synthase is a cytosolic DNA sensor that activates the type I interferon pathway, Science 339:786-791; Sun et al., 2013, Cyclic GMP-AMP is an endogenous second messenger in innate immune signaling by cytosolic DNA, Science 339: 826-830). Expression of full-length (amino acids (aa) 1-522) and truncated (catalytic domain, 'cd') *Homo sapiens* (h) (aa 155-522) and *Mus musculus* (m) (aa 141-507) cGAS, with and without N-terminal His6 and/or MBP (maltose-binding protein) fusion protein expression are described by Civril, F. et al. 2013 (Structural mechanism of cytosolic DNA sensing by cGAS. Nature 498, 332-337). The cGAS may be functionally expressed in its entirety (Tao et al., 2017, Nonspecific DNA binding of cGAS N terminus promotes cGAS activation, J. Immunol 198: 3627-3636) or as a truncation of up to the first 160 amino acids, such as amino acids 157-522 expressed by Kranzusch et al., 2013 (Structure of human cGAS reveals a conserved family of second-messenger enzymes in innate immunity, Cell Reports 3:1362-1368).

The cGAS may be further co-expressed with either a mitochondrial or bacterial HU nucleoid protein or mitochondrial transcription factor A (TFAM) or the high-mobility group box protein (HMGB) that thereby activates the cGAS (Andreeva et al., 2017, cGAS senses long and HMGB/

TFAM-bound U-turn DNA by forming protein-DNA ladders, Nature doi:10.1038/nature23890).

Activity of cGAS is determined as described by Bose et al., 2016, An RNA-based fluorescent biosensor for high-throughput analysis of the cGAS-cGAMP-STING pathway, Cell Chem Biol 23:1539-1549), using a thin layer chromatography assay.

In another preferred embodiment, the enzyme the DncV *Vibrio cholerae* which catalyzes the production of 33'-cGAMP (Davies et al., 2012, Coordinated regulation of accessory genetic elements produces cyclic di-nucleotides for *V. cholerae* virulence. Cell: 149:358-370) is expressed. Also encompassed are homologues of the *Vibrio cholerae* DncV of other species, including but not limited to *Vibrio* sp., *Vibrio metoecus, V. mimicus, V. albensis, V. harveyi, V. parahaemolyticus, V. anguillanum, V. alginolyticus, V. diazotrophicus Salinivibrio* sp., *Salinivibrio kushneri, Moritella* sp., *Moritella marina, Kosakonia* sp., *Kosakonia radicincitans, Dykeya* sp., *Dykeya chrsanthemi, Alcanivorax* sp., *Aeromona* ssp., *Aeromonas salmonicida, Idomarina* sp., *Idomarina loihiensis, Pantoea* sp., *Pantoea stewartia, Escherichia* sp., *Escherichia coli, E. alberti, Klebsiella* sp, *K. pneumoniae, K. varicola, Cronobacter* sp., *Cronobacter sakazakii, Cronobacter dublinensis, Yersinia* sp., *Yersinia enterocolitica, Yersinia kristensenii, Enterobacter* sp., *Enterobacter cloacae, Lonsdalea* sp., *Lonsdalea populi, Pseudomonas* sp., *Pseudomonas simiae, P. syringae, Aliivibrio* sp., *Alivibrio fisheri, Photobacterium* sp., *Photobacterium kishitanii, Rahnella* sp., *Acinetobacter* sp.

Multiple diguanylate cyclases may be express using promoters of different activities. When expressed by a tumor targeted bacterium, the CDNs stimulate the immune system, most particularly the stimulators of interferon gamma known as STING and/or their homologues and orthologues, and are thereby associated with an enhanced immune response against the cancerous tissue. Because the CDNs are expressed and produced locally by a tumor-localized bacterium following administration, the therapy is distinct from systemic administration of purified CDNs.

In another embodiment, the overexpression of CDNs is enhanced by deletion of phosphodiesterase degrading c-di-GMP enzymes, such as yhjH (Lamprokostopouiou et al., 2010, Cyclic di-GMP signaling controls virulence properties of *Salmonella enterica* serovar Typhimurium at the mucosal lining, Experimental Microbiology 12: 40-53).

In another embodiment, the overexpression of CDNs is accompanied by deletions in c-di-GMP regulated functions, such as those involved in the transition from virulence to biofilm formation, including either the CsgD regulator (encoded by csgD), or individual biofilm components bcsABZC (cellulose synthase), csgBA (curli fimbriae subunits), bapA (large secreted surface protein) and/or yihQ (glycosyl transferase for O-antigen capsule), or the YcgR associated with c-di-GMP inhibition of motility in combination with any of the bcsABZC genes, especially bcsA (Zorraquino et al., 2013 Coordinated Cyclic-Di-GMP Repression of *Salmonella* Motility through YcgR and Cellulose, J Bacteriol 195: 417-428).

These functions may serve to increase virulence, increase invasion, increase proinflammatory IL8 stimulation and enhance motility, also thereby increasing immunostimulation by flagellin through toll like receptor 5 (TLR5), and thereby recruiting the immune system to attach the cancerous tissue associated with the presence of the bacteria and throughout the body.

Bacteria that express multifunctional immunotherapeutic cytotoxic proteins. Bacteria that deliver multifunctional cytotoxins have the potential to both directly kill tumor cells and recruit the immune system (FIGS. 9A-9L, 10A-10E, 11A-11C, 12A-12E and 13A-13B). The cytotoxins may have immunostimulatory activity on their own and may further stimulate the immune system through immunogenic cell death. The cytotoxins and multifunctional cytotoxins of the technology may be expressed using known promoters and/or the regulatory circuits described herein and have enhanced immunostimulatory properties. The enhanced stimulation of the immune system is recognizable by several different means using known immunological techniques. Immunostimulatory cytotoxins expressed by tumor-targeted bacteria result in enhanced numbers of CD4+ and CD8+ T-cells within the tumor, and decreased numbers of myeloid derived suppressor cells (MDSC) are detected in the spleen. Peptide vaccine fusions are detected by peptide-specific CD8+ cells. Tumor infiltrating cells and lymphoid cells are stained with a mixture of an IgG antibody loaded with the peptide and a fluorescently labeled secondary antibody to the IgG and analyzed by flow cytotometry. Similarly, HLA-A2 dimers loaded with the peptide may be used to analyze CD8+ T-cell responses, and may be further correlated with IFN-gamma release, lymphocyte proliferation, and cytotoxicity (Woll et al., 2004, Direct measurement of peptide-specific CD8+ T cells using HLA-A2:lg dimer for monitoring the in vivo immune response to a HER2/neu vaccine in breast and prostate cancer patients, J Clin Immunol. 2004 July; 24(4): 449-61). The overall effect can be determined by treating tumor models with the bacteria expressing the cytotoxin with and without the immune peptide.

Tripeptide tyroserleutide (YSL) effects can be determined I, as YSL enhances the antitumor effects of macrophages and stimulates macrophage secretion of IL-1beta, TNF-alpha, and NO (YAO et al., 2006, Cancer Immunol Immunother. 2006 January; 55(1):56-60). The effect of tyroserleutide is also measured according to CN182737 (Method for detecting ant-liver cancer efficacy of tyroserleutide, kit and gene chip used thereby), which describes determining the expression level of the genes NDUFA2, NDUFA10, NDUFS1, SUCLG1, Calreticulin, PTEN, Akt1, Akt2, P21 and P27 following treatment by tyr-ser-leu peptide; with reduced gene expression of NDUFA2, NDUFA10, NDUFS1, SUCLG1, Akt1, Akt2 and increased gene expression Calreticulin, PTEN, P21, P27. The effect of tryrserleutide is also determined by assessing antitumor effect of the effector gene alone or in combination with the tyrserlutide peptide fusion.

Peptide fusion may further be modified by the addition of a targeting moiety, such as RGD-4C (SEQ ID NO: 005 ACDCRGDCFCG). The toxins may be further modified by addition of a targeting moiety. Thus, *Pasteurella* multocita toxin (PMT) that consists of 1285 amino acids which in its naturally occurring form is encoded as a single open reading frame, can be expressed with a peptide fusion such as SEQ ID NO: 154 LKYSL to create an immunotherapeutic cytotoxin.

In another embodiment of the present technology, PMT is artificially "split", i.e., separated into more than one independent open reading frame, with the appropriate initiating methionine and stop codon, as needed, together with one or more pairs of dimerizing peptides, such as leucine zipper peptides and linkers, as illustrated below, and those encompassed by Chica 2019 (Designer sense-response systems, Science 366: 952-953; Glasgow et al., Science 366, 1024 (2019); Guo et al., J. Am. Chem. Soc. 141, 8128 (2019); Taylor et al., Nat. Methods 13,177 (2016); Fegan et al., Chem. Rev. 110, 3315 (2010); Pelletier, F.-X. Campbell-Valois, S. W. Michnick, Proc. Natl. Acad. Sci. U.S.A. 95, 12141 (1998); Bick et al., eLife 6, e28909 (2017); Feng et al., eLife 4, e10606 (2015); Davey, R. A. Chica, Protein Sci. 21, 1241 (2012). These multiple open reading frames may then be expressed independently as components of a regulatory circuit. The two fragment peptide combinations may consist of amino acids 1-574 together with 575-1285; 1-719 together with 72-1285; or 1-1104 together with 1105-1285. The three peptide combinations may consist of 1-574 together with 575-719 and 720-1285; or 1-719 and 720-1104 and 1105-1285. The four peptide combinations may consist of 1-574, together with 575-719, 720-1104, and 1105-1285.

Secreted PMT divided into two components with leucine zippers (underlined). Amino acids of the nucleic acid open reading, for the first of a two part regulatory circuit 1-574=PMT N-term; 575-580=linker (in large italics); 581-609=leucine zipper (in bold), SEQ ID NO: 118

MKTKHFFNSDFTVKGKSADEIFRRLCTDHPDKQLNNVKWKEVFINRFGQ
MMLDTPNPRKIVEKIINEGLEKQGLKNIDPETTYFNIFSSSDSSDGNVF
HYNSLSESYRVTDACLMNIFVERYFDDWDLLNSLASNGIYSVGKEGAYY
PDHDYGPEYNPVWGPNEQIYHSRVIADILYARSVWDEFKKYFMEYWQKY
AQLYTEMLSDTFLAMAIQQYTRQTLTDEGFLMVCNTYYGNKEEVQITLL
DIYGYPSTDIICIEQKGLPTPKVILYIPGGTQPFVEFLNTDDLKQWIAW
HLKDNKHMVAFRKHFSLKQRQEGETFTGIDKALQYIAEESPEWPANKYI
LYNPTHLETENLFNIMMKRTEQRMLEDSDVQIRSNSEATRDYALSLLET
FISQLSAIDMLVPAVGIPINFALSATALGLSSDIWNGDSYEKRKYGIGS
LVQSALFTGINLIPVISETAEILSSFSRTEEDIPAFFTEEQALAQRFEI
VEEELHSISPDDPPREITDENLHKIRLVRLNNENQPLVVLRRLGGNKFI
RIEPITFQEIKGSLVSEVINPVTNKTYYVSNAKL*GGSGSG*<u>ALKKELQAN</u>
<u>KKELAQLKWELQALKKELAQ</u>

Amino acids of the nucleic acid open reading, for the second of a two-part regulatory circuit 1-119=YebF; 120-121 "LK"=cleavage signal; 122-151=leucine zipper (in bold); 152-155=linker (large type italics); 156-866=C-term PMT. SEQ ID NO: 119

MAKKRGAFLGLLLVSACASVFAANNETSKSVTFPKCEDLDAAGIAASVK
RDYQQNRVARWADDQKIVGQADPVAWVSLQDIQGKDDKWSVPLTVRGKS
ADIHYQVSVDCKAGMAEYQRR<u>LK</u>EQLEKKLQALEKKLAQLEWKNQALEK
KLAQ*GGSG*LGGSPYSPFRIGLEGVWTPEVLKARASVIGKPIGESYKRIL
AKLQRIHNSNILDERQGLMHELMELIDLYEESQPSSERLNAFRELRTQL
EKALYLPEMEALKKQILQIPNKGSGAARFLLRTAMNEMAGKTSESTADL
IRFALQDTVISAPFRGYAGAIPEAIDFPVKYVIEDISVFDKIQTNYWEL
PAYESWNEGSNSALLPGLLRESQSKGMLSKCRIIENSLYIGHSYEEMFY
SISPYSNQVGGPYELYPFTFFSMLQEVQGDLGFEQAFATRNFFNTLVSD
RLSLMENTMLLTESFDYTPWDAIYGDINYDEQFAAMSINERIEKCMNTY
RGVAFQNSSKSIDFFLNNLTTFIDNGLTEIAISDLPYDIVQQEISQFLQ
GSNEWKTLDAMLFNLDKGDINGAFRKLLQSAKDNNIKFRAIGHSDNSVP
PFNNPYKSLYYKGNIIAEAIEKLDREGQKFWVFADSSLLNSTPGTGRPM

-continued

PGLVQYLKIPATWVDSDGAWQFLPDVASSRVPIEVTELENWQVLTPPQG
KILGLKQFKLTAGFPTEQSRLPLLENSVSEDLREELMQKIDAIKNDVKM
NSLVCMEAGSCDSVSPKVAARLKDMGLEAGMGASITWWRREGGMEFSHQ
MHTTASFKFAGKEFAVDASHLQFVHDQLDTTILILPVDDWALEIAQRNR
AINPFVEYVSKTGNMLALFMPPLFTKPRLTRAL

Released PMT divided into two components with leucine zippers (underlined). Split PMTs may also be expressed without engineered secretion of the non-secretion component through bacterial cell lysis. Programmed loss of bacterial cell wall structural integrity by disruption of the asd gene can be used for release of cytoplasmic contents (Kong et al., 2008). Through utilization of arabinose inducible control to keep the gene on, cell lysis occurs in the absence of the inducer. Programmed lysis has been enhanced by arabinose control of the cell wall biosynthesis genes murA and asd coupled with expression of the p22 phage c2 gene (Kong et al., 2012). Subsequent to removal of the arabinose inducer caused by introduction of the bacteria into an arabinose-free host, murA and asd are further inhibited through loss of repression of PR, which then drives an antisense murA and asd. High lysis efficiencies were engineered using the bacteriophage lambda lysis gene cluster SRRz for tumor-targeted delivery with anhydrotetracycline induction coupled in parallel with salicylate induction for therapeutic gene expression (Camacho et al., 2016).

Amino acids of the nucleic acid open reading, for the first of a two-part regulatory circuit; 1-574=PMT N-term; 575-580=linker (in large italics); 581-609=leucine zipper (in bold) SEQ ID NO: 118.

Amino acids of the nucleic acid open reading, for the second of a two part regulatory circuit; 1, initiating methionine; 2-31 leucine zipper; 32-35, linker; 36-746, PMT C-term SEQ ID NO: 120

MEQLEKKLQALEKKLAQLEWKNQALEKKLAQ*GGSG*LGGSPYSPFRIGLE
GVWTPEVLKARASVIGKPIGESYKRILAKLQRIHNSNILDERQGLMHEL
MELIDLYEESQPSSERLNAFRELRTQLEKALYLPEMEALKKQILQIPNK
GSGAARFLLRTAMNEMAGKTSESTADLIRFALQDTVISAPFRGYAGAIP
EAIDFPVKYVIEDISVFDKIQTNYWELPAYESWNEGSNSALLPGLLRES
QSKGMLSKCRIIENSLYIGHSYEEMFYSISPYSNQVGGPYELYPFTFFS
MLQEVQGDLGFEQAFATRNFFNTLVSDRLSLMENTMLLTESFDYTPWDA
IYGDINYDEQFAAMSINERIEKCMNTYRGVAFQNSSKSIDFFLNNLTTF
IDNGLTEIAISDLPYDIVQQEISQFLQGSNEWKTLDAMLFNLDKGDING
AFRKLLQSAKDNNIKFRAIGHSDNSVPPFNNPYKSLYYKGNIIAEAIEK
LDREGQKFWVFADSSLLNSTPGTGRPMPGLVQYLKIPATWDSDGAWQFL
PDVASSRVPIEVTELENWQVLTPPQGKILGLKQFKLTAGFPTEQSRLPL
LENSVSEDLREELMQKIDAIKNDVKMNSLVCMEAGSCDSVSPKVAARLK
DMGLEAGMGASITWWRREGGMEFSHQMHTTASFKFAGKEFAVDASHLQF
VHDQLDTTILILPVDDWALEIAQRNRAINPFVEYVSKTGNMLALFMPPL
FTKPRLTRAL

A secreted therapeutic *Escherichia coli* cytotoxic necrotizing factor (CNF) toxin under control of a gene expression circuit, optionally with lysis protein co-expression.

In another embodiment, various forms of CNF are incorporated. *E. coli* cytotoxic necrotic factor 1 (CNF1) consists of 1014 amino acids which in its naturally occurring form is encoded as a single open reading frame. The amino acid sequence shown contains the CNF with an internal pertussis S3 binding domain (underlined) with flanking short flexible linkers (bold) SEQ ID NO: 121.

MGNQWQQKYLLEYNELVSNFPSPERWVSDYIKNCFKTDLPWFSRIDPDN
AYFICFSQNRSNSRSYTGWDHLGKYKTEVLTLTQAALINIGYRFDVFDD
ANSSTGIYKTKSADVFNEENEEKMLPSEYLHFLQKCDFAGVYGKTLSDY
WSKYYDKFKLLLKNYYISSALYLYKNGELDEREYNFSMNALNRSDNISL
LFFDIYGYYASDIFVAKNNDKVMLFIPGAKKPFLFKKNIADLRLTLKEL
IKDSDKQQLLSQHFSLYSRQDGVSYAGVNSVLHAIENDGNFNESYFLYS
NKTLSNKDVFDAIAISVKKRSFSDGDIVIKSNSEAQRDYALTILQTILS
MTPIFDIVVPEVSVPLGLGIITSSMGISFDQLINGDTYEERRSAIPGLA
TNAVLLGLSFAIPLLISKAGINQEVLSSVINNEGRTLNETNIDIFLKEY
GIAEDSISSTNLLDVKLKSSGQHVNIVKLSDEDNQIVAVKGSSLSGIYY
EVDIETGYEILSRRIYRTEYNNEILWTRGGGLKGGQPFDFESLNIPVFF
KDEPYSAVTGSPLSFINDDSSLLYPDTNPKLPQPTSEMDIVNYVKGSGS
FGDRFVTLMRGATEEEAWNIASYHTAGGSTEELHEILLGQGPQSSLGFT
EYTSNVNSADAASRRHFLWVIKVHVKYITNNNVSYVNHWAIPDEAPVEV
LAVVDRRFNFPEPSTPPDISTIggggsapgivippkalftqqggaygrc
pngtraltvaelrgnaelgtylrgitpgwsiyglydgtylgqayggiik
dappgagfiyretfcitsggggsgKLSRGNIDVLKGRGSISSTRQRAIY
PYFEAANADEQQPLFFYIKKDRFDNHGYDQYFYDNTVGLNGIPTLNTYT
GEIPSDSSSLGSTYWKKYNLTNETSIIRVSNSARGANGIKIALEEVQEG
KPVIITSGNLSGCTTIVARKEGYIYKVHTGTTKSLAGFTSTTGVKKAVE
VLELLTKEPIPRVEGIMSNDFLVDYLSENFEDSLITYSSSEKKPDSQIT
IIRDNVSVFPYFLDNIPEHGFGTSATVLVRVDGNVWRSLSESYSLNADA
SEISVLKVFSKKF A split secreted or released form of therapeutic *Escherichia coli* cytotoxic necrotizing factor (CNF) toxin under control of a gene expression circuit, optionally with lysis protein expression.

1-539 CNF1 N-term; 540-574=linker and leucine zipper SEQ ID NO: 122

MGNQWQQKYLLEYNELVSNFPSPERVVSDYIKNCFKTDLPWFSRIDPDN
AYFICFSQNRSNSRSYTGWDHLGKYKTEVLTLTQAALINIGYRFDVFDD
ANSSTGIYKTKSADVFNEENEEKMLPSEYLHFLQKCDFAGVYGKTLSDY
WSKYYDKFKLLLKNYYISSALYLYKNGELDEREYNFSMNALNRSDNISL
LFFDIYGYYASDIFVAKNNDKVMLFIPGAKKPFLFKKNIADLRLTLKEL
IKDSDKQQLLSQHFSLYSRQDGVSYAGVNSVLHAIENDGNFNESYFLYS
NKTLSNKDVFDAIAISVKKRSFSDGDIVIKSNSEAQRDYALTILQTILS
MTPIFDIVVPEVSVPLGLGIITSSMGISFDQLINGDTYEERRSAIPGLA

-continued

TNAVLLGLSFAIPLLISKAGINQEVLSSVINNEGRTLNETNIDIFLKEY
GIAEDSISSTNLLDVKLKSSGQHVNIVKLSDEDNQIVAVKGSSLSGIYY
EVDIETGYEILSRRIYRTEYNNEILWTRGGGLKGGQPFDFESLNIPVFF
*GGSGSG*ALKKELQANKKELAQLKWELQALKKELAQ

Amino acids of the nucleic acid open reading, for the second of a two part regulatory circuit; 1-119=YebF; 120-121 "LK"=cleavage signal; 122-151=leucine zipper (in bold); 152-155=linker (large type italics); followed by C-term CNF UniProtKB (Q47106_ECOLX) amino acids 540-1013 SEQ ID NO: 123.

MAKKRGAFLGLLLVSACASVFAANNETSKSVTFPKCEDLDAAGIAASVK
RDYQQNRVARWADDQKIVGQADPVAWVSLQDIQGKDDKWSVPLTVRGKS
ADIHYQVSVDCKAGMAEYQRRLKEQLEKKLQALEKKLAQLEWKNQALEK
KLAQ*GGSG*KDEPYSAVTGSPLSFINDDSSLLYPDTNPKLPQPTSEMDIV
NYVKGSGSFGDRFVTLMRGATEEEAWNIASYHTAGGSTEELHEILLGQG
PQSSLGFTEYTSNVNSADAASRRHFLVVIKVHVKYITNNNVSYVNHWAI
PDEAPVEVLAWDRRFNFPEPSTPPDISTIRKLLSLRYFKESIESTSKSN
FQKLSRGNIDVLKGRGSISSTRQRAIYPYFEAANADEQQPLFFYIKKDR
FDNHGYDQYFYDNTVGLNGIPTLNTYTGEIPSDSSSLGSTYWKKYNLTN
ETSIIRVSNSARGANGIKIALEEVQEGKPVIITSGNLSGCTTIVARKEG
YIYKVHTGTTKSLAGFTSTTGVKKAVEVLELLTKEPIPRVEGIMSNDFL
VDYLSENFEDSLITYSSSEKKPDSQITIIRDNVSVFPYFLDNIPEHGFG
TSATVLVRVDGNWWVRSLSESYSLNADASEISVLKVFSKKF

A released and/or secreted split therapeutic *Escherichia coli* cytotoxic necrotizing factor (CNF) toxin under control of a gene expression circuit, optionally with lysis protein(s).

First component: 1-539 CNF1 N-term; 540-574=linker and leucine zipper SEQ ID NO: 122. The second component of a released and/or split therapeutic *Escherichia coli* CNF: SEQ ID NO: 124

**MEQLEKKLQALEKKLAQLEWKNQALEKKLAQ*GGSG***KDEPYSAVTGSPLS
FINDDSSLLYPDTNPKLPQPTSEMDIVNYVKGSGSFGDRFVTLMRGATE
EEAWNIASYHTAGGSTEELHEILLGQGPQSSLGFTEYTSNVNSADAASR
RHFLWIKVHVKYITNNNVSYVNHWAIPDEAPVEVLAVVDRRFNFPEPST
PPDISTIRKLLSLRYFKESIESTSKSNFQKLSRGNIDVLKGRGSISSTR
QRAIYPYFEAANADEQQPLFFYIKKDRFDNHGYDQYFYDNTVGLNGIPT
LNTYTGEIPSDSSSLGSTYWKKYNLTNETSIIRVSNSARGANGIKIALE
EVQEGKPVIITSGNLSGCTTIVARKEGYIYKVHTGTTKSLAGFTSTTGV
KKAVEVLELLTKEPIPRVEGIMSNDFLVDYLSENFEDSLITYSSSEKKP
DSQITIIRDNVSVFPYFLDNIPEHGFGTSATVLVRVDGNWVVRSLSESY
SLNADASEISVLKVFSKKF

A released (no secretion signal) therapeutic *Escherichia coli* cytotoxic necrotizing factor (CNF) toxin under control of a gene expression circuit and lysis protein(s) SEQ ID NO: 125

```
MCFSQNRSNSRSYTGWDHLGKYKTEVLTLTQAALINIGYRFDVFDDANS

STGIYKTKSADVFNEENEEKMLPSEYLHFLQKCDFAGVYGKTLSDYWSK

YYDKFKLLLKNYYISSALYLYKNGELDEREYNFSMNALNRSDNISLLFF

DIYGYYASDIFVAKNNDKVMLFIPGAKKPFLFKKNIADLRLTLKELIKD

SDKQQLLSQHFSLYSRQDGVSYAGVNSVLHAIENDGNFNESYFLYSNKT

LSNKDVFDAIAISVKKRSFSDGDIVIKSNSEAQRDYALTILQTILSMTP

IFDIWPEVSVPLGLGIITSSMGISFDQLINGDTYEERRSAIPGLATNAV

LLGLSFAIPLLISKAGINQEVLSSVINNEGRTLNETNIDIFLKEYGIAE

DSISSTNLLDVKLKSSGQHVNIVKLSDEDNQIVAVKGSSLSGIYYEVDI

ETGYEILSRRIYRTEYNNEILWTRGGGLKGGQPFDFESLNIPVFFKDEP

YSAVTGSPLSFINDDSSLLYPDTNPKLPQPTSEMDIVNYVKGSGSFGDR

FVTLMRGATEEEAWNIASYHTAGGSTEELHEILLGQGPQSSLGFTEYTS

NVNSADAASRRHFLVVIKVHVKYITNNNVSYVNHWAIPDEAPVEVLAWD

RRFNFPEPSTPPDISTIRKLLSLRYFKESIESTSKSNFQKLSRGNIDVL

KGRGSISSTRQRAIYPYFEAANADEQQPLFFYIKKDRFDNHGYDQYFYD

NTVGLNGIPTLNTYTGEIPSDSSSLGSTYWKKYNLTNETSIIRVSNSAR

GANGIKIALEEVQEGKPVIITSGNLSGCTTIVARKEGYIYKVHTGTTKS

LAGFTSTTGVKKAVEVLELLTKEPIPRVEGIMSNDFLVDYLSENFEDSL

ITYSSSEKKPDSQITIIRDNVSVFPYFLDNIPEHGFGTSATVLVRVDGN

VVVRSLSESYSLNADASEISVLKVFSKKF
```

Therapeutics with alternative targeting moieties. See Peptide Ligands, supra.

Diagrams of targeted toxins are shown in FIGS. 9A-9L, 11A-11C, 12A-12E and 13A-13B. The toxins may be expressed by known expression systems or by the expression systems described herein. The amino acid sequence of an RGD-targeted therapeutic *Escherichia coli* cytotoxic necrotizing factor (CNF) toxin, which can be expressed under control of a gene expression circuit, optionally co-expressed with one or more lysis proteins (FIGS. 9A-9L) SEQ ID NO: 121.

Bacteria that express therapeutic enhancers. Bacterial production of metabolites that are toxic to tumor cells such as indol, a product of tryptophanase, is used to enhance bacterial spread within the tumor by killing tumor cells by the production of the indol metabolite that the bacteria are not themselves affected by. The tumor cells are further starved for tryptophane by the depletion of tryptophan by tryptophanse. The combination of these effects is further enhanced by the other pharmacokinetic enhancements, tumor penetration, persistence and intra-tumoral spreading. Expression of tryptophanase may use the *Escherichia coli* genes or any homologous genes; those of the enterobacteriaceae are a preferred embodiment. In *E. coli* which are encoded by a transcribed leader region, tnaL (also known as tnaC), and two larger structural genes, where tnaA, which encodes the degradative enzyme and tnaB which together with the tnaL product are involved in tryptophane transport. It is understood that other enzymes, such as tyrosinase, may be genetically engineered within the *Salmonella*, instead of or together with the tryptophanase, in accordance with known principles and the discussion herein.

The therapeutic enhancers used in the technology are able to enhance the immunostimulatory and/or cytotoxicity of the immunotherapeutics and cytotoxins. The enhancers may also increase the spread of the bacteria, and thereby increase the immunostimulatory and/or cytotoxicity of the immunotherapeutics and cytotoxins. Therapeutic enhancers may be expressed independently or dependently (polycistronically) with the immunotherapeutics and cytotoxins. Therapeutic enhancers include but are not limited to TAT-apoptin (Bermudes et al., U.S. Pat. No. 7,452,531), a TAT-apoptin with an OmpA "8L" signal sequence SEQ ID NO: 126 AKKTA-LALLLLLLALTSVAQAYGRKKRRQRRRMNALQED-TPPGPSTVFRPPTSSRPLETPHCREIRIGIAGITITLSL-CG CANARAPTLRSATADNSENTGFKNVPDLRTD-QPKPPSKKRSCDPSEYRVSELKESLITTTPSRPRTARR-CIRL, TAT-bim, TAT-bax, TAT-p53 peptide (Justesen et al., 2007, Immunology 122: 326-334; (as well as other therapeutic peptides and cell penetrating peptides, see Table 2, Marqus et al., 2017, Evaluation of the use of therapeutic peptides for cancer treatment, J Biomed Sci 24: Article number: 21 (2017); Protease inhibitors (e.g., Bermudes U.S. Pat. No. 9,878,023; Quimbar et al., 2013, High-affinity cyclic peptide matriptase inhibitors, J. Biological Chemistry doi/10.1074/jbc.M113.460030; Korsinczky et al., 2001, Solution Structures by 1H NMR of the Novel CyclicTrypsin Inhibitor SFTI-1 from Sunflower Seeds and an Acyclic Permutant, J. Mol. Biol. (2001) 311, 579±591), E3 periplasmic lysis, the peptide pentastatin-1 (SEQ ID NO: 066 LRRFSTMPFMFCNINNVCNF) (Koskimaki et al., 2010 Pentastating-1, a collagen IV derived 20-mer peptide, suppresses tumor growth in a small cell lung cancer xenograft model, BMC Cancer 10: 29 doi: 10.1186/1471-2407-10-29, and Noxa (Jeong et al., Anti-tumoral effect of the mitochondrial target domain of Noxa delivered by an engineered *Salmonella typhimurium*, PLoS One (2014) 9, issue 1, e80050).

Human hyaluronidase amino acid sequence (BC026163), with the functional portion for use in the present technology underlined, SEQ ID NO: 127

```
MGVLKFKHIFFRSFVKSSGVSQIVFTFLLIPCCLTLNFRAPPVIPNVPF

LWAWNAPSEFCLGKFDEPLDMSLFSFIGSPRINATGQGVTIFYVDRLGY

YPYIDSITGVTVNGGIPQKISLQDHLDKAKKDITFYMPVDNLGMAVIDW

EEWRPTWARNWKPKDVYKNRSIELVQQQNVQLSLTEATEKAKQEFEKAG

KDFLVETIKLGKLLRPNHLWGYYLFPDCYNHHYKKPGYNGSCFNVEIKR

NDDLSWLWNESTALYPSIYLNTQQSPVAATLYVRNRVREAIRVSKIPDA

KSPLPVFAYTRIVFTDQVLKFLSQDELVYTFGETVALGASGIVIWGTLS

IMRSMKSCLLLDNYMETILNPYIINVTLAAKMCSQVLCQEQGVCIRKNW

NSSDYLHLNPDNFAIQLEKGGKFTVRGKPTLEDLEQFSEKFYCSCYSTL

SCKEKADVKDTDAVDVCIADGVCIDAFLKPPMETEEPQIFYNASPSTLS

ATMFIWRLEVWDQGISRIGFF
```

Bacterial genetic backgrounds improving immunotherapeutic effects. The present technology also provides a unique combination of bacteria that enhance the immunostimulation by preventing inhibition of proinflammatory response together with agents and enhancers described above. These mutations include but are not limited to steE, ssaV, and combinations of steE and ssaV (Stapels et al., *Salmonella* persisters undermine host immune defenses during antibiotic treatment, Science 362:1156-1160).

The figures show compositions and methods to modify bacteria of the present technology.

FIGS. 1A and 1B show AND Gates. AND gates require more than one (two or more) inputs for activation. The inputs may consist of promoter regulatory elements, which, under the appropriate conditions of exogenous induction, tissue or tumor specific induction, or constitutive induction, result in gene expression. A symbolic logic depiction of a two component AND gate and output table (FIG. 1A) and a symbolic logic depiction of a three component AND gate and output table (FIG. 1B). A two input, positively regulated tumor-selective AND gate, where the first promoter is pAcidic, and the second promoter is hypoxic promoter (e.g., pepT). The coding sequence controlled by the two promoters may be any such bipartite protein, such as an AB toxin (Alouf et al., 2005 and 2015 editions, The Comprehensive Sourcebook of Bacterial Protein Toxins, Academic Press, Elsevier), such as *Shigella* toxin (Melton-Celsa 2014, Shiga toxin (Stx) classification, structure and function, Microbiol Spectr doi:10.1128/microbiospec.EHEC-0024-2013). The two input AND gates may also control more than 2 components, such as the *Salmonella* typhoid toxin/cytolethal distending toxin (CLDT), that consists of cldtB, pltA and pltB, where the pltA and pltB are controlled simultaneously by one promoter when operably linked with a Shine-Dalgarno ribosomal binding site. This multigene format may be applied to each of the other regulatory systems described. A three-input, positively regulated tumor-selective AND gate, where the promoter 1 is pAcidic, promoter 2 is a hypoxic promoter, and promoter 3 is exogenously inducible. The coding sequences may consist of any tripartite or greater number of subunit multimeric protein, such as the *Salmonella* cytolethal distending toxin (CLDT) that consists of cldtB, pltA and pltB, or a reporter gene system such as the lux operon that can be imaged, and thereby indicating the dual acidic and hypoxic conditions.

FIG. 2A shows an OR Gate, which have regulation of a single entity, monomeric, or multimeric (when operably linked with a Shine-Delgarno ribosomal binding site) by more than one regulatory element. A symbolic logic depiction of a two component OR gate, the output table and example of genetic constructs that result in the expression of a therapeutic PMT (CNF or other monomeric, or multimeric polycistronic, e.g., CLDT) under either pHypoxia or pAcidic control. FIG. 2B shows a NOT Gate (inverter). A promoter such as pSpleen is used to drive a repressor of an otherwise constitute promoter. Expression of PMT (or others) occurs when there is no input.

FIG. 3 shows a two simple gene expression circuit, that acts collectively as a NOT AND gate. Growth, and therefore expression, is limited in normal tissue such as spleen, mediated by expression of sulA. Expression is promoted in the tumor, but not in the spleen. The combined activity is NOT in spleen, AND in tumor. The two-circuit system shown in FIG. 3 can further be combined with the two component and three component AND gates shown in FIGS. 1A and 1B, such as for expression of cytolethal distending toxin.

FIGS. 4A-4B show NOR AND Gates. FIG. 4A, a NOT AND Gate, not expressed in spleen and positively expressed in tumors. In the NOR AND gate depicted in FIG. 4B, expression occurs Not in normal tissues (e.g., spleen) OR other normal tissue or fluid (e.g., bile). Normal tissues drive one or another repressor (or alternatively a growth reducing protein such as a lysis protein or a growth reducing protein such as SulA), such that positive expression for the first two subunits of CLDT only occurs when both normal tissue environments are not present. Expression further requires positive expression of a tumor-activated promoter such as pSTM1787 in order that the third subunit of a cytolethal distending toxin is expressed. Thus, the holotoxin is only active under conditions of the lack of two negative and the presence of one positive inputs.

FIGS. 5A-5C show NOT (1 negative) AND (2 positive input) gates. In the NOT AND gate depicted in FIG. 5A, expression occurs Not in normal tissues (e.g., Arrach et al., 2008). FIG. 5B; normal spleen tissue drives a repressor (sulA), whereby lack of the repressor allows constitutive expression of the first component (cldtB shown). Second and third components (pltB and pltA) are expressed by positive regulatory elements such that positive expression for the subsequent two subunits of CLDT only occurs with both stimuli are present. Expression further requires positive expression of a tumor-activated promoter (pSTM1787) in order that the second and third subunits of a typhoid toxin. Thus, the holotoxin is only active under conditions of the lack of one negative and the presence of two positive inputs.

FIGS. 6A-6C shows NOR Gates. The NOR gates shown use more than one method to limit expression. In FIG. 6A, expression occurs Not in either Or of two normal tissues (e.g., bile induced in the gut or in the spleen). FIG. 6B: Normal gut (bile) tissue or fluid drives bacterial lysis limiting bacterial growth, while normal spleen drives a repressor, such that positive expression only occurs with both normal tissue environments are not present Diagram of a genetic construct that results in the expression of a therapeutic *Pasteurella multocita* toxin (PMT), but only when pBile and pSpleen are not activated. FIG. 6C: Diagram of genetic constructs that result in the expression of a therapeutic typhoid cytolethal distending toxin under combined control of pSpleen which represses the CldtB subunit, and pBile, which represses the pltBA subunits; thus, the therapeutic toxin, which requires all three subunits, is only activated when neither promoter is active.

FIG. 7A shows NOT (1 negative) AND (1 positive input) Gates. A promoter such as pSpleen is used to drive a repressor of an otherwise constitutive promoter, and results in expression of a first monomer (CldtB). Expression occurs when there is no repressor and when there is the positive input of a second promoter (e.g., pTet with addition of tetracycline per FIG. 7B, or pTumor pSTM1787 activated within tumors per FIG. 7C) resulting in the expression of both of the other components PltB and PltA or a monomer such as CNF1.

FIGS. 8A-8D show wild type lux operon with addition of cldtABC. Per FIG. 8A, the toxin is produced under density dependent conditions (Anderson et al., 2006; Swofford et al., 2014), and allows for tumor imaging, and therefore also indicates the location of therapeutic protein (e.g., CldtABC). Per FIG. 8B, a lux operon where the repressor is selectively produced in the tumor, limiting density dependent expression to the tumor, with a reduced monodirectional lux promoter. Per FIG. 8C, a lux operon where the luxR is under negative regulatory control for normal tissue such as spleen. Per FIG. 8D, a lux operon where the luxR is under negative regulatory control for normal tissue such as spleen and positive regulatory control of the tumor. The lux operon under normal tissue regulation, positive tumor regulation, and/or negative and positive regulation can be used for tumor selective diagnostic imaging. Synchronized cycles of lysis and release may optionally be utilized by inclusion of a lysis gene (Din et al., 2016). These circuits provide for the expression of therapeutic genes by bacteria, including tumor-specific density dependence and normal tissue density independence.

Figures 9A, 9B, 9C, 9D, 9E, 9F, 9G, 9H, 9I, 9J, 9K, 9L:
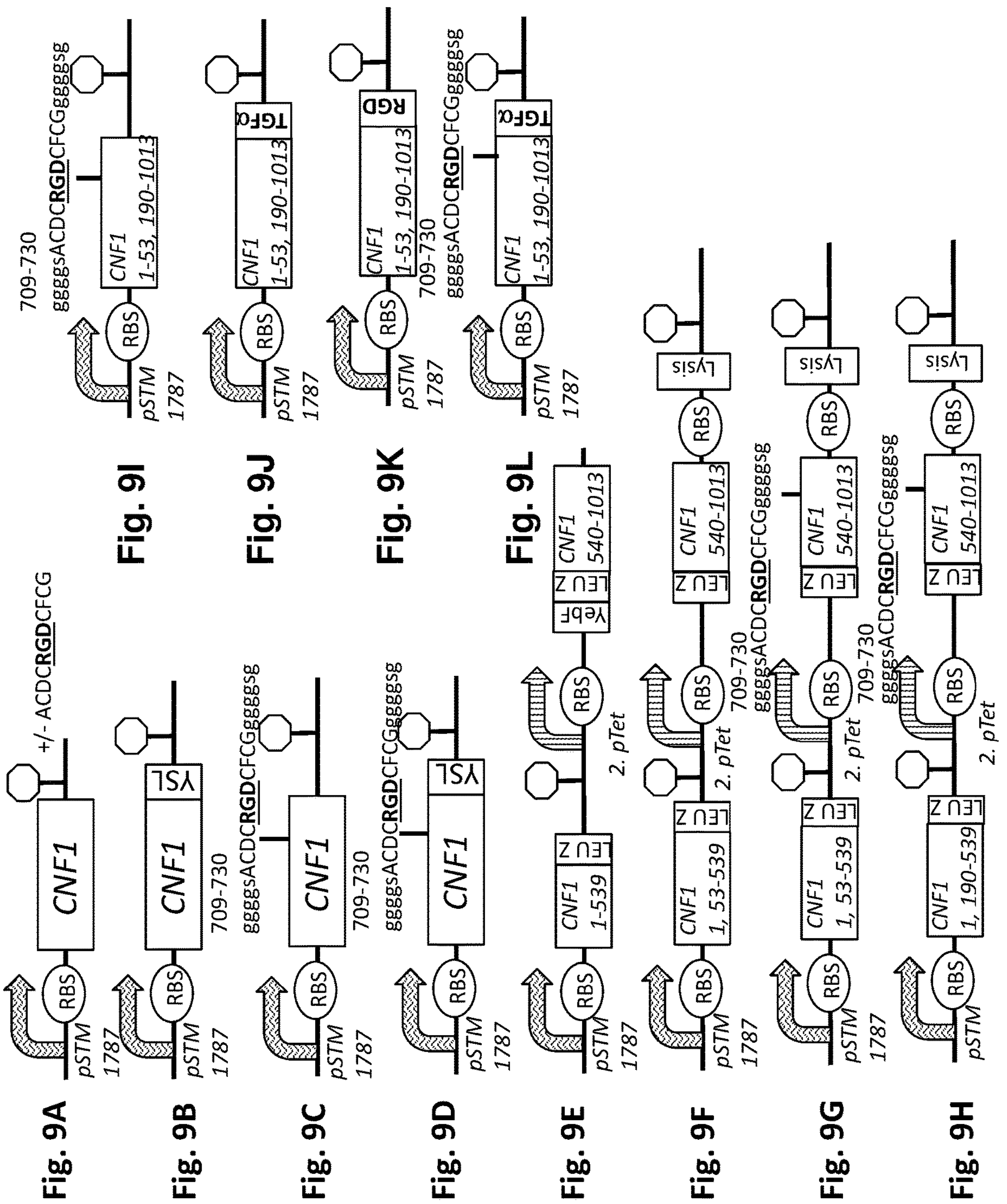
FIGS. 9A-9L show various logical circuits controlling production of modified cytotoxic necrotizing factors (CNFs).

FIGS. 9A-9L show tumor selective forms of CNF. FIG. 9A: wild type CNF1 expressed by the tumor specific promoter STM1787. FIG. 9B: CNF1 with a C-terminal YSL peptide expressed by the tumor specific promoter STM1787. FIG. 9C: CNF1 with RGD peptide expressed by the tumor specific promoter STM1787. FIG. 9D: CNF1 with RGD peptide and YSL expressed by the tumor specific promoter STM1787. FIG. 9E: A secreted form of split CNF. FIG. 9F: A released form of split CNF. FIG. 9G: A released form of split CNF with an RGD targeting peptide. FIG. 9H: A released form of split CNF with an RGD targeting peptide lacking N-terminal binding, FIG. 9I: A secreted form of CNF with an RGD targeting peptide at amino acids 709-730 based on wildtype) lacking N-terminal binding (amino acids 54-189; optionally, N-terminal binding may be retained), FIG. 9J, A secreted form of CNF with a C-terminal targeting peptide (e.g., TGFα shown) lacking N-terminal binding (optionally, N-terminal binding may be retained), FIG. 9K: A secreted form of CNF with an RGD targeting peptide lacking N-terminal binding (optionally, N-terminal binding may be retained). FIG. 9L: A secreted form of CNF with a C-terminal TGFα targeting peptide and an internal RGD targeting peptide lacking N-terminal binding (optionally, N-terminal binding may be retained). pSTM1787 is exemplary; promoter elements include known promoter elements and systems including quorum sensing cyclical lysis (Din et al., doi: 10.1038/nature18930).

Figures 10A, 10B, 10C, 10D, 10E, 11A, 11B, 11C:
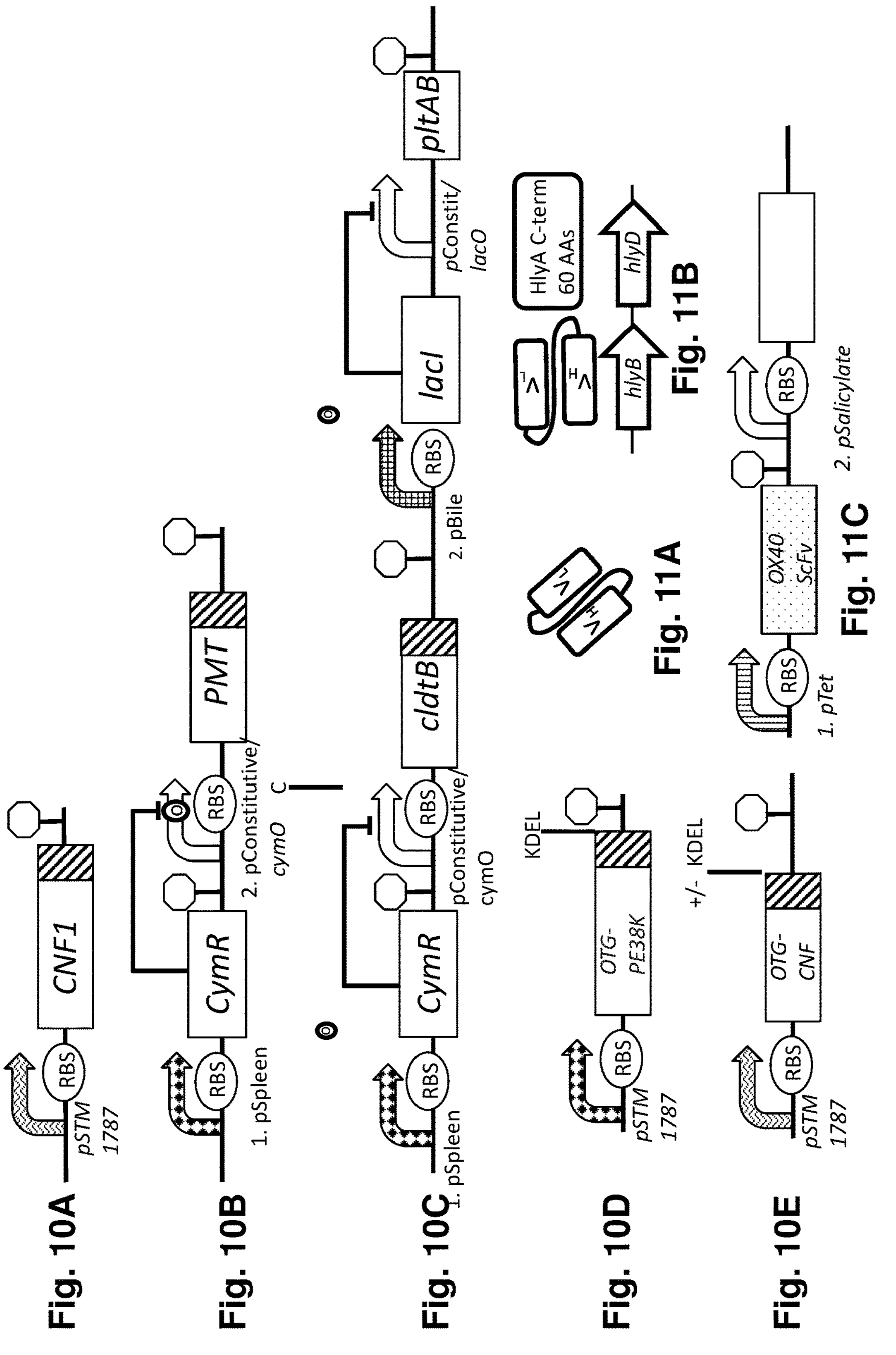
FIGS. 10A-10E show various logical circuits controlling production of cytotoxins modified with immune peptides.
FIG. 11A shows an immune enhancing single chain antibodies (ScFv) against checkpoint inhibitors and CD47.
FIG. 11B shows the ScFv produced with HlyA.
FIG. 11C shows a logical circuit for effecting the scenario of FIG. 11B.

FIGS. 10A-10E show cytotoxins modified with immune peptides. Cytoxins such as CNF1 (FIG. 10A), PMT (FIG. 10B), cldtB (FIG. 10C), OTG-PE38K (derived from ToxA) (FIG. 10D) and OTG-CNF (FIG. 10E) are modified by creating gene fusions with immune peptides such as YSL (Yao et al., 2005, Tripeptide tyroserleutide enhances the antitumor effects of macrophages and stimulates macrophage secretion of IL-1b, TNF-a, and NO in vitro. Cancer Immunol Immunother 55: 56-60), survivin, Bcl-2, Mcl-1 (Garg et al., 2016, Survivin: a unique target for tumor therapy, Cancer Cell Int 2016; 16: 49; Onodi et al., 2018, High therapeutic efficacy of a new surviving LSP-cancer vaccine containing CD4+ and CD8+ T-cell epitopes, Frontiers in oncology 2018 doi: 10.3389/fonc.2018.00517' Ciesielski et al., 2008, Therapeutic effect of a T-helper cell supported CTL response induced by a surviving peptide vaccine against murine cerebral glioma, Cancer Immunol Immunother 57:1827-1835; Mohammad et al., 2015, Broad targeting of resistance to apoptosis in cancer, Seminars in Cancer Biology 35: S78-S103) and the N-domain of carcinoembryonic antigen (CEA; Abdul-Wahid et al., US Patent Application 20150044218). Cytoxins such as CNF1 with a peptide (FIG. 10A). a NOT gate controlling expression of a PMT with an immune peptide (FIG. 10B); CltB requires addition of a C-terminal cysteine (C) and is followed by a normal tissue promoter driving a repressor lacI that stops expression of a constitutive promoter with the lac operator (FIG. 10C). OTG-PE38K is modified with a C-terminal KDEL endoplasmic reticulum retention signal, shown as expressed by a tumor specific promoter (FIG. 10D). OTG-PE38K is modified the active portion of CNF with a C-terminal KDEL endoplasmic reticulum retention signal (FIG. 10E). Additional antigens include EMR2, CD33, IL10RB, PLXNC1, PIEZO1, CD300LF, CPM, ITFG3, TTYH3, ITGA4, SLC9A1, MBOAT7, CD38, SLC6A6, ENG, SIRPB1, MRP1, ITGA5, SLC43A3, MYADM, ICAM1, SLC44A1, CCR1, SLC22A5, TFR2, KCNN4, LILRB4, LTB4R, CD70, GYPA, FCGR1A, CD123, CLEC12A, ITGB5, PTPRJ, SLC30A1, EMC10, TNFRSF1B, CD82, ITGAX, CR1, DAGLB, SEMA4A, TLR2, P2RY13, LILRB2, EMB, CD96, LILRB3, LILRA6, LILRA2, WT1, PRAME and SLC19A1.

The active domain of OTG-PE38K corresponds to amino acids 404-613 of the wild type (Wolf and Elsasser-Beile 2009, doi.org/10.1016/j.ijmm.2008.08.003) substituted with *Yersinia* CNF active domain (735-1014, Haywood et al. J. Biol. Chem. 2018; 293:3860-3870.

In FIGS. 10A-10E, the cross-hashed region represents the Immune Peptide YSL, Survivin 49-71 SEQ ID NO: 055 ENEPDLAQCFFCFKELEGWEPDD, CAE N-domain, Bcl-2, Mcl-1, Mesothelin, CNF 735-1014, or KRAS Peptides Kpep-2 SEQ ID NO: 067 RRCPLYISYDPVCRR; KRpep-2d SEQ ID NO: 068 RRRRCPLYISYDPVCRRRR.

δ-toxins and phenol soluble modulins (PMS; a-type and b-type) from Staphalococcus *aureus* (Sa) and *S. epidermidis* (Se) are useful in the technology. The corresponding DNA sequences may be used in the genetic circuits described herein. They may be further modified by expression as a fusion with YebF(LK), and may be further modified with the immunostimulatory tyroserleutide (YSL) peptide, SEQ ID NO: 154 LKYSL, preferably at the C-terminus (Peschel and Otto, Nat Rev Microbiol 11: 667-673, doi:10.1038/nrmicro3110; Bermudes U.S. Pat. No. 8,241,623; Doung et al., 2012 Pathogens 1: 3-11 DOI: 10.3390/pathogens1010003 Jiang et al., 2011, Experimental and Therapeutic Medicine 3:195-199 DOI: 10.3892/etm.2011.401, or RGD peptide SEQ ID NO: 005 ACDCRGDCFCG.

α-type

| | | |
|---|---|---|
| Sα δ-toxin | SEQ ID NO: 167 | MAQDIISTIGDLVKWIIDTVNKFTKK |
| Se δ-toxin | SEQ ID NO: 168 | MAADIISTIGDLVKWIIDTVNKFKK |
| Sα PSMa1 | SEQ ID NO: 169 | MGIIAGIIKVIKSLIEQFTGK |
| Sα PSMa2 | SEQ ID NO: 170 | MGIIAGIIKFIKGLIEKFTGK |
| Sα PSMa3 | SEQ ID NO: 171 | MEFVAKLFKFFKDLLGKFLGNN |
| Sα PSMa4 | SEQ ID NO: 172 | MAIVGTIIKIIKAIIDIFAK |
| Se PSMa | SEQ ID NO: 173 | MADVIAKIVEIVKGLIDQFTQK |
| Se PSMO | SEQ ID NO: 174 | MSIVSTIIEVVKTIVDIVKKFKK |
| Se PSME | SEQ ID NO: 175 | MFIINLVKKVISFIKGLFGNNENE |
| Sα/SePSM-me c | SEQ ID NO: 176 | MDFTGVITSIIDLIKTCIQAFG |

β-type

| | | |
|---|---|---|
| Sα PSMβ1 | SEQ ID NO: 177 | MEGLFNAIKDTVTAAINNDGAKLGTSIV-SIVENGVGLLGKLFGF |

-continued

| | |
|---|---|
| Sα PSMβ2 | SEQ ID NO: 178 MTGLAEAIANTVQAAQQHDSVKLGTSIV-DIVANGVGLLGKLFGF |
| Se PSMβ1 | SEQ ID NO: 179 MSKLAEAIANTVKAAQDQDWTKLGTSIVDIVESGVSVLG-KIFGF |
| Se PSMβ2 | SEQ ID NO: 180 MEQLFDAIRSWDAGINQDWSQLASGIAGIVENGISVISKLLGQ |

Immune checkpoint antibodies are provided as follows.

an IgG antibody agonist with $V_H$ and $V_L$ domains specific for PD-L1 ScFv derived from Atezolizumab SEQ ID NO: 181

MAEVOLVESGGGLVQPGGSLRLSCAASGFTFSDSWIHWVRQAPGKGLEW
VAWISPYGGSTYYADSVKGRFTISADTSKNTAYLQMNSLRAEDTAVYYC
ARRHWPGGFDYWGQGTLVTSSGGGGSGGGGSGGGGSDIQMTQSPSSLSA
SVGDRVTITCRASQDVSTAVAWYQQKPGKAPKLLIYSASFLYSGVPSRF
SGSGSGTDFTLTISSLOPEDFATYYCQQYLYHPATFGQGTKVEIKRHHH
HHHAALAYGSQGNLNPLINEISKIISAAGNFDVKEERAAASLLQLSGNA
SDFSYGRNSITLTASA

An IgG antibody agonist with $V_H$ and $V_L$ domains specific for OX-40 SC02023 Bakker et al. (2012) SEQ ID NO: 182

MAEVOLVESGGGLVHPGGSLRLSCAGSGFTFSSYAMHWVRQAPGKGLEW
VSAIGTGGGTYYADSVMGRFTISRDNSKNTLYLQMNSLRAEDTAVYYCA
RYDNVMGLYWFDYWGQGTLVTVSSGGGGSGGGGSGGGGSEIELTQSPAT
LSLSPGERATLSCRASQSVSSYLAWYQQKPGQAPRLLIYDASNRATGIP
ARFSGSGSGTDFTLTISSLEPEPEDFAVYYCQQRSNWPPAFGGGTKVEI
KR*HHHHHHAA*LAYGSQGNLNPLINEISKIISAAGNFDVKEERAAASLLQ
LSGNASDFSYGRNSITLTASA an IgG antibody agonist with $V_H$ and $V_L$ domains specific for CD47, 5F9 anti-CD47 diabody A chain (pdb 5IWL) SEQ ID NO: 188

MAXVQLVQSGAEVKKPGASVKVSCKASGYTFTNYNMHWVRQAPGQRLEW
MGTIYPGNDDTSYNQKFKDRVTITADTSASTAYMELSSLRSEDTAVYYC
ARGGYRAMDYWGQGTLVTVSSGGSGGDIVMTQSPLSLPVTPGEPASISC
RSSQSIVYSNGNTYLGWYLQKPGQSPQLLIYKVSNRFSGVPDRFSGSGS
GTDFTLKISRVEAEDVGVYYCFQGSHVPYTFGQGTKLEIK*HHHHHH*AAL
AYGSQGNLNPLINEISKIISAAGNFDVKEERAAASLLQLSGNASDFSYG
RNSITLTASA an IgG antibody agonist with $V_H$ and $V_L$ domains specific for CD47, 5F9 anti-CD47 diabody B chain (pdb 5IWL) SEQ ID NO: 183

QVQLVQSGAEVKKPGASVKVSCKASGYTFTNYNMHWVRQAPGQRLEWMG
TIYPGNDDTSYNQKFKDRVTITADTSASTAYMELSSLRSEDTAVYYCAR
GGYRAMDYWGQGTLVTVSSGGSGGDIVMTQSPLSLPVTPGEPASISCRS

-continued

SQSIVYSNGNTYLGWYLQKPGQSPQLLIYKVSNRFSGVPDRFSGSGSGT
DFTLKISRVEAEDVGVYYCFQGSHVPYTFGQGTKLEIK*HHHHHHAA*LAY
GSQGNLNPLINEISKIISAAGNFDVKEERAAASLLQLSGNASDFSYGRN
SITLTASA an ScFv from U.S. Pat. No. 7,488,802 against PD-1 SEQ ID NO: 184

DIQMTQSPSSLSASVGDRVTITCRASQSISSYLNWYQQKPGKAPKLLIYA
ASSLQSGVPSRFSGSGSGTDFTLTISSLQPEDFATYYCQQSYSTPLTFGG
GTKVEIKRSRGGGGSGGGGGGGGSEVQLVESGGGLVQPGGSLRLSCAASG
FTSSSYWMSWVRQAPGRGLEWVANIKQDGSEKYYVDSVKGRFTISRDNAK
NSLYLQMNSLRAEDTAVYYCARGGWSYDMWGQGTLVTVSSHHHHHHGAYP
YDVPDYAS an ScFv against CTLA-4 derived from ipilimumab SEQ ID NO: 185

MAQVQLVESGGGVVQPGRSLRLSCAASGFTFSSYTMHWVRQAPGKGLEWV
TFISYDGNNKYYADSVKGRFTISRDNSKNTLYLQMNSLRAEDTAIYYCAR
TGWLGPFDYWGQGTLVTVSSGGGGSGGGGSGGGGSEIVLTQSPGTLSLSP
GERATLSCRASQSVGSSYLAWYQQKPGQAPRLLIYGAFSRATGIPDRFSG
SGSGTDFTLTISRLEPEDFAVYYCQQYGSSPWTFGQGTKVEIKRHHHHHH
AALAYGSQGNLNPLINEISKIISAAGNFDVKEERAAASLLQLSGNASDFS
YGRNSITLTASA

FIG. 11A shows a diagram of a single chain variable fragment (scFv) consisting of the $V_H$ and $V_L$ domains fused with a flexible linker. FIG. 11B shows a hexahistidine (SEQ ID NO: 166 HHHHHH) tag has been added for detection and the scFv is a fusion protein with the secretory carrier HlyA. The fusion is shown with the HlyA C-terminal 60 amino acid secretion signal SEQ ID NO: 113. The genes hlyB and hlyD are also required in trans, and is expressed in a strain that also expresses TolC. Bakker A B H, Meeter-Rood P M L, and Bakker A Q, 2012, Agonist binding molecules to the human OX40 receptor, U.S. Pat. No. 8,133,983. Fernández L A, Solal, Enjuanes L, de Lorenzo V, 2000, Specific secretion of active single-chain Fv antibodies into the supernatants of *Escherichia coli* cultures by use of the hemolysin system. Applied Environ Microbiol 66: 5024-5029. C) An expression circuit for alternating expression is shown in the lower left, e.g., OX40 followed by PD-1 (Messenheimer et al., 2017, doi: 10.1158/1078-0432.CCR-16-2677), by sequentially administering tetracycline and then subsequently salicylate when preadministered the bacterium carrying the expression circuit.

FIGS. 12A-12E show CLDT Chimeras. Examples of a reorganized *Salmonella* thyphoid toxin operon consisting of cldtB, pltB and pltA (FIG. 12). A fusion with *Bordetella* S3 protein gene in different locations (S3 new N-terminus of pltB FIG. 12B; S3 at C-terminus of cldtB FIG. 12C; S3 at N-terminus of cldtB FIG. 12D; S3 near N-terminus of pltA FIG. 12E), acting as a ligand. When fused to the C-terminus of CldtB (e.g., FIG. 12C), a terminal cysteine is provided.

Figures 12A, 12B, 12C, 12D, 12E, 13A, 13B:
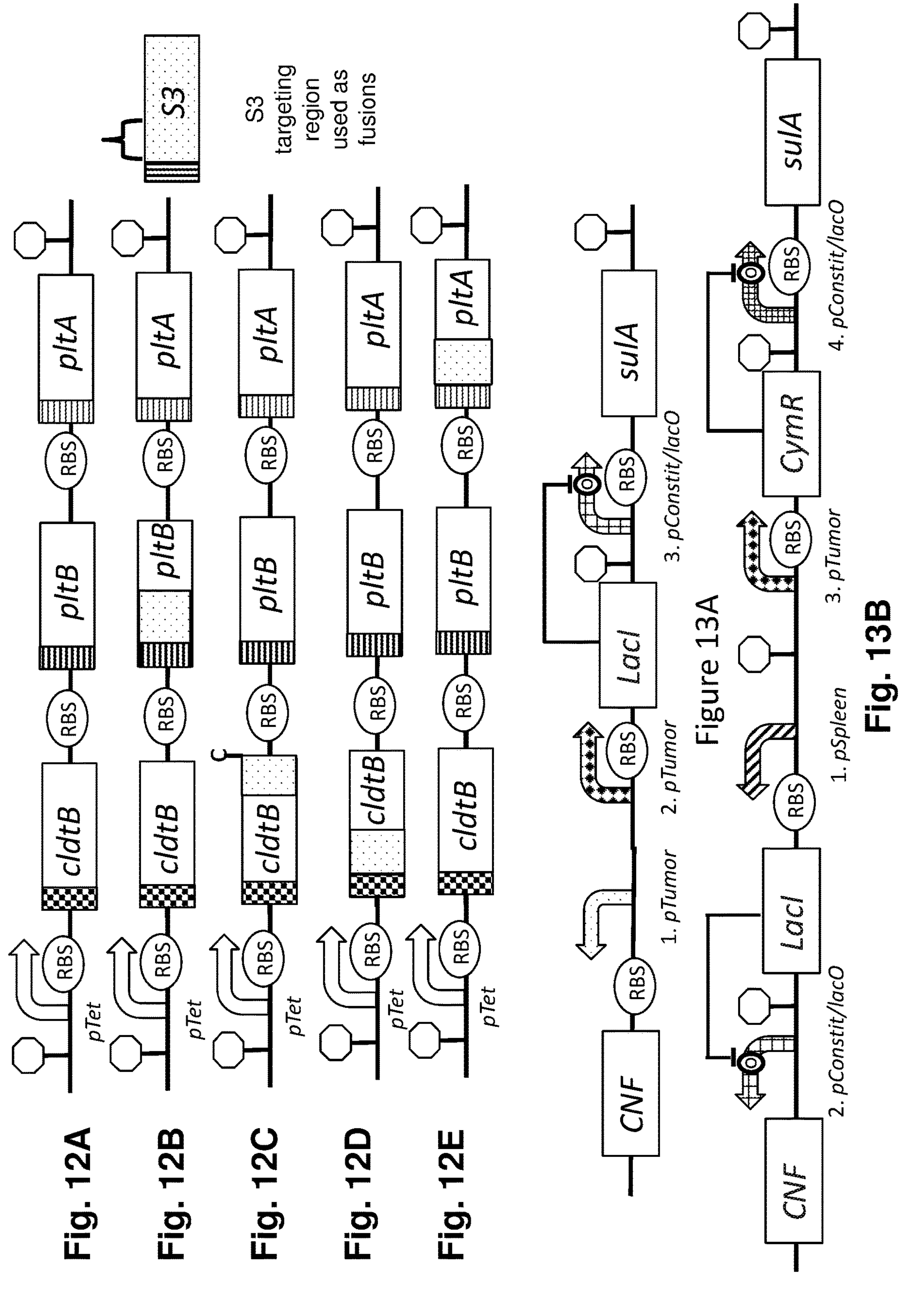
FIGS. 12A-12E show logical circuits for controlling production of *Salmonella* cytolethal distending toxin (CLDT; typhoid toxin) chimeras.
FIGS. 13A and 13B show use of tumor-specific and spleen specific promoters as inverters.

FIG. 13A shows a tumor selective toxin expression and normal tissue growth repression expression construct 1. A tumor-selective promoter expresses CNF in the tumor. 2. A tumor selective promotor expresses LacI which represses expression of sulA in the tumor and allows expression of sulA in non-tumor tissue. FIG. 13B shows a double inverter system, where the tumor-selective promoter results in expression within normal tissue, and a spleen selective promoter that results in expression in tumor tissue. 1. A spleen specific promoter that results in expression of Lad which represses 2, a constitutive promoter with the lac operator. CNF is expressed when not in the spleen. 3. A tumor specific promoter that results in expression of CymR that represses a different constitutive promoter 4 with the cym operator and allows expression not in the tumor.

EXAMPLES In order to more fully illustrate the technology, the following examples are provided.

EXAMPLE 1. Expression of the cytotoxic protein holotoxin, *Salmonella* cytolethal distending toxin (typhoid toxin) by a two component AND gate (FIG. 1A).

A cytotoxic multimer, e.g., *Salmonella* CLDT (typhoid toxin), is expressed with improved specificity using an AND gate combination of tumor selective acid induction combined with tumor selective hypoxic induction, whereby the complete holotoxin is only formed when both environmental signals are present. The genetic circuit is cloned into a plasmid or expressed on the chromosome as previously described (Low et al., 2004, Construction of VNP20009: a novel, genetically stable antibiotic-sensitive strain of tumor-targeting *Salmonella* for parenteral administration in humans, Methods Mol Med 90: 47-60), and used to treat tumors as previously described (Toso et al., 2002, Phase I study of the intravenous administration of attenuated *Salmonella* typhimurium to patients with metastatic melanoma, J. Clin. Oncol 20:142-152; Nemunaitis et al., 2003, Pilot trial of genetically modified, attenuated *Salmonella* expressing the *E. coli* cytosine deaminase gene in refractory cancer patients, Cancer Gene Therapy 10: 737-744; King, I., Ittensohn, M. and Bermudes, D. 2009. Tumor-targeted *Salmonella* typhimurium over-expressing cytosine deaminase: A novel, tumor-selective therapy. *Methods Mol Biol.* 542: 649-659).

Operable portions of the circuit include:

1) A tumor-selective acidic promoter (the *Salmonella* homologue of the asr promoter (Suziedeliene et al., 1999, The acid inducible asr gene in *Escherichia coli*. Transcriptional control by the phoBR operon, J. Bacteriol 181: 2084-2093), whereby the *Salmonella* typhimurium 14028 sequence is given below splenic promoter (upstream from STM14_1795): SEQ ID NO: 128 tacatgccgaaaccaatcactcacggaagccttttgataacagcgatatagt-catticaccggccccgcagtggggttgaatgaaaaccaaatcgagggtat-caaa
2) A 5' UT and RBS of US2011/0195847 SEQ ID NO: 077 TCGAGAGATCTCCATCGAATTCGTGGGTCG-ACCCCGGGAGGCCTAAAGAGGAGAAAT-TAACT
3) The sequence of the CLDT, cldtB and stop codon SEQ ID NO: 129

```
ATGGTCAAAAAACCTGTTTTTTTCCTTCTGACCATGATCATCTGCAGCTA
TATTTCTTTTGCCTGCGCTAATATCAGTGACTACAAAGTTATGACCTGGA
ATCTTCAGGGCTCTTCAGCATCTACAGAAAGTAAATGGAATGTCAATGTC
AGACAGCTTTTAAGCGGTACTGCCGGTGTGGATATTCTTATGGTACAGGA
GGCCGGTGCTGTTCCCACCTCAGCGGTTCCTACCGGACGACATATTCAGC
CTTTTGGAGTGGGTATTCCCATTGATGAATACACCTGGAATCTCGGAACC
ACCAGCCGTCAGGATATAAGATATATCTACTACTCGGCTATTGATGTTGG
AGCACGCCGTGTTAATCTGGCAATAGTTTCCAGACAAAGAGCGGATAATG
TTTATGTCTTGCGTCCGACAACTGTCGCATCTCGCCCCGTCATTGGCATC
GGACTGGGTAATGATGTTTTTCTGACAGCGCACGCACTGGCTAGTGGAGG
TCCGGATGCTGCAGCTATTGTCAGGGTTACCATTAATTTTTTTAGACAAC
CTCAGATGCGGCATTTATCCTGGTTTCTTGCCGGGGATTTTAATCGCAGC
CCAGACAGACTTGAAAATGACCTGATGACTGAGCATCTGGAACGAGTTGT
AGCCGTACTCGCACCTACAGAACCCACGCAAATTAGCGGTGGTATTTTAG
ATTATGGGGTCATTGTCGATCGAGCACCTTATTCACAAAGGGTCGAAGCA
TTACGTAATCCACAACTCGCTTCTGATCATTATCCCGTAGCCTTTTTGGC
ACGAAGCTGTTAA
```

4) A double terminator PartBBa_B0015: SEQ ID NO: 075

```
ccaggcatcaaataaaacgaaaggctcagtcgaaagactgggcctttcgt
tttatctgttgtttgtcggtgaacgctctctactagagtcacactggctc
accttcgggggcctttctgcgtttata
```

5) A hypoxic promoter (Mengesha et al., 2006, Development of a flexible and potent hypoxia-inducible promoter for tumor-targeted gene express in attenuated *Salmonella*, Cancer Biology and Therapy 5:1120-1128; HIP-1): SEQ ID NO: 130 GGA-TAAAAGTGACCTGACGCAATAT-TTGTCTTTTCTTGCTTAATAATGTTGTCA
6) A 5'UT and RBS SEQ ID NO: 076

ACCGTAGTTAAAGCACCTAACC<u>GAGCT</u>C*ggtacc*AAAGGAGGTTGGC<u>CC</u>

7) The sequence of the polycistronic CLDT, pltB, pltA SEQ ID NO: 131

```
ATGTATATAAATAAGTTTGTGCCTGTTTATACATTATTAATTCTCATTTA
TTCTTTTAATGCCAGCGCTGAGTGGACAGGAGATAATACGAACGCCTATT
ACTCAGACGAAGTTATCAGTGAATTACATGTTGGTCAGATAGATACTAGT
CCTTATTTTTGCATAAAAACGGTTAAAGCTAACGGTAGTGGTACACCAGT
TGTTGCATGTGCGGTATCAAAGCAGAGCATATGGGCGCCCTCCTTTAAAG
AACTTCTTGATCAGGCAAGATATTTTTACAGTACAGGGCAATCCGTAAGG
ATTCATGTTCAAAAAAATATCTGGACCTATCCGCTTTTTGTTAATACCTT
TTCAGCAAATGCTCTTGTGGGACTATCATCGTGCAGTGCGACACAATGCT
TTGGACCCAAGTAAgaggggagaagaaataATGAAAAAGTTAATATTCTT
```

-continued

```
AACCTTATCTATAGTTAGCTTTAATAACTATGCTGTAGATTTTGTGTATC
GTGTGGACTCAACCCCGCCGGACGTTATTTTTCGCGATGGGTTTTCACTA
CTTGGGTATAACCGTAACTTTCAGCAATTTATTAGTGGAAGGTCATGTAG
TGGTGGAAGTAGTGACAGTCGCTATATTGCAACAACCTCAAGTGTTAATC
AAACATATGCTATAGCCAGAGCGTACTATTCTCGCTCAACATTCAAAGGT
AATTTATACAGATATCAGATTCGTGCAGATAATAATTTCTACAGCTTGCT
CCCATCCATCACCTATCTGGAAACGCAAGGTGGTCACTTTAATGCTTATG
AAAAAACGATGATGCGATTGCAAAGAGAGTATGTTTCCACATTATCTATT
TTACCCGAGAATATTCAAAAGGCCGTGGCGCTAGTTTATGATAGCGCAAC
CGGTCTGGTAAAGGATGGTGTAAGCACAATGAATGCCAGTTATTTAGGTT
TAAGCACTACGTCTAATCCTGGTGTGATACCTTTTCTTCCGGAACCGCAG
ACGTATACCCAACAACGAATTGATGCATTCGGCCCATTAATAAGTTCATG
CTTTTCAATAGGTAGCGTATGTCAGTCACATCGAGGGCAAAGAGCTGACG
TATACAACATGTCTTTTTATGATGCAAGACCTGTAATAGAACTTATACTT
TCTAAATAA
```

The complete sequence of the genetic circuit, consists of items 1-7 above in continuous sequence, as chemically synthesized by a commercial vendor. The DNA sequences, shown as a linear sequence that is either a component of a circular plasmid capable of being carried by the bacterial species, such as *Salmonella* VNP20009, or as a chromosomal integrant, such that the genetic circuit may be selectively expressed within neoplastic tissue, requiring both hypoxic and acidic conditions, and have a therapeutic benefit against neoplastic tissue.

EXAMPLE 2: A positively and negatively regulated gene circuit for expression of a toxic monomer or multimer (e.g., a NOT gate, FIG. 2B).

A therapeutic or reporter monomer, e.g., *E. coli* CNF (GFP, *Staphylococcus aureus* alpha-hemolysin, or others), is expressed with improved specificity using a combination of tumor selectivity with repression of grown and expression in splenic normal tissue. The genetic circuit below is cloned into a plasmid or expressed on the chromosome as previously described (Low et al., 2004, Construction of VNP20009: a novel, genetically stable antibiotic-sensitive strain of tumor-targeting *Salmonella* for parenteral administration in humans, Methods Mol Med 90: 47-60), and used to treat tumors as previously described (Toso et al., 2002, Phase I study of the intravenous administration of attenuated *Salmonella* typhimurium to patients with metastatic melanoma, J. Clin. Oncol 20:142-152; Nemunaitis et al., 2003, Pilot trial of genetically modified, attenuated *Salmonella* expressing the *E. coli* cytosine deaminase gene in refractory cancer patients, Cancer Gene Therapy 10: 737-744). The operator may be repositioned more proximally to the +1 of the promoter based upon RACE or RNA transcriptomics. Mapping of transcriptional start locations is known (e.g., Mattaeu and Rodrigue 2015, Precise Identification of Genome-Wide Transcription Start Sites in Bacteria by 5'-Rapid Amplification of cDNA Ends (5-RACE), Methods Mol Biol 143-159; Klerk et al., 2014, RNA sequencing: from tag-based profiling to resolving complete transcript structure, Cell Mol Life Sci 71: 3537-3551).

Functional portions of the circuit include:

1) A splenic promoter (from US2011/0195847 TonB) SEQ ID NO: 083

```
GTTCGCCGTCCATTTTTACCTCTGGGGCTGTTTCTTAGCGCGCCCTCCCC
CGGAAAAACAAAATATAATGAACAAAAAACATACAAACCATCATCTTTTA
AAAATAAATTACATTAAAACAGAGAGTTACAACATGATGATGATGCATGA
AAAATCAAAAATGCGCCAAATCCCGCGCCGCTGCCGCCCCGTGGCAGGCC
GCCCCGCCGGGAGTACCTTTTTAAAATGCGAACAATTATCAACAACTACC
ACTTAATGATTATTTATTTCATTTTGCGATATTGATTATCATTTTCAATA
A
```

2) A 5'UT and RBS SEQ ID NO: 076

ACCGTAGTTAAAGCACCTAACCGAGCTC*ggtacc*AAAGGAGGTTGGCCC

3) The lac repressor, encoded by the DNA sequence SEQ ID NO: 133

```
atgaaaccagtaacgctgtacgatgtcgcagagtatgccggtgtctctta
tcagaccgtttcccgcgtggtgaaccaggccagccacgtttctgcgaaaa
cgcgggaaaaagtggaagcggcgatggcggagctgaattacattcccaac
cgcgtggcacaacaactggcgggcaaacagtcgttgctgattggcgttgc
cacctccagtctggccctgcacgcgccgtcgcaaattgtcgcggcgatta
aatctcgcgccgatcaactgggtgccagcgtggtggtgtcgatggtagaa
cgaagcggcgtcgaagcctgtaaagcggcggttcacaatcttctcgcgca
gcgcgtcagtgggctgatcattaactatccgctggatgaccaggatgcca
ttgctgtggaagctgcctgcactaatgttccggcgttatttcttgatgtc
tctgaccagacacccatcaacagtattattttctcccatgaagacggtac
gcgactgggcgtggagcatctggtcgcattgggtcaccagcaaatcgcgc
tgttagcgggcccattaagttctgtctcggcgcgtctgcgtctggctggc
tggcataaatatctcactcgcaatcaaattcagccgatagcggaacggga
aggcgactggagtgccatgtccggttttcaacaaaccatgcaaatgctga
atgagggcatcgttcccactgcgatgctggttgccaacgatcagatggcg
ctgggcgcaatgcgcgccattaccgagtccgggctgcgcgttggtgcgga
catctcggtagtgggatacgacgataccgaagacagctcatgttatatcc
cgccgttaaccaccatcaaacaggattttcgcctgctggggcaaaccagc
gtggaccgcttgctgcaactctctcagggccaggcggtgaagggcaatca
actgttgcccgtctcactggtgaaaagaaaaaccaccctggcgcccaata
cgcaaaccgcctctccccgcgcgttggccgattcattaatgcaactggca
cgacaggtttcccgactggaaagcgggcaggcggcgaacaaaaacgaaga
aaacaccaacgaagtgccgacctttatgctgaacgcgggccaggcgaact
acctgtctcaataa
```

4) A double terminator PartBBa_B0015 SEQ ID NO: 075

```
ccaggcatcaaataaaacgaaaggctcagtcgaaagactgggcctttcgt
tttatctgttgtttgtcggtgaacgctctctactagagtcacactggctc
accttcgggggcctttctgcgttata
```

5) A tumor selective promoter, Deyneko et al., 2016 SEQ ID NO: 030 taacgcctCTTTGTCAGAacctctccattcGTTGATCATGATCAAgaTAG

CTTtcattcgaaagtaa**TTTAAT*CTTTAT*GATACA*TAAGAG***aggccgttt where the promoter has been trimmed to allow the following operator sequence overlap with the +1 of the 5' UT.

6) The symmetrical lac operator SEQ ID NO: 010 tgtgtggaattgtgagcgctcacaattccacaca 7) A 5'UT and RBS SEQ ID NO: 077

TCGAGAGATCTCCATCGAATTCGTGGGTCGACCCCGGGAGGCCTAAAGAG

GAGAAATTAACT

8) The effector gene cytotoxic necrotic factor (CNF) coding sequence GenBank: X70670.1

EXAMPLE 3A: Two simple circuits that collectively act as a NOT AND gate. The circuits are not integrated except through their collective action, whereby CNF is selectively expressed in the tumor and growth is not suppressed in the tumor, while independently, CNF is not selectively expressed in the spleen, and growth is selectively expressed in the spleen (FIG. 3). Collectively, systemic activity is suppressed and intratumoral activity is promoted. A positively regulated and negatively regulated proliferation set of gene circuits for expression of a therapeutic or reporter monomer or polycistronic therapeutic or reporter (e.g., a simple NOT AND gate, FIG. 3).

A toxic monomer, e.g., *E. coli* CNF (or polycistronic multimer such as CLDT typhoid toxin), is expressed with improved specificity using a combination of tumor selectivity with repression of grown and expression in splenic normal tissue in combination with a tumor-selective promoter. The genetic circuit is cloned into a plasmid or expressed on the chromosome as previously described (Low et al., 2004, Construction of VNP20009: a novel, genetically stable antibiotic-sensitive strain of tumor-targeting *Salmonella* for parenteral administration in humans, Methods Mol Med 90: 47-60), and used to treat tumors as previously described (Toso et al., 2002, Phase I study of the intravenous administration of attenuated *Salmonella* typhimurium to patients with metastatic melanoma, J. Clin. Oncol 20:142-152; Nemunaitis et al., 2003, Pilot trial of genetically modified, attenuated *Salmonella* expressing the *E. coli* cytosine deaminase gene in refractory cancer patients, Cancer Gene Therapy 10: 737-744).

Operable portions of the circuit include:

1) The sulA gene in the reverse complement SEQ ID NO: 134 ctaattttacttaatgatacaaattagagtgaatttttagcccggaatgc tgtctcctgggtaaagcgtgcgcacgtacagggcgcatgataaaccctac cgcattacctaccttcgctgcttcaaccaggctggcatgttcttcttctg tcagttcttcagtcatccaaccaattaccacgctgtaatttcctgtacgc aaagcgcggatcatcgactccagcgtatgacgaggcgcaagctggctaat ttgcatcactttcgttaatggcaaacctgaagactgtacccattcacggc tgagcttttgctgcggcgtgagccagagctgccatcgtgattgttggcct -continued aactgacggagtaaaggcaaaagcaggagttgcgccatcatgggctggtc ttcgtggtagacaacttcactgaccagtcctgccgcggcattttccgtag cggtgcgcgcagcgttgtgggtagtggtaggaaatgacgaagaacgattt gcataacctgaagtgtacat 2) The 5'UT of US2011/0195847 PRL1-F1 in the reverse complement SEQ ID NO: 135

GGGCCAACCTCCTTT*ggtacc*GAGCTCGGTTAGGTGCTTTAACTACGGT

3) A splenic promoter from TonB in the reverse complement SEQ ID NO: 136

TTATTGAAAATGATAATCAATATCGCAAAATGAAATAAATAATCATTAAG

TGGTAGTTGTTGATAATTGTTCGCATTTTAAAAAGGTACTCCCGGCGGGG

CGGCCTGCCACGGGGCGGCAGCGGCGCGGGATTTGGCGCATTTTTGATTT

TTCATGCATCATCATCATGTTGTAACTCTCTGTTTTAATGTAATTTATTT

TTAAAAGATGATGGTTTGTATGTTTTTTGTTCATTATATTTTGTTTTTCC

GGGGGAGGGCGCGCTAAGAAACAGCCCCAGAGGTAAAAATGGACGGCGAA

C

4) A terminator>BBa_B0012 SEQ ID NO: 074 tcacactggctcaccttcgggtgggcctttctgcgtttata 5) A tumor-selective promoter US2011/0195847 STM1382-STM1383 SEQ ID NO: 070.

6) The 5'UT of US2011/0195847 PRL1-F1 SEQ ID NO: 077

TCGAGAGATCTCCATCGAATTCGTGGGTCGACCCCGGGAGGCCTAAAGA

GGAGAAATTAACT

7) Cytotoxic necrotic factor coding sequence and stop codon.

8) A terminator, >BBa_B0004 SEQ ID NO: 073 cgccgaaaaccccgcttcggcggggttttgccgc

The complete sequence of the genetic circuit, consists of items above in continuous sequence, as chemically synthesized by a commercial vendor. The DNA sequences, shown as a linear sequence that is either a component of a circular plasmid capable of being carried by the bacterial species, such as *Salmonella* VNP20009, or as a chromosomal integrant, such that the genetic circuit may be selectively expressed within neoplastic tissue, requiring both hypoxic and acidic conditions, and have a therapeutic benefit against neoplastic tissue.

The genetic circuit is cloned into a plasmid or expressed on the chromosome as previously described (Low et al., 2004, Construction of VNP20009: a novel, genetically stable antibiotic-sensitive strain of tumor-targeting *Salmonella* for parenteral administration in humans, Methods Mol Med 90: 47-60), and used to treat tumors as previously described (Toso et al., 2002, Phase I study of the intravenous administration of attenuated *Salmonella* typhimurium to patients with metastatic melanoma, J. Clin. Oncol 20:142-152; Nemunaitis et al., 2003, Pilot trial of genetically modified, attenuated *Salmonella* expressing the *E. coli* cytosine deaminase gene in refractory cancer patients, Cancer Gene Therapy 10: 737-744; King, I., Ittensohn, M. and Bermudes, D. 2009. Tumor-targeted *Salmonella* typhimurium over-expressing cytosine deaminase: A novel, tumor-selective therapy. *Methods Mol Biol.* 542: 649-659).

EXAMPLE 3B: Another embodiment provides two simple circuits that collectively act as a NOT AND gate. The circuits are not integrated except through their collective action, whereby carboxylesterase Est55 is selectively expressed in the tumor and growth is not suppressed in the tumor, while independently, Est55 is not selectively expressed in the spleen, and growth is selectively expressed in the spleen (FIG. 3). Collectively, systemic activity is suppressed and intratumoral activity is promoted. A positively regulated and negatively regulated proliferation set of gene circuits for expression of a therapeutic or reporter monomer or polycistronic therapeutic or reporter (e.g, a simple NOT AND gate, FIG. 3).

A monomer, e.g., *E. coli* Est55 that activates CPT-11 (or polycistronic multimer such as CLDT typhoid toxin), is expressed with improved specificity using a combination of tumor selectivity with repression of grown and expression in splenic normal tissue in combination with a tumor-selective promoter. The genetic circuit is cloned into a plasmid or expressed on the chromosome as previously described (Low et al., 2004, Construction of VNP20009: a novel, genetically stable antibiotic-sensitive strain of tumor-targeting *Salmonella* for parenteral administration in humans, Methods Mol Med 90: 47-60), and used to treat tumors as previously described (Toso et al., 2002, Phase I study of the intravenous administration of attenuated *Salmonella* typhimurium to patients with metastatic melanoma, J. Clin. Oncol 20:142-152; Nemunaitis et al., 2003, Pilot trial of genetically modified, attenuated *Salmonella* expressing the *E. coli* cytosine deaminase gene in refractory cancer patients, Cancer Gene Therapy 10: 737-744).

Operable portions of the circuit include:

1) The sulA gene in the reverse complement SEQ ID NO: 134.
2) The 5'UT of US2011/0195847 PRL1-F1 in the reverse complement SEQ ID NO: 135.
3) A splenic promoter (from TonB) in the reverse complement SEQ ID NO: 136.
4) A terminator >BBa_B0012 SEQ ID NO: 074 tcacactggctcaccttcgggtgggcctttctgcgtttata
5) A tumor-selective promoter US2011/0195847 STM1382-STM1383 SEQ ID NO: 070.
6) The 5'UT of US2011/0195847 PRL1-F1 SEQ ID NO: 077

TCGAGAGATCTCCATCGAATTCGTGGGTCGACCCCGGG<u>AGGCCT</u>AAAGA

GGAGAAATTAACT

7) *Geobacillus* carboxylesterase Est55 and stop codon SEQ ID. NO: 137 MERTVVETRYGRLRG-EMNEGVFVWKGIPYAKAPVGERRFLPPEPP-DAWDGVREATSFGPWMQPSDPIFSGLLGR MSEAPSEDGLYLNIWSPAADGKKRPVLFWIHG-GAFLFGSGSSPWYDGTAFAKHGDVVVVTI-NYRMNVFGFLHLGDS FGEAYAQAGNLGILD-QVAALRWVKENIAAFGGDPDNITIFGESAGAA-SVGVLLSLPEASGLFRRAMLQSGSGSLLLRS PETAMAMTERILDKAGIRPGDRERLLSIPAEELL-RAALSLGPGVMYGPWDGRVLRRHPIEAL-RYGAASGIPILIGVTKD EYNLFTLTDPSWT-KLGEKELLDRINREVGPVPEEAIRYYKETAEP-SAPTWQTWLRIMTYRVFVEGMLRTADAQAAQG ADVYMYRFDYETPVFGGQLKACHALEL-PFVFHNLHQPGVANFVGNRPEREAIANEMHY-AWLSFARTGDPNGAHLP EAWPAYTNERKAAF-VFSAASHVEDDPFGRERAAWQGR
8) A terminator, >BBa_B0004 SEQ ID NO: 073 cgccgaaaaccccgcttcggcggggttttgccgc The complete sequence of the genetic circuit, consists of items above in continuous sequence, as chemically synthesized by a commercial vendor. The DNA sequences, shown as a linear sequence that is either a component of a circular plasmid capable of being carried by the bacterial species, such as *Salmonella* VNP20009, or as a chromosomal integrant, such that the genetic circuit may be selectively expressed within neoplastic tissue, requiring both hypoxic and acidic conditions, and have a therapeutic benefit against neoplastic tissue.

The genetic circuit is cloned into a plasmid or expressed on the chromosome as previously described (Low et al., 2004, Construction of VNP20009: a novel, genetically stable antibiotic-sensitive strain of tumor-targeting *Salmonella* for parenteral administration in humans, Methods Mol Med 90: 47-60), and used to treat tumors as previously described (Toso et al., 2002, Phase I study of the intravenous administration of attenuated *Salmonella* typhimurium to patients with metastatic melanoma, J. Clin. Oncol 20:142-152; Nemunaitis et al., 2003, Pilot trial of genetically modified, attenuated *Salmonella* expressing the *E. coli* cytosine deaminase gene in refractory cancer patients, Cancer Gene Therapy 10: 737-744; King, I., Ittensohn, M. and Bermudes, D. 2009. Tumor-targeted *Salmonella* typhimurium over-expressing cytosine deaminase: A novel, tumor-selective therapy. *Methods Mol Biol.* 542: 649-659).

EXAMPLE 4: Expression of a KRAS inhibitory peptide.

A K-RAS inhibitory peptide is expressed and secreted, having an anti-neoplastic activity against K-RAS mutant neoplasias. A DNA sequence encoding KRAS inhibitory peptide, KRpep-2d SEQ ID NO: 068 RRRRCPLYI-SYDPVCRRRR is operably fused to the sequence encoding YebF, preceded by an LK trypsin cleavage signal, as described by Quintero et al. 2018 (Co-Expression of a Chimeric Protease Inhibitor Secreted by a Tumor-Targeted *Salmonella* Protects Therapeutic Proteins from Proteolytic Degradation J. Microbiol. Biotechnol. (2018), 28(12), 2079-2094 doi.org/10.4014/jmb.1807.08036). The genetic construct and regulatory elements may be any of those previously described, e.g., tetracycline inducible, or any of the regulatory elements described herein. This genetic construct can be expressed in *Salmonella* VNP20009 cloned into a plasmid or expressed on the chromosome as previously described (Low et al., 2004, Construction of VNP20009: a novel, genetically stable antibiotic-sensitive strain of tumor-targeting *Salmonella* for parenteral administration in humans, Methods Mol Med 90: 47-60), and used to treat tumors as previously described (Toso et al., 2002, Phase I study of the intravenous administration of attenuated *Salmonella* typhimurium to patients with metastatic melanoma, J. Clin. Oncol 20:142-152; Nemunaitis et al., 2003, Pilot trial of genetically modified, attenuated *Salmonella* expressing the *E. coli* cytosine deaminase gene in refractory cancer patients, Cancer Gene Therapy 10: 737-744; King, I., Ittensohn, M. and Bermudes, D. 2009. Tumor-targeted *Salmonella* typhimurium over-expressing cytosine deaminase: A novel, tumor-selective therapy. *Methods Mol Biol.* 542: 649-659).

EXAMPLE 5: Expression of GMCSF by a therapeutic bacterium.

The immunostimulatory peptide corresponding to the mature GMCSF is expressed by a therapeutic bacterium, thereby improving antitumor efficacy through immune simulation. The mature GMCSF peptide SEQ ID NO: 034 APARSPSPSTQPWEHVNAIQEARRLLNLSRDTAAE-MNETVEVISEMFDLQEPTCLQTRLELYKQGLRGSL-TKLKGPLT MMASHYKQHCPPTPETSCATQIITFES-FKENLKDFLLVIPFDCWEPVQE via its corresponding DNA sequence, ending in a stop codon, is expressed using an inducible promoter, or one of the genetic circuits described herein, and is expressed by a therapeutic bacterium, such as VNP20009, optionally, either polycistronically with the lysis protein E from bacteriophage φ-X174, or individually, with an upstream ribosomal binding site SEQ ID NO: 139 agatctgtactCTAGAAAGGA- GTCGTT (or modified to increase or decrease translational initiation; Salis 2011, The ribosome binding site calculator, Methods Enzymol 498: 19-42) as in the GMCSF expressed by a tumor-selective hypoxic promoter, e.g., FF+20 (Ryan, R. M., J. Green, P. J. Williams, S. Tazzyman, S. Hunt, J. H. Harmey, S. C. Kehoe, and C. E. Lewis. "Bacterial delivery of a novel cytolysin to hypoxic areas of solid tumors." Gene therapy 16, no. 3 (2009): 329-339), with a point mutation in the −10 element from SEQ ID NO. 187 CATAAT to SEQ ID NO: 138 CATCAT, and the lysis gene expressed by a tumor-selective acidic promoter, resulting in expression and release only in hypoxic and acidic environments, such as within tumors. The bacteria are used in treating tumors.

EXAMPLE 6: Expression of GMCSF by a therapeutic bacterium with an N-terminal signal sequence.

The immunostimulatory peptide corresponding to the mature GMCSF is expressed by a therapeutic bacterium as an N-terminal secretion fusion, thereby improving antitumor efficacy through immune simulation.

The OmpA signal sequence SEQ ID NO: 140 MKKTA-IAIAVALAGFATVAQA is operably fused in-frame with the mature GMCSF peptide SEQ ID NO: 138 via its corresponding DNA sequence, ending in a stop codon. The GMCSF is expressed polycistronically with the colicin E3 lysis protein SEQ ID NO: 141 MKKITGIILLLLAVIILS-ACQANYIRDVQGGTVSPSSTAEVTGLATQ via its corresponding DNA sequence, ending in a stop codon, and preceded upstream by the sequence SEQ ID NO: 139 agatctgtactCTAGAAAGGAGTCGTT containing its ribosomal binding site (GenBank: KM287568.1). The system further consists operable linking resulting in gene expression using known bacterial expression systems, or those expression systems described here in, and is expressed in a therapeutic bacterium such as VNP20009 and used to treat neoplasia.

EXAMPLE 7: Expression of a C-terminal HlyA:GMCSF fusion by a therapeutic bacterium.

The immunostimulatory peptide corresponding to the mature GMCSF is expressed by a therapeutic bacterium as a C-terminal secretion fusion, thereby improving antitumor efficacy through immune simulation.

The HlyA C-terminal 60 amino acids SEQ ID NO: 113 LAYGSQGNLNPLINEISKIISAAGNFDVKEER-AAASLLQLSGNASDFSYGRNSITLTASA is operably fused in-frame at the C-terminus of the mature GMCSF peptide SEQ ID NO: 138 via its corresponding DNA sequence, ending in a stop codon. The GMCSF is co-expressed heterologously with the HlyBD genes (U.S. Pat. No. 5,143,830) in a strain that also expresses tolC, such as VNP20009, and used to treat neoplasia.

EXAMPLE 8: Expression of a secreted adenosine deaminase by a therapeutic bacterium.

The secreted adenosine deaminase of *Eizabethkingia anophelis/meningoseptica* SEQ ID NO: 115.

via its corresponding DNA sequence, ending in a stop codon, is expressed by a therapeutic bacterium. In the present example, the adenosine deaminase is expressed polycistronically with the colicin E3 lysis protein SEQ ID NO: 141 MKKITGIILLLLAVIILS-ACQANYIRDVQGGTVSPSSTAEVTGLATQ via its corresponding DNA sequence, ending in a stop codon, and preceded upstream by the sequence SEQ ID NO: 139 agatctgtactCTAGAAAGGAGTCGTT containing its ribosomal binding site GenBank: KM287568.1). The system further consists operable linking resulting in gene expression using known bacterial expression systems such as a tetracycline inducible promoter, or those expression systems described herein, and is expressed in a therapeutic bacterium such as VNP20009, and used to treat neoplasia.

EXAMPLE 9: Expression of a PMN peptide fusion cytotoxic and immunostimulatory peptide.

A DNA sequence encoding *Staphylococcus aureus* phenol soluble modulin (Sa PSM alpha 1) fused with the immunostimulatory peptide YSL preceded by LK, SEQ ID NO: 142 MGIIAGIIKVIKSLIEQFTGKLKYSL is operably fused to the sequence encoding YebF, preceded by an LK trypsin cleavage signal, as described by Quintero et al. 2018 (Co-Expression of a Chimeric Protease Inhibitor Secreted by a Tumor-Targeted *Salmonella* Protects Therapeutic Proteins from Proteolytic Degradation J. Microbiol. Biotechnol. (2018), 28(12), 2079-2094 doi.org/10.4014/jmb.1807.08036). Alternatively, any of the secretion mechanisms described may be substituted. The genetic construct and regulatory elements may be any of those previously described, e.g., tetracycline inducible, or any of the regulatory elements described herein. This genetic construct can be expressed in *Salmonella* VNP20009 cloned into a plasmid or expressed on the chromosome as previously described (Low et al., 2004, Construction of VNP20009: a novel, genetically stable antibiotic-sensitive strain of tumor-targeting *Salmonella* for parenteral administration in humans, Methods Mol Med 90: 47-60), and used to treat tumors as previously described (Toso et al., 2002, Phase I study of the intravenous administration of attenuated *Salmonella* typhimurium to patients with metastatic melanoma, J. Clin. Oncol 20:142-152; Nemunaitis et al., 2003, Pilot trial of genetically modified, attenuated *Salmonella* expressing the *E. coli* cytosine deaminase gene in refractory cancer patients, Cancer Gene Therapy 10: 737-744; King, I., Ittensohn, M. and Bermudes, D. 2009. Tumor-targeted *Salmonella* typhimurium over-expressing cytosine deaminase: A novel, tumor-selective therapy. *Methods Mol Biol.* 542: 649-659).

EXAMPLE 10: Expression of a PMN peptide fusion cytotoxic targeted peptide.

A DNA sequence encoding *Staphylococcus aureus* phenol soluble modulin (Sa PSM alpha 1) fused with the RGD peptide SEQ ID NO: 005 ACDCRGDCFCG, SEQ ID NO: 143 MGIIAGIIKVIKSLIEQFTGKLKYSLACDCRGD-CFCG is operably fused to the sequence encoding YebF, preceded by an LK trypsin cleavage signal, as described by Quintero et al. 2018 (Co-Expression of a Chimeric Protease Inhibitor Secreted by a Tumor-Targeted *Salmonella* Protects Therapeutic Proteins from Proteolytic Degradation J. Microbiol. Biotechnol. (2018), 28(12), 2079-2094 doi.org/10.4014/jmb.1807.08036). Alternatively, any of the secretion mechanisms described may be substituted. The genetic construct and regulatory elements may be any of those previously described, e.g., tetracycline inducible, or any of the regulatory elements described herein. This genetic construct can be expressed in *Salmonella* VNP20009 cloned into a plasmid or expressed on the chromosome as previously described (Low et al., 2004, Construction of VNP20009: a novel, genetically stable antibiotic-sensitive strain of tumor-targeting *Salmonella* for parenteral administration in humans, Methods Mol Med 90: 47-60), and used to treat tumors as previously described (Toso et al., 2002, Phase I study of the intravenous administration of attenuated *Salmonella* typhimurium to patients with metastatic melanoma, J. Clin. Oncol 20:142-152; Nemunaitis et al., 2003, Pilot trial of genetically modified, attenuated *Salmonella* expressing the *E. coli* cytosine deaminase gene in refractory cancer patients, Cancer Gene Therapy 10: 737-744; King, I., Ittensohn, M. and Bermudes, D. 2009. Tumor-targeted *Salmonella* typhimurium over-expressing cytosine deaminase: A novel, tumor-selective therapy. Methods Mol Biol. 542: 649-659).

EXAMPLE 11: Alternating expression of OX40 scFv and PD-1 scFv.

A DNA sequence encoding the amino acids as shown in SEQ ID NO: 181-185 are operably linked to the two inducible promoter system. This genetic construct can be expressed in *Salmonella* VNP20009 cloned into a plasmid or expressed on the chromosome as previously described (Low et al., 2004, Construction of VNP20009: a novel, genetically stable antibiotic-sensitive strain of tumor-targeting *Salmonella* for parenteral administration in humans, Methods Mol Med 90: 47-60), and used to treat tumors as previously described (Toso et al., 2002, Phase I study of the intravenous administration of attenuated *Salmonella* typhimurium to patients with metastatic melanoma, J. Clin. Oncol 20:142-152; Nemunaitis et al., 2003, Pilot trial of genetically modified, attenuated *Salmonella* expressing the *E. coli* cytosine deaminase gene in refractory cancer patients, Cancer Gene Therapy 10: 737-744; King, I., Ittensohn, M. and Bermudes, D. 2009. Tumor-targeted *Salmonella* typhimurium over-expressing cytosine deaminase: A novel, tumor-selective therapy. *Methods Mol Biol.* 542: 649-659). Alternating induction is achieved by first injecting a first inducer, pTet, thereby inducing Ox40 but not PD-1, followed by a waiting period, before independently inducing anti-PD-1 with salicylic acid.

EXAMPLE 12A: Expression of a hybrid CLDT typhoid holotoxin with PltB:S3 hybrid.

A hybrid PltB:S3 consisting of the PltB signal sequence and 5 post cleavage amino acids that improve signal cleavage (Nielsen 2017, Predicting secretory proteins with SignalP, IN: Kidhara D (ed) Protein function prediction, Springer, New York pp 59-73; Petersen et al., 2011, SignalP 4.0: discriminating signal peptides from transmembrane regions, Nat Methods 8: 785-786), a portion of S3 consisting of the amino acids in lowercase, non-PltB non-S3 amino acids improving disulfide bonding (Ceronia et al., 2006; DISULFIND: a disulfide bonding state and cysteine connectivity prediction server, Nucleic Acids Res 34 (Web Server issue):W177-81) and creating a flexible linker (in italics), and the PltB C-terminus (FIG. 12B) SEQ ID NO: 144 MYlNKFVPVYTLLILIYSFNASAEWTGDapgivippkalftqqggaygrcpngtraltvaelrgnaelqtylrqitpgwsiyglydgtylgqayggiikdappg agfiyretfcitSGGGGsGGGGSKQSIWAPSFKELLDQARYFYSTGQSVRIHVQKNIWTYPLFVNTFSANALVGLSSCSATQ CFGPK The system further consists operable linking resulting in gene expression using known bacterial expression systems such as a tetracycline inducible promoter, or those expression systems described herein, and is expressed in a therapeutic bacterium such as VNP20009, and used to treat neoplasia.

EXAMPLE 12B: Expression of a hybrid CLDT typhoid holotoxin with PltB:HST (heat stable toxin) hybrid.

A hybrid PltB:S3 consisting of the PltB signal sequence and 5 post cleavage amino acids that improve signal cleavage (Nielsen 2017, Predicting secretory proteins with SignalP, IN: Kidhara D (ed) Protein function prediction, Springer, New York pp 59-73; Petersen et al., 2011, SignalP 4.0: discriminating signal peptides from transmembrane regions, Nat Methods 8: 785-786), a portion of S3 consisting of the amino acids in lowercase, non-PltB creating a flexible linker (in italics), and the PltB C-terminus (FIG. 12B) SEQ ID NO: 145

MYINKFVPVYTLLILIYSFNASAEWTGDnssnyccelccnpactgcfSG
GGGGGGGSKQSIWAPSFKELLDQARYFYSTGQSVRIHVQKNIWTYPLFV
NTFSANALVGLSSCSATQCFGPK The system further consists operable linking resulting in gene expression using known bacterial expression systems such as a tetracycline inducible promoter, or those expression systems described herein, and is expressed in a therapeutic bacterium such as VNP20009 and used to treat neoplasia.

EXAMPLE 12C: Expression of a hybrid CLDT typhoid holotoxin with PltB:*clostridium* targeting peptide hybrid.

A hybrid PltB:S3 consisting of the PltB signal sequence and 5 post cleavage amino acids that improve signal cleavage (Nielsen 2017, Predicting secretory proteins with SignalP, IN: Kidhara D (ed) Protein function prediction, Springer, New York pp 59-73; Petersen et al., 2011, SignalP 4.0: discriminating signal peptides from transmembrane regions, Nat Methods 8: 785-786), a portion of S3 consisting of the amino acids in lowercase, non-PltB creating a flexible linker (in italics), and the PltB C-terminus (FIG. 12B) SEQ ID NO: 146

MYINKFVPVYTLLILIYSFNASAEWTGDsldagqyvlvmkanssysgny
pysilfqkfSGGGGGGGSGGGGKQSIWAPSFKELLDQARYFYSTGQSV
RIHVQKNIWTYPLFVNTFSANALVGLSSCSATQCFGPK The system further consists operable linking resulting in gene expression using known bacterial expression systems such as a tetracycline inducible promoter, or those expression systems described herein, and is expressed in a therapeutic bacterium such as VNP20009, and used to treat neoplasia.

EXAMPLE 13: Expression of a PE38K with a heat stable toxin targeting moiety.

The OmpA signal sequence with post cleavage amino acids SEQ ID NO: 147 MKKTAIAIAVALAGFATVAQAAV, followed by the HST mature peptide amino acids SEQ ID NO: 002 NSSNYCCELCCNPACTGCF, followed by a flexible linker SEQ ID NO: 148 GGGGSGGGGSGGGGSRGGS, followed by PE38K SEQ ID NO: 150

LAALTAHQACHLPLETFTRHRQPRGWEQLEQCGYPVQRLVALYLAARLS
WNQVDQVIRNALASPGSGGDLGEAIREQPEQARLALTLAAAESERFVRQ
GTGNDEAGAANAPADSGDALLERNYPTGAEFLGDGGDVSFSTRGTQNWT
VERLLQAHRQLEERGYVFVGYHGTFLEAAQSIVFGGVRARSQDLDAIWR

-continued

GFYIAGDPALAYGYAQDQEPDARGRIRNGALLRVYVPRSSLPGFYRTSL

TLAAPEAAGEVERLIGHPLPLRLDAITGPEEEGGRLETILGWPLAERTW

VIPSAIPTDPRNVGGDLDPSSIPDKEQAISALPDYASQPGKPPKDEL*

The system further consists operable linking resulting in gene expression using known bacterial expression systems such as a tetracycline inducible promoter, or those expression systems described herein, and is expressed in a therapeutic bacterium such as VNP20009, and used to treat neoplasia.

EXAMPLE 14: Expression of a PE38K with an RGD targeting moiety.

The OmpA signal sequence with post cleavage amino acids SEQ ID NO: 147 MKKTAIAIAVALAGFATVAQAAV, followed by the HST mature peptide amino acids SEQ ID NO: 151 ggggsACDCRGDCFCGggggs, followed by a flexible linker SEQ ID NO: 148 GGGGSGGGGSGGGGSRGGS, followed by PE38K SEQ ID NO: 150.

The system further consists operable linking resulting in gene expression using known bacterial expression systems such as a tetracycline inducible promoter, or those expression systems described herein, and is expressed in a therapeutic bacterium such as VNP20009, and used to treat neoplasia.

EXAMPLE 15: Expression of a PE38K with a pertussis S3 targeting moiety.

The OmpA signal sequence with post cleavage amino acids SEQ ID NO: 147

The OmpA signal sequence with post cleavage amino acids

SEQ ID NO: 147
MKKTAIAIAVALAGFATVAQAAV, followed by the HST mature peptide amino acids SEQ ID NO: 152
MYINKFVPVYTLLILIYSFNASAEWTGDapgivippkalftqqggaygr cpngtraltvaelrgnaelqtylrqitpgwsiyglydgtylgqayggii kdappgagfiyretfcit, followed by a flexible linker SEQ ID NO: 153
*SGGGGsGGGGSGGGGS*, followed by PE38K SEQ ID NO: 150.

agfiyretfcit, followed by a flexible linker SEQ ID NO: 153 SGGGGsGGGGSGGGGS, followed by PE38K SEQ ID NO: 150.

The system further consists operable linking resulting in gene expression using known bacterial expression systems such as a tetracycline inducible promoter, or those expression systems described herein, and is expressed in a therapeutic bacterium such as VNP20009, and used to treat neoplasia.

EXAMPLE 16: Expression of a therapeutic *Pasteurella multocita* toxin.

*Pasteurella multocita* toxin (PMT) consists of 1285 amino acids which in its naturally occurring form is encoded as a single open reading frame. The corresponding DNA sequence of complete amino acid sequence UniProtKB—P17452 (TOXA_PASMD) ending in a stop codon, can be expressed in *Salmonella* VNP20009 cloned into a plasmid or expressed on the chromosome as previously described (Low et al., 2004, Construction of VNP20009: a novel, genetically stable antibiotic-sensitive strain of tumor-targeting *Salmonella* for parenteral administration in humans, Methods Mol Med 90: 47-60), and used to treat tumors as previously described (Toso et al., 2002, Phase I study of the intravenous administration of attenuated *Salmonella* typhimurium to patients with metastatic melanoma, J. Clin. Oncol 20:142-152; Nemunaitis et al., 2003, Pilot trial of genetically modified, attenuated *Salmonella* expressing the *E. coli* cytosine deaminase gene in refractory cancer patients, Cancer Gene Therapy 10: 737-744; King, I., Ittensohn, M. and Bermudes, D. 2009. Tumor-targeted *Salmonella* typhimurium over-expressing cytosine deaminase: A novel, tumor-selective therapy. *Methods Mol Biol.* 542: 649-659). The system further consists operable linking resulting in gene expression using known bacterial expression systems such as a tetracycline inducible promoter, or those expression systems described herein, and is expressed in a therapeutic bacterium such as VNP20009 and used to treat neoplasia.

EXAMPLE 17: A therapeutic *Pasteurella multocita* toxin as an immune-therapeutic toxin.

The complete PMT sequence UniProtKB—P17452 (TOXA_PASMD) with an immune stimulating peptide (tyroserleutide YSL) fusion preceded by a protease cleavage site (leucine lysine; LK), SEQ ID NO: 154 LKYSL is expressed in *Salmonella* VNP20009 cloned into a plasmid or expressed on the chromosome as previously described (Low et al., 2004, Construction of VNP20009: a novel, genetically stable antibiotic-sensitive strain of tumor-targeting *Salmonella* for parenteral administration in humans, Methods Mol Med 90: 47-60), and used to treat tumors as previously described (Toso et al., 2002, Phase I study of the intravenous administration of attenuated *Salmonella* typhimurium to patients with metastatic melanoma, J. Clin. Oncol 20:142-152; Nemunaitis et al., 2003, Pilot trial of genetically modified, attenuated *Salmonella* expressing the *E. coli* cytosine deaminase gene in refractory cancer patients, Cancer Gene Therapy 10: 737-744; King, I., Ittensohn, M. and Bermudes, D. 2009. Tumor-targeted *Salmonella* typhimurium over-expressing cytosine deaminase: A novel, tumor-selective therapy. *Methods Mol Biol.* 542: 649-659). The system further consists operable linking resulting in gene expression using known bacterial expression systems such as a tetracycline inducible promoter, or those expression systems described herein, and is expressed in a therapeutic bacterium such as VNP20009 and used to treat neoplasia.

EXAMPLE 18. Expression of secreted split PMTs.

Multiple open reading frames are generated based on the amino acid sequences below are expressed independently as components of a regulatory circuit. The two fragment peptide combinations may consist of amino acids 1-574 together with 575-1285; 1-719 together with 72-1285; or 1-1104, together with 1105-1285. The three peptide combinations may consist of 1-574 together with 575-719 and 720-1285; or 1-719 and 720-1104 and 1105-1285. The four peptide combinations may consist of 1-574, together with 575-719, 720-1104, and 1105-1285.

Secreted PMT divided into two components with leucine zippers (underlined). Amino acids of the nucleic acid open reading, for the first of a two-part regulatory circuit; 1-574=PMT N-term; 575-580=linker (in large italics); 581-609=leucine zipper (in bold), SEQ ID NO: 118.

Amino acids of the nucleic acid open reading, for the second of a two-part regulatory circuit 1-119=YebF; 120-121 "LK"=cleavage signal; 122-151=leucine zipper (in bold); 152-155=linker (large type italics); 156-866=C-term PMT, SEQ ID NO: 119.

EXAMPLE 19A: Expression of released split PMTs.

The multiple amino acid sequences and their corresponding DNA sequences as open reading frames as listed below are expressed independently as components of a regulatory circuit as described herein and in previous examples. The released PMT is divided into two components with leucine zippers (underlined). Split PMTs may also be expressed without engineered secretion of the non-secretion component through bacterial cell lysis. Programmed loss of bacterial cell wall structural integrity by disruption of the asd gene can be used for release of cytoplasmic contents (Kong et al., 2008). Through utilization of arabinose inducible control to keep the gene on, cell lysis occurs in the absence of the inducer. Programmed lysis has been enhanced by arabinose control of the cell wall biosynthesis genes murA and asd coupled with expression of the p22 phage c2 gene (Kong et al., 2012). Subsequent to removal of the arabinose inducer caused by introduction of the bacteria into an arabinose-free host, murA and asd are further inhibited through loss of repression of PR, which then drives an antisense murA and asd. High lysis efficiencies were engineered using the bacteriophage lambda lysis gene cluster SRRz for tumor-targeted delivery with anhydrotetracycline induction coupled in parallel with salicylate induction for therapeutic gene expression (Camacho et al., 2016).

Amino acids of the nucleic acid open reading, for the first of a two-part regulatory circuit; 1-574=PMT N-term; 575-580=linker (in large italics); 581-609=leucine zipper (in bold): SEQ ID NO: 118.

Amino acids of the nucleic acid open reading, for the second of a two-part regulatory circuit 1, initiating methionine; 2-31 leucine zipper; 32-35, linker; 36-746, PMT C-term. SEQ ID NO: 120.

The system further consists operable linking resulting in gene expression using known bacterial expression systems such as a tetracycline inducible promoter, or those expression systems described herein, and is expressed in a therapeutic bacterium such as VNP20009 and used to treat neoplasia.

EXAMPLE 19B: Secreted split therapeutic *Escherichia coli* cytotoxic necrotizing factors (CNFs) toxin under control of a gene expression circuit, optionally with lysis protein co-expression.

One or more forms of CNF are incorporated. *E. coli* cytotoxic necrotic factor 1 (CNF1) consists of 1014 amino acids and its corresponding DNA sequence followed by a stop codon which in its naturally occurring form is encoded as a single open reading frame. The amino acid sequence shown contains the CNF with an internal pertussis S3 binding domain (underlined) with flanking short flexible linkers (bold) SEQ ID NO: 121.

A split secreted or released form of therapeutic *Escherichia coli* cytotoxic necrotizing factor (CNF) toxin under control of a gene expression circuit, optionally with lysis protein expression.

1-539 CNF1 N-term; 540-574=linker and leucine zipper SEQ ID NO: 122.

Amino acids of the nucleic acid open reading, for the second of a two-part regulatory circuit 1-119=YebF; 120-121 "LK"=cleavage signal; 122-151=leucine zipper (in bold); 152-155=linker (large type italics); followed by C-term CNF amino acids 540-1013 SEQ ID NO: 123.

EXAMPLE 20: A released and/or secreted split therapeutic *Escherichia coli* cytotoxic necrotizing factor (CNF) toxin under control of a gene expression circuit, optionally with lysis protein(s).

The multiple open reading frames generated below may then be expressed independently as components of a regulatory circuit as described in previous examples.

First component: 1-539 CNF1 N-term; 540-574=linker and leucine zipper SEQ ID NO: 122. The second component of a released and/or split therapeutic *Escherichia coli* CNF SEQ ID NO: 124.

The system further consists operable linking resulting in gene expression using known bacterial expression systems such as a tetracycline inducible promoter, or those expression systems described herein, and is expressed in a therapeutic bacterium such as VNP20009, and used to treat neoplasia.

EXAMPLE 21: A released (no secretion signal) therapeutic *Escherichia coli* cytotoxic necrotizing factor (CNF) toxin under control of a gene expression circuit and lysis protein(s).

The multiple open reading frames generated below may then be expressed independently as components of a regulatory circuit as described in previous examples. SEQ ID NO. 125.

The system further consists operable linking resulting in gene expression using known bacterial expression systems such as a tetracycline inducible promoter, or those expression systems described herein, and is expressed in a therapeutic bacterium such as VNP20009, and used to treat neoplasia.

EXAMPLE 22: an RGD-targeted therapeutic *Escherichia coli* cytotoxic necrotizing factor (CNF) toxin expressed under control of a gene expression circuit, optionally co-expressed with one or more lysis proteins (FIGS. 9A-9L). All constructs with or without enhancers, e.g., colicin or bacteriocin release peptide expressed polycistronically, e.g., SEQ ID NO: 141 MKKITGIILLLLAVIILSACQANYIRDVQGGTVSPSSTAEVTGLATQ, GenBank: KM287568.1 pSTM1787 is exemplary; and promoter elements may include known promoter elements and systems including quorum sensing cyclical lysis (Din et al., doi: 10.1038/nature18930).

The single or multiple open reading frames generated below may then be expressed independently as components of a regulatory circuit as described in previous examples. Diagrams of targeted toxins are shown in FIGS. 9A-9L, 12A-12E and 13A-13B, α-type PSM peptides, and p-type PSM peptides, The toxins may be expressed by known expression systems or by the expression systems described herein. The amino acid sequence shown contains the CNF with an internal 4C RGD peptide (bold) with flanking short flexible liners SEQ ID NO: 126.

The modified toxin is expressed via its corresponding DNA sequence, followed by a stop codon, using known inducible promoters such as the tetracycline promoter, or by one of the genetic circuits described herein, such as a combination of negative regulation for expression or bacterial growth within normal (e.g., spleen) tissue combined with positive regulation for expression within tumor tissue.

EXAMPLE 23: A pertussis S3:therapeutic *Escherichia coli* cytotoxic necrotizing factor (CNF) toxin expressed under control of a gene expression circuit, optionally co-expressed with one or more lysis proteins (FIGS. 8A-8D).

The single or multiple open reading frames generated below may then be expressed independently as components of a regulatory circuit as described in previous examples. Diagrams of targeted toxins are shown in FIGS. 9A-9L, 12A-12E and 13A-13B, and α-type PSM peptides, p-type PSM peptides. The toxins may be expressed by known expression systems or by the expression systems described herein. The amino acid sequence shown contains the CNF with an internal pertussis S3 binding domain (underlined) with flanking short flexible linkers (bold) SEQ ID NO: 121.

The modified toxin is expressed via its corresponding DNA sequence, followed by a stop codon, using known inducible promoters such as the tetracycline promoter, or by one of the genetic circuits described herein, such as a combination of negative regulation for expression or bacterial growth within normal (e.g., spleen) tissue combined with positive regulation for expression within tumor tissue.

EXAMPLE 24A: A HST:therapeutic *Escherichia coli* cytotoxic necrotizing factor (CNF) toxin expressed under control of a gene expression circuit, optionally co-expressed with one or more lysis proteins (FIGS. 8A-8D).

The single or multiple open reading frames generated below may then be expressed independently as components of a regulatory circuit as described in previous examples. Diagrams of targeted toxins are shown in FIGS. 9A-9L, 12A-12E and 13A-13B, and α-type PSM peptides, p-type PSM peptides. The toxins may be expressed by known expression systems or by the expression systems described herein. The amino acid sequence shown contains the CNF with an internal 4C RGD peptide (bold) with flanking short flexible linkers (italics) SEQ ID NO: 126.

The modified toxin is expressed via its corresponding DNA sequence, followed by a stop codon, using known inducible promoters such as the tetracycline promoter, or by one of the genetic circuits described herein, such as a combination of negative regulation for expression or bacterial growth within normal (e.g., spleen) tissue combined with positive regulation for expression within tumor tissue.

EXAMPLE 24B: A parasporin toxin expressed under control of a gene expression circuit, optionally co-expressed with one or more lysis proteins.

The single or multiple open reading frames generated may then be expressed independently as components of a regulatory circuit as described in previous examples. Diagrams of targeted toxins are shown in FIGS. 9A-9L, 12A-12E and 13A-13B, and α-type PSM peptides, p-type PSM peptides. The toxins may be expressed by known expression systems or by the expression systems described herein. The amino acid sequence shown contains parasporin 1 SEQ ID NO: 155

```
MDPFSNYSEQKYPDSNNNQELITKSSSFYSDTTNENAKNYHPIEQDILK

FTNQEFSDNHYQHSDVSNDINSMRNTLCKDLPPETNMSIYDNLRSTVTV

PSFSNQFDPIKFLHDIEIAIQTGSFSASTQSNMNQGGTDINPMLISTFF

KVASSLLPFPLSSLGALASFYVTDSQTGAMANLWRQMVDYVEKRIDSKI

LDYHNFIMGAELAALNASLKEYARWKIFENDMNRMAEPPSTGVITQFRI

LNDNFIKYIAKLQFSTNQSDLQYPVLTLPLRAQACVMHLMLLKDATTSV

WGQQIDSQQLNGYKAELIRLIKVYTNDVNTTYNQGLELEKAKPLNYSDP

EEYLQARRPDISVLRSNFKEVMKWNRVAKYKRGMAMSALSLAALFPTFG

PNYPKQALKWVQSRQIFAPVIGIPGGITSQDHSGTFGSMRFDVKTYDQI

DALRRLMELYIQPLKSAYFYIYESDWKVRATYVNDYIGKRGSNTGLAWG

MWSSDPSVIYTSALGAAGYAPNWGVRYSHGGSYTKGMAPPNTNAYAPFE

FKYPGYKLHSVSAYGLSKAPDTADSVMFGFRPVLLENEANQLLTDTALQ

IPAEIGITDWPAFGRTEEPINGQDAIIIWESFTSGFGFTYTVDSPQKQK
```

-continued

```
YKIIYRSANNLSASTVSLTDNNQTFFTDILNPSLDPNGVRGNYGSYTLV

EGPIIEFSQGTNIFKLRSQKGEFAIDSIIFSPVS
```

The toxin is expressed via its corresponding DNA sequence, followed by a stop codon, using known inducible promoters such as the tetracycline promoter, or by one of the genetic circuits described herein, such as a combination of negative regulation for expression or bacterial growth within normal (e.g., spleen) tissue combined with positive regulation for expression within tumor tissue. Optionally, the gene may be co-expressed polycistronically with a lysis protein or as a quorum-sensing cyclical lysis system.

EXAMPLE 25: PEGylation of therapeutic bacteria.

PEGylation is accomplished by known means. A technical guide is provided by Lee et al., 2007 (Investigations of PEGylated recombinant adenovirus, using fluorescein-labeled polyethylene glycol, Hum Gene Ther 18: 286-300). By way of example, the method of Tesfay et al., 2013 is illustrated. Bacteria are covalently modified with activated monomethoxy-polyethylene glycol ($PEG_{5000}$) succinimidyl succinate (Jenkem Technology, Beijing, China). A range of concentrations of PEG (0 to 20 mg) is added to $5\times10^6$-$5\times10^{12}$ colony forming units (CFU) of a therapeutic bacterium, such as VNP200009, with or without additional therapeutic modifications such as those described herein. By way of specific example, $5\times10^8$ CFU with a final volume of 500 μl in 100 mM potassium PBS (pH 7.4) for each preparation. PEG conjugation reactions are performed as described previously (Croyle M A, Yu Q-C, Wilson J M. 2000. Development of a rapid method for the PEGylation of adenoviruses with enhanced transduction and improved stability under harsh storage conditions. Hum. Gene Ther. 11:1713-1722; O'Riordan C R, Lachapelle A, Delado C, Parkes V, Wadsworth S C, Smith A E, Francis G E. 1999. PEGylation of adenovirus with retention of infectivity and protection from neutralizing antibody in vitro and in vivo. Hum. Gene Ther. 10:1349-1358; Blake D A, Bovin N V, Bess D, Henry S M. 2011. FSL constructs: a simple method for modifying cell/virion surfaces with a range of biological markers without affecting their viability. J. Vis54:e3289 doi:10.3791/3289). Briefly, all conjugation reactions are performed at 25° C. with gentle agitation. The reactions are stopped by 15 min incubation at 4° C. Reaction products are purified by buffer exchange over a Micro-Bio Spin P-30 chromatography column (Bio-Rad) equilibrated with 100 mM potassium PBS (pH 7.4) following the supplier's protocol. A similar approach may be used to modify VNP20009 and other bacteria with FSL-$PEG_{2000}$ (KODE Biotech, Auckland, New Zealand), to noncovalently used to modify bacteria by simple direct contact (Blake et al., 2011. FSL constructs: a simple method for modifying cell/virion surfaces with a range of biological markers without affecting their viability. J. Vis. Exp. 54:e3289 doi:10.3791/3289; Hadac et al., 2011. Fluorescein and radiolabeled function-spacer-lipid constructs allow for simple in vitro and in vivo bioimaging of enveloped virions. J. Virol. Methods 176:78-84). For comparison, VNP20009 is incubated with 100 mM potassium PBS (pH 7.4) without PEG or FSL-PEG under similar conditions and processed in the same manner to that for the PEG-conjugated virus. PEGylation status is assessed by in vitro infectivity assay on cultured cells (Elsinghorst 1994, Measurement of invasion by gentamycin resistance, Methods in Enzymology 236: 405-420). Serum and antibody interaction assay are performed after exposing bacteria as described for poly(allylamine hydrochloride) (PAH) coating (Lee et al., 2013, A polymer coating applied to *Salmonella* prevents the binding of *Salmonella*-specific antibodies, *Int J Cancer.* 2013 Feb. 1; 132(3):717-25. doi: 10.1002/ijc.27700). The therapeutic bacteria, such as VNP20009, and used to treat neoplasia.

EXAMPLE 26: Example. Expression of human cGAS.

Heterologous expression of human cGAS is used to stimulate interferon, in order to result in an improved immune stimulation against neoplastic tissue. The 157-522 amino acids of human cGAS are indicated as SEQ ID NO: 156

```
DAAPGASKLRAVLEKLKLSRDDISTAAGMVKGVVDHLLLRLKCDSAFRG

VGLLNTGSYYEHVKISAPNEFDVMFKLEVPRIQLEEYSNTRAYYFVKFK

RNPKENPLSQFLEGEILSASKMLSKFRKIIKEEINDIKDTDVIMKRKRG

GSPAVTLLISEKISVDITLALESKSSWPASTQEGLRIQNWLSAKVRKQL

RLKPFYLVPKHAKEGNGFQEETWRLSFSHIEKEILNNHGKSKTCCENKE

EKCCRKDCLKLMKYLLEQLKERFKDKKHLDKFSSYHVKTAFFHVCTQNP

QDSQWDRKDLGLCFDNCVTYFLQCLRTEKLENYFIPEFNLFSSNLIDKR

SKEFLTKQIEYERNNEFPVFDEF
```

A nucleotide sequence, obtained by commercial DNA synthesis, corresponding to the cGAS amino acids above, with added initiating methionine and second amino acid (A) to result in an NcoI site at the 5' end (underlined) is indicated by the following sequence, that further contains a stop codon followed by a HindIII restriction site at the 3' end (underlined) SEQ ID NO: 157

```
ccATGGCGGACGCAGCTCCGGGTGCATCCAAACTGCGTGCGGTITTAGA

AAAACTGAAACTGTCCAGGGATGATATCTCCACCGCTGCGGGTATGGTC

AAGGGCGTGGTGGACCACCTGCTGCTGCGCCTGAAATGTGACTCGGCTT

TTCGTGGTGTAGGTCTGCTGAACACTGGCAGCTATTACGAACACGTGAA

AATTTCGGCCCCTAATGAATTCGACGTCATGTTCAAATTGGAAGTCCCG

CGTATTCAGCTGGAGGAATATTCCAACACTCGTGCCTACTATTTCGTAA

AATTCAAACGCAACCCTAAAGAGAACCCGCTGTCCCAGTTCCTGGAAGG

CGAGATTCTGTCCGCTTCTAAAATGCTGTCCAAATTCCGTAAAATTATT

AAGGAGGAAATCAACGACATCAAAGACACGGACGTAATCATGAAACGCA

AAAGAGGTGGTTCTCCGGCCGTCACGCTGCTGATTTCTGAAAAAATTTC

CGTGGATATTACCCTGGCCCTGGAATCCAAGTCTTCCTGGCCGGCCTCC

ACGCAGGAAGGTCTGCGCATTCAGAACTGGCTGTCTGCAAAGGTACGTA

AACAGCTGCGTTTGAAACCGTTCTATTTAGTGCCGAAGCATGCGAAAGA

AGGTAACGGTTTCCAAGAAGAAACCTGGCGTCTGAGCTTCTCTCACATC

GAAAAAGAAATCCTTAACAAtCATGGCAAAAGCAAAACTTGCTGTGAAA

ACAAAGAAGAGAAATGCTGTCGTAAGGACTGTCTGAAACTGATGAAATA

TCTGCTGGAACAGCTGAAAGAACGTTTCAAGGACAAAAAACACCTGGAC

AAATTCTCTAGCTACCACGTAAAAACCGCCTTCTTCCACGTGTGTACTC

AGAACCCGCAGGACAGCCAGTGGGACCGCAAAGACCTGGGTCTGTGCTT

CGACAACTGTGTTACCTACTTCCTGCAGTGCCTCCGTACCGAAAAACTG
```

-continued

```
GAGAACTATTTCATCCCGGAATTTAACCTGTTCTCTTCTAACCTGATCG

ACAAGCGCTCTAAAGAATTCCTGACCAAACAAATTGAATACGAACGTAA

CAACGAGTTTCCTGTGTTCGACGAGTTTtaaAAGCTT
```

Optionally, the bacterial strain may be deleted in the cellulase synthetase gene bcsA, thereby reducing biofilm formation. The system further consists operable linking resulting in gene expression using known bacterial expression systems such as a tetracycline inducible promoter, or those expression systems described herein, and is expressed in a therapeutic bacterium such as VNP20009 and used to treat neoplasia.

EXAMPLE 27: Expression of *Vibrio* DncV.

Heterologous expression a *Vibrio* gene is used to stimulate interferon, in order to result in an improved immune stimulation against neoplastic tissue. *Vibrio cholera* GenBank Accession number CP013309.1 amino acid sequence is given by SEQ ID NO: 158

```
MRMTWNFHQYYTNRNDGLMGKLVLTDEEKNNLKALRKIIRLRTRDVFEE

AKGIAKAVKKSALTFEIIQEKVSTTQIKHLSDSEQREVAKLIYEMDDDA

RDEFLGLTPRFWTQGSFQYDTLNRPFQPGQEMDIDDGTYMPMPIFESEP

KIGHSLLILLVDASLKSLVAENHGWKFEAKQTCGRIKIEAEKTHIDVPM

YAIPKDEFQKKQIALEANRSFVKGAIFESYVADSITDDSETYELDSENV

NLALREGDRKWINSDPKIVEDWFNDSCIRIGKHLRKVCRFMKAWRDAQW

DVGGPSSISLMAATVNILDSVAHDASDLGETMKIIAKHLPSEFARGVES

PDSTDEKPLFPPSYKHGPREMDIMSKLERLPEILSSAESADSKSEALKK

INMAFGNRVTNSELIVLAKALPAFAQEPSSASKPEKISSTMVSG
```

Optionally, the overexpression of cyclic dinucleotides is combined with deletion of their binding activator proteins (e.g., STM14_4357, yhjN) and/or riboswitches, which serves both to limit the physiological response of the bacteria to the CDNs, as well as limit the internal binding components, where thereby make the CDNs more available to the host immune system. Optionally, the bacterial strain may be deleted in the cellulase synthetase gene bcsA, thereby reducing biofilm formation. The system further consists operable linking resulting in gene expression using known bacterial expression systems such as a tetracycline inducible promoter, or those expression systems described herein, and is expressed in a therapeutic bacterium such as VNP20009 and used to treat neoplasia.

EXAMPLE 28: Overexpression of *Salmonella* dinucleotide cyclases.

A *Salmonella* overexpressing a dinucleotide cyclase that results in enhanced production of a cyclic dinucleotide is used to stimulate interferon, in order to result in an improved immune stimulation against neoplastic tissue. The *Salmonella* cyclic dinucleotide synthase consisting of (yaiC/AdrA), *Salmonella* YiaC amino acids SEQ ID NO: 159

```
MFPKIMNDENFYRKAVEQAVAPPDPPDDRQRSGLRFARRIRLPRAVGLG

GMFLPVAAVLVTQPVFGGWWLLLVGWSFVWPHLAWQWAAKALDPLRQEI

YNLKVDAILSGMWIALMGVNMLPAAALFMMMSMNLMGAGGRRLFTVGMG

LLLASCLVTLQLAGLPVAMRSSSLEVTLSLPVIMLYPLLFAWVSYQTAI

KLAEHKRRLQAMSSRDGMTGVYNRRHWEILLRNEFDHSRRHHREATLLI
```

-continued

IDIDHFKSINDTWGHDVGDEAIIALTRQLQITLRGSDIIGRFGGDEFAV

IMCGTPADSAITAMSRVHERLNTLRLPGAPQVMLRISVGVAPLTPQIGH

YREWLKSADMALYKAKNAGRNRTEVAA

EXAMPLE 29: Expression of a hybrid *Shigella* toxin B subunit with the mistletoe B subunit.

The mistletoe lectin is expressed by a therapeutic bacterium to improve immune stimulation and increase the anticancer effects of a therapeutic bacterium. The mistletoe (*Viscum coloratum*) lectin chain B subunit (GenBank AAM46935.1) is given by SEQ ID NO: 117.

The *Shigella* toxin B subunit UniProtKB Q7BQ98.1 is given by SEQ ID NO: 160 MKKTLLIAASLSFF-SASALATPDCVTGKVEYTKYNDDDTFTVKVGD-KELFTNRWNLQSLLLSAQITGMTVTIKTNACH NGGGFSEVIFR and is encoded by SEQ ID NO: 161 atgaaaaaaacattattaatagctgcatcgctttcatttttttcagcaa gtgcgctggcgacgcctgattgtgtaactggaaaggtggagtatacaaa atataatgatgacgatacctttacagttaaagtgggtgataaagaatta ttaccaacagatggaatcttcagtctcttcttctcagtgcgcaaattac ggggatgactgtaaccattaaaactaatgcctgtcataatggaggggga ttcagcgaagttatttttcgttga A hybrid toxin, containing the *Shigella* toxin N-terminus (in capitals) and the mistletoe lectin C-terminus (in lower case) of the technology is given by the amino acid sequence SEQ ID NO: 162

MKKTLLIAASLSFFSASALATPDCVTGKVEtvrfvgrnglcldvpegdy hdgsriqlwpcksnsdqnqlwtirrdgtirsngrclttygytagsyimi ydcnrggwdlttwqirgngilnprsmmvigtpsgsrgtrgttftlqtlg yslgqgwlasndtaprevtiygfrdhcmetsggkvwvgtcvsgkqnqrw alygdgsirpkpyqdqcltsqgdsvrsvinlfsctagsprqrwvftnkg ailnlknrlamdvaesnpslrriiifsvtgnpnqmwlpvp EXAMPLE 30: Expression of a hybrid *Shigella* toxin B subunit with the mistletoe B subunit.

The mistletoe (*Viscum coloratum*) lectin chain B subunit (GenBank AAM46935.1) is given by SEQ ID NO: 117.

The *Shigella* toxin B subunit (UniProtKB Q7BQ98.1 is given by SEQ ID NO: 160 and is encoded by SEQ ID NO: 161.

A hybrid toxin, containing the *Shigella* toxin N-terminus (in capitals) and the mistletoe lectin C-terminus (in lower case) of the technology is given by the amino acid sequence SEQ ID NO: 162.

The corresponding nucleotide sequence, with NcoI, second (V) codon, stop codon and HindIII site is given by the sequence SEQ ID NO: 163 ccatgGTCaaaaaaacattattaatagctgcatcgctttcatttttttc agcaagtgcgctggcgacgcctgattgtgtaactggaaaggtggagACG -continued

GTCCGTTTCGTTGGCCGCAACGGCCTGTGCTTGGACGTTCCGGAGGGTG

ATTACCATGATGGTTCTCGCATCCAGTTGTGGCCGTGCAAATCGAACTC

TGATCAGAACCAACTGTGGACAATCCGTCGTGACGGCACCATCCGCTCC

AACGGTCGCTGTCTGACCACATACGGCTACACCGCCGGTAGCTACATTA

TGATTTATGACTGCAATCGTGGCGGCTGGGATCTCACGACCTGGCAGAT

TCGTGGCAACGGGATCATCCTGAATCCGCGTTCCATGATGGTGATCGGC

ACTCCGTCTGGTTCTCGCGGGACTCGTGGTACTACCTTCACGCTGCAAA

CCCTGGGTTATTCTCTGGGCCAGGGGTGGTTGGCATCGAACGATACCGC

GCCGCGTGAAGTGACTATCTATGGTTTCCGTGACCACTGCATGGAAACC

TCTGGCGGCAAGGTCTGGGTGGGTACCTGCGTGTCCGGCAAACAGAACC

AGCGCTGGGCGCTGTATGGCGACGGCAGCATCCGTCCGAAGCCGTACCA

GGATCAGTGTCTGACCTCCCAGGGTGATAGCGTGCGCAGCGTGATCAAC

CTGTTTTCTTGCACTGCGGGTAGCCCGCGTCAGCGCTGGGTATTCACCA

ACAAGGGCGCTATTCTGAACCTGAAAAATCGTCTGGCTATGGATGTGGC

TGAAAGCAACCCGTCTTTGCGCCGCATCATCATCTTTTCCGTTACCGGT

AATCCGAACCAGATGTGGCTGCCAGTCCCGtaaAAGCTT

EXAMPLE 31: Co-expression of a GMCSF with ColE3 lysis.

A DNA fragment encoding a GMCSF with ColE3 lysis protein as a polycistronic message. The fragment encodes an NcoI site upstream and XbaI and HindIII sites downstream for cloning into an expression vector and expressed by a therapeutics bacterium, used to treat neoplasia. SEQ ID NO: 164 ccATGGCTAAAAAGACAGCTATCGCGATTGCAGTGGCACTGGCTGGTTT

CGCTACCGTAGCGCAGGCAGctCCGGCTCGTAGCCCGTCGCCATCCACT

CAGCCCTGGGAGCACGTCAATGCGATTCAAGAGGCTCGTCGTTTACTTA

ACCTGTCGCGGGATACCGCAGCGGAGATGAACGAAACAGTTGAAGTTAT

CTCGGAAATGTTTGATTTGCAGGAACCAACATGTTTGCAGACTCGCCTG

GAACTTTATAAGCAGGGTTTACGGGGCTCATTAACAAAACTGAAAGGCC

CTCTTACCATGATGGCCTCCCATTACAAGCAGCATTGTCCCCCCACGCC

TGAAACTTCTTGCGCGACGCAAATTATTACGTTTGAATCGTTCAAGGAG

AATCTGAAAGATTTCCTTTTGGTTATCCCCTTCGATTGCTGGGAACCTG

TACAAGAATGACTCGAGTagatctgtacaCTAGAAAGGAGTCGTTATGA

AAAAAATAACAGGGATTATTTTATTGCTTCTTGCAGTCATTATTCTGTC

TGCATGTCAGGCAAACTATATCCGGGATGTTCAGGGGGGACCGTATCTC

CGTCATCAACqGCTGAAGTGACCGGATTAGCAACGCAGTAAtctagagc gaagcttgatc

While the invention is shown by way of various examples and explanations, it should be understood that this specification and the drawings are intended to encompass the various combinations, sub-combinations, and permutations of the various features disclosed, and not limited by the particular combinations and sequences presented by way of example.

Each reference cited herein is expressly incorporated herein in its entirety. Such references provide examples representing aspects of the invention, uses of the invention, disclosure of the context of the invention and its use and application. The various aspects disclosed herein, including subject matter incorporated herein by reference, may be employed, in combination or subcombination and in various permutations, consistent with the claims.

The invention may be embodied in other specific forms without departing from its spirit or essential characteristics. The described embodiment is to be considered in all respects only illustrative and not restrictive. The scope of the invention is, therefore, indicated by the appended claims rather by the foregoing description. All changes that fall within the meaning and range of equivalency of the claims are to be embraced within their scope.

What is claimed is:

1. A live genetically engineered gram-negative bacterium, comprising:

a first heterologous gene which encodes at least a first subunit of a functional multimeric cytolethal distending toxin or a fusion of a first subunit of the functional multimeric cytolethal distending toxin, the first heterologous gene being inducible or repressible via a first promoter or operator; repressor, a second heterologous gene which encodes at least a second subunit of the functional multimeric cytolethal distending toxin or a fusion of the second subunit of the functional multimeric cytolethal distending toxin, the second heterologous gene being inducible or repressible via a second promoter or operator repressor;

the first promoter or operator repressor being independent and different from the second promoter or operator repressor;

the first heterologous gene being responsive via the first promoter or operator and the second heterologous gene being responsive via the second promoter or operator, to together implement a Boolean logic function selected from the group consisting of NOT, NOR, NAND, OR, AND, XOR, and Not XOR, with respect to formation by the live genetically engineered gram-negative bacterium of the functional multimeric cytolethal distending toxin;

being configured to functionally implement a Boolean logic function based on inputs represented by presence or absence of a first inducer or repressor for the respective first promoter or operator repressor and by presence or absence of a second inducer or repressor for the second promoter or operator repressor, the first promoter or operator repressor and the second promoter or operator repressor being adapted to selectively interact to provide a different functional outcome than independent promotion or repression of the first heterologous gene or promotion or repression of the second heterologous gene; and an output representing a gene product selectively transcribed in dependence on the presence or absence induction or repression of the first promoter or operator repressor and the second promoter or operator repressor and the Boolean logic function, wherein the output provides feedback to the Boolean logic function, the live genetically engineered gram-negative bacterium being adapted for administration to a human or animal and colonization of at least one tissue under non-lethal conditions; and the functional multimeric cytolethal distending toxin gene product has a tissue-specific therapeutic effect on the human or animal.

2. The live genetically engineered gram-negative bacterium according to claim 1, wherein the functional multimeric cytolethal distending toxin comprises a fusion of a cytolethal distending toxin subunit, and at least one of PltA, PltB, pertussis PltB S2 subunit, pertussis PltB S3 subunit, PltB:HST (heat stable toxin), PltB:*clostridium* targeting peptide, apoptin, apoptin nuclear export signal, apoptin nuclear localization signal, ArtAB, ArtAB subtilase, and *Bacillus anthracis* toxin lethal factor.

3. The live genetically engineered gram-negative bacterium according to claim 1, wherein the functional multimeric cytolethal distending toxin comprises a nuclear localization factor.

4. The live genetically engineered gram-negative bacterium according to claim 1, wherein the at least a second subunit of the functional multimeric cytolethal distending toxin or a fusion of the second subunit of the functional multimeric cytolethal distending toxin is distinct from the at least a first subunit of the functional multimeric cytolethal distending toxin or a fusion of the first subunit of the functional multimeric cytolethal distending toxin.

5. The live genetically engineered gram-negative bacterium according to claim 1, wherein the functional multimeric cytolethal distending toxin comprises a fusion of a cytolethal distending toxin subunit and at least one of PltA, PltB, pertussis PltB S2 subunit, pertussis PltB S3 subunit, PltB:HST (heat stable toxin), PltB:*clostridium* targeting peptide, apoptin, apoptin nuclear localization signal, apoptin nuclear export signal, ArtAB, ArtAB subtilase, and *Bacillus anthracis* toxin lethal factor.

6. The live genetically engineered gram-negative bacterium according to claim 1, wherein the Boolean logic function is selected from the group consisting of AND, NAND, OR and NOR.

7. The live genetically engineered gram-negative bacterium according to claim 1, wherein the Boolean logic function is selected from the group consisting of XOR and Not XOR.

8. The live genetically engineered gram-negative bacterium according to claim 1, wherein:

the first promoter or operator has greater functionality within the at least one tissue of the host and lower functionality within another tissue of the host; and the second promoter or operator is exogenously administered to the host, the first heterologous gene and the second heterologous gene are inducible or repressible in combination to provide a localized effect on the at least one tissue and are inducible or repressible independently without providing the localized effect on the at least one tissue.

9. The live genetically engineered gram-negative bacterium according to claim 1, wherein the first promoter or operator is selectively induced or expressed in a tumor of a host and the second promoter or operator is selectively induced or expressed in a normal tissue of the host, and act together to selectively reduce formation of the functional multimeric cytolethal distending toxin in the normal tissue and to selectively increase formation of the functional multimeric cytolethal distending toxin in the tumor tissue.

10. The live genetically engineered gram-negative bacterium according to claim 1, wherein the at least the first subunit of a functional multimeric cytolethal distending toxin or a fusion of the first subunit of the functional multimeric cytolethal distending toxin, and the at least the second subunit of the functional multimeric cytolethal distending toxin or the fusion of the second subunit of the functional multimeric cytolethal distending toxin, are coexpressed under control of the first promoter or operator and the second promoter or operator to form the functional multimeric cytolethal distending toxin.

11. The live genetically engineered gram-negative bacterium according to claim 1, wherein at least one of the first promoter or operator and the second promoter or operator comprises a tumor selective promoter selected from the group consisting of: STM1787, STM1791 STM1793, ydiH, lpT, csG, mltD, mdh, mtfA, frdA, pfkA, pflE, nirB, ptsG, glpA, and ydiH.

12. The live genetically engineered gram-negative bacterium according to claim 1, wherein at least one of the first promoter or operator and the second promoter or operator comprises a tissue-selective promoter selected from the group consisting of a bile activated gene promoter, a spleen activated promoter, STM0006 yaaJ, STM0006, STM0007 talB, STM0080, STM0080, STM0081, STM0390 aroM, STM0391 yaiE, STM0605 ybdN, STM0605, STM0606 ybdO, STM0892 ybjP, STM0893, STM1044 sodC, STM1044, STM1045, STM1231 phoP, STM1231, STM1232 purB, STM1249, STM1249, STM1250, STM1583, STM1583, STM1584, STM1584 ansP, STM1736 yciA, STM1736, STM1737, STM1737 tonB, STM1868, STM1876 holE, STM1876, STM1877, STM2153 yehE, STM2153, STM2154, STM2154 mrp, STM2169 yohC, STM2169, STM2170 yohD, STM2349 yfcG, STM2349, STM2350, STM2366 accD, STM2367 dedA, STM3047 ygfY, STM3047, STM3048, STM3048 ygfZ, STM3231 yqjK, STM3231, STM3232, STM3805 yidH, STM3805, STM3806, STM4286 lpxO, STM4286, STM4287, STM4290 proP, STM4290, STM4291, STM4291 basS, STM4328 yjeH, STM4329, STM4362 hflX, STM4362, STM4363, STM4363 hflK, PSLT006, PSLT007, PSLT024, PSLT025, PSLT025, PSLT026, PSLT040 spvA, PSLT040, PSLT041, PSLT045, PSLT046, and PSLT047.

13. The live genetically engineered gram-negative bacterium according to claim 1, wherein at least one of the first heterologous gene and the second heterologous gene encode at least one peptide selected from the group consisting of *Pseudomonas* ToxA, cytotoxic necrotic factor cnf1, cytotoxic necrotic factor cnf2, cytotoxic necrotic factor cnf3, cytotoxic necrotic factor dnf, cytotoxic necrotic factor CNFY, phenol soluble modulin toxin (PSM), parasporin, *Staphylococcus* leukotoxin, *Pasteurella* multocita toxin (PMT) *Actinobacillus* leukotoxin, *Phaseolus vulgaris* leukoagglutinin (L-PHA), *Helix pomatia* lectin (HPA), mistletoe lectin, GMCSF, human cGAS, *Vibrio* DncV, *Salmonella* AdrA, K-Ras inhibitory peptide, carboxylesterase Est55, carboxylesterase Est55 C408V mutant, carboxylesterase Est55 C408A mutant, secreted adenosine deaminase, tryptophanase, antibody against checkpoint inhibitor, and checkpoint inhibitor peptide.

14. The live genetically engineered gram-negative bacterium according to claim 1, wherein at least one of the first heterologous gene and the second heterologous gene encode an enhancer selected from the group comprising of apoptin, TAT-apoptin, TAT-bim, TAT-bax, TAT-p53, antennapedia homeodomain (penetraxin), Kaposi fibroblast growth factor (FGF) membrane-translocating sequence (MTS), herpes simplex virus VP22, hexahistidine, hexalysine, hexaarginine, herpes simplex virus thymidine kinase nuclear localization signal (NLS), nuclear localization signal from apoptin, nuclear export signal from apoptin, SV40 large T antigen monopartite NLS, and nucleoplamin bipartite NLS.

15. The live genetically engineered gram-negative bacterium according to claim 1, wherein at least one of the first heterologous gene and the second heterologous gene encodes a therapeutic toxin modified with an immunotherapeutic peptide selected from the group consisting of tyroserleutide, survivin, melanoma associated antigen Melan A/MART 1, tyrosinase, gp100, tyrosine-related protein-2 (TRYP-2), EGFR, human epidermal receptor-2 (HER2), carcinoembryonic antigen (CEA), mucin 1 (MUC-1), New York-esophagus antigen (NY-ESO), and mesothelin.

16. The live genetically engineered gram-negative bacterium according to claim 1, wherein at least one of the first promoter or operator and the second promoter or operator comprises MarA, which is induced by presence of acetyl salicylic acid.

17. The live genetically engineered gram-negative bacterium according to claim 1, wherein the live genetically engineered gram-negative bacterium has a selective tropism for at least one type of tumor in a human or animal, and the functional multimeric cytolethal distending toxin is effective for treating the at least one type of tumor of the human or animal, the live genetically engineered gram-negative bacterium being provided within a pharmaceutically acceptable formulation for administration to the human or animal.

18. The live genetically engineered gram-negative bacterium according to claim 1, wherein the live genetically engineered gram-negative bacterium is provided in a pharmaceutically acceptable formulation suitable for administration to a human or animal, and the genetically engineered gram-negative bacterium is subject to PEGylation effective for increasing a serum half-life of the live genetically engineered gram-negative bacterium after administration to the human or animal in the pharmaceutically acceptable formulation.

19. Live genetically engineered gram-negative bacterium according to claim 1, wherein the Boolean logic function comprises at least three logical inputs.

20. A method of treating a tumor, comprising:

administering the live genetically engineered gram-negative bacterium according to claim 1 to a human or animal having the tumor in need of treatment; and administering at least one of the first inducer or repressor and the second inducer or repressor to the human or animal, to establish conditions that cause the live genetically engineered gram-negative bacterium to selectively express the functional multimeric cytolethal distending toxin within the tumor, to thereby deliver a selective treatment comprising delivery of the functional multimeric cytolethal distending toxin to the tumor.

* * * * *

SEQUENCE LISTING

```
<160> NUMBER OF SEQ ID NOS: 188

<210> SEQ ID NO 1
<211> LENGTH: 11
<212> TYPE: PRT
<213> ORGANISM: Artificial Sequence
<220> FEATURE:
<223> OTHER INFORMATION: HIV TAT protein amino acids 47-57

<400> SEQUENCE: 1

Tyr Gly Arg Lys Lys Arg Arg Gln Arg Arg Arg
1               5                   10


<210> SEQ ID NO 2
<211> LENGTH: 19
<212> TYPE: PRT
<213> ORGANISM: Artificial Sequence
<220> FEATURE:
<223> OTHER INFORMATION: Heat stable enterotoxin targeting peptide

<400> SEQUENCE: 2

Asn Ser Ser Asn Tyr Cys Cys Glu Leu Cys Cys Asn Pro Ala Cys Thr
1               5                   10                  15

Gly Cys Phe


<210> SEQ ID NO 3
<211> LENGTH: 313
<212> TYPE: PRT
<213> ORGANISM: Canis familiaris

<400> SEQUENCE: 3

Met Val Arg Gly His Leu Val Ala Ala Val Gly Ala Ser Ser Lys Val
1               5                   10                  15

Arg Glu Glu Ser Ser Pro Ser Ala Cys Pro Ser Gly His Arg Val Cys
            20                  25                  30

Gly Arg Gln Thr Arg Val Arg Val Leu Pro Glu Leu Ser Arg Arg Asp
        35                  40                  45

Gly Leu Gln Gly Glu Ala Arg Arg Asp Arg Ser Ser Ser Ser Pro Gln
    50                  55                  60

Arg Pro Pro Arg Gly Pro Trp Ser Ala Pro Pro Pro Pro Cys Arg Arg
65                  70                  75                  80

Pro Asp Pro Leu Ala Leu Trp Arg Glu Gly Thr Glu His Pro Arg Arg
                85                  90                  95

Arg Ala Trp Arg Pro Gln Tyr Gly Ala Ala Ala Gly Ala Val Ile Pro
            100                 105                 110

Ser Trp Gln Leu Arg Gly Lys Ala Ser Val Leu Leu Ala Ala Gly Gln
        115                 120                 125

Ala Leu Glu Asn Ser Thr Ser Ala Leu Ser Ala Arg Pro Pro Val Ala
    130                 135                 140

Ala Ala Val Val Ser His Phe Asn Asp Cys Pro Asp Ser His Ser Gln
145                 150                 155                 160
```

```
Phe Cys Phe His Gly Thr Cys Arg Phe Leu Val Gln Glu Asp Lys Pro
                165                 170                 175

Ala Cys Val Cys His Ser Gly Tyr Val Gly Ala Arg Cys Glu His Ala
            180                 185                 190

Asp Leu Leu Ala Val Val Ala Ala Ser Gln Lys Lys Gln Ala Ile Thr
        195                 200                 205

Ala Leu Val Val Val Ser Ile Val Ala Leu Ala Val Leu Ile Ile Ala
    210                 215                 220

Cys Val Leu Ile His Cys Cys Gln Val Arg Lys His Cys Glu Trp Cys
225                 230                 235                 240

Gln Ala Leu Leu Cys Arg His Glu Lys Pro Ser Ala Leu Leu Lys Gly
                245                 250                 255

Arg Ala Ala Cys Cys His Ser Glu Thr Gly Lys Gly Arg Lys Gly Pro
            260                 265                 270

Arg Gln Gly His Ser Gly Arg Arg Ser Pro Leu Pro Pro Pro Leu Thr
        275                 280                 285

Ser Pro Gly Gln Gly Pro Gly Arg Gly Gly Leu Phe Asn Leu Gln Glu
    290                 295                 300

Pro Leu Lys Arg Pro Pro Gln Gly Cys
305                 310


<210> SEQ ID NO 4
<211> LENGTH: 30
<212> TYPE: PRT
<213> ORGANISM: Clostridium perfringens

<400> SEQUENCE: 4

Ser Leu Asp Ala Gly Gln Tyr Val Leu Val Met Lys Ala Asn Ser Ser
1               5                   10                  15

Tyr Ser Gly Asn Tyr Pro Tyr Ser Ile Leu Phe Gln Lys Phe
            20                  25                  30


<210> SEQ ID NO 5
<211> LENGTH: 11
<212> TYPE: PRT
<213> ORGANISM: Artificial Sequence
<220> FEATURE:
<223> OTHER INFORMATION: RGD-C4

<400> SEQUENCE: 5

Ala Cys Asp Cys Arg Gly Asp Cys Phe Cys Gly
1               5                   10


<210> SEQ ID NO 6
<211> LENGTH: 10
<212> TYPE: PRT
<213> ORGANISM: Artificial Sequence
<220> FEATURE:
<223> OTHER INFORMATION: MMP2/9 inhibitor

<400> SEQUENCE: 6

Cys Thr Thr His Trp Gly Phe Thr Leu Cys
1               5                   10


<210> SEQ ID NO 7
<211> LENGTH: 15
<212> TYPE: PRT
<213> ORGANISM: Artificial Sequence
<220> FEATURE:
<223> OTHER INFORMATION: MMP2/9 derivative

<400> SEQUENCE: 7
```

Arg Gly Asp Ser Tyr Cys Thr Thr His Trp Gly Phe Thr Leu Cys
1 5 10 15

<210> SEQ ID NO 8
<211> LENGTH: 12
<212> TYPE: PRT
<213> ORGANISM: Artificial Sequence
<220> FEATURE:
<223> OTHER INFORMATION: Peptide that binds epithelial cell adhesion molecule EP133 US 9,815,866

<400> SEQUENCE: 8

Glu His Leu His Cys Leu Gly Ser Leu Cys Trp Pro
1 5 10

<210> SEQ ID NO 9
<211> LENGTH: 12
<212> TYPE: PRT
<213> ORGANISM: Artificial Sequence
<220> FEATURE:
<223> OTHER INFORMATION: Peptide that binds epithelial cell adhesion molecule EP114 US 9,815,866

<400> SEQUENCE: 9

Lys His Leu Gln Cys Val Arg Asn Ile Cys Trp Ser
1 5 10

<210> SEQ ID NO 10
<211> LENGTH: 34
<212> TYPE: DNA
<213> ORGANISM: Artificial Sequence
<220> FEATURE:
<223> OTHER INFORMATION: Symmetrical lacO operator

<400> SEQUENCE: 10
tgtgtggaat tgtgagcgct cacaattcca caca 34

<210> SEQ ID NO 11
<211> LENGTH: 21
<212> TYPE: DNA
<213> ORGANISM: Artificial Sequence
<220> FEATURE:
<223> OTHER INFORMATION: Tumor-specific bacterial promoter element
<220> FEATURE:
<221> NAME/KEY: Y
<222> LOCATION: (1)..(1)
<223> OTHER INFORMATION: Y is T or C
<220> FEATURE:
<221> NAME/KEY: H
<222> LOCATION: (2)..(2)
<223> OTHER INFORMATION: H is A or T or C
<220> FEATURE:
<221> NAME/KEY: N
<222> LOCATION: (3)..(3)
<223> OTHER INFORMATION: N is A or T or G or C
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: Y
<222> LOCATION: (4)..(4)
<223> OTHER INFORMATION: Y is T or C
<220> FEATURE:
<221> NAME/KEY: D
<222> LOCATION: (5)..(5)
<223> OTHER INFORMATION: D is A or T or G
<220> FEATURE:
<221> NAME/KEY: K
<222> LOCATION: (7)..(7)
<223> OTHER INFORMATION: K is G or T
<220> FEATURE:
<221> NAME/KEY: W
<222> LOCATION: (10)..(10)
<223> OTHER INFORMATION: W is A or T
<220> FEATURE:
<221> NAME/KEY: W
<222> LOCATION: (13)..(13)
<223> OTHER INFORMATION: W is A or T
<220> FEATURE:
<221> NAME/KEY: N
<222> LOCATION: (15)..(15)
<223> OTHER INFORMATION: N is A or T or G or C
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: S
<222> LOCATION: (17)..(17)
<223> OTHER INFORMATION: S is G or C
<220> FEATURE:
<221> NAME/KEY: R
<222> LOCATION: (18)..(18)
<223> OTHER INFORMATION: R is G or A
<220> FEATURE:
<221> NAME/KEY: W
<222> LOCATION: (19)..(19)
<223> OTHER INFORMATION: W is A or T
<220> FEATURE:
<221> NAME/KEY: M
<222> LOCATION: (21)..(21)
<223> OTHER INFORMATION: M is A or C

<400> SEQUENCE: 11
yhnydtkttw ttwanasrwa m 21

<210> SEQ ID NO 12
<211> LENGTH: 21
<212> TYPE: DNA
<213> ORGANISM: Artificial Sequence
<220> FEATURE:
<223> OTHER INFORMATION: Tumor-specific bacterial promoter element

<400> SEQUENCE: 12
cagtatttta tttaaaggta a 21

<210> SEQ ID NO 13
<211> LENGTH: 21
<212> TYPE: DNA
<213> ORGANISM: Artificial Sequence
<220> FEATURE:
<223> OTHER INFORMATION: Tumor-specific bacterial promoter element

<400> SEQUENCE: 13
ccatatttta tttagaggta a 21

<210> SEQ ID NO 14
<211> LENGTH: 21
<212> TYPE: DNA
<213> ORGANISM: Artificial Sequence
<220> FEATURE:
<223> OTHER INFORMATION: Tumor-specific bacterial promoter element

<400> SEQUENCE: 14
ttttgtttaa aaaaaataca g 21

<210> SEQ ID NO 15
<211> LENGTH: 21
<212> TYPE: DNA
<213> ORGANISM: Artificial Sequence
<220> FEATURE:

<223> OTHER INFORMATION: Tumor-specific bacterial promoter element

<400> SEQUENCE: 15
ttacctctaa ataaaatatg g 21

<210> SEQ ID NO 16
<211> LENGTH: 21
<212> TYPE: DNA
<213> ORGANISM: Artificial Sequence
<220> FEATURE:
<223> OTHER INFORMATION: Tumor-specific bacterial promoter element

<400> SEQUENCE: 16
cactgtgatt ttttgaggta a 21

<210> SEQ ID NO 17
<211> LENGTH: 21
<212> TYPE: DNA
<213> ORGANISM: Artificial Sequence
<220> FEATURE:
<223> OTHER INFORMATION: Tumor-specific bacterial promoter element

<400> SEQUENCE: 17
ttacgtgtaa aaaaacaaat g 21

<210> SEQ ID NO 18
<211> LENGTH: 22
<212> TYPE: DNA
<213> ORGANISM: Artificial Sequence
<220> FEATURE:
<223> OTHER INFORMATION: Tumor-specific bacterial promoter element

<400> SEQUENCE: 18
ttacttttaa aaaaccaacc tg 22

<210> SEQ ID NO 19
<211> LENGTH: 21
<212> TYPE: DNA
<213> ORGANISM: Artificial Sequence
<220> FEATURE:
<223> OTHER INFORMATION: Tumor-specific bacterial promoter element

<400> SEQUENCE: 19
tctcattttt tctcaacgtg a 21

<210> SEQ ID NO 20
<211> LENGTH: 20
<212> TYPE: DNA
<213> ORGANISM: Artificial Sequence
<220> FEATURE:
<223> OTHER INFORMATION: Tumor-specific bacterial promoter element

<400> SEQUENCE: 20
gcacgtttta ataaattggg 20

<210> SEQ ID NO 21
<211> LENGTH: 21
<212> TYPE: DNA
<213> ORGANISM: Artificial Sequence
<220> FEATURE:
<223> OTHER INFORMATION: Tumor-specific bacterial promoter element

<400> SEQUENCE: 21
cagcattttg tgtataaatt a 21

<210> SEQ ID NO 22
<211> LENGTH: 21
<212> TYPE: DNA
<213> ORGANISM: Artificial Sequence
<220> FEATURE:
<223> OTHER INFORMATION: Tumor-specific bacterial promoter element

<400> SEQUENCE: 22
taatctttat atgaaataag a 21

<210> SEQ ID NO 23
<211> LENGTH: 21
<212> TYPE: DNA
<213> ORGANISM: Artificial Sequence
<220> FEATURE:
<223> OTHER INFORMATION: Tumor-specific bacterial promoter element

<400> SEQUENCE: 23
ttgtatgtta tttgtacaaa c 21

<210> SEQ ID NO 24
<211> LENGTH: 21
<212> TYPE: DNA
<213> ORGANISM: Artificial Sequence
<220> FEATURE:
<223> OTHER INFORMATION: Tumor-specific bacterial promoter element

<400> SEQUENCE: 24
gtatcttttt ataaaacaca a 21

<210> SEQ ID NO 25
<211> LENGTH: 17
<212> TYPE: DNA
<213> ORGANISM: Artificial Sequence
<220> FEATURE:
<223> OTHER INFORMATION: Dyneko et al., 2016, (Composing a tumor specific bacterial promoter, 11(5): e0155338) FNR''

<400> SEQUENCE: 25
cgttgatcaa tgatcaa 17

<210> SEQ ID NO 26
<211> LENGTH: 29
<212> TYPE: DNA
<213> ORGANISM: Artificial Sequence
<220> FEATURE:
<223> OTHER INFORMATION: Dyneko et al., 2016, (Composing a tumor specific bacterial promoter, 11(5): e0155338) functional tumor-selective promoter

<400> SEQUENCE: 26
ttttaagact ataccaactt gatttaatt 29

<210> SEQ ID NO 27
<211> LENGTH: 100
<212> TYPE: DNA
<213> ORGANISM: Artificial Sequence
<220> FEATURE:
<223> OTHER INFORMATION: Dyneko et al., 2016, (Composing a tumor specific bacterial promoter, 11(5): e0155338) tumor specific promoter po.112

<400> SEQUENCE: 27
taacgcctct ttgtcagaac ctctccattc gttgacgcac atcaagatag ctttcattcg 60
aaagtaattt aatctttata tgaaataaga gaggccgttt 100

<210> SEQ ID NO 28
<211> LENGTH: 100
<212> TYPE: DNA
<213> ORGANISM: Artificial Sequence
<220> FEATURE:
<223> OTHER INFORMATION: mutation of NagC

<400> SEQUENCE: 28
taacgcctct ttgtcagaac ctctccattc gttgacgcac atcaagatag ctttcattcg 60
aaagtaattt aatctttata tgaaatgcga gaggccgttt 100

<210> SEQ ID NO 29
<211> LENGTH: 99
<212> TYPE: DNA
<213> ORGANISM: Artificial Sequence
<220> FEATURE:
<223> OTHER INFORMATION: deletion in TGIF

<400> SEQUENCE: 29
taacgcctct tttcagaacc tctccattcg ttgacgcaca tcaagatagc tttcattcga 60
aagtaattta atctttatat gaaataagag aggccgttt 99

<210> SEQ ID NO 30
<211> LENGTH: 100
<212> TYPE: DNA
<213> ORGANISM: Artificial Sequence
<220> FEATURE:
<223> OTHER INFORMATION: mutation of insignificant nucleotides in FNR
and NagC

<400> SEQUENCE: 30
taacgcctct ttgtcagaac ctctccattc gttgatcatg atcaagatag ctttcattcg 60
aaagtaattt aatctttatg atacataaga gaggccgttt 100

<210> SEQ ID NO 31
<211> LENGTH: 100
<212> TYPE: DNA
<213> ORGANISM: Artificial Sequence
<220> FEATURE:
<223> OTHER INFORMATION: mutation of regions between motifs

<400> SEQUENCE: 31
taagtcacct ttgtcagaac aacgctactc gttgacgcac atcaagatag ctttcactag 60
taagtaattt aatctttata tgaaataaga gaggccgttt 100

<210> SEQ ID NO 32
<211> LENGTH: 97
<212> TYPE: DNA
<213> ORGANISM: Artificial Sequence
<220> FEATURE:
<223> OTHER INFORMATION: mutation of regions between motifs

<400> SEQUENCE: 32
agaccaatgg acatccacgg cgattattac gttgatcatg atcaagcagt tttaagacta 60
taccaacttg atttaattct tgtaataaac gaatgcc 97

<210> SEQ ID NO 33
<211> LENGTH: 143
<212> TYPE: PRT
<213> ORGANISM: Artificial Sequence
<220> FEATURE:
<223> OTHER INFORMATION: GMCSF

<400> SEQUENCE: 33

```
Met Trp Leu Gln Ser Leu Leu Leu Leu Gly Thr Val Ala Cys Ser Ile
1               5                   10                  15

Ser Ala Pro Ala Arg Ser Pro Ser Pro Ser Thr Gln Pro Trp Glu His
            20                  25                  30

Val Asn Ala Ile Gln Glu Ala Arg Arg Leu Leu Asn Leu Ser Arg Asp
        35                  40                  45

Thr Ala Ala Glu Met Asn Glu Thr Val Glu Val Ile Ser Glu Met Phe
    50                  55                  60

Asp Gln Glu Pro Thr Cys Leu Gln Thr Arg Leu Glu Leu Tyr Lys Gln
65                  70                  75                  80

Gly Leu Arg Gly Ser Leu Thr Lys Leu Lys Gly Pro Leu Thr Met Met
                85                  90                  95

Ala Ser His Tyr Lys Gln His Cys Pro Pro Thr Pro Glu Thr Ser Cys
            100                 105                 110

Ala Thr Gln Ile Ile Thr Phe Glu Ser Phe Lys Glu Asn Leu Lys Asp
        115                 120                 125

Phe Leu Leu Val Ile Pro Phe Asp Cys Trp Glu Pro Val Gln Glu
    130                 135                 140
```

<210> SEQ ID NO 34
<211> LENGTH: 127
<212> TYPE: PRT
<213> ORGANISM: Artificial Sequence
<220> FEATURE:
<223> OTHER INFORMATION: Mature GMCSF peptide

<400> SEQUENCE: 34

```
Ala Pro Ala Arg Ser Pro Ser Pro Ser Thr Gln Pro Trp Glu His Val
1               5                   10                  15

Asn Ala Ile Gln Glu Ala Arg Arg Leu Leu Asn Leu Ser Arg Asp Thr
            20                  25                  30

Ala Ala Glu Met Asn Glu Thr Val Glu Val Ile Ser Glu Met Phe Asp
        35                  40                  45

Leu Gln Glu Pro Thr Cys Leu Gln Thr Arg Leu Glu Leu Tyr Lys Gln
    50                  55                  60

Gly Leu Arg Gly Ser Leu Thr Lys Leu Lys Gly Pro Leu Thr Met Met
65                  70                  75                  80

Ala Ser His Tyr Lys Gln His Cys Pro Pro Thr Pro Glu Thr Ser Cys
                85                  90                  95

Ala Thr Gln Ile Ile Thr Phe Glu Ser Phe Lys Glu Asn Leu Lys Asp
            100                 105                 110

Phe Leu Leu Val Ile Pro Phe Asp Cys Trp Glu Pro Val Gln Glu
        115                 120                 125
```

<210> SEQ ID NO 35
<211> LENGTH: 9
<212> TYPE: PRT
<213> ORGANISM: Artificial Sequence
<220> FEATURE:
<223> OTHER INFORMATION: enterokinase signal followed by glycine and threonine plus a leucine lysine cleavage signal

<400> SEQUENCE: 35

```
Asp Asp Asp Asp Lys Gly Thr Leu Lys
1               5
```

<210> SEQ ID NO 36
<211> LENGTH: 8

<212> TYPE: PRT
<213> ORGANISM: Artificial Sequence
<220> FEATURE:
<223> OTHER INFORMATION: Survivin 9-16

<400> SEQUENCE: 36

Ala Trp Gln Pro Phe Leu Lys Asp
1               5

<210> SEQ ID NO 37
<211> LENGTH: 8
<212> TYPE: PRT
<213> ORGANISM: Artificial Sequence
<220> FEATURE:
<223> OTHER INFORMATION: Survivin 18-25

<400> SEQUENCE: 37

Arg Ile Ser Thr Phe Lys Asn Trp
1               5

<210> SEQ ID NO 38
<211> LENGTH: 8
<212> TYPE: PRT
<213> ORGANISM: Artificial Sequence
<220> FEATURE:
<223> OTHER INFORMATION: Survivin 39-46

<400> SEQUENCE: 38

Ala Glu Ala Gly Phe Ile His Cys
1               5

<210> SEQ ID NO 39
<211> LENGTH: 15
<212> TYPE: PRT
<213> ORGANISM: Artificial Sequence
<220> FEATURE:
<223> OTHER INFORMATION: Survivin 53-57

<400> SEQUENCE: 39

Asp Leu Ala Gln Cys Phe Phe Cys Phe Lys Glu Leu Glu Gly Trp
1               5                   10                  15

<210> SEQ ID NO 40
<211> LENGTH: 10
<212> TYPE: PRT
<213> ORGANISM: Artificial Sequence
<220> FEATURE:
<223> OTHER INFORMATION: Survivin 55-64

<400> SEQUENCE: 40

Ala Gln Cys Phe Phe Cys Phe Lys Glu Leu
1               5                   10

<210> SEQ ID NO 41
<211> LENGTH: 9
<212> TYPE: PRT
<213> ORGANISM: Artificial Sequence
<220> FEATURE:
<223> OTHER INFORMATION: Survivin 56-64

<400> SEQUENCE: 41

Gln Cys Phe Phe Cys Phe Lys Glu Leu
1               5

<210> SEQ ID NO 42
<211> LENGTH: 8
<212> TYPE: PRT

```
<213> ORGANISM: Artificial Sequence
<220> FEATURE:
<223> OTHER INFORMATION: Survivin 57-64

<400> SEQUENCE: 42

Cys Phe Phe Cys Phe Lys Glu Leu
1               5


<210> SEQ ID NO 43
<211> LENGTH: 8
<212> TYPE: PRT
<213> ORGANISM: Artificial Sequence
<220> FEATURE:
<223> OTHER INFORMATION: Survivin 82-89

<400> SEQUENCE: 43

Ser Gly Cys Ala Phe Leu Ser Val
1               5


<210> SEQ ID NO 44
<211> LENGTH: 8
<212> TYPE: PRT
<213> ORGANISM: Artificial Sequence
<220> FEATURE:
<223> OTHER INFORMATION: Survivin 97-104

<400> SEQUENCE: 44

Thr Leu Gly Glu Phe Leu Lys Leu
1               5


<210> SEQ ID NO 45
<211> LENGTH: 8
<212> TYPE: PRT
<213> ORGANISM: Artificial Sequence
<220> FEATURE:
<223> OTHER INFORMATION: Survivin 57-64/M57

<400> SEQUENCE: 45

Met Phe Phe Cys Phe Lys Glu Leu
1               5


<210> SEQ ID NO 46
<211> LENGTH: 8
<212> TYPE: PRT
<213> ORGANISM: Artificial Sequence
<220> FEATURE:
<223> OTHER INFORMATION: Survivin 82-89/L82

<400> SEQUENCE: 46

Leu Gly Cys Ala Phe Leu Ser Val
1               5


<210> SEQ ID NO 47
<211> LENGTH: 15
<212> TYPE: PRT
<213> ORGANISM: Artificial Sequence
<220> FEATURE:
<223> OTHER INFORMATION: Survivin 17-31

<400> SEQUENCE: 47

His Arg Ile Ser Thr Phe Lys Asn Trp Pro Phe Leu Glu Gly Cys
1               5                   10                  15


<210> SEQ ID NO 48
<211> LENGTH: 15
<212> TYPE: PRT
<213> ORGANISM: Artificial Sequence
```

<220> FEATURE:
<223> OTHER INFORMATION: Survivin 20-34

<400> SEQUENCE: 48

Ser Thr Phe Lys Asn Trp Pro Phe Leu Glu Gly Cys Ala Cys Thr
1 5 10 15

<210> SEQ ID NO 49
<211> LENGTH: 15
<212> TYPE: PRT
<213> ORGANISM: Artificial Sequence
<220> FEATURE:
<223> OTHER INFORMATION: Survivin 84-98

<400> SEQUENCE: 49

Cys Ala Phe Leu Ser Val Lys Lys Gln Phe Glu Glu Leu Thr Leu
1 5 10 15

<210> SEQ ID NO 50
<211> LENGTH: 15
<212> TYPE: PRT
<213> ORGANISM: Artificial Sequence
<220> FEATURE:
<223> OTHER INFORMATION: Survivin 90-104

<400> SEQUENCE: 50

Lys Lys Gln Phe Glu Glu Leu Thr Leu Gly Glu Phe Leu Lys Leu
1 5 10 15

<210> SEQ ID NO 51
<211> LENGTH: 15
<212> TYPE: PRT
<213> ORGANISM: Artificial Sequence
<220> FEATURE:
<223> OTHER INFORMATION: Survivin 93-107

<400> SEQUENCE: 51

Phe Glu Glu Leu Thr Leu Gly Glu Phe Leu Lys Leu Asp Arg Glu
1 5 10 15

<210> SEQ ID NO 52
<211> LENGTH: 15
<212> TYPE: PRT
<213> ORGANISM: Artificial Sequence
<220> FEATURE:
<223> OTHER INFORMATION: Survivin 96-110

<400> SEQUENCE: 52

Leu Thr Leu Gly Glu Phe Leu Lys Leu Asp Arg Glu Phe Ala Lys
1 5 10 15

<210> SEQ ID NO 53
<211> LENGTH: 15
<212> TYPE: PRT
<213> ORGANISM: Artificial Sequence
<220> FEATURE:
<223> OTHER INFORMATION: Survivin 122-136

<400> SEQUENCE: 53

Lys Glu Phe Glu Glu Thr Ala Lys Lys Val Arg Arg Ala Ile Glu
1 5 10 15

<210> SEQ ID NO 54
<211> LENGTH: 15
<212> TYPE: PRT
<213> ORGANISM: Artificial Sequence
<220> FEATURE:

<223> OTHER INFORMATION: Survivin 128-142

<400> SEQUENCE: 54

Ala Lys Lys Val Arg Arg Ala Ile Glu Gln Leu Ala Ala Met Asp
1 5 10 15

<210> SEQ ID NO 55
<211> LENGTH: 23
<212> TYPE: PRT
<213> ORGANISM: Artificial Sequence
<220> FEATURE:
<223> OTHER INFORMATION: Survivin 49-71

<400> SEQUENCE: 55

Glu Asn Glu Pro Asp Leu Ala Gln Cys Phe Phe Cys Phe Lys Glu Leu
1 5 10 15

Glu Gly Trp Glu Pro Asp Asp
20

<210> SEQ ID NO 56
<211> LENGTH: 10
<212> TYPE: PRT
<213> ORGANISM: Artificial Sequence
<220> FEATURE:
<223> OTHER INFORMATION: Mesothelin 540-549

<400> SEQUENCE: 56

Lys Leu Leu Gly Pro His Glu Val Gly Leu
1 5 10

<210> SEQ ID NO 57
<211> LENGTH: 9
<212> TYPE: PRT
<213> ORGANISM: Artificial Sequence
<220> FEATURE:
<223> OTHER INFORMATION: Mesothelin 530-538

<400> SEQUENCE: 57

Val Leu Pro Leu Thr Val Ala Glu Val
1 5

<210> SEQ ID NO 58
<211> LENGTH: 9
<212> TYPE: PRT
<213> ORGANISM: Artificial Sequence
<220> FEATURE:
<223> OTHER INFORMATION: Mesothelin 20-28

<400> SEQUENCE: 58

Ser Leu Leu Phe Leu Leu Phe Ser Leu
1 5

<210> SEQ ID NO 59
<211> LENGTH: 9
<212> TYPE: PRT
<213> ORGANISM: Artificial Sequence
<220> FEATURE:
<223> OTHER INFORMATION: Mesothelin 435-443

<400> SEQUENCE: 59

Phe Tyr Pro Gly Tyr Leu Cys Ser Leu
1 5

<210> SEQ ID NO 60
<211> LENGTH: 9
<212> TYPE: PRT

<213> ORGANISM: Artificial Sequence
<220> FEATURE:
<223> OTHER INFORMATION: Mesothelin 83-91

<400> SEQUENCE: 60

Glu Leu Ala Val Ala Leu Ala Gln Lys
1 5

<210> SEQ ID NO 61
<211> LENGTH: 9
<212> TYPE: PRT
<213> ORGANISM: Artificial Sequence
<220> FEATURE:
<223> OTHER INFORMATION: mesothelin 225-233

<400> SEQUENCE: 61

Ala Leu Gln Gly Gly Gly Pro Pro Tyr
1 5

<210> SEQ ID NO 62
<211> LENGTH: 73
<212> TYPE: PRT
<213> ORGANISM: Artificial Sequence
<220> FEATURE:
<223> OTHER INFORMATION: Domain 1 of ICAM-1 (mature peptide)

<400> SEQUENCE: 62

Gln Thr Ser Val Ser Pro Ser Lys Val Ile Leu Pro Arg Gly Gly Ser
1 5 10 15

Val Leu Val Thr Cys Ser Thr Ser Cys Asp Gln Pro Lys Leu Leu Gly
20 25 30

Ile Glu Thr Pro Leu Pro Lys Lys Glu Leu Leu Leu Pro Gly Asn Asn
35 40 45

Arg Lys Val Tyr Glu Leu Ser Asn Val Gln Glu Asp Ser Gln Pro Met
50 55 60

Cys Tyr Ser Asn Cys Pro Asp Gly Gln
65 70

<210> SEQ ID NO 63
<211> LENGTH: 36
<212> TYPE: PRT
<213> ORGANISM: Artificial Sequence
<220> FEATURE:
<223> OTHER INFORMATION: Chlorotoxin

<400> SEQUENCE: 63

Met Cys Met Pro Cys Phe Thr Thr Asp His Gln Met Ala Arg Lys Cys
1 5 10 15

Asp Asp Cys Cys Gly Gly Lys Gly Arg Gly Lys Cys Tyr Gly Pro Gln
20 25 30

Cys Leu Cys Arg
35

<210> SEQ ID NO 64
<211> LENGTH: 14
<212> TYPE: PRT
<213> ORGANISM: Artificial Sequence
<220> FEATURE:
<223> OTHER INFORMATION: Sunflower trypsin inhibitor (SFTI)

<400> SEQUENCE: 64

Gly Arg Cys Thr Lys Ser Ile Pro Pro Ile Cys Phe Pro Asp
1 5 10

<210> SEQ ID NO 65
<211> LENGTH: 13
<212> TYPE: PRT
<213> ORGANISM: Artificial Sequence
<220> FEATURE:
<223> OTHER INFORMATION: BulA conotoxin

<400> SEQUENCE: 65

Gly Cys Cys Ser Thr Pro Pro Cys Ala Val Leu Tyr Cys
1 5 10

<210> SEQ ID NO 66
<211> LENGTH: 20
<212> TYPE: PRT
<213> ORGANISM: Artificial Sequence
<220> FEATURE:
<223> OTHER INFORMATION: Pentastatin-1

<400> SEQUENCE: 66

Leu Arg Arg Phe Ser Thr Met Pro Phe Met Phe Cys Asn Ile Asn Asn
1 5 10 15

Val Cys Asn Phe
20

<210> SEQ ID NO 67
<211> LENGTH: 15
<212> TYPE: PRT
<213> ORGANISM: Artificial Sequence
<220> FEATURE:
<223> OTHER INFORMATION: KRAS inhibitory peptide KRpep-2

<400> SEQUENCE: 67

Arg Arg Cys Pro Leu Tyr Ile Ser Tyr Asp Pro Val Cys Arg Arg
1 5 10 15

<210> SEQ ID NO 68
<211> LENGTH: 19
<212> TYPE: PRT
<213> ORGANISM: Artificial Sequence
<220> FEATURE:
<223> OTHER INFORMATION: KRAS inhibitory peptide KRpep-2d

<400> SEQUENCE: 68

Arg Arg Arg Arg Cys Pro Leu Tyr Ile Ser Tyr Asp Pro Val Cys Arg
1 5 10 15

Arg Arg Arg

<210> SEQ ID NO 69
<211> LENGTH: 1053
<212> TYPE: DNA
<213> ORGANISM: Artificial Sequence
<220> FEATURE:
<223> OTHER INFORMATION: MarA ending with start codon ATG

<400> SEQUENCE: 69
cagtgtgcaa gttaatatcc tctacaacct ataacctgta attatcaatt agttacaagt 60
tatcacagca caataccccg gacgcctttt agcaaatcgt ggcatcggcc aattcattta 120
gttgacttat acttgcctgg gcaatagtat ctgacgaaat taattacttg ccggggcaac 180
cattttgaaa agcaccagtg atctgttcaa tgaaatcatt ccgctgggtc gcttgatcta 240
catggtaaat cagaaaaaag atcgcctgtt aaataactat ttatccccgc tggatatcac 300
cgcaacacag tttaaagtgc tttgctcgat acgctgcgcg ggatgtatta ccccggttga 360
acttaaaaaa gtgctgtctg tcgatctcgg cgcattgacg cggatgctcg accgcctgct 420
gtgcaaaggc tggatcgaaa gactgccgaa tcctaatgac aaacgcggcg tactggtgaa 480
gctaacgccg gacggcgcgg caatttgtga gcaatgtcat caacgaccag ggcaagacct 540
gcatcaggaa ttaacaaaaa acttaacggc ggacgaagtg gcaacgcttg agtatttgct 600
caagaaaatt ctgccgtaga caaaaaagag gtatgacgat gtccagacgc aacactgacg 660
ctattactat tcatagcatt ttggactgga tcgaggataa cctggagtcg ccgctctcac 720
tggaaaaagt gtctgagcgt tcaggatatt ccaaatggca cctgcaacgg atgtttaaaa 780
aagagaccgg tcattcatta ggccaataca tccgcagccg taaaatgacg gaaatcgcgc 840
aaaaattaaa agagagcaac gagcccattc tctatctggc ggaacgctat ggctttgagt 900
cacagcaaac attgacccgg acgttcaaaa actattttga tgtgccgcca cacaaatacc 960
ggatcaccaa tatgcatggc gaatcacggt atatgctgcc gctgaaccat ggcaactact 1020
agtttgttta tgcgccacgc gaagagcacc atg 1053

<210> SEQ ID NO 70
<211> LENGTH: 300
<212> TYPE: DNA
<213> ORGANISM: Artificial Sequence
<220> FEATURE:
<223> OTHER INFORMATION: Aarach and McClelland Patent Application Table 2A, STM1382-STM1383

<400> SEQUENCE: 70
tgaagcatac ctgatttctg gaaatagcgt agatcggaac gaatagtctc ctggctaacc 60
ttataaaggt ctgaaagttt actgacgcta acactattat cctttatcag taaattaatg 120
atggcatgac gtctttcttc tttaaacata ttgcctccgg gtagtgagtt gaattgtatt 180
tatggcaatg ttgtcatgcg gtgaattcaa tcacagatta tgcggtcacc ggaagtaacc 240
ccaaatgaat gtcaataatc agaagcgcag ccaatgtgtt aaatattaat tgcttacaga 300

<210> SEQ ID NO 71
<211> LENGTH: 54
<212> TYPE: DNA
<213> ORGANISM: Artificial Sequence
<220> FEATURE:
<223> OTHER INFORMATION: hypoxic inducible promoter “pHypoxic” (Mengesha et al., 2006, Development of a flexible and potent hypoxia-inducible promoter for tumor-targeted gene expression in Salmonella. Cancer Biology and Therapy 5: 1120-1128)

<400> SEQUENCE: 71
ggataaaagt gacctgacgc aatatttgtc ttttcttgct taataatgtt gtca 54

<210> SEQ ID NO 72
<211> LENGTH: 264
<212> TYPE: DNA
<213> ORGANISM: Artificial Sequence
<220> FEATURE:
<223> OTHER INFORMATION: Acid (low pH; “pAcidic”) inducible promoter (Tucker et al., 2002, Gene expression profiling of the pH response in Escherichia coli, J Bacteriol 184: 6551-6558) GadA-RBS >BBa_K1231001

<400> SEQUENCE: 72
ctttcctgca cagtctgaac ggggtgtaca cgccgtatat gcaggataaa caataattaa 60
tttgatcgcc cgaacagcaa tgtttgggcg atttttatta cgataataaa gtctgttttt 120
aatattatca tgttaaatgt ttatattata aaaagtcgtt tttctgctta ggattttgtt 180
atttaaatta agcctgtaat gccttgcttc cattgcggat aaatcctact tttttattgc 240
cttcaaataa atttaaggag ttcg 264

<210> SEQ ID NO 73
<211> LENGTH: 34
<212> TYPE: DNA
<213> ORGANISM: Artificial Sequence
<220> FEATURE:
<223> OTHER INFORMATION: Transcriptional terminator >BBa_B0004

<400> SEQUENCE: 73
cgccgaaaac cccgcttcgg cggggttttg ccgc 34

<210> SEQ ID NO 74
<211> LENGTH: 41
<212> TYPE: DNA
<213> ORGANISM: Artificial Sequence
<220> FEATURE:
<223> OTHER INFORMATION: Transcriptional terminator >BBa_B0012

<400> SEQUENCE: 74
tcacactggc tcaccttcgg gtgggccttt ctgcgtttat a 41

<210> SEQ ID NO 75
<211> LENGTH: 129
<212> TYPE: DNA
<213> ORGANISM: Artificial Sequence
<220> FEATURE:
<223> OTHER INFORMATION: Trascriptional terminator, Part:BBa_B0015
(double terminator; B0010-B0012)

<400> SEQUENCE: 75
ccaggcatca aataaaacga aaggctcagt cgaaagactg ggcctttcgt tttatctgtt 60
gtttgtcggt gaacgctctc tactagagtc acactggctc accttcgggt gggcctttct 120
gcgtttata 129

<210> SEQ ID NO 76
<211> LENGTH: 49
<212> TYPE: DNA
<213> ORGANISM: Artificial Sequence
<220> FEATURE:
<223> OTHER INFORMATION: 5' untranslated (5'UT) region with a ribosomal
binding site (RBS)

<400> SEQUENCE: 76
accgtagtta aagcacctaa ccgagctcgg taccaaagga ggttggccc 49

<210> SEQ ID NO 77
<211> LENGTH: 62
<212> TYPE: DNA
<213> ORGANISM: Artificial Sequence
<220> FEATURE:
<223> OTHER INFORMATION: 5'UT deduced from McClelland and Arrach PRL1-F1

<400> SEQUENCE: 77
tcgagagatc tccatcgaat tcgtgggtcg accccgggag gcctaaagag gagaaattaa 60
ct 62

<210> SEQ ID NO 78
<211> LENGTH: 745
<212> TYPE: DNA
<213> ORGANISM: Artificial Sequence
<220> FEATURE:
<223> OTHER INFORMATION: pTet with TetR, Tet operator and 5' untranslated region with a ribosomal binding site

<400> SEQUENCE: 78
ttaagaccca ctttcacatt taagttgttt ttctaatccg catataatca attcaaggcc 60
gaataagaag gctggctctg caccttggtg atcaaataat tcgatagctt gtcgtaataa 120
tggcggcata ctatcagtag taggtgtttc cctttcttct ttagcgactt gatgctcttg 180
atcttccaat acgcaaccta aagtaaaatg ccccacagcg ctgagtgcat ataatgcatt 240
ctctagtgaa aaaccttgtt ggcataaaaa ggctaattga ttttcgagag tttcatactg 300
tttttctgta ggccgtgtac ctaaatgtac ttttgctcca tcgcgatgac ttagtaaagc 360
acatctaaaa cttttagcgt tattacgtaa aaaatcttgc cagctttccc cttctaaagg 420
gcaaaagtga gtatggtgcc tatctaacat ctcaatggct aaggcgtcga gcaaagcccg 480
cttatttttt acatgccaat acaatgtagg ctgctctaca cctagcttct gggcgagttt 540
acgggttgtt aaaccttcga ttccgacctc attaagcagc tctaatgcgc tgttaatcac 600
tttactttta tctaatctcg acatcattaa ttcctcagct tttgttgaca ctctatcgtt 660
gatagagtta ttttaccact ccctatcagt gatagaaccg tagttaaagc acctaaccga 720
gctcggtacc aaaggaggtt ggccc 745

<210> SEQ ID NO 79
<211> LENGTH: 81
<212> TYPE: DNA
<213> ORGANISM: Artificial Sequence
<220> FEATURE:
<223> OTHER INFORMATION: SOS (DNA damage, X-ray, alkylating agent)
induced promoter, >BBa_K819017 sulA promoter

<400> SEQUENCE: 79
cgaggctctt tccgaaaata gggttgatct ttgttgtcac tggatgtacc gtacatccat 60
acggtaactc acaggggctg g 81

<210> SEQ ID NO 80
<211> LENGTH: 301
<212> TYPE: DNA
<213> ORGANISM: Artificial Sequence
<220> FEATURE:
<223> OTHER INFORMATION: Spleen activated (“pSpleen”) promoter, Aarach
and McClelland Patent Application Table 4, yaaJ

<400> SEQUENCE: 80
gtatttcgtt aataaaactg aaaaactcag gcattaacgt ccctcttgtt gatgccggca 60
cgctttgata atcctgtata agcgtgaccc atgatgtaga tgaccttgtc agactaatat 120
taacggcagt ttaccataaa tacggtggta tcctttaatt gcgcatcaac cgtcggcaga 180
tacgcaaaca gtgcacaagg gcagccaggt gcatgtaggc ggttgcgctg tgagtgcgtc 240
gtgttatcat cagggtagac cggttacatc ccctaacaag ctgtttaaag agaaactcta 300
t 301

<210> SEQ ID NO 81
<211> LENGTH: 301
<212> TYPE: DNA
<213> ORGANISM: Artificial Sequence
<220> FEATURE:
<223> OTHER INFORMATION: pSpleen promoter, Aarach and McClelland Patent
Application Table 4, talB

<400> SEQUENCE: 81
tgcgaataaa cggatgcctg aacaggcagg gacgccggaa aacgtcgaaa tacgttagac 60
cattcgcccg tgttcccgct ttccccaccg cgctgtccgc ttacatgagg ttacactcat 120
cgacatttct ctgaacagcg gctcaacatt tcccggaaaa aaacatatcg cagggcattt 180
atccttatga ttaggtataa atgatgaggt ataaggaaca ggagtctgta atgaaaccaa 240
taccttttta tttgctcgcg ctattttctg ccgcctccgg ggctacggag ataaacgtct 300
g 301

<210> SEQ ID NO 82
<211> LENGTH: 301
<212> TYPE: DNA
<213> ORGANISM: Artificial Sequence
<220> FEATURE:
<223> OTHER INFORMATION: Spleen activated ("pSpleen") promoter, Aarach and McClelland Patent Application Table 4, aroM

<400> SEQUENCE: 82
tcaaggcgcg gacgtcatta tgctggattg tctgggtttt catcagcgtc atcgggatat 60
tttacagcag gcgctggatg tgccggtttt actctctaac gttttgattg cgcggttagc 120
ttcagaactg cttgtctaat tttacgtgac aggccgaacg tcaggactct atattgggtg 180
ttaatttaat aatgagacgg ggcctgatta tgctacaaag caatgaatac ttttccggga 240
aagttaagtc tattggattt accagcagta gcaccggccg ggccagcgtt ggtgtgatgg 300
c 301

<210> SEQ ID NO 83
<211> LENGTH: 301
<212> TYPE: DNA
<213> ORGANISM: Artificial Sequence
<220> FEATURE:
<223> OTHER INFORMATION: pSpleen promoter, Aarach and McClelland Patent Application Table 4, tonB

<400> SEQUENCE: 83
gttcgccgtc catttttacc tctggggctg tttcttagcg cgccctcccc cggaaaaaca 60
aaatataatg aacaaaaaac atacaaacca tcatctttta aaaataaatt acattaaaac 120
agagagttac aacatgatga tgatgcatga aaaatcaaaa atgcgccaaa tcccgcgccg 180
ctgccgcccc gtggcaggcc gccccgccgg gagtaccttt ttaaaatgcg aacaattatc 240
aacaactacc acttaatgat tatttatttc attttgcgat attgattatc attttcaata 300
a 301

<210> SEQ ID NO 84
<211> LENGTH: 276
<212> TYPE: DNA
<213> ORGANISM: Artificial Sequence
<220> FEATURE:
<223> OTHER INFORMATION: PhiX174E lysis protein gene ("Lysis"), BBa_K2685005

<400> SEQUENCE: 84
atggttcgtt ggaccctgtg ggacaccctg gctttcctgc tgctgctgtc tctgctgctg 60
ccgtctctgc tgatcatgtt catcccgtct accttcaaac gtccggtttc ttcttggaaa 120
gctctgaacc tgcgtaaaac cctgctgatg gcttcttctg ttcgtctgaa accgctgaac 180
tgctctcgtc tgccgtgcgt ttacgctcag gaaaccctga ccttcctgct gacccagaaa 240
aaaacctgcg ttaaaaacta cgttcgtaaa gaataa 276

<210> SEQ ID NO 85
<211> LENGTH: 1599
<212> TYPE: DNA
<213> ORGANISM: Artificial Sequence
<220> FEATURE:
<223> OTHER INFORMATION: lac promoter ("pLac") BBa_K389050 sequence, consisting of the p(Lac) IQ promoter I14032, RBS B0034, LacI C0012, double stop B0010,and LacI regulated promoter R0010

<400> SEQUENCE: 85
tggtgcaaaa cctttcgcgg tatggcatga tagcgcctac tagagaaaga ggagaaatac 60
tagatggtga atgtgaaacc agtaacgtta tacgatgtcg cagagtatgc cggtgtctct 120
tatcagaccg tttcccgcgt ggtgaaccag gccagccacg tttctgcgaa aacgcggaaa 180
aagtggaagc ggcgatggcg gagctgaatt acattcccaa ccgcgtggca caacaactgg 240
cgggcaaaca gtcgttgctg attggcgttg ccacctccag tctggccctg cacgcgccgt 300
cgcaaattgt cgcggcgatt aaatctcgcg ccgatcaact gggtgccagc gtggtggtgt 360
cgatggtaga acgaagcggc gtcgaagcct gtaaagcggc ggtgcacaat cttctcgcgc 420
aacgcgtcag tgggctgatc attaactatc cgctggatga ccaggatgcc attgctgtgg 480
aagctgcctg cactaatgtt ccggcgttat ttcttgatgt ctctgaccag acacccatca 540
acagtattat tttctcccat gaagacggta cgcgactggg cgtggagcat ctggtcgcat 600
tgggtcacca gcaaatcgcg ctgttagcgg gcccattaag ttctgtctcg gcgcgtctgc 660
gtctggctgg ctggcataaa tatctcactc gcaatcaaat tcagccgata gcggaacggg 720
aaggcgactg gagtgccatg tccggttttc aacaaaccat gcaaatgctg aatgagggca 780
tcgttcccac tgcgatgctg gttgccaacg atcagatggc gctgggcgca atgcgcgcca 840
ttaccgagtc cgggctgcgc gttggtgcgg atatctcggt agtgggatac gacgataccg 900
aagacagctc atgttatatc ccgccgttaa ccaccatcaa acaggatttt cgcctgctgg 960
ggcaaaccag cgtggaccgc ttgctgcaac tctctcaggg ccaggcggtg aagggcaatc 1020
agctgttgcc cgtctcactg gtgaaaagaa aaaccaccct ggcgcccaat acgcaaaccg 1080
cctctccccg cgcgttggcc gattcattaa tgcagctggc acgacaggtt tcccgactgg 1140
aaagcgggca ggctgcaaac gacgaaaact acgctttagt agcttaataa ctctgatagt 1200
gctagtgtag atctctacta gagccaggca tcaaataaaa cgaaaggctc agtcgaaaga 1260
ctgggccttt cgttttatct gttgtttgtc ggtgaacgct ctctactaga gccaggcatc 1320
aaataaaacg aaaggctcag tcgaaagact gggcctttcg ttttatctgt tgtttgtcgg 1380
tgaacgctct ctactagagc aatacgcaaa ccgcctctcc ccgcgcgttg gccgattcat 1440
taatgcagct ggcacgacag gtttcccgac tggaaagcgg gcagtgagcg caacgcaatt 1500
aatgtgagtt agctcactca ttaggcaccc caggctttac actttatgct tccggctcgt 1560
atgttgtgtg gaattgtgag cggataacaa tttcacaca 1599

<210> SEQ ID NO 86
<211> LENGTH: 835
<212> TYPE: DNA
<213> ORGANISM: Artificial Sequence
<220> FEATURE:
<223> OTHER INFORMATION: bile salt (normal gut) sensing promoter ("pBile") >BBa_K318514 Part-only sequence

<400> SEQUENCE: 86
ttatcagggg gagccgttga ccgtcgacgc gcgcagcgtc ggacacaatt gatacatctc 60

```
cagcaggatc gtgacgtagg cgcgagcttc tttttttaaa tcaaacgatt gcggagcaaa    120

taaccagttt tccatgagcc ctgaaataaa gctgcgcatc agtatcgccg cacgacgggt    180

cagcagattt tcaggcagca ttttagcatt aatacaatgt tttaacgttt gttcaatccg    240

atcgtaactt tccagacaaa ggctacgttg cgcctgttga accacaacca tttctccgac    300

aaactcacat ttatggaata taatctccat caataagcgg cgtcgttctt ctgttacagt    360

agcttcaaga atatgaacta aaatttctct taatacagat agtggatcgt cggggaattt    420

tgcctgatac tcaatctcaa gctcaccaat attggattct gatagctccc agatctcact    480

gaataaatcc gacttatttt tgaaatgcca atagattgcg ccgcgcgtca cgccagcagc    540

gttcgcaatc tccgccagcg aggttgccga tacgccttgc tgcgagaaca aacgcagggc    600

cacatccagg atgtgttgtc gtgtctccag cgcttgttgt ttggtttttc gtgccatatg    660

tcggtgaatt tacaggcgtt agatttacat acatttatgg atgtatgtac catagcacga    720

cgataatata aacgcagcaa tgggtttaag gacctttgac cattgaccaa tttgaaatcg    780

gacactcgag gtttacatat gaacaaaaac agagggttaa cgcctctggc ggtcg         835
```

<210> SEQ ID NO 87
<211> LENGTH: 35
<212> TYPE: DNA
<213> ORGANISM: Artificial Sequence
<220> FEATURE:
<223> OTHER INFORMATION: Constitutive (pConstitutive) promoter
      BBa_J23105

<400> SEQUENCE: 87

```
tttacggcta gctcagtcct aggtactatg ctagc                              35
```

<210> SEQ ID NO 88
<211> LENGTH: 169
<212> TYPE: PRT
<213> ORGANISM: Artificial Sequence
<220> FEATURE:
<223> OTHER INFORMATION: Growth inhibitory gene sulA Salmonella amino
      acids

<400> SEQUENCE: 88

```
Met Tyr Thr Ser Gly Tyr Ala Asn Arg Ser Ser Ser Phe Pro Thr Thr
1               5                   10                  15

Thr His Asn Ala Ala Arg Thr Ala Thr Glu Asn Ala Ala Ala Gly Leu
            20                  25                  30

Val Ser Glu Val Val Tyr His Glu Asp Gln Pro Met Met Ala Gln Leu
        35                  40                  45

Leu Leu Leu Pro Leu Leu Arg Gln Leu Gly Gln Gln Ser Arg Trp Gln
    50                  55                  60

Leu Trp Leu Thr Pro Gln Gln Lys Leu Ser Arg Glu Trp Val Gln Ser
65                  70                  75                  80

Ser Gly Leu Pro Leu Thr Lys Val Met Gln Ile Ser Gln Leu Ala Pro
                85                  90                  95

Arg His Thr Leu Glu Ser Met Ile Arg Ala Leu Arg Thr Gly Asn Tyr
            100                 105                 110

Ser Val Val Ile Gly Trp Met Thr Glu Glu Leu Thr Glu Glu Glu His
        115                 120                 125

Ala Ser Leu Val Glu Ala Ala Lys Val Gly Asn Ala Val Gly Phe Ile
    130                 135                 140

Met Arg Pro Val Arg Ala His Ala Leu Pro Arg Arg Gln His Ser Gly
145                 150                 155                 160
```

```
Leu Lys Ile His Ser Asn Leu Tyr His
                165


<210> SEQ ID NO 89
<211> LENGTH: 507
<212> TYPE: DNA
<213> ORGANISM: Artificial Sequence
<220> FEATURE:
<223> OTHER INFORMATION: Salmonella sulA

<400> SEQUENCE: 89

atgtacactt caggctatgc acatcgttct tcgtcgttct catccgcagc aagtaaaatt      60

gcgcgtgtct ctacggaaaa cactacagcc gggcttatca gtgaagttgt ctatcgcgaa     120

gatcagccca tgatgacgca acttctactg ttgccattgt tacagcaact cggtcagcaa     180

tcgcgctggc aactctggtt aacaccgcaa caaaaactga gtcgggaatg ggttcaggca     240

tctgggctac ccttaacgaa agtaatgcag attagccagc tctccccttg ccacactgtg     300

gagtcaatgg ttcgcgcttt acgcacgggc aattacagtg tggtgatcgg ttggttggca     360

gatgatttga ctgaagaaga gcatgctgaa cttgttgatg cggcaaatga aggtaacgct     420

atggggttta ttatgcgtcc ggtaagcgca tcctctcacg ccacgagaca actttccggg     480

ctaaaaattc actctaattt gtatcat                                         507


<210> SEQ ID NO 90
<211> LENGTH: 235
<212> TYPE: PRT
<213> ORGANISM: Artificial Sequence
<220> FEATURE:
<223> OTHER INFORMATION: Salmonella MinC

<400> SEQUENCE: 90

Met Ser Asn Thr Pro Ile Glu Leu Lys Gly Ser Ser Phe Thr Leu Ser
1               5                   10                  15

Val Val His Leu His Glu Ala Glu Pro Glu Val Ile Arg Gln Ala Leu
            20                  25                  30

Glu Asp Lys Ile Ala Gln Ala Pro Ala Phe Leu Lys His Ala Pro Val
        35                  40                  45

Val Ile Asn Val Ser Gly Leu Glu Ser Pro Val Asn Trp Pro Glu Leu
    50                  55                  60

His Lys Ile Val Thr Ser Thr Gly Leu Arg Ile Ile Gly Val Ser Gly
65                  70                  75                  80

Cys Lys Asp Ala Ser Leu Lys Val Glu Ile Asp Arg Met Gly Leu Pro
                85                  90                  95

Leu Leu Thr Glu Gly Lys Glu Lys Ala Val Arg Pro Ala Pro Val Glu
            100                 105                 110

Pro Ala Thr Pro Ser Glu Pro Pro Gln Asn Ala Asn Pro Ile Thr Lys
        115                 120                 125

Thr Arg Leu Ile Asp Val Pro Val Arg Ser Gly Gln Arg Ile Tyr Ala
    130                 135                 140

Pro Gln Cys Asp Leu Ile Val Thr Ser His Val Ser Ala Gly Ala Glu
145                 150                 155                 160

Leu Ile Ala Asp Gly Asn Ile His Val Tyr Gly Met Met Arg Gly Arg
                165                 170                 175

Ala Leu Ala Gly Ala Ser Gly Asp Arg Glu Ala Gln Ile Phe Cys Thr
            180                 185                 190

His Leu Thr Ala Glu Leu Val Ser Ile Ala Gly Val Tyr Trp Leu Ser
```

```
        195                 200                 205

Asp Lys Ile Pro Ala Glu Phe Tyr Gly Lys Ala Ala Arg Leu Arg Leu
    210                 215                 220

Ala Asp Asn Ala Leu Thr Val Gln Pro Leu Asn
225                 230                 235


<210> SEQ ID NO 91
<211> LENGTH: 270
<212> TYPE: PRT
<213> ORGANISM: Artificial Sequence
<220> FEATURE:
<223> OTHER INFORMATION: Salmonella MinD

<400> SEQUENCE: 91

Met Ala Arg Ile Ile Val Val Thr Ser Gly Lys Gly Gly Val Gly Lys
1               5                   10                  15

Thr Thr Ser Ser Ala Ala Ile Ala Thr Gly Leu Ala Gln Lys Gly Lys
            20                  25                  30

Lys Thr Val Val Ile Asp Phe Asp Ile Gly Leu Arg Asn Leu Asp Leu
        35                  40                  45

Ile Met Gly Cys Glu Arg Arg Val Val Tyr Asp Phe Val Asn Val Ile
    50                  55                  60

Gln Gly Asp Ala Thr Leu Asn Gln Ala Leu Ile Lys Asp Lys Arg Thr
65                  70                  75                  80

Glu Asn Leu Phe Ile Leu Pro Ala Ser Gln Thr Arg Asp Lys Asp Ala
                85                  90                  95

Leu Thr Arg Glu Gly Val Ala Lys Val Leu Asp Ser Leu Lys Ala Met
            100                 105                 110

Asp Phe Glu Phe Ile Val Cys Asp Ser Pro Ala Gly Ile Glu Thr Gly
        115                 120                 125

Ala Leu Met Ala Leu Tyr Phe Ala Asp Glu Ala Ile Ile Thr Thr Asn
    130                 135                 140

Pro Glu Val Ser Ser Val Arg Asp Ser Asp Arg Ile Leu Gly Ile Leu
145                 150                 155                 160

Ala Ser Lys Ser Arg Arg Ala Glu Asn Gly Glu Glu Pro Ile Lys Glu
                165                 170                 175

His Leu Leu Leu Thr Arg Tyr Asn Pro Gly Arg Val Asn Lys Gly Asp
            180                 185                 190

Met Leu Ser Met Glu Asp Val Leu Glu Ile Leu Arg Ile Lys Leu Val
        195                 200                 205

Gly Val Ile Pro Glu Asp Gln Ser Val Leu Arg Ala Ser Asn Gln Gly
    210                 215                 220

Glu Pro Val Ile Leu Asp Ala Thr Ala Asp Ala Gly Lys Ala Tyr Ala
225                 230                 235                 240

Asp Thr Val Asp Arg Leu Leu Gly Glu Glu Arg Pro Phe Arg Phe Ile
                245                 250                 255

Glu Glu Glu Lys Lys Gly Phe Leu Lys Arg Leu Phe Gly Gly
            260                 265                 270


<210> SEQ ID NO 92
<211> LENGTH: 201
<212> TYPE: DNA
<213> ORGANISM: Artificial Sequence
<220> FEATURE:
<223> OTHER INFORMATION: Salmonella DicF encoding an antisense RNA

<400> SEQUENCE: 92
```

```
gaggacgcga taatgaaaac gttattacca aacgttaata cgtctgaagg ttgttttgaa      60

attggtgtca ctatcagtaa cccagtattt actgaagatg ccattaacaa gagaaaacaa     120

gaacgggagc tattaaataa aatatgcatt gtttcaatgc tggctcgttt acgtctgatg     180

ccaaaaggat gtgcacaatg a                                               201


<210> SEQ ID NO 93
<211> LENGTH: 62
<212> TYPE: PRT
<213> ORGANISM: Artificial Sequence
<220> FEATURE:
<223> OTHER INFORMATION: Salmonella P22 phage kil

<400> SEQUENCE: 93

Met Thr Ile Val Pro Val Asn Gly Thr Ile Leu Val Gln Gln Gly Asn
1               5                   10                  15

Arg Glu Phe Asn Lys Leu Tyr Glu Ala Ser Phe Pro Asp Thr Lys Glu
            20                  25                  30

Gly Asn Ser Ala Ala Tyr Ala Trp Ala Ser Ser Ile Ala Met Gly Trp
        35                  40                  45

Glu Asp Cys Gln Asp Glu Asp Trp Asn Arg Asn His Ala Ala
    50                  55                  60


<210> SEQ ID NO 94
<211> LENGTH: 88
<212> TYPE: PRT
<213> ORGANISM: Artificial Sequence
<220> FEATURE:
<223> OTHER INFORMATION: lamda kil

<400> SEQUENCE: 94

Met Pro Leu Gln Gly Gly Leu Leu Leu Ala Ala Leu Pro Asn Leu Tyr
1               5                   10                  15

Leu Asn Glu Ser Pro Val Asn Tyr Val Thr Asp Gly Asn Ala Leu Ser
            20                  25                  30

Thr Tyr Leu Ile Ser Gln Glu Ser Gln Arg Met Asp Gln Thr Leu Met
        35                  40                  45

Ala Ile Gln Thr Lys Phe Thr Ile Ala Thr Phe Ile Gly Asp Glu Lys
    50                  55                  60

Met Phe Arg Glu Ala Val Asp Ala Tyr Lys Lys Trp Ile Leu Ile Leu
65                  70                  75                  80

Lys Leu Arg Ser Ser Lys Ser Ile
                85


<210> SEQ ID NO 95
<211> LENGTH: 89
<212> TYPE: PRT
<213> ORGANISM: Artificial Sequence
<220> FEATURE:
<223> OTHER INFORMATION: Multispecies: host cell division inhibitory
      peptide Kil

<400> SEQUENCE: 95

Met Pro Leu Gln Gly Gly Leu Leu Leu Ala Ala Leu Pro Asn Leu Tyr
1               5                   10                  15

Leu Asn Glu Ser Pro Val Asn Tyr Val Thr Asp Gly Asn Ala Leu Ser
            20                  25                  30

Thr Tyr Leu Ile Ser Gln Glu Ser Gln Arg Met Asp Gln Thr Leu Met
        35                  40                  45

Ala Ile Gln Thr Lys Phe Thr Ile Ala Thr Phe Ile Gly Asp Glu Lys
```

50 55 60

Met Phe Arg Glu Ala Val Asp Ala Tyr Lys Lys Trp Ile Leu Ile Leu
65 70 75 80

Lys Leu Arg Ser Ser Lys Ser Ile His
85

<210> SEQ ID NO 96
<211> LENGTH: 74
<212> TYPE: PRT
<213> ORGANISM: Artificial Sequence
<220> FEATURE:
<223> OTHER INFORMATION: phage Mu cell division inhibitor gp5

<400> SEQUENCE: 96

Met Ala Arg Asn Ile Lys Met Ala Thr Asp Ala Gln Asn Trp Leu Gln
1 5 10 15

Ala Arg Gly Ser His Val Asn Glu Ser Tyr Leu Gly Val Ala Arg Pro
20 25 30

Ile Leu Glu Ile Thr Tyr Pro Pro Val Glu Leu Val Lys Asn Ala Val
35 40 45

Arg Ile Met Glu His Lys Ser Gly Val Ala Arg Ser Val Trp Thr Ala
50 55 60

Arg Leu Asn Gly Cys Gln Ile Ile Trp Arg
65 70

<210> SEQ ID NO 97
<211> LENGTH: 73
<212> TYPE: PRT
<213> ORGANISM: Artificial Sequence
<220> FEATURE:
<223> OTHER INFORMATION: phage Rac cell division inhibitor KilR

<400> SEQUENCE: 97

Met Ile Ala His His Phe Gly Thr Asp Glu Ile Pro Arg Gln Cys Val
1 5 10 15

Thr Pro Gly Asp Tyr Val Leu His Glu Gly Arg Thr Tyr Ile Ala Ser
20 25 30

Ala Asn Asn Ile Lys Lys Arg Lys Leu Tyr Ile Arg Asn Leu Thr Thr
35 40 45

Lys Thr Cys Ile Thr Asp Cys Met Ile Lys Val Phe Leu Gly Arg Asp
50 55 60

Gly Leu Pro Val Lys Ala Glu Ser Trp
65 70

<210> SEQ ID NO 98
<211> LENGTH: 49
<212> TYPE: PRT
<213> ORGANISM: Artificial Sequence
<220> FEATURE:
<223> OTHER INFORMATION: Salmonella (NCBI: EBU7160853)

<400> SEQUENCE: 98

Met Lys His Gln His Tyr Gly Thr Met Glu Val Ile Arg Gln Cys Ala
1 5 10 15

Val Pro Gly Thr Met Val Lys Tyr Asn Asp Arg Ile Tyr Lys Ala Thr
20 25 30

Ala Asn Thr Arg Gly Lys Leu Thr Leu Thr Asn Ile Arg Glu Asn Ile
35 40 45

Thr

<210> SEQ ID NO 99
<211> LENGTH: 124
<212> TYPE: PRT
<213> ORGANISM: Artificial Sequence
<220> FEATURE:
<223> OTHER INFORMATION: GenBank: EBY8247551.1

<400> SEQUENCE: 99

Thr Met Glu Val Ile Arg Gln Cys Ala Val Pro Gly Thr Met Val Lys
1 5 10 15

Tyr Asn Asp Arg Ile Tyr Lys Ala Thr Ala Asn Thr Arg Gly Lys Leu
20 25 30

Thr Leu Thr Asn Ile Arg Glu Asn Ile Thr Ile Arg Asp Leu Val Ile
35 40 45

Glu Ile Tyr Leu Asp Gly Lys Gly Glu Pro Leu Thr Asn Met Lys His
50 55 60

Gln His Tyr Gly Thr Met Glu Val Ile Arg Gln Cys Ala Val Pro Gly
65 70 75 80

Thr Met Val Lys Tyr Asn Asp Arg Ile Tyr Lys Ala Thr Ala Asn Thr
85 90 95

Arg Gly Lys Leu Thr Leu Thr Asn Ile Arg Glu Asn Ile Thr Ile Arg
100 105 110

Asp Leu Val Ile Glu Ile Tyr Leu Asp Gly Lys Gly
115 120

<210> SEQ ID NO 100
<211> LENGTH: 68
<212> TYPE: PRT
<213> ORGANISM: Artificial Sequence
<220> FEATURE:
<223> OTHER INFORMATION: GenBank: EBK1720184.1

<400> SEQUENCE: 100

Met Lys His Gln His Tyr Gly Thr Met Lys Val Ile Arg Gln Cys Ala
1 5 10 15

Val Pro Gly Thr Met Val Lys Tyr Asn Asp Arg Ile Tyr Lys Ala Thr
20 25 30

Ala Asn Thr Arg Gly Lys Leu Thr Leu Thr Asn Ile Arg Glu Asn Ile
35 40 45

Thr Ile Arg Asp Leu Val Ile Glu Ile Tyr Leu Asp Gly Lys Gly Glu
50 55 60

Pro Leu Thr Asn
65

<210> SEQ ID NO 101
<211> LENGTH: 64
<212> TYPE: PRT
<213> ORGANISM: Artificial Sequence
<220> FEATURE:
<223> OTHER INFORMATION: GenBank AKG31181.1

<400> SEQUENCE: 101

Met Gln Asn Thr Leu Thr Val Ile Arg Gln Cys Val Thr Pro Gly Met
1 5 10 15

Leu Val Ile His His Gly Lys Pro Trp Arg Ala Ala Val Asn Lys Asp
20 25 30

Gly Lys Leu His Ile His Thr Leu Thr Glu Ala Lys Pro Leu Lys Asp
35 40 45

Leu Leu Val Asp Ile Val Leu Asn His Lys Asn Glu Pro Glu Ile Ile 50 55 60

<210> SEQ ID NO 102
<211> LENGTH: 68
<212> TYPE: PRT
<213> ORGANISM: Artificial Sequence
<220> FEATURE:
<223> OTHER INFORMATION: GenBank: EBH8280910.1

<400> SEQUENCE: 102

Met Lys His Gln His Tyr Gly Thr Met Glu Val Ile Arg Gln Cys Ala
1 5 10 15

Val Pro Gly Thr Met Val Lys Tyr Asn Asp Arg Ile Tyr Lys Ala Thr
20 25 30

Ala Asn Thr Arg Gly Lys Leu Thr Leu Thr Asn Ile Arg Glu Asn Ile
35 40 45

Thr Ile Arg Asp Leu Val Ile Glu Phe Tyr Leu Asp Gly Lys Gly Glu
50 55 60

Pro Leu Thr Asn
65

<210> SEQ ID NO 103
<211> LENGTH: 68
<212> TYPE: PRT
<213> ORGANISM: Artificial Sequence
<220> FEATURE:
<223> OTHER INFORMATION: GenBank: AHX77645.1

<400> SEQUENCE: 103

Met Lys His Gln His Tyr Gly Thr Met Glu Val Ile Arg Gln Cys Ala
1 5 10 15

Val Pro Gly Thr Met Val Lys Tyr Asn Asp Arg Ile Tyr Lys Ala Thr
20 25 30

Ala Asn Thr Arg Gly Lys Leu Thr Leu Thr Asn Ile Arg Glu Asn Ile
35 40 45

Thr Ile Arg Asp Leu Val Ile Glu Ile Tyr Leu Asp Gly Lys Gly Glu
50 55 60

Pro Leu Thr Asn
65

<210> SEQ ID NO 104
<211> LENGTH: 68
<212> TYPE: PRT
<213> ORGANISM: Artificial Sequence
<220> FEATURE:
<223> OTHER INFORMATION: GenBank: CQB84553.1

<400> SEQUENCE: 104

Met Lys His Gln His Tyr Gly Thr Met Glu Val Ile Arg Gln Cys Ala
1 5 10 15

Val Pro Gly Thr Met Val Lys Tyr Asn Asp Arg Ile Tyr Lys Ala Thr
20 25 30

Ala Asn Thr Arg Gly Lys Leu Thr Leu Thr Asn Ile Arg Glu Asn Ile
35 40 45

Thr Ile Arg Asp Leu Val Ile Glu Ile Tyr Leu Asp Gly Lys Gly Glu
50 55 60

Pro Leu Ser Asn
65

<210> SEQ ID NO 105

<211> LENGTH: 68
<212> TYPE: PRT
<213> ORGANISM: Artificial Sequence
<220> FEATURE:
<223> OTHER INFORMATION: GenBank: ECM3647222.1

<400> SEQUENCE: 105

Met Lys His Gln His Tyr Gly Thr Met Glu Val Ile Arg Gln Cys Ala
1 5 10 15

Val Pro Gly Thr Met Val Lys Tyr Asn Asp Arg Ile Tyr Lys Ala Thr
20 25 30

Ala Asn Thr Arg Gly Lys Leu Thr Leu Thr Asn Ile Arg Glu Asn Ile
35 40 45

Thr Ile Arg Asp Leu Val Ile Glu Ile Tyr Leu Asp Asp Lys Gly Glu
50 55 60

Pro Leu Thr Asn
65

<210> SEQ ID NO 106
<211> LENGTH: 67
<212> TYPE: PRT
<213> ORGANISM: Artificial Sequence
<220> FEATURE:
<223> OTHER INFORMATION: GenBank: ECH8747869.1

<400> SEQUENCE: 106

Met Lys His Gln His Tyr Gly Thr Met Glu Val Ile Arg Gln Cys Ala
1 5 10 15

Val Pro Gly Thr Met Val Lys Tyr Asn Asp Arg Ile Tyr Lys Ala Thr
20 25 30

Ala Asn Thr Lys Gly Lys Leu Thr Leu Thr Asn Ile Arg Glu Asn Ile
35 40 45

Thr Ile Arg Asp Leu Val Ile Glu Ile Tyr Leu Asp Lys Gly Glu Pro
50 55 60

Leu Thr Asn
65

<210> SEQ ID NO 107
<211> LENGTH: 64
<212> TYPE: PRT
<213> ORGANISM: Artificial Sequence
<220> FEATURE:
<223> OTHER INFORMATION: GenBank: ECM8575082.1

<400> SEQUENCE: 107

Glu Ile Pro Arg Gln Cys Ile Thr Pro Gly Asp Tyr Val Ile His Asp
1 5 10 15

Gly Arg Thr Tyr Ile Ala Ser Ala Asn Asn Ile Lys Lys Arg Arg Leu
20 25 30

Tyr Ile Arg Asp Leu Thr Thr Gln Arg Cys Ile Thr Asp Cys Met Val
35 40 45

Lys Val Trp Leu Asn Arg Asn Gly Leu Pro Ala Lys Ala Glu Ser Trp
50 55 60

<210> SEQ ID NO 108
<211> LENGTH: 73
<212> TYPE: PRT
<213> ORGANISM: Artificial Sequence
<220> FEATURE:
<223> OTHER INFORMATION: GenBank: EBU6838365.1

<400> SEQUENCE: 108

Met Ile Ala His His Phe Gly Thr Asp Glu Ile Pro Arg Gln Cys Ile
1               5                   10                  15

Thr Pro Gly Asp Tyr Val Ile His Asp Gly Arg Thr Tyr Ile Ala Ser
            20                  25                  30

Ala Asn His Ile Lys Lys Arg Arg Leu Tyr Ile Arg Asp Leu Thr Thr
        35                  40                  45

Gln Arg Cys Ile Thr Asp Cys Met Val Lys Val Trp Leu Asn Arg Asn
    50                  55                  60

Gly Leu Pro Ala Lys Ala Glu Ser Trp
65                  70

<210> SEQ ID NO 109
<211> LENGTH: 73
<212> TYPE: PRT
<213> ORGANISM: Artificial Sequence
<220> FEATURE:
<223> OTHER INFORMATION: zinc sigma-54-dependent two-component system
      Response regulator, GenBank: AUC49429.1

<400> SEQUENCE: 109

Met Ile Ala His His Phe Gly Thr Asp Glu Ile Pro Arg Gln Cys Ile
1               5                   10                  15

Thr Pro Gly Asp Tyr Val Ile His Asp Gly Arg Thr Tyr Ile Ala Ser
            20                  25                  30

Ala Asn Asn Ile Lys Lys Arg Arg Leu Tyr Ile Arg Asp Leu Thr Thr
        35                  40                  45

Gln Arg Cys Ile Thr Asp Cys Met Val Lys Val Trp Leu Asn Arg Asn
    50                  55                  60

Gly Leu Pro Ala Lys Ala Glu Ser Trp
65                  70

<210> SEQ ID NO 110
<211> LENGTH: 73
<212> TYPE: PRT
<213> ORGANISM: Artificial Sequence
<220> FEATURE:
<223> OTHER INFORMATION: GenBank: EBB4754385.1

<400> SEQUENCE: 110

Met Ile Ala His His Phe Gly Thr Asp Glu Ile Pro Arg Gln Cys Val
1               5                   10                  15

Thr Pro Gly Asp Tyr Val Leu His Glu Gly Arg Thr Tyr Ile Ala Ser
            20                  25                  30

Ala Asn Asn Ile Lys Lys Arg Lys Leu Tyr Ile Arg Ser Leu Thr Thr
        35                  40                  45

Lys Thr Cys Ile Ser Asp Cys Met Ile Lys Val Phe Leu Gly Arg Asp
    50                  55                  60

Gly Leu Pro Val Lys Ala Glu Ser Trp
65                  70

<210> SEQ ID NO 111
<211> LENGTH: 1455
<212> TYPE: DNA
<213> ORGANISM: Artificial Sequence
<220> FEATURE:
<223> OTHER INFORMATION: Silicatin, Facile fabrication of uniform silica
      films with tunable physical properties using silicatein protein
      from sponges. Languir 26(6): 4152-4159)

<400> SEQUENCE: 111

```
atgaaggcta caaaattggt gttgggagcg gtaatcctgg gttcgactct gttggcaggc      60
tgttcttcca atgcgaagat cgaccagtta tccagtgatg tggggatcaa cccatacgtc     120
ggtttcgaga tgggttatga ctggctgggc cgcatgccat ataagggatc cgtggaaaac     180
ggcgcatata aggcacaagg agtccaattg accgcaaagt tgggttaccc cattactgat     240
gatttggaca tctacacgcg tctgggtggg atggtgtggc gcgcagacac aaaaagtaat     300
gtttatggta agaatcacga tacaggagtt tctcccgttt ttgctggagg agtggagtat     360
gcgatcacgc cggaaatcgc gacgcgcttg gagtaccaat ggactaacaa cattggcgac     420
gcgcacacga ttggcactcg tcctgacaac ggcatcccag gtatgtatct cggcacgttg     480
gttgttttgt gtgttttggg ggctgctatt ggagagccaa tgcctcagta tgagttcaag     540
gaggaatggc agctgtggaa gaaacaacat gacaagtctt acagcaccaa cttggaggaa     600
ctggagaaac atcttgtctg gctctccaac aagaagtaca ttgaactgca caatgccaat     660
gcagacacct ttggattcac tctagctatg aaccatctag gagatatgac tgaccatgaa     720
tacaaggaga gatacctcac atacactaac agcaaatctg gtaactacac caaggtgttc     780
aaacgtgagc catggatggc ctacccggag actgtagatt ggagaacaaa gggcgctgtg     840
actggtatca agagccaggg agattgtggt gccagctatg cattcagtgc catgggtgca     900
cttgaaggaa tcaatgcact tgctactgga aagctgacct atctcagtga acagaacatc     960
attgattgct ctgtacctta tggtaaccat ggttgcaagg gtggaaacat gtatgtggct    1020
ttcctctatg ttgttgctaa cgaaggagtt gatgatgggg gttcctatcc atttagagga    1080
aagcaatcca gttgtacgta tcaagagcag taccgtggtg caagtatgtc tggctcagtt    1140
caaatcaaca gtggtagtga atctgatctg gaagcagctg tagccaatgt tggtccagtt    1200
gcagtagcta ttgatggaga gtcaaatgct ttcagattct attacagtgg agtgtacgac    1260
tcctccagat gttctagtag cagtctcaac cacgccatgg tgatcactgg ctatggaatt    1320
tcaaataacc aggaatactg gcttgcaaag aacagctggg gtgagaactg gggagaactg    1380
ggctatgtga agatggccag gaacaagtac aatcaatgtg ggattgctag tgatgcctcc    1440
taccccactc tctag                                                     1455
```

<210> SEQ ID NO 112
<211> LENGTH: 272
<212> TYPE: PRT
<213> ORGANISM: Artificial Sequence
<220> FEATURE:
<223> OTHER INFORMATION: mistletoe lectin Pha-L

<400> SEQUENCE: 112

```
Met Ala Ser Ser Lys Phe Phe Thr Val Leu Phe Leu Val Leu Leu Thr
1               5                   10                  15

His Ala Asn Ser Ser Asn Asp Ile Tyr Phe Ser Phe Asp Arg Phe Asn
            20                  25                  30

Glu Thr Asn Leu Ile Leu Gln Gly Asp Ala Ser Val Ser Ser Ser Gly
        35                  40                  45

Gln Leu Arg Leu Thr Asn Val Asn Ser Asn Gly Glu Pro Arg Val Gly
    50                  55                  60

Ser Leu Gly Arg Ala Phe Tyr Ser Ala Pro Ile Gln Ile Trp Asp Asn
65                  70                  75                  80

Thr Thr Gly Thr Val Ala Ser Phe Ala Thr Ser Phe Thr Phe Asn Ile
                85                  90                  95

Gln Val Pro Asn Asn Ala Gly Pro Ala Asp Gly Leu Ala Phe Ala Leu
```

```
            100                 105                 110

Val Pro Val Gly Ser Gln Pro Lys Asp Lys Gly Gly Phe Leu Gly Leu
        115                 120                 125

Phe Asp Gly Ser Asn Ser Asn Phe His Thr Val Ala Val Glu Phe Asp
    130                 135                 140

Thr Leu Tyr Asn Lys Asp Trp Asp Pro Thr Glu Arg His Ile Gly Ile
145                 150                 155                 160

Asp Val Asn Ser Ile Arg Ser Ile Lys Thr Thr Arg Trp Asp Phe Val
                165                 170                 175

Asn Gly Glu Asn Ala Glu Val Leu Ile Thr Tyr Glu Ser Ser Thr Asn
            180                 185                 190

Leu Leu Val Ala Ser Leu Val Tyr Pro Ser Gln Lys Thr Ser Phe Ile
        195                 200                 205

Val Ser Asp Thr Val Asp Leu Lys Ser Val Leu Pro Glu Trp Val Ser
    210                 215                 220

Val Gly Phe Ser Ala Thr Thr Gly Ile Asn Lys Gly Asn Val Glu Thr
225                 230                 235                 240

Asn Asp Val Leu Ser Trp Ser Phe Ala Ser Lys Leu Ser Asp Gly Thr
                245                 250                 255

Thr Ser Glu Gly Leu Asn Leu Ala Asn Leu Val Leu Asn Gln Ile Leu
            260                 265                 270


<210> SEQ ID NO 113
<211> LENGTH: 60
<212> TYPE: PRT
<213> ORGANISM: Artificial Sequence
<220> FEATURE:
<223> OTHER INFORMATION: Single chain variable fraction (ScFv) antibody

<400> SEQUENCE: 113

Leu Ala Tyr Gly Ser Gln Gly Asn Leu Asn Pro Leu Ile Asn Glu Ile
1               5                   10                  15

Ser Lys Ile Ile Ser Ala Ala Gly Asn Phe Asp Val Lys Glu Glu Arg
            20                  25                  30

Ala Ala Ala Ser Leu Leu Gln Leu Ser Gly Asn Ala Ser Asp Phe Ser
        35                  40                  45

Tyr Gly Arg Asn Ser Ile Thr Leu Thr Ala Ser Ala
    50                  55                  60


<210> SEQ ID NO 114
<211> LENGTH: 333
<212> TYPE: PRT
<213> ORGANISM: Artificial Sequence
<220> FEATURE:
<223> OTHER INFORMATION: Salmonella enterica serotype Typhimurium,
      adenosine deaminase

<400> SEQUENCE: 114

Met Ile Asp Ile Thr Leu Pro Leu Thr Asp Ile His Arg His Leu Asp
1               5                   10                  15

Gly Asn Ile Arg Ala Gln Thr Ile Leu Asp Leu Gly Arg Gln Phe Asn
            20                  25                  30

Ile Ala Leu Pro Ala Gln Thr Leu Glu Thr Leu Ile Pro His Val Gln
        35                  40                  45

Val Thr Ser Thr Glu Pro Asp Leu Val Ser Phe Leu Thr Lys Leu Asp
    50                  55                  60

Trp Gly Val Lys Val Leu Ala Ser Leu Asp Ala Cys Arg Arg Val Ala
65                  70                  75                  80
```

```
Phe Glu Asn Ile Glu Asp Ala Ala Arg Asn Gly Leu His Tyr Val Glu
                85                  90                  95

Leu Arg Phe Ser Pro Gly Tyr Met Ala Met Ala His Gln Leu Pro Ile
            100                 105                 110

Ala Gly Val Val Glu Ala Val Ile Asp Gly Val Arg Asp Gly Cys Asn
        115                 120                 125

Thr Phe Gly Val Glu Ala Arg Leu Ile Gly Ile Met Ser Arg Thr Phe
    130                 135                 140

Gly Glu Ala Ala Cys Leu Gln Glu Leu Asp Ala Leu Leu Ala His Arg
145                 150                 155                 160

Glu Asn Ile Thr Ala Leu Asp Leu Ala Gly Asp Glu Leu Gly Phe Pro
                165                 170                 175

Gly Ser Leu Phe Leu Ser His Phe Asn Arg Ala Arg Asp Ala Gly Trp
            180                 185                 190

His Ile Thr Val His Ala Gly Glu Ala Ala Gly Pro Glu Ser Ile Trp
        195                 200                 205

Gln Ala Ile Arg Glu Leu Gly Ala Glu Arg Ile Gly His Gly Val Lys
    210                 215                 220

Ala Val Glu Asp Arg Ala Leu Met Asp Phe Leu Ala Gln Gln Arg Ile
225                 230                 235                 240

Gly Ile Glu Ser Cys Leu Thr Ser Asn Ile Gln Thr Ser Thr Val Ala
                245                 250                 255

Ser Leu Ala Asp His Pro Leu Lys Thr Phe Leu Glu His Gly Val Leu
            260                 265                 270

Ala Ser Leu Asn Thr Asp Asp Pro Ala Val Gln Gly Val Asp Ile Ile
        275                 280                 285

His Glu Tyr His Val Ala Ala Pro Ala Ala Gly Leu Ser Arg Glu Gln
    290                 295                 300

Ile Arg Gln Ala Gln Ile Asn Gly Leu Glu Ile Ala Phe Leu Ser Asp
305                 310                 315                 320

Ser Glu Lys Arg Ala Leu Arg Glu Lys Val Ala Glu Ala
                325                 330
```

<210> SEQ ID NO 115
<211> LENGTH: 502
<212> TYPE: PRT
<213> ORGANISM: Artificial Sequence
<220> FEATURE:
<223> OTHER INFORMATION: Secreted adenosine deaminase of Elizabethkingia anophelis/meningoseptica

<400> SEQUENCE: 115

```
Met Met Lys Lys Thr Leu Ile Tyr Ile Leu Leu Leu Gly Leu Pro Leu
1               5                   10                  15

Thr Gly Asn Gln Tyr Ile Thr Ala Gln Glu Leu Ser Tyr Gln Gln Lys
            20                  25                  30

Ile Asn Leu Leu Asp Gln Glu Asn Gln Ala Leu Gly Phe Asp Ser Asp
        35                  40                  45

Leu Lys Leu Ser Asp Ala Glu Ser Val Leu Asp Lys Lys Leu Phe Gln
    50                  55                  60

Leu Arg Lys Glu Phe Leu Thr Glu Thr Glu Lys Gln Lys Ile Pro Leu
65                  70                  75                  80

Tyr Asn Ser Ser Phe Asn Gln Ile Lys Pro Leu Ile Glu Asn Ser Lys
                85                  90                  95

Leu Phe Asn Ile Ile Gln Ser Met Pro Lys Gly Gly Leu Leu His Thr
```

```
            100                 105                 110

His Ser Gly Gly Ile Thr Asp Ala Lys Trp Ile Ile Glu Thr Ala Arg
        115                 120                 125

Lys Tyr Lys Glu Ser Tyr Ile Tyr Val Gln Lys Asp Asn Asp Gln Tyr
    130                 135                 140

Ile Phe Gly Gln Met Ala Phe Phe Ala Lys Asp Lys Val Pro Ala Gly
145                 150                 155                 160

Phe Val Asn Leu Asp Glu Lys Leu Ser Ala Asp Pro Gly Phe Glu Lys
                165                 170                 175

Gln Leu Gln Glu Leu Leu Ile Leu Lys Arg Asp Gln Leu Cys Asn Tyr
            180                 185                 190

Thr Asp Tyr Trp Ile Glu Phe Glu Lys Arg Phe Lys Arg Thr Gly Ser
        195                 200                 205

Leu Leu Ser Tyr Arg Pro Phe Phe Lys Ala Tyr Tyr Leu Lys Gly Phe
    210                 215                 220

Gln Asp Leu Ile Lys Asp Asn Val Gln His Gly Glu Ile Arg Phe Ile
225                 230                 235                 240

Phe Asp Gln Leu Tyr Asp Phe Glu His Gly Lys Tyr Ser Leu Asn Thr
                245                 250                 255

Ser Ile Thr Asp Leu Gln Asp Ile Leu Lys Glu Ile His Lys Thr Ala
            260                 265                 270

Pro Gln Phe Thr Leu Lys Leu Ile Tyr Ser Ser Phe Lys Phe Leu Asp
        275                 280                 285

Pro Lys Gly Val Asp Gln Gln Leu Glu Ala Ala Phe Gln Leu Lys Lys
    290                 295                 300

Glu Phe Pro Asp Met Ile Thr Gly Phe Asp Leu Val Ala Asp Glu Ala
305                 310                 315                 320

Ala Gly Asn Ser Ile Tyr Ser Phe Arg Glu Ser Trp Met Lys Leu Asn
                325                 330                 335

Asp Leu Ser Lys Lys Tyr Gly Val Asp Met Pro Leu Phe Leu His Ala
            340                 345                 350

Gly Glu Ser Asn Ser Val Phe Asn Lys Asn Val Val Asp Leu Ala Leu
        355                 360                 365

Leu Asn Asn Lys Arg Ile Gly His Gly Leu Asn Leu Ile Tyr Phe Pro
    370                 375                 380

Lys Thr Leu Glu Leu Ile Lys Lys Gln Asn Lys Leu Val Glu Val Ser
385                 390                 395                 400

Pro Ile Ser Asn Gln Ile Leu Gly Tyr Val Ser Asp Met Arg Asn His
                405                 410                 415

Pro Ala Arg Val Leu Leu Ser Asn Gly Val Gln Cys Ser Ile Asn Ser
            420                 425                 430

Asp Asp Pro Gly Val Tyr Gly Tyr Glu Gly Leu Ser Tyr Asp Phe Trp
        435                 440                 445

Val Ala Phe Val Tyr Trp Glu Leu Asp Ile Lys Ala Leu Lys Lys Leu
    450                 455                 460

Val Tyr Asn Ser Ile Asn Tyr Ser Ser Leu Asn Glu Lys Glu Lys Lys
465                 470                 475                 480

Glu Ala Ile Leu Tyr Leu Asn Lys Gln Trp Thr Asp Phe Val Thr Lys
                485                 490                 495

Met Asn Gln Lys Leu Ser
            500
```

<210> SEQ ID NO 116

<211> LENGTH: 274
<212> TYPE: PRT
<213> ORGANISM: Artificial Sequence
<220> FEATURE:
<223> OTHER INFORMATION: Eubacterium ramulus phloretin hydrolase (phy) gene GenBank: AF548616.1
<220> FEATURE:
<221> NAME/KEY: misc_feature
<222> LOCATION: (17)..(17)
<223> OTHER INFORMATION: Xaa can be any naturally occurring amino acid

<400> SEQUENCE: 116

```
Met Glu Glu Asp Phe Asn Met Ser Thr Pro Gly Val Lys Val Gly Val
1               5                   10                  15

Xaa Glu Glu Glu Lys Lys Leu Ser Tyr Tyr Lys Tyr Tyr Glu Gln Asp
            20                  25                  30

Leu Ala Pro Val Pro Ala Glu Lys Ile Ala Ile Leu Gln Gly Gly Pro
        35                  40                  45

Ile Ala Pro Glu Lys Cys Ile Pro Phe Asp Glu Arg Asn Lys Phe Leu
    50                  55                  60

Lys Gly Glu Asp Asp Glu Tyr Ala Asn Ile Gly Phe Gly Val Ala Ala
65                  70                  75                  80

Asp Gly Thr Ala Leu Val Cys Asn Thr Thr Tyr Met Pro Gly Val Thr
                85                  90                  95

Gly Glu Met Leu Asp Trp Trp Phe Pro Trp His Ser Val Gly Ser Asp
            100                 105                 110

Leu Arg Tyr Lys Ile Trp Asp Pro Glu Asp His Tyr Phe Ala Arg Ala
        115                 120                 125

Tyr Pro Ala Ser Tyr Val Val Asp Pro Asn Val Pro Met Asn Gln Lys
    130                 135                 140

Thr Trp Gly Val Asp His Tyr Ile Met Glu Asp Val Gly Pro Gly Pro
145                 150                 155                 160

Glu Phe Leu Lys Leu Cys Phe Lys Arg Pro Ala Asp Phe Gly Tyr Asp
                165                 170                 175

Glu Ser Ile Ile Gly Thr Glu Lys Cys Glu Ser Leu Val Cys Ala Ile
            180                 185                 190

Gly Glu Ser Ser Cys Ala Ala Ala Met Thr His Lys Trp His Pro Tyr
        195                 200                 205

Lys Asp Gly Val Leu Phe Glu Ser Arg Phe Trp Ile Gly Tyr Arg Ile
    210                 215                 220

Asp Glu Glu Gly Asn Ile Val Lys Ala Ile Pro Glu Gly Val Ser Ile
225                 230                 235                 240

Pro Pro Phe Val Pro Gln Gly Leu Phe Ala His Asn Ile Lys Glu Phe
                245                 250                 255

Thr Asn Leu Ala Ala Ile Leu Pro Thr Leu Tyr Ala Glu Glu Lys Asp
            260                 265                 270

Thr Phe
```

<210> SEQ ID NO 117
<211> LENGTH: 266
<212> TYPE: PRT
<213> ORGANISM: Artificial Sequence
<220> FEATURE:
<223> OTHER INFORMATION: Mistletoe B chain

<400> SEQUENCE: 117

```
Asp Asp Val Thr Cys Thr Thr Ser Glu Pro Thr Val Arg Phe Val Gly
1               5                   10                  15
```

```
Arg Asn Gly Leu Cys Leu Asp Val Pro Glu Gly Asp Tyr His Asp Gly
            20                  25                  30

Ser Arg Ile Gln Leu Trp Pro Cys Lys Ser Asn Ser Asp Gln Asn Gln
        35                  40                  45

Leu Trp Thr Ile Arg Arg Asp Gly Thr Ile Arg Ser Asn Gly Arg Cys
    50                  55                  60

Leu Thr Thr Tyr Gly Tyr Thr Ala Gly Ser Tyr Ile Met Ile Tyr Asp
65                  70                  75                  80

Cys Asn Arg Gly Gly Trp Asp Leu Thr Thr Trp Gln Ile Arg Gly Asn
                85                  90                  95

Gly Ile Ile Leu Asn Pro Arg Ser Met Met Val Ile Gly Thr Pro Ser
            100                 105                 110

Gly Ser Arg Gly Thr Arg Gly Thr Thr Phe Thr Leu Gln Thr Leu Gly
        115                 120                 125

Tyr Ser Leu Gly Gln Gly Trp Leu Ala Ser Asn Asp Thr Ala Pro Arg
    130                 135                 140

Glu Val Thr Ile Tyr Gly Phe Arg Asp His Cys Met Glu Thr Ser Gly
145                 150                 155                 160

Gly Lys Val Trp Val Gly Thr Cys Val Ser Gly Lys Gln Asn Gln Arg
                165                 170                 175

Trp Ala Leu Tyr Gly Asp Gly Ser Ile Arg Pro Lys Pro Tyr Gln Asp
            180                 185                 190

Gln Cys Leu Thr Ser Gln Gly Asp Ser Val Arg Ser Val Ile Asn Leu
        195                 200                 205

Phe Ser Cys Thr Ala Gly Ser Pro Arg Gln Arg Trp Val Phe Thr Asn
    210                 215                 220

Lys Gly Ala Ile Leu Asn Leu Lys Asn Arg Leu Ala Met Asp Val Ala
225                 230                 235                 240

Glu Ser Asn Pro Ser Leu Arg Arg Ile Ile Ile Phe Ser Val Thr Gly
                245                 250                 255

Asn Pro Asn Gln Met Trp Leu Pro Val Pro
            260                 265


<210> SEQ ID NO 118
<211> LENGTH: 609
<212> TYPE: PRT
<213> ORGANISM: Artificial Sequence
<220> FEATURE:
<223> OTHER INFORMATION: Pasteurella multocita toxin (PMT)

<400> SEQUENCE: 118

Met Lys Thr Lys His Phe Phe Asn Ser Asp Phe Thr Val Lys Gly Lys
1               5                   10                  15

Ser Ala Asp Glu Ile Phe Arg Arg Leu Cys Thr Asp His Pro Asp Lys
            20                  25                  30

Gln Leu Asn Asn Val Lys Trp Lys Glu Val Phe Ile Asn Arg Phe Gly
        35                  40                  45

Gln Met Met Leu Asp Thr Pro Asn Pro Arg Lys Ile Val Glu Lys Ile
    50                  55                  60

Ile Asn Glu Gly Leu Glu Lys Gln Gly Leu Lys Asn Ile Asp Pro Glu
65                  70                  75                  80

Thr Thr Tyr Phe Asn Ile Phe Ser Ser Ser Asp Ser Ser Asp Gly Asn
                85                  90                  95

Val Phe His Tyr Asn Ser Leu Ser Glu Ser Tyr Arg Val Thr Asp Ala
            100                 105                 110
```

```
Cys Leu Met Asn Ile Phe Val Glu Arg Tyr Phe Asp Asp Trp Asp Leu
        115                 120                 125

Leu Asn Ser Leu Ala Ser Asn Gly Ile Tyr Ser Val Gly Lys Glu Gly
    130                 135                 140

Ala Tyr Tyr Pro Asp His Asp Tyr Gly Pro Glu Tyr Asn Pro Val Trp
145                 150                 155                 160

Gly Pro Asn Glu Gln Ile Tyr His Ser Arg Val Ile Ala Asp Ile Leu
                165                 170                 175

Tyr Ala Arg Ser Val Trp Asp Glu Phe Lys Lys Tyr Phe Met Glu Tyr
            180                 185                 190

Trp Gln Lys Tyr Ala Gln Leu Tyr Thr Glu Met Leu Ser Asp Thr Phe
        195                 200                 205

Leu Ala Met Ala Ile Gln Gln Tyr Thr Arg Gln Thr Leu Thr Asp Glu
    210                 215                 220

Gly Phe Leu Met Val Cys Asn Thr Tyr Tyr Gly Asn Lys Glu Glu Val
225                 230                 235                 240

Gln Ile Thr Leu Leu Asp Ile Tyr Gly Tyr Pro Ser Thr Asp Ile Ile
                245                 250                 255

Cys Ile Glu Gln Lys Gly Leu Pro Thr Pro Lys Val Ile Leu Tyr Ile
            260                 265                 270

Pro Gly Gly Thr Gln Pro Phe Val Glu Phe Leu Asn Thr Asp Asp Leu
        275                 280                 285

Lys Gln Trp Ile Ala Trp His Leu Lys Asp Asn Lys His Met Val Ala
    290                 295                 300

Phe Arg Lys His Phe Ser Leu Lys Gln Arg Gln Glu Gly Glu Thr Phe
305                 310                 315                 320

Thr Gly Ile Asp Lys Ala Leu Gln Tyr Ile Ala Glu Glu Ser Pro Glu
                325                 330                 335

Trp Pro Ala Asn Lys Tyr Ile Leu Tyr Asn Pro Thr His Leu Glu Thr
            340                 345                 350

Glu Asn Leu Phe Asn Ile Met Met Lys Arg Thr Glu Gln Arg Met Leu
        355                 360                 365

Glu Asp Ser Asp Val Gln Ile Arg Ser Asn Ser Glu Ala Thr Arg Asp
    370                 375                 380

Tyr Ala Leu Ser Leu Leu Glu Thr Phe Ile Ser Gln Leu Ser Ala Ile
385                 390                 395                 400

Asp Met Leu Val Pro Ala Val Gly Ile Pro Ile Asn Phe Ala Leu Ser
                405                 410                 415

Ala Thr Ala Leu Gly Leu Ser Ser Asp Ile Val Val Asn Gly Asp Ser
            420                 425                 430

Tyr Glu Lys Arg Lys Tyr Gly Ile Gly Ser Leu Val Gln Ser Ala Leu
        435                 440                 445

Phe Thr Gly Ile Asn Leu Ile Pro Val Ile Ser Glu Thr Ala Glu Ile
    450                 455                 460

Leu Ser Ser Phe Ser Arg Thr Glu Glu Asp Ile Pro Ala Phe Phe Thr
465                 470                 475                 480

Glu Glu Gln Ala Leu Ala Gln Arg Phe Glu Ile Val Glu Glu Glu Leu
                485                 490                 495

His Ser Ile Ser Pro Asp Asp Pro Pro Arg Glu Ile Thr Asp Glu Asn
            500                 505                 510

Leu His Lys Ile Arg Leu Val Arg Leu Asn Asn Glu Asn Gln Pro Leu
        515                 520                 525

Val Val Leu Arg Arg Leu Gly Gly Asn Lys Phe Ile Arg Ile Glu Pro
```

```
    530                 535                 540

Ile Thr Phe Gln Glu Ile Lys Gly Ser Leu Val Ser Glu Val Ile Asn
545                 550                 555                 560

Pro Val Thr Asn Lys Thr Tyr Tyr Val Ser Asn Ala Lys Leu Gly Gly
                565                 570                 575

Ser Gly Ser Gly Ala Leu Lys Lys Glu Leu Gln Ala Asn Lys Lys Glu
            580                 585                 590

Leu Ala Gln Leu Lys Trp Glu Leu Gln Ala Leu Lys Lys Glu Leu Ala
        595                 600                 605

Gln


<210> SEQ ID NO 119
<211> LENGTH: 866
<212> TYPE: PRT
<213> ORGANISM: Artificial Sequence
<220> FEATURE:
<223> OTHER INFORMATION: Amino acids of the nucleic acid open reading,
      for the second of a two-part regulatory circuit; 1-119 = YebF;
      120-121 "LK" = cleavage signal; 122-151 = leucine zipper (in
      bold); 152-155 = linker (large type italics); 156-866 = C-term PMT

<400> SEQUENCE: 119

Met Ala Lys Lys Arg Gly Ala Phe Leu Gly Leu Leu Leu Val Ser Ala
1               5                   10                  15

Cys Ala Ser Val Phe Ala Ala Asn Asn Glu Thr Ser Lys Ser Val Thr
            20                  25                  30

Phe Pro Lys Cys Glu Asp Leu Asp Ala Ala Gly Ile Ala Ala Ser Val
        35                  40                  45

Lys Arg Asp Tyr Gln Gln Asn Arg Val Ala Arg Trp Ala Asp Asp Gln
    50                  55                  60

Lys Ile Val Gly Gln Ala Asp Pro Val Ala Trp Val Ser Leu Gln Asp
65                  70                  75                  80

Ile Gln Gly Lys Asp Asp Lys Trp Ser Val Pro Leu Thr Val Arg Gly
                85                  90                  95

Lys Ser Ala Asp Ile His Tyr Gln Val Ser Val Asp Cys Lys Ala Gly
            100                 105                 110

Met Ala Glu Tyr Gln Arg Arg Leu Lys Glu Gln Leu Glu Lys Lys Leu
        115                 120                 125

Gln Ala Leu Glu Lys Lys Leu Ala Gln Leu Glu Trp Lys Asn Gln Ala
    130                 135                 140

Leu Glu Lys Lys Leu Ala Gln Gly Gly Ser Gly Leu Gly Gly Ser Pro
145                 150                 155                 160

Tyr Ser Pro Phe Arg Ile Gly Leu Glu Gly Val Trp Thr Pro Glu Val
                165                 170                 175

Leu Lys Ala Arg Ala Ser Val Ile Gly Lys Pro Ile Gly Glu Ser Tyr
            180                 185                 190

Lys Arg Ile Leu Ala Lys Leu Gln Arg Ile His Asn Ser Asn Ile Leu
        195                 200                 205

Asp Glu Arg Gln Gly Leu Met His Glu Leu Met Glu Leu Ile Asp Leu
    210                 215                 220

Tyr Glu Glu Ser Gln Pro Ser Ser Glu Arg Leu Asn Ala Phe Arg Glu
225                 230                 235                 240

Leu Arg Thr Gln Leu Glu Lys Ala Leu Tyr Leu Pro Glu Met Glu Ala
                245                 250                 255

Leu Lys Lys Gln Ile Leu Gln Ile Pro Asn Lys Gly Ser Gly Ala Ala
            260                 265                 270
```

```
Arg Phe Leu Leu Arg Thr Ala Met Asn Glu Met Ala Gly Lys Thr Ser
        275                 280                 285

Glu Ser Thr Ala Asp Leu Ile Arg Phe Ala Leu Gln Asp Thr Val Ile
    290                 295                 300

Ser Ala Pro Phe Arg Gly Tyr Ala Gly Ala Ile Pro Glu Ala Ile Asp
305                 310                 315                 320

Phe Pro Val Lys Tyr Val Ile Glu Asp Ile Ser Val Phe Asp Lys Ile
                325                 330                 335

Gln Thr Asn Tyr Trp Glu Leu Pro Ala Tyr Glu Ser Trp Asn Glu Gly
            340                 345                 350

Ser Asn Ser Ala Leu Leu Pro Gly Leu Leu Arg Glu Ser Gln Ser Lys
        355                 360                 365

Gly Met Leu Ser Lys Cys Arg Ile Ile Glu Asn Ser Leu Tyr Ile Gly
    370                 375                 380

His Ser Tyr Glu Glu Met Phe Tyr Ser Ile Ser Pro Tyr Ser Asn Gln
385                 390                 395                 400

Val Gly Gly Pro Tyr Glu Leu Tyr Pro Phe Thr Phe Phe Ser Met Leu
                405                 410                 415

Gln Glu Val Gln Gly Asp Leu Gly Phe Glu Gln Ala Phe Ala Thr Arg
            420                 425                 430

Asn Phe Phe Asn Thr Leu Val Ser Asp Arg Leu Ser Leu Met Glu Asn
        435                 440                 445

Thr Met Leu Leu Thr Glu Ser Phe Asp Tyr Thr Pro Trp Asp Ala Ile
    450                 455                 460

Tyr Gly Asp Ile Asn Tyr Asp Glu Gln Phe Ala Ala Met Ser Ile Asn
465                 470                 475                 480

Glu Arg Ile Glu Lys Cys Met Asn Thr Tyr Arg Gly Val Ala Phe Gln
                485                 490                 495

Asn Ser Ser Lys Ser Ile Asp Phe Phe Leu Asn Asn Leu Thr Thr Phe
            500                 505                 510

Ile Asp Asn Gly Leu Thr Glu Ile Ala Ile Ser Asp Leu Pro Tyr Asp
        515                 520                 525

Ile Val Gln Gln Glu Ile Ser Gln Phe Leu Gln Gly Ser Asn Glu Trp
    530                 535                 540

Lys Thr Leu Asp Ala Met Leu Phe Asn Leu Asp Lys Gly Asp Ile Asn
545                 550                 555                 560

Gly Ala Phe Arg Lys Leu Leu Gln Ser Ala Lys Asp Asn Asn Ile Lys
                565                 570                 575

Phe Arg Ala Ile Gly His Ser Asp Asn Ser Val Pro Pro Phe Asn Asn
            580                 585                 590

Pro Tyr Lys Ser Leu Tyr Tyr Lys Gly Asn Ile Ile Ala Glu Ala Ile
        595                 600                 605

Glu Lys Leu Asp Arg Glu Gly Gln Lys Phe Val Val Phe Ala Asp Ser
    610                 615                 620

Ser Leu Leu Asn Ser Thr Pro Gly Thr Gly Arg Pro Met Pro Gly Leu
625                 630                 635                 640

Val Gln Tyr Leu Lys Ile Pro Ala Thr Val Val Asp Ser Asp Gly Ala
                645                 650                 655

Trp Gln Phe Leu Pro Asp Val Ala Ser Ser Arg Val Pro Ile Glu Val
            660                 665                 670

Thr Glu Leu Glu Asn Trp Gln Val Leu Thr Pro Pro Gln Gly Lys Ile
        675                 680                 685
```

Leu Gly Leu Lys Gln Phe Lys Leu Thr Ala Gly Phe Pro Thr Glu Gln
    690                 695                 700

Ser Arg Leu Pro Leu Leu Glu Asn Ser Val Ser Glu Asp Leu Arg Glu
705                 710                 715                 720

Glu Leu Met Gln Lys Ile Asp Ala Ile Lys Asn Asp Val Lys Met Asn
                725                 730                 735

Ser Leu Val Cys Met Glu Ala Gly Ser Cys Asp Ser Val Ser Pro Lys
            740                 745                 750

Val Ala Ala Arg Leu Lys Asp Met Gly Leu Glu Ala Gly Met Gly Ala
        755                 760                 765

Ser Ile Thr Trp Trp Arg Arg Glu Gly Gly Met Glu Phe Ser His Gln
    770                 775                 780

Met His Thr Thr Ala Ser Phe Lys Phe Ala Gly Lys Glu Phe Ala Val
785                 790                 795                 800

Asp Ala Ser His Leu Gln Phe Val His Asp Gln Leu Asp Thr Thr Ile
                805                 810                 815

Leu Ile Leu Pro Val Asp Asp Trp Ala Leu Glu Ile Ala Gln Arg Asn
            820                 825                 830

Arg Ala Ile Asn Pro Phe Val Glu Tyr Val Ser Lys Thr Gly Asn Met
        835                 840                 845

Leu Ala Leu Phe Met Pro Pro Leu Phe Thr Lys Pro Arg Leu Thr Arg
    850                 855                 860

Ala Leu
865

<210> SEQ ID NO 120
<211> LENGTH: 746
<212> TYPE: PRT
<213> ORGANISM: Artificial Sequence
<220> FEATURE:
<223> OTHER INFORMATION: Amino acids of the nucleic acid open reading, for the second of a two part regulatory circuit; 1, initiating methionine; 2-31 leucine zipper; 32-35, linker; 36 - 746, PMT C-term

<400> SEQUENCE: 120

Met Glu Gln Leu Glu Lys Lys Leu Gln Ala Leu Glu Lys Lys Leu Ala
1               5                   10                  15

Gln Leu Glu Trp Lys Asn Gln Ala Leu Glu Lys Lys Leu Ala Gln Gly
            20                  25                  30

Gly Ser Gly Leu Gly Gly Ser Pro Tyr Ser Pro Phe Arg Ile Gly Leu
        35                  40                  45

Glu Gly Val Trp Thr Pro Glu Val Leu Lys Ala Arg Ala Ser Val Ile
    50                  55                  60

Gly Lys Pro Ile Gly Glu Ser Tyr Lys Arg Ile Leu Ala Lys Leu Gln
65                  70                  75                  80

Arg Ile His Asn Ser Asn Ile Leu Asp Glu Arg Gln Gly Leu Met His
                85                  90                  95

Glu Leu Met Glu Leu Ile Asp Leu Tyr Glu Glu Ser Gln Pro Ser Ser
            100                 105                 110

Glu Arg Leu Asn Ala Phe Arg Glu Leu Arg Thr Gln Leu Glu Lys Ala
        115                 120                 125

Leu Tyr Leu Pro Glu Met Glu Ala Leu Lys Lys Gln Ile Leu Gln Ile
    130                 135                 140

Pro Asn Lys Gly Ser Gly Ala Ala Arg Phe Leu Leu Arg Thr Ala Met
145                 150                 155                 160

-continued

```
Asn Glu Met Ala Gly Lys Thr Ser Glu Ser Thr Ala Asp Leu Ile Arg
                165                 170                 175

Phe Ala Leu Gln Asp Thr Val Ile Ser Ala Pro Phe Arg Gly Tyr Ala
            180                 185                 190

Gly Ala Ile Pro Glu Ala Ile Asp Phe Pro Val Lys Tyr Val Ile Glu
        195                 200                 205

Asp Ile Ser Val Phe Asp Lys Ile Gln Thr Asn Tyr Trp Glu Leu Pro
    210                 215                 220

Ala Tyr Glu Ser Trp Asn Glu Gly Ser Asn Ser Ala Leu Leu Pro Gly
225                 230                 235                 240

Leu Leu Arg Glu Ser Gln Ser Lys Gly Met Leu Ser Lys Cys Arg Ile
                245                 250                 255

Ile Glu Asn Ser Leu Tyr Ile Gly His Ser Tyr Glu Glu Met Phe Tyr
            260                 265                 270

Ser Ile Ser Pro Tyr Ser Asn Gln Val Gly Gly Pro Tyr Glu Leu Tyr
        275                 280                 285

Pro Phe Thr Phe Phe Ser Met Leu Gln Glu Val Gln Gly Asp Leu Gly
    290                 295                 300

Phe Glu Gln Ala Phe Ala Thr Arg Asn Phe Phe Asn Thr Leu Val Ser
305                 310                 315                 320

Asp Arg Leu Ser Leu Met Glu Asn Thr Met Leu Leu Thr Glu Ser Phe
                325                 330                 335

Asp Tyr Thr Pro Trp Asp Ala Ile Tyr Gly Asp Ile Asn Tyr Asp Glu
            340                 345                 350

Gln Phe Ala Ala Met Ser Ile Asn Glu Arg Ile Glu Lys Cys Met Asn
        355                 360                 365

Thr Tyr Arg Gly Val Ala Phe Gln Asn Ser Ser Lys Ser Ile Asp Phe
    370                 375                 380

Phe Leu Asn Asn Leu Thr Thr Phe Ile Asp Asn Gly Leu Thr Glu Ile
385                 390                 395                 400

Ala Ile Ser Asp Leu Pro Tyr Asp Ile Val Gln Gln Glu Ile Ser Gln
                405                 410                 415

Phe Leu Gln Gly Ser Asn Glu Trp Lys Thr Leu Asp Ala Met Leu Phe
            420                 425                 430

Asn Leu Asp Lys Gly Asp Ile Asn Gly Ala Phe Arg Lys Leu Leu Gln
        435                 440                 445

Ser Ala Lys Asp Asn Asn Ile Lys Phe Arg Ala Ile Gly His Ser Asp
    450                 455                 460

Asn Ser Val Pro Pro Phe Asn Asn Pro Tyr Lys Ser Leu Tyr Tyr Lys
465                 470                 475                 480

Gly Asn Ile Ile Ala Glu Ala Ile Glu Lys Leu Asp Arg Glu Gly Gln
                485                 490                 495

Lys Phe Val Val Phe Ala Asp Ser Ser Leu Leu Asn Ser Thr Pro Gly
            500                 505                 510

Thr Gly Arg Pro Met Pro Gly Leu Val Gln Tyr Leu Lys Ile Pro Ala
        515                 520                 525

Thr Val Val Asp Ser Asp Gly Ala Trp Gln Phe Leu Pro Asp Val Ala
    530                 535                 540

Ser Ser Arg Val Pro Ile Glu Val Thr Glu Leu Glu Asn Trp Gln Val
545                 550                 555                 560

Leu Thr Pro Pro Gln Gly Lys Ile Leu Gly Leu Lys Gln Phe Lys Leu
                565                 570                 575

Thr Ala Gly Phe Pro Thr Glu Gln Ser Arg Leu Pro Leu Leu Glu Asn
```

```
            580                 585                 590

Ser Val Ser Glu Asp Leu Arg Glu Glu Leu Met Gln Lys Ile Asp Ala
        595                 600                 605

Ile Lys Asn Asp Val Lys Met Asn Ser Leu Val Cys Met Glu Ala Gly
    610                 615                 620

Ser Cys Asp Ser Val Ser Pro Lys Val Ala Ala Arg Leu Lys Asp Met
625                 630                 635                 640

Gly Leu Glu Ala Gly Met Gly Ala Ser Ile Thr Trp Trp Arg Arg Glu
                645                 650                 655

Gly Gly Met Glu Phe Ser His Gln Met His Thr Thr Ala Ser Phe Lys
            660                 665                 670

Phe Ala Gly Lys Glu Phe Ala Val Asp Ala Ser His Leu Gln Phe Val
        675                 680                 685

His Asp Gln Leu Asp Thr Thr Ile Leu Ile Leu Pro Val Asp Asp Trp
    690                 695                 700

Ala Leu Glu Ile Ala Gln Arg Asn Arg Ala Ile Asn Pro Phe Val Glu
705                 710                 715                 720

Tyr Val Ser Lys Thr Gly Asn Met Leu Ala Leu Phe Met Pro Pro Leu
                725                 730                 735

Phe Thr Lys Pro Arg Leu Thr Arg Ala Leu
            740                 745


<210> SEQ ID NO 121
<211> LENGTH: 1092
<212> TYPE: PRT
<213> ORGANISM: Artificial Sequence
<220> FEATURE:
<223> OTHER INFORMATION: CNF with an internal pertussis S3 binding
      domain with flanking short flexible linkers

<400> SEQUENCE: 121

Met Gly Asn Gln Trp Gln Gln Lys Tyr Leu Leu Glu Tyr Asn Glu Leu
1               5                   10                  15

Val Ser Asn Phe Pro Ser Pro Glu Arg Val Val Ser Asp Tyr Ile Lys
            20                  25                  30

Asn Cys Phe Lys Thr Asp Leu Pro Trp Phe Ser Arg Ile Asp Pro Asp
        35                  40                  45

Asn Ala Tyr Phe Ile Cys Phe Ser Gln Asn Arg Ser Asn Ser Arg Ser
    50                  55                  60

Tyr Thr Gly Trp Asp His Leu Gly Lys Tyr Lys Thr Glu Val Leu Thr
65                  70                  75                  80

Leu Thr Gln Ala Ala Leu Ile Asn Ile Gly Tyr Arg Phe Asp Val Phe
                85                  90                  95

Asp Asp Ala Asn Ser Ser Thr Gly Ile Tyr Lys Thr Lys Ser Ala Asp
            100                 105                 110

Val Phe Asn Glu Glu Asn Glu Glu Lys Met Leu Pro Ser Glu Tyr Leu
        115                 120                 125

His Phe Leu Gln Lys Cys Asp Phe Ala Gly Val Tyr Gly Lys Thr Leu
    130                 135                 140

Ser Asp Tyr Trp Ser Lys Tyr Tyr Asp Lys Phe Lys Leu Leu Leu Lys
145                 150                 155                 160

Asn Tyr Tyr Ile Ser Ser Ala Leu Tyr Leu Tyr Lys Asn Gly Glu Leu
                165                 170                 175

Asp Glu Arg Glu Tyr Asn Phe Ser Met Asn Ala Leu Asn Arg Ser Asp
            180                 185                 190
```

```
Asn Ile Ser Leu Leu Phe Phe Asp Ile Tyr Gly Tyr Tyr Ala Ser Asp
        195                 200                 205

Ile Phe Val Ala Lys Asn Asn Asp Lys Val Met Leu Phe Ile Pro Gly
    210                 215                 220

Ala Lys Lys Pro Phe Leu Phe Lys Lys Asn Ile Ala Asp Leu Arg Leu
225                 230                 235                 240

Thr Leu Lys Glu Leu Ile Lys Asp Ser Asp Lys Gln Gln Leu Leu Ser
                245                 250                 255

Gln His Phe Ser Leu Tyr Ser Arg Gln Asp Gly Val Ser Tyr Ala Gly
            260                 265                 270

Val Asn Ser Val Leu His Ala Ile Glu Asn Asp Gly Asn Phe Asn Glu
        275                 280                 285

Ser Tyr Phe Leu Tyr Ser Asn Lys Thr Leu Ser Asn Lys Asp Val Phe
    290                 295                 300

Asp Ala Ile Ala Ile Ser Val Lys Lys Arg Ser Phe Ser Asp Gly Asp
305                 310                 315                 320

Ile Val Ile Lys Ser Asn Ser Glu Ala Gln Arg Asp Tyr Ala Leu Thr
                325                 330                 335

Ile Leu Gln Thr Ile Leu Ser Met Thr Pro Ile Phe Asp Ile Val Val
            340                 345                 350

Pro Glu Val Ser Val Pro Leu Gly Leu Gly Ile Ile Thr Ser Ser Met
        355                 360                 365

Gly Ile Ser Phe Asp Gln Leu Ile Asn Gly Asp Thr Tyr Glu Glu Arg
    370                 375                 380

Arg Ser Ala Ile Pro Gly Leu Ala Thr Asn Ala Val Leu Leu Gly Leu
385                 390                 395                 400

Ser Phe Ala Ile Pro Leu Leu Ile Ser Lys Ala Gly Ile Asn Gln Glu
                405                 410                 415

Val Leu Ser Ser Val Ile Asn Asn Glu Gly Arg Thr Leu Asn Glu Thr
            420                 425                 430

Asn Ile Asp Ile Phe Leu Lys Glu Tyr Gly Ile Ala Glu Asp Ser Ile
        435                 440                 445

Ser Ser Thr Asn Leu Leu Asp Val Lys Leu Lys Ser Ser Gly Gln His
    450                 455                 460

Val Asn Ile Val Lys Leu Ser Asp Glu Asp Asn Gln Ile Val Ala Val
465                 470                 475                 480

Lys Gly Ser Ser Leu Ser Gly Ile Tyr Tyr Glu Val Asp Ile Glu Thr
                485                 490                 495

Gly Tyr Glu Ile Leu Ser Arg Arg Ile Tyr Arg Thr Glu Tyr Asn Asn
            500                 505                 510

Glu Ile Leu Trp Thr Arg Gly Gly Gly Leu Lys Gly Gly Gln Pro Phe
        515                 520                 525

Asp Phe Glu Ser Leu Asn Ile Pro Val Phe Phe Lys Asp Glu Pro Tyr
    530                 535                 540

Ser Ala Val Thr Gly Ser Pro Leu Ser Phe Ile Asn Asp Asp Ser Ser
545                 550                 555                 560

Leu Leu Tyr Pro Asp Thr Asn Pro Lys Leu Pro Gln Pro Thr Ser Glu
                565                 570                 575

Met Asp Ile Val Asn Tyr Val Lys Gly Ser Gly Ser Phe Gly Asp Arg
            580                 585                 590

Phe Val Thr Leu Met Arg Gly Ala Thr Glu Glu Glu Ala Trp Asn Ile
        595                 600                 605

Ala Ser Tyr His Thr Ala Gly Gly Ser Thr Glu Glu Leu His Glu Ile
```

```
    610                 615                 620

Leu Leu Gly Gln Gly Pro Gln Ser Ser Leu Gly Phe Thr Glu Tyr Thr
625                 630                 635                 640

Ser Asn Val Asn Ser Ala Asp Ala Ala Ser Arg Arg His Phe Leu Val
                645                 650                 655

Val Ile Lys Val His Val Lys Tyr Ile Thr Asn Asn Asn Val Ser Tyr
            660                 665                 670

Val Asn His Trp Ala Ile Pro Asp Glu Ala Pro Val Glu Val Leu Ala
        675                 680                 685

Val Val Asp Arg Arg Phe Asn Phe Pro Glu Pro Ser Thr Pro Pro Asp
    690                 695                 700

Ile Ser Thr Ile Gly Gly Gly Gly Ser Ala Pro Gly Ile Val Ile Pro
705                 710                 715                 720

Pro Lys Ala Leu Phe Thr Gln Gln Gly Gly Ala Tyr Gly Arg Cys Pro
                725                 730                 735

Asn Gly Thr Arg Ala Leu Thr Val Ala Glu Leu Arg Gly Asn Ala Glu
            740                 745                 750

Leu Gln Thr Tyr Leu Arg Gln Ile Thr Pro Gly Trp Ser Ile Tyr Gly
        755                 760                 765

Leu Tyr Asp Gly Thr Tyr Leu Gly Gln Ala Tyr Gly Gly Ile Ile Lys
    770                 775                 780

Asp Ala Pro Pro Gly Ala Gly Phe Ile Tyr Arg Glu Thr Phe Cys Ile
785                 790                 795                 800

Thr Ser Gly Gly Gly Gly Ser Gly Lys Leu Ser Arg Gly Asn Ile Asp
                805                 810                 815

Val Leu Lys Gly Arg Gly Ser Ile Ser Ser Thr Arg Gln Arg Ala Ile
            820                 825                 830

Tyr Pro Tyr Phe Glu Ala Ala Asn Ala Asp Glu Gln Gln Pro Leu Phe
        835                 840                 845

Phe Tyr Ile Lys Lys Asp Arg Phe Asp Asn His Gly Tyr Asp Gln Tyr
    850                 855                 860

Phe Tyr Asp Asn Thr Val Gly Leu Asn Gly Ile Pro Thr Leu Asn Thr
865                 870                 875                 880

Tyr Thr Gly Glu Ile Pro Ser Asp Ser Ser Ser Leu Gly Ser Thr Tyr
                885                 890                 895

Trp Lys Lys Tyr Asn Leu Thr Asn Glu Thr Ser Ile Ile Arg Val Ser
            900                 905                 910

Asn Ser Ala Arg Gly Ala Asn Gly Ile Lys Ile Ala Leu Glu Glu Val
        915                 920                 925

Gln Glu Gly Lys Pro Val Ile Ile Thr Ser Gly Asn Leu Ser Gly Cys
    930                 935                 940

Thr Thr Ile Val Ala Arg Lys Glu Gly Tyr Ile Tyr Lys Val His Thr
945                 950                 955                 960

Gly Thr Thr Lys Ser Leu Ala Gly Phe Thr Ser Thr Thr Gly Val Lys
                965                 970                 975

Lys Ala Val Glu Val Leu Glu Leu Leu Thr Lys Glu Pro Ile Pro Arg
            980                 985                 990

Val Glu Gly Ile Met Ser Asn Asp  Phe Leu Val Asp Tyr  Leu Ser Glu
        995                 1000                1005

Asn Phe  Glu Asp Ser Leu Ile  Thr Tyr Ser Ser Ser  Glu Lys Lys
    1010                1015                1020

Pro Asp  Ser Gln Ile Thr Ile  Ile Arg Asp Asn Val  Ser Val Phe
    1025                1030                1035
```

Pro Tyr Phe Leu Asp Asn Ile Pro Glu His Gly Phe Gly Thr Ser
1040 1045 1050

Ala Thr Val Leu Val Arg Val Asp Gly Asn Val Val Val Arg Ser
1055 1060 1065

Leu Ser Glu Ser Tyr Ser Leu Asn Ala Asp Ala Ser Glu Ile Ser
1070 1075 1080

Val Leu Lys Val Phe Ser Lys Lys Phe
1085 1090

<210> SEQ ID NO 122
<211> LENGTH: 574
<212> TYPE: PRT
<213> ORGANISM: Artificial Sequence
<220> FEATURE:
<223> OTHER INFORMATION: Split secreted or released form of therapeutic Escherichia coli cytotoxic necrotizing factor (CNF) toxin

<400> SEQUENCE: 122

Met Gly Asn Gln Trp Gln Gln Lys Tyr Leu Leu Glu Tyr Asn Glu Leu
1 5 10 15

Val Ser Asn Phe Pro Ser Pro Glu Arg Val Val Ser Asp Tyr Ile Lys
20 25 30

Asn Cys Phe Lys Thr Asp Leu Pro Trp Phe Ser Arg Ile Asp Pro Asp
35 40 45

Asn Ala Tyr Phe Ile Cys Phe Ser Gln Asn Arg Ser Asn Ser Arg Ser
50 55 60

Tyr Thr Gly Trp Asp His Leu Gly Lys Tyr Lys Thr Glu Val Leu Thr
65 70 75 80

Leu Thr Gln Ala Ala Leu Ile Asn Ile Gly Tyr Arg Phe Asp Val Phe
85 90 95

Asp Asp Ala Asn Ser Ser Thr Gly Ile Tyr Lys Thr Lys Ser Ala Asp
100 105 110

Val Phe Asn Glu Glu Asn Glu Glu Lys Met Leu Pro Ser Glu Tyr Leu
115 120 125

His Phe Leu Gln Lys Cys Asp Phe Ala Gly Val Tyr Gly Lys Thr Leu
130 135 140

Ser Asp Tyr Trp Ser Lys Tyr Tyr Asp Lys Phe Lys Leu Leu Leu Lys
145 150 155 160

Asn Tyr Tyr Ile Ser Ser Ala Leu Tyr Leu Tyr Lys Asn Gly Glu Leu
165 170 175

Asp Glu Arg Glu Tyr Asn Phe Ser Met Asn Ala Leu Asn Arg Ser Asp
180 185 190

Asn Ile Ser Leu Leu Phe Phe Asp Ile Tyr Gly Tyr Tyr Ala Ser Asp
195 200 205

Ile Phe Val Ala Lys Asn Asn Asp Lys Val Met Leu Phe Ile Pro Gly
210 215 220

Ala Lys Lys Pro Phe Leu Phe Lys Lys Asn Ile Ala Asp Leu Arg Leu
225 230 235 240

Thr Leu Lys Glu Leu Ile Lys Asp Ser Asp Lys Gln Gln Leu Leu Ser
245 250 255

Gln His Phe Ser Leu Tyr Ser Arg Gln Asp Gly Val Ser Tyr Ala Gly
260 265 270

Val Asn Ser Val Leu His Ala Ile Glu Asn Asp Gly Asn Phe Asn Glu
275 280 285

Ser Tyr Phe Leu Tyr Ser Asn Lys Thr Leu Ser Asn Lys Asp Val Phe

```
    290                 295                 300

Asp Ala Ile Ala Ile Ser Val Lys Lys Arg Ser Phe Ser Asp Gly Asp
305                 310                 315                 320

Ile Val Ile Lys Ser Asn Ser Glu Ala Gln Arg Asp Tyr Ala Leu Thr
                325                 330                 335

Ile Leu Gln Thr Ile Leu Ser Met Thr Pro Ile Phe Asp Ile Val Val
            340                 345                 350

Pro Glu Val Ser Val Pro Leu Gly Leu Gly Ile Ile Thr Ser Ser Met
        355                 360                 365

Gly Ile Ser Phe Asp Gln Leu Ile Asn Gly Asp Thr Tyr Glu Glu Arg
    370                 375                 380

Arg Ser Ala Ile Pro Gly Leu Ala Thr Asn Ala Val Leu Leu Gly Leu
385                 390                 395                 400

Ser Phe Ala Ile Pro Leu Leu Ile Ser Lys Ala Gly Ile Asn Gln Glu
                405                 410                 415

Val Leu Ser Ser Val Ile Asn Asn Glu Gly Arg Thr Leu Asn Glu Thr
            420                 425                 430

Asn Ile Asp Ile Phe Leu Lys Glu Tyr Gly Ile Ala Glu Asp Ser Ile
        435                 440                 445

Ser Ser Thr Asn Leu Leu Asp Val Lys Leu Lys Ser Ser Gly Gln His
    450                 455                 460

Val Asn Ile Val Lys Leu Ser Asp Glu Asp Asn Gln Ile Val Ala Val
465                 470                 475                 480

Lys Gly Ser Ser Leu Ser Gly Ile Tyr Tyr Glu Val Asp Ile Glu Thr
                485                 490                 495

Gly Tyr Glu Ile Leu Ser Arg Arg Ile Tyr Arg Thr Glu Tyr Asn Asn
            500                 505                 510

Glu Ile Leu Trp Thr Arg Gly Gly Gly Leu Lys Gly Gly Gln Pro Phe
        515                 520                 525

Asp Phe Glu Ser Leu Asn Ile Pro Val Phe Phe Gly Gly Ser Gly Ser
    530                 535                 540

Gly Ala Leu Lys Lys Glu Leu Gln Ala Asn Lys Lys Glu Leu Ala Gln
545                 550                 555                 560

Leu Lys Trp Glu Leu Gln Ala Leu Lys Lys Glu Leu Ala Gln
                565                 570


<210> SEQ ID NO 123
<211> LENGTH: 630
<212> TYPE: PRT
<213> ORGANISM: Artificial Sequence
<220> FEATURE:
<223> OTHER INFORMATION: Amino acids of the nucleic acid open reading,
      for the second of a two part regulatory circuit; 1-119 = YebF;
      120-121 "LK" = cleavage signal; 122-151 = leucine zipper;
      152-155 = linker (followed by C-term CNF amino acids 540-1013)

<400> SEQUENCE: 123

Met Ala Lys Lys Arg Gly Ala Phe Leu Gly Leu Leu Leu Val Ser Ala
1               5                   10                  15

Cys Ala Ser Val Phe Ala Ala Asn Asn Glu Thr Ser Lys Ser Val Thr
            20                  25                  30

Phe Pro Lys Cys Glu Asp Leu Asp Ala Ala Gly Ile Ala Ala Ser Val
        35                  40                  45

Lys Arg Asp Tyr Gln Gln Asn Arg Val Ala Arg Trp Ala Asp Asp Gln
    50                  55                  60

Lys Ile Val Gly Gln Ala Asp Pro Val Ala Trp Val Ser Leu Gln Asp
```

-continued

```
65                  70                  75                  80

Ile Gln Gly Lys Asp Asp Lys Trp Ser Val Pro Leu Thr Val Arg Gly
                85                  90                  95

Lys Ser Ala Asp Ile His Tyr Gln Val Ser Val Asp Cys Lys Ala Gly
            100                 105                 110

Met Ala Glu Tyr Gln Arg Arg Leu Lys Glu Gln Leu Glu Lys Lys Leu
        115                 120                 125

Gln Ala Leu Glu Lys Lys Leu Ala Gln Leu Glu Trp Lys Asn Gln Ala
    130                 135                 140

Leu Glu Lys Lys Leu Ala Gln Gly Gly Ser Gly Lys Asp Glu Pro Tyr
145                 150                 155                 160

Ser Ala Val Thr Gly Ser Pro Leu Ser Phe Ile Asn Asp Asp Ser Ser
                165                 170                 175

Leu Leu Tyr Pro Asp Thr Asn Pro Lys Leu Pro Gln Pro Thr Ser Glu
            180                 185                 190

Met Asp Ile Val Asn Tyr Val Lys Gly Ser Gly Ser Phe Gly Asp Arg
        195                 200                 205

Phe Val Thr Leu Met Arg Gly Ala Thr Glu Glu Glu Ala Trp Asn Ile
    210                 215                 220

Ala Ser Tyr His Thr Ala Gly Gly Ser Thr Glu Glu Leu His Glu Ile
225                 230                 235                 240

Leu Leu Gly Gln Gly Pro Gln Ser Ser Leu Gly Phe Thr Glu Tyr Thr
                245                 250                 255

Ser Asn Val Asn Ser Ala Asp Ala Ala Ser Arg Arg His Phe Leu Val
            260                 265                 270

Val Ile Lys Val His Val Lys Tyr Ile Thr Asn Asn Asn Val Ser Tyr
        275                 280                 285

Val Asn His Trp Ala Ile Pro Asp Glu Ala Pro Val Glu Val Leu Ala
    290                 295                 300

Val Val Asp Arg Arg Phe Asn Phe Pro Glu Pro Ser Thr Pro Pro Asp
305                 310                 315                 320

Ile Ser Thr Ile Arg Lys Leu Leu Ser Leu Arg Tyr Phe Lys Glu Ser
                325                 330                 335

Ile Glu Ser Thr Ser Lys Ser Asn Phe Gln Lys Leu Ser Arg Gly Asn
            340                 345                 350

Ile Asp Val Leu Lys Gly Arg Gly Ser Ile Ser Ser Thr Arg Gln Arg
        355                 360                 365

Ala Ile Tyr Pro Tyr Phe Glu Ala Ala Asn Ala Asp Glu Gln Gln Pro
    370                 375                 380

Leu Phe Phe Tyr Ile Lys Lys Asp Arg Phe Asp Asn His Gly Tyr Asp
385                 390                 395                 400

Gln Tyr Phe Tyr Asp Asn Thr Val Gly Leu Asn Gly Ile Pro Thr Leu
                405                 410                 415

Asn Thr Tyr Thr Gly Glu Ile Pro Ser Asp Ser Ser Ser Leu Gly Ser
            420                 425                 430

Thr Tyr Trp Lys Lys Tyr Asn Leu Thr Asn Glu Thr Ser Ile Ile Arg
        435                 440                 445

Val Ser Asn Ser Ala Arg Gly Ala Asn Gly Ile Lys Ile Ala Leu Glu
    450                 455                 460

Glu Val Gln Glu Gly Lys Pro Val Ile Ile Thr Ser Gly Asn Leu Ser
465                 470                 475                 480

Gly Cys Thr Thr Ile Val Ala Arg Lys Glu Gly Tyr Ile Tyr Lys Val
                485                 490                 495
```

His Thr Gly Thr Thr Lys Ser Leu Ala Gly Phe Thr Ser Thr Thr Gly
500 505 510

Val Lys Lys Ala Val Glu Val Leu Glu Leu Leu Thr Lys Glu Pro Ile
515 520 525

Pro Arg Val Glu Gly Ile Met Ser Asn Asp Phe Leu Val Asp Tyr Leu
530 535 540

Ser Glu Asn Phe Glu Asp Ser Leu Ile Thr Tyr Ser Ser Ser Glu Lys
545 550 555 560

Lys Pro Asp Ser Gln Ile Thr Ile Ile Arg Asp Asn Val Ser Val Phe
565 570 575

Pro Tyr Phe Leu Asp Asn Ile Pro Glu His Gly Phe Gly Thr Ser Ala
580 585 590

Thr Val Leu Val Arg Val Asp Gly Asn Val Val Val Arg Ser Leu Ser
595 600 605

Glu Ser Tyr Ser Leu Asn Ala Asp Ala Ser Glu Ile Ser Val Leu Lys
610 615 620

Val Phe Ser Lys Lys Phe
625 630

<210> SEQ ID NO 124
<211> LENGTH: 510
<212> TYPE: PRT
<213> ORGANISM: Artificial Sequence
<220> FEATURE:
<223> OTHER INFORMATION: The second component of a released and/or split therapeutic Escherichia coli CNF

<400> SEQUENCE: 124

Met Glu Gln Leu Glu Lys Lys Leu Gln Ala Leu Glu Lys Lys Leu Ala
1 5 10 15

Gln Leu Glu Trp Lys Asn Gln Ala Leu Glu Lys Lys Leu Ala Gln Gly
20 25 30

Gly Ser Gly Lys Asp Glu Pro Tyr Ser Ala Val Thr Gly Ser Pro Leu
35 40 45

Ser Phe Ile Asn Asp Asp Ser Ser Leu Leu Tyr Pro Asp Thr Asn Pro
50 55 60

Lys Leu Pro Gln Pro Thr Ser Glu Met Asp Ile Val Asn Tyr Val Lys
65 70 75 80

Gly Ser Gly Ser Phe Gly Asp Arg Phe Val Thr Leu Met Arg Gly Ala
85 90 95

Thr Glu Glu Glu Ala Trp Asn Ile Ala Ser Tyr His Thr Ala Gly Gly
100 105 110

Ser Thr Glu Glu Leu His Glu Ile Leu Leu Gly Gln Gly Pro Gln Ser
115 120 125

Ser Leu Gly Phe Thr Glu Tyr Thr Ser Asn Val Asn Ser Ala Asp Ala
130 135 140

Ala Ser Arg Arg His Phe Leu Val Val Ile Lys Val His Val Lys Tyr
145 150 155 160

Ile Thr Asn Asn Asn Val Ser Tyr Val Asn His Trp Ala Ile Pro Asp
165 170 175

Glu Ala Pro Val Glu Val Leu Ala Val Val Asp Arg Arg Phe Asn Phe
180 185 190

Pro Glu Pro Ser Thr Pro Pro Asp Ile Ser Thr Ile Arg Lys Leu Leu
195 200 205

Ser Leu Arg Tyr Phe Lys Glu Ser Ile Glu Ser Thr Ser Lys Ser Asn

```
    210                 215                 220

Phe Gln Lys Leu Ser Arg Gly Asn Ile Asp Val Leu Lys Gly Arg Gly
225                 230                 235                 240

Ser Ile Ser Ser Thr Arg Gln Arg Ala Ile Tyr Pro Tyr Phe Glu Ala
                245                 250                 255

Ala Asn Ala Asp Glu Gln Gln Pro Leu Phe Phe Tyr Ile Lys Lys Asp
            260                 265                 270

Arg Phe Asp Asn His Gly Tyr Asp Gln Tyr Phe Tyr Asp Asn Thr Val
        275                 280                 285

Gly Leu Asn Gly Ile Pro Thr Leu Asn Thr Tyr Thr Gly Glu Ile Pro
    290                 295                 300

Ser Asp Ser Ser Ser Leu Gly Ser Thr Tyr Trp Lys Lys Tyr Asn Leu
305                 310                 315                 320

Thr Asn Glu Thr Ser Ile Ile Arg Val Ser Asn Ser Ala Arg Gly Ala
                325                 330                 335

Asn Gly Ile Lys Ile Ala Leu Glu Glu Val Gln Glu Gly Lys Pro Val
            340                 345                 350

Ile Ile Thr Ser Gly Asn Leu Ser Gly Cys Thr Thr Ile Val Ala Arg
        355                 360                 365

Lys Glu Gly Tyr Ile Tyr Lys Val His Thr Gly Thr Thr Lys Ser Leu
    370                 375                 380

Ala Gly Phe Thr Ser Thr Thr Gly Val Lys Lys Ala Val Glu Val Leu
385                 390                 395                 400

Glu Leu Leu Thr Lys Glu Pro Ile Pro Arg Val Glu Gly Ile Met Ser
                405                 410                 415

Asn Asp Phe Leu Val Asp Tyr Leu Ser Glu Asn Phe Glu Asp Ser Leu
            420                 425                 430

Ile Thr Tyr Ser Ser Ser Glu Lys Lys Pro Asp Ser Gln Ile Thr Ile
        435                 440                 445

Ile Arg Asp Asn Val Ser Val Phe Pro Tyr Phe Leu Asp Asn Ile Pro
    450                 455                 460

Glu His Gly Phe Gly Thr Ser Ala Thr Val Leu Val Arg Val Asp Gly
465                 470                 475                 480

Asn Val Val Val Arg Ser Leu Ser Glu Ser Tyr Ser Leu Asn Ala Asp
                485                 490                 495

Ala Ser Glu Ile Ser Val Leu Lys Val Phe Ser Lys Lys Phe
            500                 505                 510


<210> SEQ ID NO 125
<211> LENGTH: 962
<212> TYPE: PRT
<213> ORGANISM: Artificial Sequence
<220> FEATURE:
<223> OTHER INFORMATION: A released (no secretion signal) therapeutic
      Escherichia coli cytotoxic necrotizing factor (CNF) toxin

<400> SEQUENCE: 125

Met Cys Phe Ser Gln Asn Arg Ser Asn Ser Arg Ser Tyr Thr Gly Trp
1               5                   10                  15

Asp His Leu Gly Lys Tyr Lys Thr Glu Val Leu Thr Leu Thr Gln Ala
            20                  25                  30

Ala Leu Ile Asn Ile Gly Tyr Arg Phe Asp Val Phe Asp Asp Ala Asn
        35                  40                  45

Ser Ser Thr Gly Ile Tyr Lys Thr Lys Ser Ala Asp Val Phe Asn Glu
    50                  55                  60
```

```
Glu Asn Glu Glu Lys Met Leu Pro Ser Glu Tyr Leu His Phe Leu Gln
65                  70                  75                  80

Lys Cys Asp Phe Ala Gly Val Tyr Gly Lys Thr Leu Ser Asp Tyr Trp
                85                  90                  95

Ser Lys Tyr Tyr Asp Lys Phe Lys Leu Leu Leu Lys Asn Tyr Tyr Ile
            100                 105                 110

Ser Ser Ala Leu Tyr Leu Tyr Lys Asn Gly Glu Leu Asp Glu Arg Glu
        115                 120                 125

Tyr Asn Phe Ser Met Asn Ala Leu Asn Arg Ser Asp Asn Ile Ser Leu
    130                 135                 140

Leu Phe Phe Asp Ile Tyr Gly Tyr Tyr Ala Ser Asp Ile Phe Val Ala
145                 150                 155                 160

Lys Asn Asn Asp Lys Val Met Leu Phe Ile Pro Gly Ala Lys Lys Pro
                165                 170                 175

Phe Leu Phe Lys Lys Asn Ile Ala Asp Leu Arg Leu Thr Leu Lys Glu
            180                 185                 190

Leu Ile Lys Asp Ser Asp Lys Gln Gln Leu Leu Ser Gln His Phe Ser
        195                 200                 205

Leu Tyr Ser Arg Gln Asp Gly Val Ser Tyr Ala Gly Val Asn Ser Val
    210                 215                 220

Leu His Ala Ile Glu Asn Asp Gly Asn Phe Asn Glu Ser Tyr Phe Leu
225                 230                 235                 240

Tyr Ser Asn Lys Thr Leu Ser Asn Lys Asp Val Phe Asp Ala Ile Ala
                245                 250                 255

Ile Ser Val Lys Lys Arg Ser Phe Ser Asp Gly Asp Ile Val Ile Lys
            260                 265                 270

Ser Asn Ser Glu Ala Gln Arg Asp Tyr Ala Leu Thr Ile Leu Gln Thr
        275                 280                 285

Ile Leu Ser Met Thr Pro Ile Phe Asp Ile Val Val Pro Glu Val Ser
    290                 295                 300

Val Pro Leu Gly Leu Gly Ile Ile Thr Ser Ser Met Gly Ile Ser Phe
305                 310                 315                 320

Asp Gln Leu Ile Asn Gly Asp Thr Tyr Glu Glu Arg Arg Ser Ala Ile
                325                 330                 335

Pro Gly Leu Ala Thr Asn Ala Val Leu Leu Gly Leu Ser Phe Ala Ile
            340                 345                 350

Pro Leu Leu Ile Ser Lys Ala Gly Ile Asn Gln Glu Val Leu Ser Ser
        355                 360                 365

Val Ile Asn Asn Glu Gly Arg Thr Leu Asn Glu Thr Asn Ile Asp Ile
    370                 375                 380

Phe Leu Lys Glu Tyr Gly Ile Ala Glu Asp Ser Ile Ser Ser Thr Asn
385                 390                 395                 400

Leu Leu Asp Val Lys Leu Lys Ser Ser Gly Gln His Val Asn Ile Val
                405                 410                 415

Lys Leu Ser Asp Glu Asp Asn Gln Ile Val Ala Val Lys Gly Ser Ser
            420                 425                 430

Leu Ser Gly Ile Tyr Tyr Glu Val Asp Ile Glu Thr Gly Tyr Glu Ile
        435                 440                 445

Leu Ser Arg Arg Ile Tyr Arg Thr Glu Tyr Asn Asn Glu Ile Leu Trp
    450                 455                 460

Thr Arg Gly Gly Gly Leu Lys Gly Gly Gln Pro Phe Asp Phe Glu Ser
465                 470                 475                 480

Leu Asn Ile Pro Val Phe Phe Lys Asp Glu Pro Tyr Ser Ala Val Thr
```

```
                485                 490                 495

Gly Ser Pro Leu Ser Phe Ile Asn Asp Asp Ser Ser Leu Leu Tyr Pro
            500                 505                 510

Asp Thr Asn Pro Lys Leu Pro Gln Pro Thr Ser Glu Met Asp Ile Val
        515                 520                 525

Asn Tyr Val Lys Gly Ser Gly Ser Phe Gly Asp Arg Phe Val Thr Leu
    530                 535                 540

Met Arg Gly Ala Thr Glu Glu Glu Ala Trp Asn Ile Ala Ser Tyr His
545                 550                 555                 560

Thr Ala Gly Gly Ser Thr Glu Glu Leu His Glu Ile Leu Leu Gly Gln
                565                 570                 575

Gly Pro Gln Ser Ser Leu Gly Phe Thr Glu Tyr Thr Ser Asn Val Asn
            580                 585                 590

Ser Ala Asp Ala Ala Ser Arg Arg His Phe Leu Val Val Ile Lys Val
        595                 600                 605

His Val Lys Tyr Ile Thr Asn Asn Asn Val Ser Tyr Val Asn His Trp
    610                 615                 620

Ala Ile Pro Asp Glu Ala Pro Val Glu Val Leu Ala Val Val Asp Arg
625                 630                 635                 640

Arg Phe Asn Phe Pro Glu Pro Ser Thr Pro Pro Asp Ile Ser Thr Ile
                645                 650                 655

Arg Lys Leu Leu Ser Leu Arg Tyr Phe Lys Glu Ser Ile Glu Ser Thr
            660                 665                 670

Ser Lys Ser Asn Phe Gln Lys Leu Ser Arg Gly Asn Ile Asp Val Leu
        675                 680                 685

Lys Gly Arg Gly Ser Ile Ser Ser Thr Arg Gln Arg Ala Ile Tyr Pro
    690                 695                 700

Tyr Phe Glu Ala Ala Asn Ala Asp Glu Gln Gln Pro Leu Phe Phe Tyr
705                 710                 715                 720

Ile Lys Lys Asp Arg Phe Asp Asn His Gly Tyr Asp Gln Tyr Phe Tyr
                725                 730                 735

Asp Asn Thr Val Gly Leu Asn Gly Ile Pro Thr Leu Asn Thr Tyr Thr
            740                 745                 750

Gly Glu Ile Pro Ser Asp Ser Ser Ser Leu Gly Ser Thr Tyr Trp Lys
        755                 760                 765

Lys Tyr Asn Leu Thr Asn Glu Thr Ser Ile Ile Arg Val Ser Asn Ser
    770                 775                 780

Ala Arg Gly Ala Asn Gly Ile Lys Ile Ala Leu Glu Glu Val Gln Glu
785                 790                 795                 800

Gly Lys Pro Val Ile Ile Thr Ser Gly Asn Leu Ser Gly Cys Thr Thr
                805                 810                 815

Ile Val Ala Arg Lys Glu Gly Tyr Ile Tyr Lys Val His Thr Gly Thr
            820                 825                 830

Thr Lys Ser Leu Ala Gly Phe Thr Ser Thr Thr Gly Val Lys Lys Ala
        835                 840                 845

Val Glu Val Leu Glu Leu Leu Thr Lys Glu Pro Ile Pro Arg Val Glu
    850                 855                 860

Gly Ile Met Ser Asn Asp Phe Leu Val Asp Tyr Leu Ser Glu Asn Phe
865                 870                 875                 880

Glu Asp Ser Leu Ile Thr Tyr Ser Ser Ser Glu Lys Lys Pro Asp Ser
                885                 890                 895

Gln Ile Thr Ile Ile Arg Asp Asn Val Ser Val Phe Pro Tyr Phe Leu
            900                 905                 910
```

Asp Asn Ile Pro Glu His Gly Phe Gly Thr Ser Ala Thr Val Leu Val
915 920 925

Arg Val Asp Gly Asn Val Val Val Arg Ser Leu Ser Glu Ser Tyr Ser
930 935 940

Leu Asn Ala Asp Ala Ser Glu Ile Ser Val Leu Lys Val Phe Ser Lys
945 950 955 960

Lys Phe

<210> SEQ ID NO 126
<211> LENGTH: 153
<212> TYPE: PRT
<213> ORGANISM: Artificial Sequence
<220> FEATURE:
<223> OTHER INFORMATION: TAT-apoptin with an OmpA “8L” signal sequence

<400> SEQUENCE: 126

Ala Lys Lys Thr Ala Leu Ala Leu Leu Leu Leu Leu Leu Ala Leu Thr
1 5 10 15

Ser Val Ala Gln Ala Tyr Gly Arg Lys Lys Arg Arg Gln Arg Arg Arg
20 25 30

Met Asn Ala Leu Gln Glu Asp Thr Pro Pro Gly Pro Ser Thr Val Phe
35 40 45

Arg Pro Pro Thr Ser Ser Arg Pro Leu Glu Thr Pro His Cys Arg Glu
50 55 60

Ile Arg Ile Gly Ile Ala Gly Ile Thr Ile Thr Leu Ser Leu Cys Gly
65 70 75 80

Cys Ala Asn Ala Arg Ala Pro Thr Leu Arg Ser Ala Thr Ala Asp Asn
85 90 95

Ser Glu Asn Thr Gly Phe Lys Asn Val Pro Asp Leu Arg Thr Asp Gln
100 105 110

Pro Lys Pro Pro Ser Lys Lys Arg Ser Cys Asp Pro Ser Glu Tyr Arg
115 120 125

Val Ser Glu Leu Lys Glu Ser Leu Ile Thr Thr Thr Pro Ser Arg Pro
130 135 140

Arg Thr Ala Arg Arg Cys Ile Arg Leu
145 150

<210> SEQ ID NO 127
<211> LENGTH: 511
<212> TYPE: PRT
<213> ORGANISM: Artificial Sequence
<220> FEATURE:
<223> OTHER INFORMATION: Human hyaluronidase amino acid sequence
(BC026163)

<400> SEQUENCE: 127

Met Gly Val Leu Lys Phe Lys His Ile Phe Phe Arg Ser Phe Val Lys
1 5 10 15

Ser Ser Gly Val Ser Gln Ile Val Phe Thr Phe Leu Leu Ile Pro Cys
20 25 30

Cys Leu Thr Leu Asn Phe Arg Ala Pro Pro Val Ile Pro Asn Val Pro
35 40 45

Phe Leu Trp Ala Trp Asn Ala Pro Ser Glu Phe Cys Leu Gly Lys Phe
50 55 60

Asp Glu Pro Leu Asp Met Ser Leu Phe Ser Phe Ile Gly Ser Pro Arg
65 70 75 80

Ile Asn Ala Thr Gly Gln Gly Val Thr Ile Phe Tyr Val Asp Arg Leu

```
                85                  90                  95

Gly Tyr Tyr Pro Tyr Ile Asp Ser Ile Thr Gly Val Thr Val Asn Gly
            100                 105                 110

Gly Ile Pro Gln Lys Ile Ser Leu Gln Asp His Leu Asp Lys Ala Lys
        115                 120                 125

Lys Asp Ile Thr Phe Tyr Met Pro Val Asp Asn Leu Gly Met Ala Val
    130                 135                 140

Ile Asp Trp Glu Glu Trp Arg Pro Thr Trp Ala Arg Asn Trp Lys Pro
145                 150                 155                 160

Lys Asp Val Tyr Lys Asn Arg Ser Ile Glu Leu Val Gln Gln Gln Asn
                165                 170                 175

Val Gln Leu Ser Leu Thr Glu Ala Thr Glu Lys Ala Lys Gln Glu Phe
            180                 185                 190

Glu Lys Ala Gly Lys Asp Phe Leu Val Glu Thr Ile Lys Leu Gly Lys
        195                 200                 205

Leu Leu Arg Pro Asn His Leu Trp Gly Tyr Tyr Leu Phe Pro Asp Cys
    210                 215                 220

Tyr Asn His His Tyr Lys Lys Pro Gly Tyr Asn Gly Ser Cys Phe Asn
225                 230                 235                 240

Val Glu Ile Lys Arg Asn Asp Asp Leu Ser Trp Leu Trp Asn Glu Ser
                245                 250                 255

Thr Ala Leu Tyr Pro Ser Ile Tyr Leu Asn Thr Gln Gln Ser Pro Val
            260                 265                 270

Ala Ala Thr Leu Tyr Val Arg Asn Arg Val Arg Glu Ala Ile Arg Val
        275                 280                 285

Ser Lys Ile Pro Asp Ala Lys Ser Pro Leu Pro Val Phe Ala Tyr Thr
    290                 295                 300

Arg Ile Val Phe Thr Asp Gln Val Leu Lys Phe Leu Ser Gln Asp Glu
305                 310                 315                 320

Leu Val Tyr Thr Phe Gly Glu Thr Val Ala Leu Gly Ala Ser Gly Ile
                325                 330                 335

Val Ile Trp Gly Thr Leu Ser Ile Met Arg Ser Met Lys Ser Cys Leu
            340                 345                 350

Leu Leu Asp Asn Tyr Met Glu Thr Ile Leu Asn Pro Tyr Ile Ile Asn
        355                 360                 365

Val Thr Leu Ala Ala Lys Met Cys Ser Gln Val Leu Cys Gln Glu Gln
    370                 375                 380

Gly Val Cys Ile Arg Lys Asn Trp Asn Ser Ser Asp Tyr Leu His Leu
385                 390                 395                 400

Asn Pro Asp Asn Phe Ala Ile Gln Leu Glu Lys Gly Gly Lys Phe Thr
                405                 410                 415

Val Arg Gly Lys Pro Thr Leu Glu Asp Leu Glu Gln Phe Ser Glu Lys
            420                 425                 430

Phe Tyr Cys Ser Cys Tyr Ser Thr Leu Ser Cys Lys Glu Lys Ala Asp
        435                 440                 445

Val Lys Asp Thr Asp Ala Val Asp Val Cys Ile Ala Asp Gly Val Cys
    450                 455                 460

Ile Asp Ala Phe Leu Lys Pro Pro Met Glu Thr Glu Glu Pro Gln Ile
465                 470                 475                 480

Phe Tyr Asn Ala Ser Pro Ser Thr Leu Ser Ala Thr Met Phe Ile Trp
                485                 490                 495

Arg Leu Glu Val Trp Asp Gln Gly Ile Ser Arg Ile Gly Phe Phe
            500                 505                 510
```

<210> SEQ ID NO 128
<211> LENGTH: 106
<212> TYPE: DNA
<213> ORGANISM: Artificial Sequence
<220> FEATURE:
<223> OTHER INFORMATION: Salmonella typhimurium 14028 sequence, splenic promoter (upstream from STM14_1795)

<400> SEQUENCE: 128
tacatgccga aaccaatcac tcacggaagc cttttgataa cagcgatata gtcatttcac 60
cggccccgca gtggggttga atgaaaacca aatcgagggt atcaaa 106

<210> SEQ ID NO 129
<211> LENGTH: 813
<212> TYPE: DNA
<213> ORGANISM: Artificial Sequence
<220> FEATURE:
<223> OTHER INFORMATION: CLDT, cldtB and stop codon

<400> SEQUENCE: 129
atggtcaaaa aacctgtttt tttccttctg accatgatca tctgcagcta tatttctttt 60
gcctgcgcta atatcagtga ctacaaagtt atgacctgga atcttcaggg ctcttcagca 120
tctacagaaa gtaaatggaa tgtcaatgtc agacagcttt taagcggtac tgccggtgtg 180
gatattctta tggtacagga ggccggtgct gttcccacct cagcggttcc taccggacga 240
catattcagc cttttggagt gggtattccc attgatgaat acacctggaa tctcggaacc 300
accagccgtc aggatataag atatatctac tactcggcta ttgatgttgg agcacgccgt 360
gttaatctgg caatagtttc cagacaaaga gcggataatg tttatgtctt gcgtccgaca 420
actgtcgcat ctcgccccgt cattggcatc ggactgggta atgatgtttt tctgacagcg 480
cacgcactgg ctagtggagg tccggatgct gcagctattg tcagggttac cattaatttt 540
tttagacaac ctcagatgcg gcatttatcc tggtttcttg ccggggattt taatcgcagc 600
ccagacagac ttgaaaatga cctgatgact gagcatctgg aacgagttgt agccgtactc 660
gcacctacag aacccacgca aattagcggt ggtattttag attatggggt cattgtcgat 720
cgagcacctt attcacaaag ggtcgaagca ttacgtaatc cacaactcgc ttctgatcat 780
tatcccgtag cctttttggc acgaagctgt taa 813

<210> SEQ ID NO 130
<211> LENGTH: 129
<212> TYPE: DNA
<213> ORGANISM: Artificial Sequence
<220> FEATURE:
<223> OTHER INFORMATION: Double terminator Part:BBa_B0015

<400> SEQUENCE: 130
ccaggcatca aataaaacga aaggctcagt cgaaagactg ggcctttcgt tttatctgtt 60
gtttgtcggt gaacgctctc tactagagtc acactggctc accttcgggt gggcctttct 120
gcgtttata 129

<210> SEQ ID NO 131
<211> LENGTH: 1159
<212> TYPE: DNA
<213> ORGANISM: Artificial Sequence
<220> FEATURE:
<223> OTHER INFORMATION: polycistronic CLDT, pltB, pltA

<400> SEQUENCE: 131

```
atgtatataa ataagtttgt gcctgtttat acattattaa ttctcattta ttcttttaat     60

gccagcgctg agtggacagg agataatacg aacgcctatt actcagacga agttatcagt    120

gaattacatg ttggtcagat agatactagt ccttattttt gcataaaaac ggttaaagct    180

aacggtagtg gtacaccagt tgttgcatgt gcggtatcaa agcagagcat atgggcgccc    240

tcctttaaag aacttcttga tcaggcaaga tatttttaca gtacagggca atccgtaagg    300

attcatgttc aaaaaaatat ctggacctat ccgctttttg ttaatacctt ttcagcaaat    360

gctcttgtgg gactatcatc gtgcagtgcg acacaatgct ttggacccaa gtaagagggg    420

agaagaaata atgaaaaagt taatattctt aaccttatct atagttagct ttaataacta    480

tgctgtagat tttgtgtatc gtgtggactc aaccccgccg gacgttattt ttcgcgatgg    540

gttttcacta cttgggtata accgtaactt tcagcaattt attagtggaa ggtcatgtag    600

tggtggaagt agtgacagtc gctatattgc aacaacctca agtgttaatc aaacatatgc    660

tatagccaga gcgtactatt ctcgctcaac attcaaaggt aatttataca gatatcagat    720

tcgtgcagat aataatttct acagcttgct cccatccatc acctatctgg aaacgcaagg    780

tggtcacttt aatgcttatg aaaaaacgat gatgcgattg caaagagagt atgtttccac    840

attatctatt ttacccgaga atattcaaaa ggccgtggcg ctagtttatg atagcgcaac    900

cggtctggta aaggatggtg taagcacaat gaatgccagt tatttaggtt taagcactac    960

gtctaatcct ggtgtgatac cttttcttcc ggaaccgcag acgtataccc aacaacgaat   1020

tgatgcattc ggcccattaa taagttcatg cttttcaata ggtagcgtat gtcagtcaca   1080

tcgagggcaa agagctgacg tatacaacat gtctttttat gatgcaagac ctgtaataga   1140

acttatactt tctaaataa                                                1159
```

<210> SEQ ID NO 132
<211> LENGTH: 37
<212> TYPE: PRT
<213> ORGANISM: Artificial Sequence
<220> FEATURE:
<223> OTHER INFORMATION: Salmonella ST64T phage the cell division inhibitor kil

<400> SEQUENCE: 132

```
Met Asp Lys Ser Leu Met Ala Ile Gln Ser Lys Phe Ala Ile Ala Val
1               5                   10                  15

Tyr Leu Gly Asp Lys Ile Met Tyr Arg Glu Ala Val Glu Ala Phe Arg
            20                  25                  30

Glu Trp Arg Leu Lys
        35
```

<210> SEQ ID NO 133
<211> LENGTH: 1164
<212> TYPE: DNA
<213> ORGANISM: Artificial Sequence
<220> FEATURE:
<223> OTHER INFORMATION: lac repressor

<400> SEQUENCE: 133

```
atgaaaccag taacgctgta cgatgtcgca gagtatgccg gtgtctctta tcagaccgtt     60

tcccgcgtgg tgaaccaggc cagccacgtt tctgcgaaaa cgcgggaaaa agtggaagcg    120

gcgatggcgg agctgaatta cattcccaac cgcgtggcac aacaactggc gggcaaacag    180

tcgttgctga ttggcgttgc cacctccagt ctggccctgc acgcgccgtc gcaaattgtc    240
```

gcggcgatta aatctcgcgc cgatcaactg ggtgccagcg tggtggtgtc gatggtagaa 300
cgaagcggcg tcgaagcctg taaagcggcg gttcacaatc ttctcgcgca gcgcgtcagt 360
gggctgatca ttaactatcc gctggatgac caggatgcca ttgctgtgga agctgcctgc 420
actaatgttc cggcgttatt tcttgatgtc tctgaccaga cacccatcaa cagtattatt 480
ttctcccatg aagacggtac gcgactgggc gtggagcatc tggtcgcatt gggtcaccag 540
caaatcgcgc tgttagcggg cccattaagt tctgtctcgg cgcgtctgcg tctggctggc 600
tggcataaat atctcactcg caatcaaatt cagccgatag cggaacggga aggcgactgg 660
agtgccatgt ccggttttca acaaaccatg caaatgctga atgagggcat cgttcccact 720
gcgatgctgg ttgccaacga tcagatggcg ctgggcgcaa tgcgcgccat taccgagtcc 780
gggctgcgcg ttggtgcgga catctcggta gtgggatacg acgataccga agacagctca 840
tgttatatcc cgccgttaac caccatcaaa caggattttc gcctgctggg gcaaaccagc 900
gtggaccgct tgctgcaact ctctcagggc caggcggtga agggcaatca actgttgccc 960
gtctcactgg tgaaaagaaa aaccaccctg gcgcccaata cgcaaaccgc ctctccccgc 1020
gcgttggccg attcattaat gcaactggca cgacaggttt cccgactgga aagcgggcag 1080
gcggcgaaca aaaacgaaga aaacaccaac gaagtgccga cctttatgct gaacgcgggc 1140
caggcgaact acctgtctca ataa 1164

<210> SEQ ID NO 134
<211> LENGTH: 520
<212> TYPE: DNA
<213> ORGANISM: Artificial Sequence
<220> FEATURE:
<223> OTHER INFORMATION: sulA gene in the reverse complement

<400> SEQUENCE: 134
ctaattttac ttaatgatac aaattagagt gaatttttag cccggaatgc tgtctcctgg 60
gtaaagcgtg cgcacgtaca gggcgcatga taaaccctac cgcattacct accttcgctg 120
cttcaaccag gctggcatgt tcttcttctg tcagttcttc agtcatccaa ccaattacca 180
cgctgtaatt tcctgtacgc aaagcgcgga tcatcgactc cagcgtatga cgaggcgcaa 240
gctggctaat ttgcatcact ttcgttaatg gcaaacctga agactgtacc cattcacggc 300
tgagcttttg ctgcggcgtg agccagagct gccatcgtga ttgttggcct aactgacgga 360
gtaaaggcaa aagcaggagt tgcgccatca tgggctggtc ttcgtggtag acaacttcac 420
tgaccagtcc tgccgcggca ttttccgtag cggtgcgcgc agcgttgtgg gtagtggtag 480
gaaatgacga agaacgattt gcataacctg aagtgtacat 520

<210> SEQ ID NO 135
<211> LENGTH: 49
<212> TYPE: DNA
<213> ORGANISM: Artificial Sequence
<220> FEATURE:
<223> OTHER INFORMATION: 5'UT of Arrach and McClelland PRL1-F1 in the reverse complement

<400> SEQUENCE: 135
gggccaacct cctttggtac cgagctcggt taggtgcttt aactacggt 49

<210> SEQ ID NO 136
<211> LENGTH: 62
<212> TYPE: DNA
<213> ORGANISM: Artificial Sequence
<220> FEATURE:

<223> OTHER INFORMATION: 5'UT of Arrach and McClelland PRL1-F1

<400> SEQUENCE: 136
tcgagagatc tccatcgaat tcgtgggtcg accccgggag gcctaaagag gagaaattaa 60
ct 62

<210> SEQ ID NO 137
<211> LENGTH: 498
<212> TYPE: PRT
<213> ORGANISM: Artificial Sequence
<220> FEATURE:
<223> OTHER INFORMATION: Geobacillus carboxylesterase Est55 and stop codon

<400> SEQUENCE: 137

Met Glu Arg Thr Val Val Glu Thr Arg Tyr Gly Arg Leu Arg Gly Glu
1 5 10 15

Met Asn Glu Gly Val Phe Val Trp Lys Gly Ile Pro Tyr Ala Lys Ala
20 25 30

Pro Val Gly Glu Arg Arg Phe Leu Pro Pro Glu Pro Pro Asp Ala Trp
35 40 45

Asp Gly Val Arg Glu Ala Thr Ser Phe Gly Pro Val Val Met Gln Pro
50 55 60

Ser Asp Pro Ile Phe Ser Gly Leu Leu Gly Arg Met Ser Glu Ala Pro
65 70 75 80

Ser Glu Asp Gly Leu Tyr Leu Asn Ile Trp Ser Pro Ala Ala Asp Gly
85 90 95

Lys Lys Arg Pro Val Leu Phe Trp Ile His Gly Gly Ala Phe Leu Phe
100 105 110

Gly Ser Gly Ser Ser Pro Trp Tyr Asp Gly Thr Ala Phe Ala Lys His
115 120 125

Gly Asp Val Val Val Val Thr Ile Asn Tyr Arg Met Asn Val Phe Gly
130 135 140

Phe Leu His Leu Gly Asp Ser Phe Gly Glu Ala Tyr Ala Gln Ala Gly
145 150 155 160

Asn Leu Gly Ile Leu Asp Gln Val Ala Ala Leu Arg Trp Val Lys Glu
165 170 175

Asn Ile Ala Ala Phe Gly Gly Asp Pro Asp Asn Ile Thr Ile Phe Gly
180 185 190

Glu Ser Ala Gly Ala Ala Ser Val Gly Val Leu Leu Ser Leu Pro Glu
195 200 205

Ala Ser Gly Leu Phe Arg Arg Ala Met Leu Gln Ser Gly Ser Gly Ser
210 215 220

Leu Leu Leu Arg Ser Pro Glu Thr Ala Met Ala Met Thr Glu Arg Ile
225 230 235 240

Leu Asp Lys Ala Gly Ile Arg Pro Gly Asp Arg Glu Arg Leu Leu Ser
245 250 255

Ile Pro Ala Glu Glu Leu Leu Arg Ala Ala Leu Ser Leu Gly Pro Gly
260 265 270

Val Met Tyr Gly Pro Val Val Asp Gly Arg Val Leu Arg Arg His Pro
275 280 285

Ile Glu Ala Leu Arg Tyr Gly Ala Ala Ser Gly Ile Pro Ile Leu Ile
290 295 300

Gly Val Thr Lys Asp Glu Tyr Asn Leu Phe Thr Leu Thr Asp Pro Ser
305 310 315 320

```
Trp Thr Lys Leu Gly Glu Lys Glu Leu Leu Asp Arg Ile Asn Arg Glu
                325                 330                 335

Val Gly Pro Val Pro Glu Glu Ala Ile Arg Tyr Tyr Lys Glu Thr Ala
            340                 345                 350

Glu Pro Ser Ala Pro Thr Trp Gln Thr Trp Leu Arg Ile Met Thr Tyr
        355                 360                 365

Arg Val Phe Val Glu Gly Met Leu Arg Thr Ala Asp Ala Gln Ala Ala
    370                 375                 380

Gln Gly Ala Asp Val Tyr Met Tyr Arg Phe Asp Tyr Glu Thr Pro Val
385                 390                 395                 400

Phe Gly Gly Gln Leu Lys Ala Cys His Ala Leu Glu Leu Pro Phe Val
                405                 410                 415

Phe His Asn Leu His Gln Pro Gly Val Ala Asn Phe Val Gly Asn Arg
            420                 425                 430

Pro Glu Arg Glu Ala Ile Ala Asn Glu Met His Tyr Ala Trp Leu Ser
        435                 440                 445

Phe Ala Arg Thr Gly Asp Pro Asn Gly Ala His Leu Pro Glu Ala Trp
    450                 455                 460

Pro Ala Tyr Thr Asn Glu Arg Lys Ala Ala Phe Val Phe Ser Ala Ala
465                 470                 475                 480

Ser His Val Glu Asp Asp Pro Phe Gly Arg Glu Arg Ala Ala Trp Gln
                485                 490                 495

Gly Arg


<210> SEQ ID NO 138
<211> LENGTH: 51
<212> TYPE: DNA
<213> ORGANISM: Artificial Sequence
<220> FEATURE:
<223> OTHER INFORMATION: taataagagg tgggattacg gctagctcag tcctaggtat
      tatgctagct a

<400> SEQUENCE: 138

taataagagg tgggattacg gctagctcag tcctaggtat tatgctagct a              51


<210> SEQ ID NO 139
<211> LENGTH: 27
<212> TYPE: DNA
<213> ORGANISM: Artificial Sequence
<220> FEATURE:
<223> OTHER INFORMATION: lysis protein E from bacteriophage phi-X174

<400> SEQUENCE: 139

agatctgtac tctagaaagg agtcgtt                                         27


<210> SEQ ID NO 140
<211> LENGTH: 21
<212> TYPE: PRT
<213> ORGANISM: Artificial Sequence
<220> FEATURE:
<223> OTHER INFORMATION: OmpA signal sequence

<400> SEQUENCE: 140

Met Lys Lys Thr Ala Ile Ala Ile Ala Val Ala Leu Ala Gly Phe Ala
1               5                   10                  15

Thr Val Ala Gln Ala
            20


<210> SEQ ID NO 141
<211> LENGTH: 47
```

```
<212> TYPE: PRT
<213> ORGANISM: Artificial Sequence
<220> FEATURE:
<223> OTHER INFORMATION: colicin E3 lysis protein

<400> SEQUENCE: 141

Met Lys Lys Ile Thr Gly Ile Ile Leu Leu Leu Leu Ala Val Ile Ile
1               5                   10                  15

Leu Ser Ala Cys Gln Ala Asn Tyr Ile Arg Asp Val Gln Gly Gly Thr
            20                  25                  30

Val Ser Pro Ser Ser Thr Ala Glu Val Thr Gly Leu Ala Thr Gln
        35                  40                  45


<210> SEQ ID NO 142
<211> LENGTH: 26
<212> TYPE: PRT
<213> ORGANISM: Artificial Sequence
<220> FEATURE:
<223> OTHER INFORMATION: Staphylococcus aureus phenol soluble modulin
      (Sa PSM alpha 1) fused with the immunostimulatory peptide YSL
      preceded by LK

<400> SEQUENCE: 142

Met Gly Ile Ile Ala Gly Ile Ile Lys Val Ile Lys Ser Leu Ile Glu
1               5                   10                  15

Gln Phe Thr Gly Lys Leu Lys Tyr Ser Leu
            20                  25


<210> SEQ ID NO 143
<211> LENGTH: 37
<212> TYPE: PRT
<213> ORGANISM: Artificial Sequence
<220> FEATURE:
<223> OTHER INFORMATION: Staphylococcus aureus phenol soluble modulin
      (Sa PSM alpha 1) fused with the RGD peptide SEQ ID NO: 005

<400> SEQUENCE: 143

Met Gly Ile Ile Ala Gly Ile Ile Lys Val Ile Lys Ser Leu Ile Glu
1               5                   10                  15

Gln Phe Thr Gly Lys Leu Lys Tyr Ser Leu Ala Cys Asp Cys Arg Gly
            20                  25                  30

Asp Cys Phe Cys Gly
        35


<210> SEQ ID NO 144
<211> LENGTH: 191
<212> TYPE: PRT
<213> ORGANISM: Artificial Sequence
<220> FEATURE:
<223> OTHER INFORMATION: PltB C-terminus

<400> SEQUENCE: 144

Met Tyr Ile Asn Lys Phe Val Pro Val Tyr Thr Leu Leu Ile Leu Ile
1               5                   10                  15

Tyr Ser Phe Asn Ala Ser Ala Glu Trp Thr Gly Asp Ala Pro Gly Ile
            20                  25                  30

Val Ile Pro Pro Lys Ala Leu Phe Thr Gln Gln Gly Gly Ala Tyr Gly
        35                  40                  45

Arg Cys Pro Asn Gly Thr Arg Ala Leu Thr Val Ala Glu Leu Arg Gly
    50                  55                  60

Asn Ala Glu Leu Gln Thr Tyr Leu Arg Gln Ile Thr Pro Gly Trp Ser
65                  70                  75                  80
```

```
Ile Tyr Gly Leu Tyr Asp Gly Thr Tyr Leu Gly Gln Ala Tyr Gly Gly
                85                  90                  95

Ile Ile Lys Asp Ala Pro Pro Gly Ala Gly Phe Ile Tyr Arg Glu Thr
            100                 105                 110

Phe Cys Ile Thr Ser Gly Gly Gly Gly Ser Gly Gly Gly Gly Ser Lys
        115                 120                 125

Gln Ser Ile Trp Ala Pro Ser Phe Lys Glu Leu Leu Asp Gln Ala Arg
    130                 135                 140

Tyr Phe Tyr Ser Thr Gly Gln Ser Val Arg Ile His Val Gln Lys Asn
145                 150                 155                 160

Ile Trp Thr Tyr Pro Leu Phe Val Asn Thr Phe Ser Ala Asn Ala Leu
                165                 170                 175

Val Gly Leu Ser Ser Cys Ser Ala Thr Gln Cys Phe Gly Pro Lys
            180                 185                 190
```

<210> SEQ ID NO 145
<211> LENGTH: 122
<212> TYPE: PRT
<213> ORGANISM: Artificial Sequence
<220> FEATURE:
<223> OTHER INFORMATION: non-PltB creating a flexible linker SGGGGSGGGGS, and the PltB C-terminus

<400> SEQUENCE: 145

```
Met Tyr Ile Asn Lys Phe Val Pro Val Tyr Thr Leu Leu Ile Leu Ile
1               5                   10                  15

Tyr Ser Phe Asn Ala Ser Ala Glu Trp Thr Gly Asp Asn Ser Ser Asn
            20                  25                  30

Tyr Cys Cys Glu Leu Cys Cys Asn Pro Ala Cys Thr Gly Cys Phe Ser
        35                  40                  45

Gly Gly Gly Gly Ser Gly Gly Gly Gly Ser Lys Gln Ser Ile Trp Ala
    50                  55                  60

Pro Ser Phe Lys Glu Leu Leu Asp Gln Ala Arg Tyr Phe Tyr Ser Thr
65                  70                  75                  80

Gly Gln Ser Val Arg Ile His Val Gln Lys Asn Ile Trp Thr Tyr Pro
                85                  90                  95

Leu Phe Val Asn Thr Phe Ser Ala Asn Ala Leu Val Gly Leu Ser Ser
            100                 105                 110

Cys Ser Ala Thr Gln Cys Phe Gly Pro Lys
        115                 120
```

<210> SEQ ID NO 146
<211> LENGTH: 137
<212> TYPE: PRT
<213> ORGANISM: Artificial Sequence
<220> FEATURE:
<223> OTHER INFORMATION: portion of S3 , non-PltB creating a flexible linker, and the PltB C-terminus

<400> SEQUENCE: 146

```
Met Tyr Ile Asn Lys Phe Val Pro Val Tyr Thr Leu Leu Ile Leu Ile
1               5                   10                  15

Tyr Ser Phe Asn Ala Ser Ala Glu Trp Thr Gly Asp Ser Leu Asp Ala
            20                  25                  30

Gly Gln Tyr Val Leu Val Met Lys Ala Asn Ser Ser Tyr Ser Gly Asn
        35                  40                  45

Tyr Pro Tyr Ser Ile Leu Phe Gln Lys Phe Ser Gly Gly Gly Gly Ser
    50                  55                  60
```

Gly Gly Gly Gly Ser Gly Gly Gly Gly Lys Gln Ser Ile Trp Ala Pro
65 70 75 80

Ser Phe Lys Glu Leu Leu Asp Gln Ala Arg Tyr Phe Tyr Ser Thr Gly
85 90 95

Gln Ser Val Arg Ile His Val Gln Lys Asn Ile Trp Thr Tyr Pro Leu
100 105 110

Phe Val Asn Thr Phe Ser Ala Asn Ala Leu Val Gly Leu Ser Ser Cys
115 120 125

Ser Ala Thr Gln Cys Phe Gly Pro Lys
130 135

<210> SEQ ID NO 147
<211> LENGTH: 23
<212> TYPE: PRT
<213> ORGANISM: Artificial Sequence
<220> FEATURE:
<223> OTHER INFORMATION: OmpA signal sequence with post cleavage amino acids

<400> SEQUENCE: 147

Met Lys Lys Thr Ala Ile Ala Ile Ala Val Ala Leu Ala Gly Phe Ala
1 5 10 15

Thr Val Ala Gln Ala Ala Val
20

<210> SEQ ID NO 148
<211> LENGTH: 19
<212> TYPE: PRT
<213> ORGANISM: Artificial Sequence
<220> FEATURE:
<223> OTHER INFORMATION: Flexible linker

<400> SEQUENCE: 148

Gly Gly Gly Gly Ser Gly Gly Gly Gly Ser Gly Gly Gly Gly Ser Arg
1 5 10 15

Gly Gly Ser

<210> SEQ ID NO 149
<211> LENGTH: 64
<212> TYPE: PRT
<213> ORGANISM: Artificial Sequence
<220> FEATURE:
<223> OTHER INFORMATION: Enterobacteria phage UAB_Phi20

<400> SEQUENCE: 149

Met Ser Met Lys Ile Gly Glu His Met Lys Pro Val Ile Glu Leu Leu
1 5 10 15

Glu Glu Leu Asn Gly Asn Asp Thr Asp Ala Lys Leu Lys Leu Leu Ala
20 25 30

Leu Val Ile Ser Glu Tyr Met Leu Asn Ala Asp Val Thr Gly Phe Glu
35 40 45

Val Ser Ala Gly Arg Met Lys Val Ala Val Asp Ile Ser Val Glu Asp
50 55 60

<210> SEQ ID NO 150
<211> LENGTH: 341
<212> TYPE: PRT
<213> ORGANISM: Artificial Sequence
<220> FEATURE:
<223> OTHER INFORMATION: PE38K

<400> SEQUENCE: 150

```
Leu Ala Ala Leu Thr Ala His Gln Ala Cys His Leu Pro Leu Glu Thr
1               5                   10                  15

Phe Thr Arg His Arg Gln Pro Arg Gly Trp Glu Gln Leu Glu Gln Cys
            20                  25                  30

Gly Tyr Pro Val Gln Arg Leu Val Ala Leu Tyr Leu Ala Ala Arg Leu
        35                  40                  45

Ser Trp Asn Gln Val Asp Gln Val Ile Arg Asn Ala Leu Ala Ser Pro
    50                  55                  60

Gly Ser Gly Gly Asp Leu Gly Glu Ala Ile Arg Glu Gln Pro Glu Gln
65                  70                  75                  80

Ala Arg Leu Ala Leu Thr Leu Ala Ala Ala Glu Ser Glu Arg Phe Val
                85                  90                  95

Arg Gln Gly Thr Gly Asn Asp Glu Ala Gly Ala Ala Asn Ala Pro Ala
            100                 105                 110

Asp Ser Gly Asp Ala Leu Leu Glu Arg Asn Tyr Pro Thr Gly Ala Glu
        115                 120                 125

Phe Leu Gly Asp Gly Gly Asp Val Ser Phe Ser Thr Arg Gly Thr Gln
    130                 135                 140

Asn Trp Thr Val Glu Arg Leu Leu Gln Ala His Arg Gln Leu Glu Glu
145                 150                 155                 160

Arg Gly Tyr Val Phe Val Gly Tyr His Gly Thr Phe Leu Glu Ala Ala
                165                 170                 175

Gln Ser Ile Val Phe Gly Gly Val Arg Ala Arg Ser Gln Asp Leu Asp
            180                 185                 190

Ala Ile Trp Arg Gly Phe Tyr Ile Ala Gly Asp Pro Ala Leu Ala Tyr
        195                 200                 205

Gly Tyr Ala Gln Asp Gln Glu Pro Asp Ala Arg Gly Arg Ile Arg Asn
    210                 215                 220

Gly Ala Leu Leu Arg Val Tyr Val Pro Arg Ser Ser Leu Pro Gly Phe
225                 230                 235                 240

Tyr Arg Thr Ser Leu Thr Leu Ala Ala Pro Glu Ala Ala Gly Glu Val
                245                 250                 255

Glu Arg Leu Ile Gly His Pro Leu Pro Leu Arg Leu Asp Ala Ile Thr
            260                 265                 270

Gly Pro Glu Glu Glu Gly Gly Arg Leu Glu Thr Ile Leu Gly Trp Pro
        275                 280                 285

Leu Ala Glu Arg Thr Val Val Ile Pro Ser Ala Ile Pro Thr Asp Pro
    290                 295                 300

Arg Asn Val Gly Gly Asp Leu Asp Pro Ser Ser Ile Pro Asp Lys Glu
305                 310                 315                 320

Gln Ala Ile Ser Ala Leu Pro Asp Tyr Ala Ser Gln Pro Gly Lys Pro
                325                 330                 335

Pro Lys Asp Glu Leu
            340


<210> SEQ ID NO 151
<211> LENGTH: 21
<212> TYPE: PRT
<213> ORGANISM: Artificial Sequence
<220> FEATURE:
<223> OTHER INFORMATION: HST mature peptide amino acids with linkers

<400> SEQUENCE: 151

Gly Gly Gly Gly Ser Ala Cys Asp Cys Arg Gly Asp Cys Phe Cys Gly
1               5                   10                  15
```

```
Gly Gly Gly Gly Ser
            20


<210> SEQ ID NO 152
<211> LENGTH: 116
<212> TYPE: PRT
<213> ORGANISM: Artificial Sequence
<220> FEATURE:
<223> OTHER INFORMATION: HST mature peptide amino acids

<400> SEQUENCE: 152

Met Tyr Ile Asn Lys Phe Val Pro Val Tyr Thr Leu Leu Ile Leu Ile
1               5                   10                  15

Tyr Ser Phe Asn Ala Ser Ala Glu Trp Thr Gly Asp Ala Pro Gly Ile
            20                  25                  30

Val Ile Pro Pro Lys Ala Leu Phe Thr Gln Gln Gly Gly Ala Tyr Gly
        35                  40                  45

Arg Cys Pro Asn Gly Thr Arg Ala Leu Thr Val Ala Glu Leu Arg Gly
    50                  55                  60

Asn Ala Glu Leu Gln Thr Tyr Leu Arg Gln Ile Thr Pro Gly Trp Ser
65                  70                  75                  80

Ile Tyr Gly Leu Tyr Asp Gly Thr Tyr Leu Gly Gln Ala Tyr Gly Gly
                85                  90                  95

Ile Ile Lys Asp Ala Pro Pro Gly Ala Gly Phe Ile Tyr Arg Glu Thr
            100                 105                 110

Phe Cys Ile Thr
        115


<210> SEQ ID NO 153
<211> LENGTH: 16
<212> TYPE: PRT
<213> ORGANISM: Artificial Sequence
<220> FEATURE:
<223> OTHER INFORMATION: Flexible linker

<400> SEQUENCE: 153

Ser Gly Gly Gly Gly Ser Gly Gly Gly Gly Ser Gly Gly Gly Gly Ser
1               5                   10                  15


<210> SEQ ID NO 154
<211> LENGTH: 5
<212> TYPE: PRT
<213> ORGANISM: Artificial Sequence
<220> FEATURE:
<223> OTHER INFORMATION: protease cleavage site LK

<400> SEQUENCE: 154

Leu Lys Tyr Ser Leu
1               5


<210> SEQ ID NO 155
<211> LENGTH: 723
<212> TYPE: PRT
<213> ORGANISM: Artificial Sequence
<220> FEATURE:
<223> OTHER INFORMATION: parasporin 1

<400> SEQUENCE: 155

Met Asp Pro Phe Ser Asn Tyr Ser Glu Gln Lys Tyr Pro Asp Ser Asn
1               5                   10                  15

Asn Asn Gln Glu Leu Ile Thr Lys Ser Ser Ser Phe Tyr Ser Asp Thr
            20                  25                  30
```

```
Thr Asn Glu Asn Ala Lys Asn Tyr His Pro Ile Glu Gln Asp Ile Leu
        35                  40                  45

Lys Phe Thr Asn Gln Glu Phe Ser Asp Asn His Tyr Gln His Ser Asp
    50                  55                  60

Val Ser Asn Asp Ile Asn Ser Met Arg Asn Thr Leu Cys Lys Asp Leu
65                  70                  75                  80

Pro Pro Glu Thr Asn Met Ser Ile Tyr Asp Asn Leu Arg Ser Thr Val
                85                  90                  95

Thr Val Pro Ser Phe Ser Asn Gln Phe Asp Pro Ile Lys Phe Leu His
            100                 105                 110

Asp Ile Glu Ile Ala Ile Gln Thr Gly Ser Phe Ser Ala Ser Thr Gln
        115                 120                 125

Ser Asn Met Asn Gln Gly Gly Thr Asp Ile Asn Pro Met Leu Ile Ser
    130                 135                 140

Thr Phe Phe Lys Val Ala Ser Ser Leu Leu Pro Phe Pro Leu Ser Ser
145                 150                 155                 160

Leu Gly Ala Leu Ala Ser Phe Tyr Val Thr Asp Ser Gln Thr Gly Ala
                165                 170                 175

Met Ala Asn Leu Trp Arg Gln Met Val Asp Tyr Val Glu Lys Arg Ile
            180                 185                 190

Asp Ser Lys Ile Leu Asp Tyr His Asn Phe Ile Met Gly Ala Glu Leu
        195                 200                 205

Ala Ala Leu Asn Ala Ser Leu Lys Glu Tyr Ala Arg Val Val Lys Ile
    210                 215                 220

Phe Glu Asn Asp Met Asn Arg Met Ala Glu Pro Pro Ser Thr Gly Val
225                 230                 235                 240

Ile Thr Gln Phe Arg Ile Leu Asn Asp Asn Phe Ile Lys Tyr Ile Ala
                245                 250                 255

Lys Leu Gln Phe Ser Thr Asn Gln Ser Asp Leu Gln Tyr Pro Val Leu
            260                 265                 270

Thr Leu Pro Leu Arg Ala Gln Ala Cys Val Met His Leu Met Leu Leu
        275                 280                 285

Lys Asp Ala Thr Thr Ser Val Trp Gly Gln Gln Ile Asp Ser Gln Gln
    290                 295                 300

Leu Asn Gly Tyr Lys Ala Glu Leu Ile Arg Leu Ile Lys Val Tyr Thr
305                 310                 315                 320

Asn Asp Val Asn Thr Thr Tyr Asn Gln Gly Leu Glu Leu Glu Lys Ala
                325                 330                 335

Lys Pro Leu Asn Tyr Ser Asp Pro Glu Glu Tyr Leu Gln Ala Arg Arg
            340                 345                 350

Pro Asp Ile Ser Val Leu Arg Ser Asn Phe Lys Glu Val Met Lys Trp
        355                 360                 365

Asn Arg Val Ala Lys Tyr Lys Arg Gly Met Ala Met Ser Ala Leu Ser
    370                 375                 380

Leu Ala Ala Leu Phe Pro Thr Phe Gly Pro Asn Tyr Pro Lys Gln Ala
385                 390                 395                 400

Leu Lys Val Val Gln Ser Arg Gln Ile Phe Ala Pro Val Ile Gly Ile
                405                 410                 415

Pro Gly Gly Ile Thr Ser Gln Asp His Ser Gly Thr Phe Gly Ser Met
            420                 425                 430

Arg Phe Asp Val Lys Thr Tyr Asp Gln Ile Asp Ala Leu Arg Arg Leu
        435                 440                 445

Met Glu Leu Tyr Ile Gln Pro Leu Lys Ser Ala Tyr Phe Tyr Ile Tyr
```

```
    450                 455                 460

Glu Ser Asp Trp Lys Val Arg Ala Thr Tyr Val Asn Asp Tyr Ile Gly
465                 470                 475                 480

Lys Arg Gly Ser Asn Thr Gly Leu Ala Trp Gly Met Trp Ser Ser Asp
                485                 490                 495

Pro Ser Val Ile Tyr Thr Ser Ala Leu Gly Ala Ala Gly Tyr Ala Pro
            500                 505                 510

Asn Val Val Gly Val Arg Tyr Ser His Gly Gly Ser Tyr Thr Lys Gly
        515                 520                 525

Met Ala Pro Pro Asn Thr Asn Ala Tyr Ala Pro Phe Glu Phe Lys Tyr
    530                 535                 540

Pro Gly Tyr Lys Leu His Ser Val Ser Ala Tyr Gly Leu Ser Lys Ala
545                 550                 555                 560

Pro Asp Thr Ala Asp Ser Val Met Phe Gly Phe Arg Pro Val Leu Leu
                565                 570                 575

Glu Asn Glu Ala Asn Gln Leu Leu Thr Asp Thr Ala Leu Gln Ile Pro
            580                 585                 590

Ala Glu Ile Gly Ile Thr Asp Val Val Pro Ala Phe Gly Arg Thr Glu
        595                 600                 605

Glu Pro Ile Asn Gly Gln Asp Ala Ile Ile Ile Trp Glu Ser Phe Thr
    610                 615                 620

Ser Gly Phe Gly Phe Thr Tyr Thr Val Asp Ser Pro Gln Lys Gln Lys
625                 630                 635                 640

Tyr Lys Ile Ile Tyr Arg Ser Ala Asn Asn Leu Ser Ala Ser Thr Val
                645                 650                 655

Ser Leu Thr Asp Asn Asn Gln Thr Phe Phe Thr Asp Ile Leu Asn Pro
            660                 665                 670

Ser Leu Asp Pro Asn Gly Val Arg Gly Asn Tyr Gly Ser Tyr Thr Leu
        675                 680                 685

Val Glu Gly Pro Ile Ile Glu Phe Ser Gln Gly Thr Asn Ile Phe Lys
    690                 695                 700

Leu Arg Ser Gln Lys Gly Glu Phe Ala Ile Asp Ser Ile Ile Phe Ser
705                 710                 715                 720

Pro Val Ser


<210> SEQ ID NO 156
<211> LENGTH: 366
<212> TYPE: PRT
<213> ORGANISM: Artificial Sequence
<220> FEATURE:
<223> OTHER INFORMATION: human cGAS 157-522

<400> SEQUENCE: 156

Asp Ala Ala Pro Gly Ala Ser Lys Leu Arg Ala Val Leu Glu Lys Leu
1               5                   10                  15

Lys Leu Ser Arg Asp Asp Ile Ser Thr Ala Ala Gly Met Val Lys Gly
            20                  25                  30

Val Val Asp His Leu Leu Leu Arg Leu Lys Cys Asp Ser Ala Phe Arg
        35                  40                  45

Gly Val Gly Leu Leu Asn Thr Gly Ser Tyr Tyr Glu His Val Lys Ile
    50                  55                  60

Ser Ala Pro Asn Glu Phe Asp Val Met Phe Lys Leu Glu Val Pro Arg
65                  70                  75                  80

Ile Gln Leu Glu Glu Tyr Ser Asn Thr Arg Ala Tyr Tyr Phe Val Lys
                85                  90                  95
```

```
Phe Lys Arg Asn Pro Lys Glu Asn Pro Leu Ser Gln Phe Leu Glu Gly
            100                 105                 110

Glu Ile Leu Ser Ala Ser Lys Met Leu Ser Lys Phe Arg Lys Ile Ile
        115                 120                 125

Lys Glu Glu Ile Asn Asp Ile Lys Asp Thr Asp Val Ile Met Lys Arg
    130                 135                 140

Lys Arg Gly Gly Ser Pro Ala Val Thr Leu Leu Ile Ser Glu Lys Ile
145                 150                 155                 160

Ser Val Asp Ile Thr Leu Ala Leu Glu Ser Lys Ser Ser Trp Pro Ala
                165                 170                 175

Ser Thr Gln Glu Gly Leu Arg Ile Gln Asn Trp Leu Ser Ala Lys Val
            180                 185                 190

Arg Lys Gln Leu Arg Leu Lys Pro Phe Tyr Leu Val Pro Lys His Ala
        195                 200                 205

Lys Glu Gly Asn Gly Phe Gln Glu Glu Thr Trp Arg Leu Ser Phe Ser
    210                 215                 220

His Ile Glu Lys Glu Ile Leu Asn Asn His Gly Lys Ser Lys Thr Cys
225                 230                 235                 240

Cys Glu Asn Lys Glu Glu Lys Cys Cys Arg Lys Asp Cys Leu Lys Leu
                245                 250                 255

Met Lys Tyr Leu Leu Glu Gln Leu Lys Glu Arg Phe Lys Asp Lys Lys
            260                 265                 270

His Leu Asp Lys Phe Ser Ser Tyr His Val Lys Thr Ala Phe Phe His
        275                 280                 285

Val Cys Thr Gln Asn Pro Gln Asp Ser Gln Trp Asp Arg Lys Asp Leu
    290                 295                 300

Gly Leu Cys Phe Asp Asn Cys Val Thr Tyr Phe Leu Gln Cys Leu Arg
305                 310                 315                 320

Thr Glu Lys Leu Glu Asn Tyr Phe Ile Pro Glu Phe Asn Leu Phe Ser
                325                 330                 335

Ser Asn Leu Ile Asp Lys Arg Ser Lys Glu Phe Leu Thr Lys Gln Ile
            340                 345                 350

Glu Tyr Glu Arg Asn Asn Glu Phe Pro Val Phe Asp Glu Phe
        355                 360                 365
```

<210> SEQ ID NO 157
<211> LENGTH: 1115
<212> TYPE: DNA
<213> ORGANISM: Artificial Sequence
<220> FEATURE:
<223> OTHER INFORMATION: initiating methionine, Human cGAS 157-522, second amino acid (A) NcoI site at 5' end, a stop codon followed by HindIII restriction site at the 3' end

<400> SEQUENCE: 157

```
ccatggcgga cgcagctccg ggtgcatcca aactgcgtgc ggttttagaa aaactgaaac     60

tgtccaggga tgatatctcc accgctgcgg gtatggtcaa gggcgtggtg gaccacctgc    120

tgctgcgcct gaaatgtgac tcggcttttc gtggtgtagg tctgctgaac actggcagct    180

attacgaaca cgtgaaaatt tcggcccct a atgaattcga cgtcatgttc aaattggaag    240

tcccgcgtat tcagctggag gaatattcca acactcgtgc ctactatttc gtaaaattca    300

aacgcaaccc taaagagaac ccgctgtccc agttcctgga aggcgagatt ctgtccgctt    360

ctaaaatgct gtccaaattc cgtaaaatta ttaaggagga aatcaacgac atcaaagaca    420

cggacgtaat catgaaacgc aaaagaggtg gttctccggc cgtcacgctg ctgatttctg    480
```

```
aaaaaatttc cgtggatatt accctggccc tggaatccaa gtcttcctgg ccggcctcca    540

cgcaggaagg tctgcgcatt cagaactggc tgtctgcaaa ggtacgtaaa cagctgcgtt    600

tgaaaccgtt ctatttagtg ccgaagcatg cgaaagaagg taacggtttc caagaagaaa    660

cctggcgtct gagcttctct cacatcgaaa aagaaatcct taacaatcat ggcaaaagca    720

aaacttgctg tgaaaacaaa gaagagaaat gctgtcgtaa ggactgtctg aaactgatga    780

aatatctgct ggaacagctg aaagaacgtt tcaaggacaa aaaacacctg gacaaattct    840

ctagctacca cgtaaaaacc gccttcttcc acgtgtgtac tcagaacccg caggacagcc    900

agtgggaccg caaagacctg ggtctgtgct tcgacaactg tgttacctac ttcctgcagt    960

gcctccgtac cgaaaaactg gagaactatt tcatcccgga atttaacctg ttctcttcta   1020

acctgatcga caagcgctct aaagaattcc tgaccaaaca aattgaatac gaacgtaaca   1080

acgagtttcc tgtgttcgac gagttttaaa agctt                              1115
```

<210> SEQ ID NO 158
<211> LENGTH: 436
<212> TYPE: PRT
<213> ORGANISM: Artificial Sequence
<220> FEATURE:
<223> OTHER INFORMATION: Vibrio cholera GenBank Accession number CP013309.1

<400> SEQUENCE: 158

```
Met Arg Met Thr Trp Asn Phe His Gln Tyr Tyr Thr Asn Arg Asn Asp
1               5                   10                  15

Gly Leu Met Gly Lys Leu Val Leu Thr Asp Glu Glu Lys Asn Asn Leu
            20                  25                  30

Lys Ala Leu Arg Lys Ile Ile Arg Leu Arg Thr Arg Asp Val Phe Glu
        35                  40                  45

Glu Ala Lys Gly Ile Ala Lys Ala Val Lys Lys Ser Ala Leu Thr Phe
    50                  55                  60

Glu Ile Ile Gln Glu Lys Val Ser Thr Thr Gln Ile Lys His Leu Ser
65                  70                  75                  80

Asp Ser Glu Gln Arg Glu Val Ala Lys Leu Ile Tyr Glu Met Asp Asp
                85                  90                  95

Asp Ala Arg Asp Glu Phe Leu Gly Leu Thr Pro Arg Phe Trp Thr Gln
            100                 105                 110

Gly Ser Phe Gln Tyr Asp Thr Leu Asn Arg Pro Phe Gln Pro Gly Gln
        115                 120                 125

Glu Met Asp Ile Asp Asp Gly Thr Tyr Met Pro Met Pro Ile Phe Glu
    130                 135                 140

Ser Glu Pro Lys Ile Gly His Ser Leu Leu Ile Leu Leu Val Asp Ala
145                 150                 155                 160

Ser Leu Lys Ser Leu Val Ala Glu Asn His Gly Trp Lys Phe Glu Ala
                165                 170                 175

Lys Gln Thr Cys Gly Arg Ile Lys Ile Glu Ala Glu Lys Thr His Ile
            180                 185                 190

Asp Val Pro Met Tyr Ala Ile Pro Lys Asp Glu Phe Gln Lys Lys Gln
        195                 200                 205

Ile Ala Leu Glu Ala Asn Arg Ser Phe Val Lys Gly Ala Ile Phe Glu
    210                 215                 220

Ser Tyr Val Ala Asp Ser Ile Thr Asp Asp Ser Glu Thr Tyr Glu Leu
225                 230                 235                 240
```

```
Asp Ser Glu Asn Val Asn Leu Ala Leu Arg Glu Gly Asp Arg Lys Trp
                245                 250                 255

Ile Asn Ser Asp Pro Lys Ile Val Glu Asp Trp Phe Asn Asp Ser Cys
            260                 265                 270

Ile Arg Ile Gly Lys His Leu Arg Lys Val Cys Arg Phe Met Lys Ala
        275                 280                 285

Trp Arg Asp Ala Gln Trp Asp Val Gly Gly Pro Ser Ser Ile Ser Leu
    290                 295                 300

Met Ala Ala Thr Val Asn Ile Leu Asp Ser Val Ala His Asp Ala Ser
305                 310                 315                 320

Asp Leu Gly Glu Thr Met Lys Ile Ile Ala Lys His Leu Pro Ser Glu
                325                 330                 335

Phe Ala Arg Gly Val Glu Ser Pro Asp Ser Thr Asp Glu Lys Pro Leu
            340                 345                 350

Phe Pro Pro Ser Tyr Lys His Gly Pro Arg Glu Met Asp Ile Met Ser
        355                 360                 365

Lys Leu Glu Arg Leu Pro Glu Ile Leu Ser Ser Ala Glu Ser Ala Asp
    370                 375                 380

Ser Lys Ser Glu Ala Leu Lys Lys Ile Asn Met Ala Phe Gly Asn Arg
385                 390                 395                 400

Val Thr Asn Ser Glu Leu Ile Val Leu Ala Lys Ala Leu Pro Ala Phe
                405                 410                 415

Ala Gln Glu Pro Ser Ser Ala Ser Lys Pro Glu Lys Ile Ser Ser Thr
            420                 425                 430

Met Val Ser Gly
        435
```

<210> SEQ ID NO 159
<211> LENGTH: 370
<212> TYPE: PRT
<213> ORGANISM: Artificial Sequence
<220> FEATURE:
<223> OTHER INFORMATION: Salmonella YiaC

<400> SEQUENCE: 159

```
Met Phe Pro Lys Ile Met Asn Asp Glu Asn Phe Tyr Arg Lys Ala Val
1               5                   10                  15

Glu Gln Ala Val Ala Pro Pro Asp Pro Pro Asp Asp Arg Gln Arg Ser
            20                  25                  30

Gly Leu Arg Phe Ala Arg Arg Ile Arg Leu Pro Arg Ala Val Gly Leu
        35                  40                  45

Gly Gly Met Phe Leu Pro Val Ala Ala Val Leu Val Thr Gln Pro Val
    50                  55                  60

Phe Gly Gly Trp Trp Leu Leu Leu Val Gly Trp Ser Phe Val Trp Pro
65                  70                  75                  80

His Leu Ala Trp Gln Trp Ala Ala Lys Ala Leu Asp Pro Leu Arg Gln
                85                  90                  95

Glu Ile Tyr Asn Leu Lys Val Asp Ala Ile Leu Ser Gly Met Trp Ile
            100                 105                 110

Ala Leu Met Gly Val Asn Met Leu Pro Ala Ala Ala Leu Phe Met Met
        115                 120                 125

Met Ser Met Asn Leu Met Gly Ala Gly Gly Arg Arg Leu Phe Thr Val
    130                 135                 140

Gly Met Gly Leu Leu Leu Ala Ser Cys Leu Val Thr Leu Gln Leu Ala
145                 150                 155                 160
```

```
Gly Leu Pro Val Ala Met Arg Ser Ser Ser Leu Glu Val Thr Leu Ser
                165                 170                 175

Leu Pro Val Ile Met Leu Tyr Pro Leu Leu Phe Ala Trp Val Ser Tyr
            180                 185                 190

Gln Thr Ala Ile Lys Leu Ala Glu His Lys Arg Arg Leu Gln Ala Met
        195                 200                 205

Ser Ser Arg Asp Gly Met Thr Gly Val Tyr Asn Arg Arg His Trp Glu
    210                 215                 220

Ile Leu Leu Arg Asn Glu Phe Asp His Ser Arg Arg His His Arg Glu
225                 230                 235                 240

Ala Thr Leu Leu Ile Ile Asp Ile Asp His Phe Lys Ser Ile Asn Asp
                245                 250                 255

Thr Trp Gly His Asp Val Gly Asp Glu Ala Ile Ile Ala Leu Thr Arg
            260                 265                 270

Gln Leu Gln Ile Thr Leu Arg Gly Ser Asp Ile Ile Gly Arg Phe Gly
        275                 280                 285

Gly Asp Glu Phe Ala Val Ile Met Cys Gly Thr Pro Ala Asp Ser Ala
    290                 295                 300

Ile Thr Ala Met Ser Arg Val His Glu Arg Leu Asn Thr Leu Arg Leu
305                 310                 315                 320

Pro Gly Ala Pro Gln Val Met Leu Arg Ile Ser Val Gly Val Ala Pro
                325                 330                 335

Leu Thr Pro Gln Ile Gly His Tyr Arg Glu Trp Leu Lys Ser Ala Asp
            340                 345                 350

Met Ala Leu Tyr Lys Ala Lys Asn Ala Gly Arg Asn Arg Thr Glu Val
        355                 360                 365

Ala Ala
    370
```

<210> SEQ ID NO 160
<211> LENGTH: 89
<212> TYPE: PRT
<213> ORGANISM: Artificial Sequence
<220> FEATURE:
<223> OTHER INFORMATION: Shigella toxin B subunit UniProtKB Q7BQ98.1

<400> SEQUENCE: 160

```
Met Lys Lys Thr Leu Leu Ile Ala Ala Ser Leu Ser Phe Phe Ser Ala
1               5                   10                  15

Ser Ala Leu Ala Thr Pro Asp Cys Val Thr Gly Lys Val Glu Tyr Thr
            20                  25                  30

Lys Tyr Asn Asp Asp Asp Thr Phe Thr Val Lys Val Gly Asp Lys Glu
        35                  40                  45

Leu Phe Thr Asn Arg Trp Asn Leu Gln Ser Leu Leu Leu Ser Ala Gln
    50                  55                  60

Ile Thr Gly Met Thr Val Thr Ile Lys Thr Asn Ala Cys His Asn Gly
65                  70                  75                  80

Gly Gly Phe Ser Glu Val Ile Phe Arg
                85
```

<210> SEQ ID NO 161
<211> LENGTH: 270
<212> TYPE: DNA
<213> ORGANISM: Artificial Sequence
<220> FEATURE:
<223> OTHER INFORMATION: Shigella toxin B subunit UniProtKB Q7BQ98.1

<400> SEQUENCE: 161
atgaaaaaaa cattattaat agctgcatcg ctttcatttt tttcagcaag tgcgctggcg 60
acgcctgatt gtgtaactgg aaaggtggag tatacaaaat ataatgatga cgataccttt 120
acagttaaag tgggtgataa agaattattt accaacagat ggaatcttca gtctcttctt 180
ctcagtgcgc aaattacggg gatgactgta accattaaaa ctaatgcctg tcataatgga 240
gggggattca gcgaagttat ttttcgttga 270

<210> SEQ ID NO 162
<211> LENGTH: 286
<212> TYPE: PRT
<213> ORGANISM: Artificial Sequence
<220> FEATURE:
<223> OTHER INFORMATION: hybrid toxin, containing the Shigella toxin N-terminus and the mistletoe lectin C-terminus

<400> SEQUENCE: 162

Met Lys Lys Thr Leu Leu Ile Ala Ala Ser Leu Ser Phe Phe Ser Ala
1 5 10 15

Ser Ala Leu Ala Thr Pro Asp Cys Val Thr Gly Lys Val Glu Thr Val
20 25 30

Arg Phe Val Gly Arg Asn Gly Leu Cys Leu Asp Val Pro Glu Gly Asp
35 40 45

Tyr His Asp Gly Ser Arg Ile Gln Leu Trp Pro Cys Lys Ser Asn Ser
50 55 60

Asp Gln Asn Gln Leu Trp Thr Ile Arg Arg Asp Gly Thr Ile Arg Ser
65 70 75 80

Asn Gly Arg Cys Leu Thr Thr Tyr Gly Tyr Thr Ala Gly Ser Tyr Ile
85 90 95

Met Ile Tyr Asp Cys Asn Arg Gly Gly Trp Asp Leu Thr Thr Trp Gln
100 105 110

Ile Arg Gly Asn Gly Ile Ile Leu Asn Pro Arg Ser Met Met Val Ile
115 120 125

Gly Thr Pro Ser Gly Ser Arg Gly Thr Arg Gly Thr Thr Phe Thr Leu
130 135 140

Gln Thr Leu Gly Tyr Ser Leu Gly Gln Gly Trp Leu Ala Ser Asn Asp
145 150 155 160

Thr Ala Pro Arg Glu Val Thr Ile Tyr Gly Phe Arg Asp His Cys Met
165 170 175

Glu Thr Ser Gly Gly Lys Val Trp Val Gly Thr Cys Val Ser Gly Lys
180 185 190

Gln Asn Gln Arg Trp Ala Leu Tyr Gly Asp Gly Ser Ile Arg Pro Lys
195 200 205

Pro Tyr Gln Asp Gln Cys Leu Thr Ser Gln Gly Asp Ser Val Arg Ser
210 215 220

Val Ile Asn Leu Phe Ser Cys Thr Ala Gly Ser Pro Arg Gln Arg Trp
225 230 235 240

Val Phe Thr Asn Lys Gly Ala Ile Leu Asn Leu Lys Asn Arg Leu Ala
245 250 255

Met Asp Val Ala Glu Ser Asn Pro Ser Leu Arg Arg Ile Ile Ile Phe
260 265 270

Ser Val Thr Gly Asn Pro Asn Gln Met Trp Leu Pro Val Pro
275 280 285

<210> SEQ ID NO 163
<211> LENGTH: 872

<212> TYPE: DNA
<213> ORGANISM: Artificial Sequence
<220> FEATURE:
<223> OTHER INFORMATION: NcoI, second (V) codon, stop codon, and HindIII site

<400> SEQUENCE: 163
ccatggtcaa aaaaacatta ttaatagctg catcgctttc attttttca gcaagtgcgc 60 tggcgacgcc tgattgtgta actggaaagg tggagacggt ccgtttcgtt ggccgcaacg 120
gcctgtgctt ggacgttccg gagggtgatt accatgatgg ttctcgcatc cagttgtggc 180
cgtgcaaatc gaactctgat cagaaccaac tgtggacaat ccgtcgtgac ggcaccatcc 240
gctccaacgg tcgctgtctg accacatacg gctacaccgc cggtagctac attatgattt 300
atgactgcaa tcgtggcggc tgggatctca cgacctggca gattcgtggc aacgggatca 360
tcctgaatcc gcgttccatg atggtgatcg gcactccgtc tggttctcgc gggactcgtg 420
gtactacctt cacgctgcaa accctgggtt attctctggg ccaggggtgg ttggcatcga 480
acgataccgc gccgcgtgaa gtgactatct atggtttccg tgaccactgc atggaaacct 540
ctggcggcaa ggtctgggtg ggtacctgcg tgtccggcaa acagaaccag cgctgggcgc 600
tgtatggcga cggcagcatc cgtccgaagc cgtaccagga tcagtgtctg acctcccagg 660
gtgatagcgt gcgcagcgtg atcaacctgt tttcttgcac tgcgggtagc ccgcgtcagc 720
gctgggtatt caccaacaag ggcgctattc tgaacctgaa aaatcgtctg gctatggatg 780
tggctgaaag caacccgtct ttgcgccgca tcatcatctt ttccgttacc ggtaatccga 840
accagatgtg gctgccagtc ccgtaaaagc tt 872

<210> SEQ ID NO 164
<211> LENGTH: 649
<212> TYPE: DNA
<213> ORGANISM: Artificial Sequence
<220> FEATURE:
<223> OTHER INFORMATION: GMCSF with ColE3 lysis protein as a polycistronic message, encoding an NcoI site upstream and XbaI and HindIII sites downstream

<400> SEQUENCE: 164
ccatggctaa aaagacagct atcgcgattg cagtggcact ggctggtttc gctaccgtag 60
cgcaggcagc tccggctcgt agcccgtcgc catccactca gccctgggag cacgtcaatg 120
cgattcaaga ggctcgtcgt ttacttaacc tgtcgcggga taccgcagcg gagatgaacg 180
aaacagttga agttatctcg gaaatgtttg atttgcagga accaacatgt ttgcagactc 240
gcctggaact ttataagcag ggtttacggg gctcattaac aaaactgaaa ggccctctta 300
ccatgatggc ctcccattac aagcagcatt gtcccccac gcctgaaact tcttgcgcga 360
cgcaaattat tacgtttgaa tcgttcaagg agaatctgaa agatttcctt ttggttatcc 420
ccttcgattg ctgggaacct gtacaagaat gactcgagta gatctgtaca ctagaaagga 480
gtcgttatga aaaaaataac agggattatt ttattgcttc ttgcagtcat tattctgtct 540
gcatgtcagg caaactatat ccgggatgtt cagggcggga ccgtatctcc gtcatcaacg 600
gctgaagtga ccggattagc aacgcagtaa tctagagcga agcttgatc 649

<210> SEQ ID NO 165
<211> LENGTH: 5
<212> TYPE: PRT
<213> ORGANISM: Artificial Sequence
<220> FEATURE:
<223> OTHER INFORMATION: Enterokinase signal

<400> SEQUENCE: 165

Asp Asp Asp Asp Lys
1 5

<210> SEQ ID NO 166
<211> LENGTH: 6
<212> TYPE: PRT
<213> ORGANISM: Artificial Sequence
<220> FEATURE:
<223> OTHER INFORMATION: Hexahistidine

<400> SEQUENCE: 166

His His His His His His
1 5

<210> SEQ ID NO 167
<211> LENGTH: 26
<212> TYPE: PRT
<213> ORGANISM: Artificial Sequence
<220> FEATURE:
<223> OTHER INFORMATION: S-alpha delta-toxin

<400> SEQUENCE: 167

Met Ala Gln Asp Ile Ile Ser Thr Ile Gly Asp Leu Val Lys Trp Ile
1 5 10 15

Ile Asp Thr Val Asn Lys Phe Thr Lys Lys
20 25

<210> SEQ ID NO 168
<211> LENGTH: 25
<212> TYPE: PRT
<213> ORGANISM: Artificial Sequence
<220> FEATURE:
<223> OTHER INFORMATION: Se delta-toxin

<400> SEQUENCE: 168

Met Ala Ala Asp Ile Ile Ser Thr Ile Gly Asp Leu Val Lys Trp Ile
1 5 10 15

Ile Asp Thr Val Asn Lys Phe Lys Lys
20 25

<210> SEQ ID NO 169
<211> LENGTH: 21
<212> TYPE: PRT
<213> ORGANISM: Artificial Sequence
<220> FEATURE:
<223> OTHER INFORMATION: S-alpha PSMa1

<400> SEQUENCE: 169

Met Gly Ile Ile Ala Gly Ile Ile Lys Val Ile Lys Ser Leu Ile Glu
1 5 10 15

Gln Phe Thr Gly Lys
20

<210> SEQ ID NO 170
<211> LENGTH: 21
<212> TYPE: PRT
<213> ORGANISM: Artificial Sequence
<220> FEATURE:
<223> OTHER INFORMATION: S-alpha PSMa2

<400> SEQUENCE: 170

Met Gly Ile Ile Ala Gly Ile Ile Lys Phe Ile Lys Gly Leu Ile Glu
1 5 10 15

Lys Phe Thr Gly Lys
20

<210> SEQ ID NO 171
<211> LENGTH: 22
<212> TYPE: PRT
<213> ORGANISM: Artificial Sequence
<220> FEATURE:
<223> OTHER INFORMATION: S-alpha PSMa3

<400> SEQUENCE: 171

Met Glu Phe Val Ala Lys Leu Phe Lys Phe Phe Lys Asp Leu Leu Gly
1 5 10 15

Lys Phe Leu Gly Asn Asn
20

<210> SEQ ID NO 172
<211> LENGTH: 20
<212> TYPE: PRT
<213> ORGANISM: Artificial Sequence
<220> FEATURE:
<223> OTHER INFORMATION: S-alpha PSMa4

<400> SEQUENCE: 172

Met Ala Ile Val Gly Thr Ile Ile Lys Ile Ile Lys Ala Ile Ile Asp
1 5 10 15

Ile Phe Ala Lys
20

<210> SEQ ID NO 173
<211> LENGTH: 22
<212> TYPE: PRT
<213> ORGANISM: Artificial Sequence
<220> FEATURE:
<223> OTHER INFORMATION: Se PSM alpha

<400> SEQUENCE: 173

Met Ala Asp Val Ile Ala Lys Ile Val Glu Ile Val Lys Gly Leu Ile
1 5 10 15

Asp Gln Phe Thr Gln Lys
20

<210> SEQ ID NO 174
<211> LENGTH: 23
<212> TYPE: PRT
<213> ORGANISM: Artificial Sequence
<220> FEATURE:
<223> OTHER INFORMATION: Se PSM delta

<400> SEQUENCE: 174

Met Ser Ile Val Ser Thr Ile Ile Glu Val Val Lys Thr Ile Val Asp
1 5 10 15

Ile Val Lys Lys Phe Lys Lys
20

<210> SEQ ID NO 175
<211> LENGTH: 24
<212> TYPE: PRT
<213> ORGANISM: Artificial Sequence
<220> FEATURE:
<223> OTHER INFORMATION: Se PSM epsilon

<400> SEQUENCE: 175

Met Phe Ile Ile Asn Leu Val Lys Lys Val Ile Ser Phe Ile Lys Gly

```
1               5                   10                  15

Leu Phe Gly Asn Asn Glu Asn Glu
            20


<210> SEQ ID NO 176
<211> LENGTH: 22
<212> TYPE: PRT
<213> ORGANISM: Artificial Sequence
<220> FEATURE:
<223> OTHER INFORMATION: S-alpha/Se PSM-me c

<400> SEQUENCE: 176

Met Asp Phe Thr Gly Val Ile Thr Ser Ile Ile Asp Leu Ile Lys Thr
1               5                   10                  15

Cys Ile Gln Ala Phe Gly
            20


<210> SEQ ID NO 177
<211> LENGTH: 44
<212> TYPE: PRT
<213> ORGANISM: Artificial Sequence
<220> FEATURE:
<223> OTHER INFORMATION: S-alpha PSM-beta1

<400> SEQUENCE: 177

Met Glu Gly Leu Phe Asn Ala Ile Lys Asp Thr Val Thr Ala Ala Ile
1               5                   10                  15

Asn Asn Asp Gly Ala Lys Leu Gly Thr Ser Ile Val Ser Ile Val Glu
            20                  25                  30

Asn Gly Val Gly Leu Leu Gly Lys Leu Phe Gly Phe
        35                  40


<210> SEQ ID NO 178
<211> LENGTH: 44
<212> TYPE: PRT
<213> ORGANISM: Artificial Sequence
<220> FEATURE:
<223> OTHER INFORMATION: S-alpha PSM-beta2

<400> SEQUENCE: 178

Met Thr Gly Leu Ala Glu Ala Ile Ala Asn Thr Val Gln Ala Ala Gln
1               5                   10                  15

Gln His Asp Ser Val Lys Leu Gly Thr Ser Ile Val Asp Ile Val Ala
            20                  25                  30

Asn Gly Val Gly Leu Leu Gly Lys Leu Phe Gly Phe
        35                  40


<210> SEQ ID NO 179
<211> LENGTH: 44
<212> TYPE: PRT
<213> ORGANISM: Artificial Sequence
<220> FEATURE:
<223> OTHER INFORMATION: Se PSM-beta1

<400> SEQUENCE: 179

Met Ser Lys Leu Ala Glu Ala Ile Ala Asn Thr Val Lys Ala Ala Gln
1               5                   10                  15

Asp Gln Asp Trp Thr Lys Leu Gly Thr Ser Ile Val Asp Ile Val Glu
            20                  25                  30

Ser Gly Val Ser Val Leu Gly Lys Ile Phe Gly Phe
        35                  40
```

<210> SEQ ID NO 180
<211> LENGTH: 44
<212> TYPE: PRT
<213> ORGANISM: Artificial Sequence
<220> FEATURE:
<223> OTHER INFORMATION: Se PSM-beta2

<400> SEQUENCE: 180

```
Met Glu Gln Leu Phe Asp Ala Ile Arg Ser Val Val Asp Ala Gly Ile
1               5                   10                  15

Asn Gln Asp Trp Ser Gln Leu Ala Ser Gly Ile Ala Gly Ile Val Glu
            20                  25                  30

Asn Gly Ile Ser Val Ile Ser Lys Leu Leu Gly Gln
        35                  40
```

<210> SEQ ID NO 181
<211> LENGTH: 310
<212> TYPE: PRT
<213> ORGANISM: Artificial Sequence
<220> FEATURE:
<223> OTHER INFORMATION: IgG antibody agonist with VH and VL domains specific for PD-L1 ScFv derived from Atezolizumab

<400> SEQUENCE: 181

```
Met Ala Glu Val Gln Leu Val Glu Ser Gly Gly Gly Leu Val Gln Pro
1               5                   10                  15

Gly Gly Ser Leu Arg Leu Ser Cys Ala Ala Ser Gly Phe Thr Phe Ser
            20                  25                  30

Asp Ser Trp Ile His Trp Val Arg Gln Ala Pro Gly Lys Gly Leu Glu
        35                  40                  45

Trp Val Ala Trp Ile Ser Pro Tyr Gly Gly Ser Thr Tyr Tyr Ala Asp
    50                  55                  60

Ser Val Lys Gly Arg Phe Thr Ile Ser Ala Asp Thr Ser Lys Asn Thr
65                  70                  75                  80

Ala Tyr Leu Gln Met Asn Ser Leu Arg Ala Glu Asp Thr Ala Val Tyr
                85                  90                  95

Tyr Cys Ala Arg Arg His Trp Pro Gly Gly Phe Asp Tyr Trp Gly Gln
            100                 105                 110

Gly Thr Leu Val Thr Ser Ser Gly Gly Gly Gly Ser Gly Gly Gly Gly
        115                 120                 125

Ser Gly Gly Gly Gly Ser Asp Ile Gln Met Thr Gln Ser Pro Ser Ser
    130                 135                 140

Leu Ser Ala Ser Val Gly Asp Arg Val Thr Ile Thr Cys Arg Ala Ser
145                 150                 155                 160

Gln Asp Val Ser Thr Ala Val Ala Trp Tyr Gln Gln Lys Pro Gly Lys
                165                 170                 175

Ala Pro Lys Leu Leu Ile Tyr Ser Ala Ser Phe Leu Tyr Ser Gly Val
            180                 185                 190

Pro Ser Arg Phe Ser Gly Ser Gly Ser Gly Thr Asp Phe Thr Leu Thr
        195                 200                 205

Ile Ser Ser Leu Gln Pro Glu Asp Phe Ala Thr Tyr Tyr Cys Gln Gln
    210                 215                 220

Tyr Leu Tyr His Pro Ala Thr Phe Gly Gln Gly Thr Lys Val Glu Ile
225                 230                 235                 240

Lys Arg His His His His His His Ala Ala Leu Ala Tyr Gly Ser Gln
                245                 250                 255

Gly Asn Leu Asn Pro Leu Ile Asn Glu Ile Ser Lys Ile Ile Ser Ala
            260                 265                 270
```

```
Ala Gly Asn Phe Asp Val Lys Glu Glu Arg Ala Ala Ala Ser Leu Leu
        275                 280                 285

Gln Leu Ser Gly Asn Ala Ser Asp Phe Ser Tyr Gly Arg Asn Ser Ile
    290                 295                 300

Thr Leu Thr Ala Ser Ala
305                 310


<210> SEQ ID NO 182
<211> LENGTH: 315
<212> TYPE: PRT
<213> ORGANISM: Artificial Sequence
<220> FEATURE:
<223> OTHER INFORMATION: IgG antibody agonist with VH and VL domains
      specific for OX-40 SC02023 Bakker et al. (2012)

<400> SEQUENCE: 182

Met Ala Glu Val Gln Leu Val Glu Ser Gly Gly Gly Leu Val His Pro
1               5                   10                  15

Gly Gly Ser Leu Arg Leu Ser Cys Ala Gly Ser Gly Phe Thr Phe Ser
            20                  25                  30

Ser Tyr Ala Met His Trp Val Arg Gln Ala Pro Gly Lys Gly Leu Glu
        35                  40                  45

Trp Val Ser Ala Ile Gly Thr Gly Gly Gly Thr Tyr Tyr Ala Asp Ser
    50                  55                  60

Val Met Gly Arg Phe Thr Ile Ser Arg Asp Asn Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Arg Tyr Asp Asn Val Met Gly Leu Tyr Trp Phe Asp Tyr Trp
            100                 105                 110

Gly Gln Gly Thr Leu Val Thr Val Ser Ser Gly Gly Gly Gly Ser Gly
        115                 120                 125

Gly Gly Gly Ser Gly Gly Gly Gly Ser Glu Ile Glu Leu Thr Gln Ser
    130                 135                 140

Pro Ala Thr Leu Ser Leu Ser Pro Gly Glu Arg Ala Thr Leu Ser Cys
145                 150                 155                 160

Arg Ala Ser Gln Ser Val Ser Ser Tyr Leu Ala Trp Tyr Gln Gln Lys
                165                 170                 175

Pro Gly Gln Ala Pro Arg Leu Leu Ile Tyr Asp Ala Ser Asn Arg Ala
            180                 185                 190

Thr Gly Ile Pro Ala Arg Phe Ser Gly Ser Gly Ser Gly Thr Asp Phe
        195                 200                 205

Thr Leu Thr Ile Ser Ser Leu Glu Pro Glu Pro Glu Asp Phe Ala Val
    210                 215                 220

Tyr Tyr Cys Gln Gln Arg Ser Asn Trp Pro Pro Ala Phe Gly Gly Gly
225                 230                 235                 240

Thr Lys Val Glu Ile Lys Arg His His His His His His Ala Ala Leu
                245                 250                 255

Ala Tyr Gly Ser Gln Gly Asn Leu Asn Pro Leu Ile Asn Glu Ile Ser
            260                 265                 270

Lys Ile Ile Ser Ala Ala Gly Asn Phe Asp Val Lys Glu Glu Arg Ala
        275                 280                 285

Ala Ala Ser Leu Leu Gln Leu Ser Gly Asn Ala Ser Asp Phe Ser Tyr
    290                 295                 300

Gly Arg Asn Ser Ile Thr Leu Thr Ala Ser Ala
```

305 310 315

<210> SEQ ID NO 183
<211> LENGTH: 302
<212> TYPE: PRT
<213> ORGANISM: Artificial Sequence
<220> FEATURE:
<223> OTHER INFORMATION: IgG antibody agonist with VH and VL domains specific for CD47, 5F9 anti-CD47 diabody B chain
<220> FEATURE:
<221> NAME/KEY: misc_feature
<222> LOCATION: (1)..(1)
<223> OTHER INFORMATION: Xaa can be any naturally occurring amino acid

<400> SEQUENCE: 183

```
Xaa Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Asn Met His Trp Val Arg Gln Ala Pro Gly Gln Arg Leu Glu Trp Met
        35                  40                  45

Gly Thr Ile Tyr Pro Gly Asn Asp Asp Thr Ser Tyr Asn Gln Lys Phe
    50                  55                  60

Lys Asp Arg Val Thr Ile Thr Ala Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Tyr Arg Ala Met Asp Tyr Trp Gly Gln Gly Thr Leu
            100                 105                 110

Val Thr Val Ser Ser Gly Gly Ser Gly Gly Asp Ile Val Met Thr Gln
        115                 120                 125

Ser Pro Leu Ser Leu Pro Val Thr Pro Gly Glu Pro Ala Ser Ile Ser
    130                 135                 140

Cys Arg Ser Ser Gln Ser Ile Val Tyr Ser Asn Gly Asn Thr Tyr Leu
145                 150                 155                 160

Gly Trp Tyr Leu Gln Lys Pro Gly Gln Ser Pro Gln Leu Leu Ile Tyr
                165                 170                 175

Lys Val Ser Asn Arg Phe Ser Gly Val Pro Asp Arg Phe Ser Gly Ser
            180                 185                 190

Gly Ser Gly Thr Asp Phe Thr Leu Lys Ile Ser Arg Val Glu Ala Glu
        195                 200                 205

Asp Val Gly Val Tyr Tyr Cys Phe Gln Gly Ser His Val Pro Tyr Thr
    210                 215                 220

Phe Gly Gln Gly Thr Lys Leu Glu Ile Lys His His His His His His
225                 230                 235                 240

Ala Ala Leu Ala Tyr Gly Ser Gln Gly Asn Leu Asn Pro Leu Ile Asn
                245                 250                 255

Glu Ile Ser Lys Ile Ile Ser Ala Ala Gly Asn Phe Asp Val Lys Glu
            260                 265                 270

Glu Arg Ala Ala Ala Ser Leu Leu Gln Leu Ser Gly Asn Ala Ser Asp
        275                 280                 285

Phe Ser Tyr Gly Arg Asn Ser Ile Thr Leu Thr Ala Ser Ala
    290                 295                 300
```

<210> SEQ ID NO 184
<211> LENGTH: 259
<212> TYPE: PRT
<213> ORGANISM: Artificial Sequence
<220> FEATURE:
<223> OTHER INFORMATION: ScFv from US 7,488,802 against PD-1

<400> SEQUENCE: 184

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gly Gly Thr Lys Val Glu Ile Lys Arg Ser Arg Gly Gly
            100                 105                 110

Gly Gly Ser Gly Gly Gly Gly Ser Gly Gly Gly Gly Ser Glu Val Gln
        115                 120                 125

Leu Val Glu Ser Gly Gly Gly Leu Val Gln Pro Gly Gly Ser Leu Arg
    130                 135                 140

Leu Ser Cys Ala Ala Ser Gly Phe Thr Ser Ser Ser Tyr Trp Met Ser
145                 150                 155                 160

Trp Val Arg Gln Ala Pro Gly Arg Gly Leu Glu Trp Val Ala Asn Ile
                165                 170                 175

Lys Gln Asp Gly Ser Glu Lys Tyr Tyr Val Asp Ser Val Lys Gly Arg
            180                 185                 190

Phe Thr Ile Ser Arg Asp Asn Ala Lys Asn Ser Leu Tyr Leu Gln Met
        195                 200                 205

Asn Ser Leu Arg Ala Glu Asp Thr Ala Val Tyr Tyr Cys Ala Arg Gly
    210                 215                 220

Gly Trp Ser Tyr Asp Met Trp Gly Gln Gly Thr Leu Val Thr Val Ser
225                 230                 235                 240

Ser His His His His His His Gly Ala Tyr Pro Tyr Asp Val Pro Asp
                245                 250                 255

Tyr Ala Ser

<210> SEQ ID NO 185
<211> LENGTH: 312
<212> TYPE: PRT
<213> ORGANISM: Artificial Sequence
<220> FEATURE:
<223> OTHER INFORMATION: ScFv against CTLA-4 derived from ipilimumab

<400> SEQUENCE: 185

Met Ala Gln Val Gln Leu Val Glu Ser Gly Gly Gly Val Val Gln Pro
1               5                   10                  15

Gly Arg Ser Leu Arg Leu Ser Cys Ala Ala Ser Gly Phe Thr Phe Ser
            20                  25                  30

Ser Tyr Thr Met His Trp Val Arg Gln Ala Pro Gly Lys Gly Leu Glu
        35                  40                  45

Trp Val Thr Phe Ile Ser Tyr Asp Gly Asn Asn Lys Tyr Tyr Ala Asp
    50                  55                  60

Ser Val Lys Gly Arg Phe Thr Ile Ser Arg Asp Asn Ser Lys Asn Thr
65                  70                  75                  80

```
Leu Tyr Leu Gln Met Asn Ser Leu Arg Ala Glu Asp Thr Ala Ile Tyr
                85                  90                  95

Tyr Cys Ala Arg Thr Gly Trp Leu Gly Pro Phe Asp Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Glu Ile Val Leu Thr Gln Ser Pro Gly
    130                 135                 140

Thr Leu Ser Leu Ser Pro Gly Glu Arg Ala Thr Leu Ser Cys Arg Ala
145                 150                 155                 160

Ser Gln Ser Val Gly Ser Ser Tyr Leu Ala Trp Tyr Gln Gln Lys Pro
                165                 170                 175

Gly Gln Ala Pro Arg Leu Leu Ile Tyr Gly Ala Phe Ser Arg Ala Thr
            180                 185                 190

Gly Ile Pro Asp Arg Phe Ser Gly Ser Gly Ser Gly Thr Asp Phe Thr
        195                 200                 205

Leu Thr Ile Ser Arg Leu Glu Pro Glu Asp Phe Ala Val Tyr Tyr Cys
    210                 215                 220

Gln Gln Tyr Gly Ser Ser Pro Trp Thr Phe Gly Gln Gly Thr Lys Val
225                 230                 235                 240

Glu Ile Lys Arg His His His His His His Ala Ala Leu Ala Tyr Gly
                245                 250                 255

Ser Gln Gly Asn Leu Asn Pro Leu Ile Asn Glu Ile Ser Lys Ile Ile
            260                 265                 270

Ser Ala Ala Gly Asn Phe Asp Val Lys Glu Glu Arg Ala Ala Ala Ser
        275                 280                 285

Leu Leu Gln Leu Ser Gly Asn Ala Ser Asp Phe Ser Tyr Gly Arg Asn
    290                 295                 300

Ser Ile Thr Leu Thr Ala Ser Ala
305                 310


<210> SEQ ID NO 186
<211> LENGTH: 61
<212> TYPE: PRT
<213> ORGANISM: Artificial Sequence
<220> FEATURE:
<223> OTHER INFORMATION: GenBank: ABF14997.1

<400> SEQUENCE: 186

Thr Met Glu Val Ile Arg Gln Cys Ala Val Pro Gly Thr Met Val Lys
1               5                   10                  15

Tyr Asn Asp Arg Ile Tyr Lys Ala Thr Ala Asn Thr Arg Gly Lys Leu
            20                  25                  30

Thr Leu Thr Asn Ile Arg Glu Asn Ile Thr Ile Arg Asp Leu Val Ile
        35                  40                  45

Glu Ile Tyr Leu Asp Gly Lys Gly Glu Pro Leu Thr Asn
    50                  55                  60


<210> SEQ ID NO 187
<211> LENGTH: 99
<212> TYPE: DNA
<213> ORGANISM: Artificial Sequence
<220> FEATURE:
<223> OTHER INFORMATION: pfdhf: fdhf promoter, a hypoxia inducible
      promoter (part:bba_k387003)

<400> SEQUENCE: 187
```

-continued tgaataaata gtgcccgtaa tatcagggaa tgaccccaca taaaatgtgg cataaaagat 60
gcatactgta gtcgagagcg cgtatgcgtg atttgatta 99

<210> SEQ ID NO 188
<211> LENGTH: 302
<212> TYPE: PRT
<213> ORGANISM: Artificial Sequence
<220> FEATURE:
<223> OTHER INFORMATION: IgG antibody agonist with VH and VL domains specific for CD47, 5F9 anti-CD47 diabody A chain

<400> SEQUENCE: 188

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Asn Met His Trp Val Arg Gln Ala Pro Gly Gln Arg Leu Glu Trp Met
        35                  40                  45

Gly Thr Ile Tyr Pro Gly Asn Asp Asp Thr Ser Tyr Asn Gln Lys Phe
    50                  55                  60

Lys Asp Arg Val Thr Ile Thr Ala Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Tyr Arg Ala Met Asp Tyr Trp Gly Gln Gly Thr Leu
            100                 105                 110

Val Thr Val Ser Ser Gly Gly Ser Gly Gly Asp Ile Val Met Thr Gln
        115                 120                 125

Ser Pro Leu Ser Leu Pro Val Thr Pro Gly Glu Pro Ala Ser Ile Ser
    130                 135                 140

Cys Arg Ser Ser Gln Ser Ile Val Tyr Ser Asn Gly Asn Thr Tyr Leu
145                 150                 155                 160

Gly Trp Tyr Leu Gln Lys Pro Gly Gln Ser Pro Gln Leu Leu Ile Tyr
                165                 170                 175

Lys Val Ser Asn Arg Phe Ser Gly Val Pro Asp Arg Phe Ser Gly Ser
            180                 185                 190

Gly Ser Gly Thr Asp Phe Thr Leu Lys Ile Ser Arg Val Glu Ala Glu
        195                 200                 205

Asp Val Gly Val Tyr Tyr Cys Phe Gln Gly Ser His Val Pro Tyr Thr
    210                 215                 220

Phe Gly Gln Gly Thr Lys Leu Glu Ile Lys His His His His His His
225                 230                 235                 240

Ala Ala Leu Ala Tyr Gly Ser Gln Gly Asn Leu Asn Pro Leu Ile Asn
                245                 250                 255

Glu Ile Ser Lys Ile Ile Ser Ala Ala Gly Asn Phe Asp Val Lys Glu
            260                 265                 270

Glu Arg Ala Ala Ala Ser Leu Leu Gln Leu Ser Gly Asn Ala Ser Asp
        275                 280                 285

Phe Ser Tyr Gly Arg Asn Ser Ile Thr Leu Thr Ala Ser Ala
    290                 295                 300
```